(12) United States Patent
Jandeleit et al.

(10) Patent No.: US 12,427,124 B1
(45) Date of Patent: Sep. 30, 2025

(54) PHENYLALANINE-BASED LAT1 INHIBITORS AND USES THEREOF

(71) Applicant: MAXYMUNE THERAPEUTICS, INC., Los Altos, CA (US)

(72) Inventors: Bernd Jandeleit, Menlo Park, CA (US); Guangyao Gao, Los Altos, CA (US); Wolf-Nicolas Fischer, Sunnyvale, CA (US); Gordon Ringold, Los Altos Hills, CA (US)

(73) Assignee: Maxymune Therapeutics, Inc., Los Altos, CA (US)

( * ) Notice: Subject to any disclaimer, the term of this patent is extended or adjusted under 35 U.S.C. 154(b) by 0 days.

(21) Appl. No.: 19/062,521

(22) Filed: Feb. 25, 2025

Related U.S. Application Data

(60) Provisional application No. 63/746,489, filed on Jan. 17, 2025, provisional application No. 63/632,130, filed on Apr. 10, 2024.

(51) Int. Cl.
| | | |
|---|---|---|
| *C07C 311/33* | (2006.01) | |
| *A61K 31/10* | (2006.01) | |
| *A61K 31/145* | (2006.01) | |
| *C07C 311/39* | (2006.01) | |
| *C07C 311/43* | (2006.01) | |
| *C07C 311/44* | (2006.01) | |
| *C07C 317/14* | (2006.01) | |

(52) U.S. Cl.
CPC ............ *A61K 31/145* (2013.01); *A61K 31/10* (2013.01); *C07C 311/33* (2013.01); *C07C 311/39* (2013.01); *C07C 311/43* (2013.01); *C07C 311/44* (2013.01); *C07C 317/14* (2013.01); *C07C 2601/14* (2017.05); *C07C 2601/16* (2017.05); *C07C 2602/10* (2017.05)

(58) Field of Classification Search
CPC ... C07C 311/33; C07C 311/39; C07C 311/43; C07C 311/44; A61K 31/145; A61K 31/10
See application file for complete search history.

(56) References Cited

U.S. PATENT DOCUMENTS

| | | | |
|---|---|---|---|
| 3,632,628 A | | 1/1972 | Suh |
| 4,065,572 A | | 12/1977 | Atkinson et al. |
| 4,156,734 A | | 5/1979 | Stone |
| 5,298,492 A | * | 3/1994 | Neustadt ............ C07D 209/20 530/331 |
| 7,056,903 B2 | * | 6/2006 | Cournoyer ........... C07D 307/80 514/159 |
| 7,345,068 B2 | | 3/2008 | Endo et al. |
| 11,279,732 B2 | | 3/2022 | Arns et al. |
| 2010/0061936 A1 | | 3/2010 | Shen |
| 2016/0038620 A1 | | 2/2016 | Nagamori et al. |

FOREIGN PATENT DOCUMENTS

| | | |
|---|---|---|
| EP | 1 481 965 B1 | 7/2015 |
| GB | 1 527 181 A | 10/1978 |
| JP | 2016-037468 A | 3/2016 |
| WO | 1994/003481 A1 | 2/1994 |
| WO | 1999/010312 A | 3/1999 |
| WO | 1999/055330 A1 | 11/1999 |
| WO | 2001/047868 A1 | 7/2001 |
| WO | 2003/082841 A1 | 10/2003 |
| WO | 2015/117147 A1 | 8/2015 |
| WO | 2017/024009 A1 | 2/2017 |
| WO | 2017/136943 A1 | 8/2017 |

OTHER PUBLICATIONS

Zeller et al., Ophidian L-Amino Acid Oxidase, The Nature of the Enzyme-Substrate Complexes, J. Biochem,, 1965, vol. 95, pp. 262-269.
Saari et al., Tyrosine Hydroxylase Inhibitors. Synthesis and Activity of Substituted Aromatic Amino Acids, Journal of Med. Chem, Nov. 1967, vol. 10, No. 6, pp. 1008-1014.
Escher et al., 128. Angiotensin II Analogues. Part II. Synthesis and Incorporation of the Sulfur-Containing Aromatic Amino Acids: L-(4'-SH)Phe, L-(4'-SO2NH2)Phe, L-(4'-SO3-)Phe and L-(4'-S—CH3)Phe$^1)^2$), Helvetica Chimica Acta, 1983, 66(5), p. 1355-1365.
Tondi et al., Structure-based discovery and in parallel optimization of novel competitive inhibitors of thymidylate synthase, Chemistry & Biology, 1999, vol. 6, No. 5, pp. 319-331.
Hohsaka et al. Position-specific incorporation of dansylated non-natural amino acids into streptavidin by using a four-base codon, FEBS Letters 560, 2004, pp. 173-177.
Skold et al., Design, synthesis and in vitro pharmacology of Gluk1 and GluK3 antagonists. Studies towards the design of subtype-selective antagonists through 2-carboxyethyl-phenylalanines with substituents interacting with non-conserved residues in the GluK binding sites, Bioorganic & Medicinal Chemistry, 2014, 22(19), pp. 5368-5377.
Augustyn et al., LAT-1 activity of meta-substituted phenylalanine and tyrosine, Bioorganic & Medicinal Chemistry Letters, 2016, vol. 26, pp. 2616-2621.
Chien et al., Reevaluating the Substrate Specificity of the L-Type Amino Acid Transporter (LAT1), Journal of Medicinal Chemistry, 2018, vol. 61, pp. 7358-7373.
Hayashi et al., L-type amino acid transporter 1 as a target for inflammatory disease and cancer immunotherapy, Journal of Pharmacological Sciences, 2022, vol. 148, pp. 31-40.
International Search Report mailed on Apr. 23, 2025, for PCT International Application No. PCT/US2025/017195, 5 pages.
Written Opinion of the International Search Authority mailed on Apr. 23, 2025, for PCT International Application No. PCT/US2025/017195, 8 pages.

(Continued)

*Primary Examiner* — Sikarl A Witherspoon
(74) *Attorney, Agent, or Firm* — Sheppard Mullin Richter & Hampton LLP

(57) ABSTRACT

Phenylalanine-based inhibitors of the Large Amino Acid Transporter 1 (LAT1) are disclosed. The compounds are useful in modulating the transcellular transport of substrates of LAT1 such as large neutral amino acids. The compounds are useful in immunomodulation therapies.

28 Claims, No Drawings

(56) References Cited

OTHER PUBLICATIONS

Database STN Chemcats, Chemical Abstracts Service, Jan. 1, 2023, XP093267934, Database accession No. 1939895360, 3 pages.

Huttunen et al., A selective and slowly reversible inhibitor of L-Type amino acid transporter 1 (LAT1) potentiates antiproliferation drug efficacy in cancer cells, Journal of Medicinal Chemistry, vol. 59, No. 12, Jun. 23, 2016, pp. 5740-5751.

Peura et al., Design, synthesis and brain uptake of LAT1-targeted amino acid prodrugs of dopamine, Pharmaceutical Research, vol. 30, No. 10, Jan. 12, 2013, pp. 2523-2537.

* cited by examiner

PHENYLALANINE-BASED LAT1 INHIBITORS AND USES THEREOF

This application claims the benefit under 35 U.S.C § 119(e) of U.S. Provisional Application No. 63/746,489 filed on Jan. 17, 2025, and U.S. Provisional Application No. 63/632,130 filed on Apr. 10, 2024, each of which is incorporated by reference in its entirety.

FIELD

Substituted phenylalanine derivatives are disclosed. The substituted phenylalanine derivatives are inhibitors of the Large Amino Acid Transporter 1 (LAT1). The derivatives can be useful in treating a inflammatory diseases, autoimmune diseases, graft-vs.-host disease, and solid organ transplant rejection.

BACKGROUND

The LAT1-mediated transport of neutral, large aliphatic and aromatic amino acids such as leucine, phenylalanine, isoleucine, tryptophan, tyrosine, and methionine has been implicated in modulation of the immune response and immune metabolism suggesting the potential of LAT1 as a target for inflammatory and autoimmune diseases.

A small molecule LAT1 inhibitor with improved drug-like properties has the potential to be a novel therapy for treating, for example, inflammatory diseases, autoimmune diseases, graft-vs-host-disease, and solid organ transplant rejection.

SUMMARY

A compound provided by the present disclosure can have the structure of Formula (1):

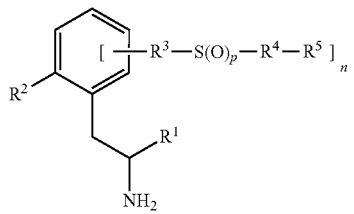

(1)

or a pharmaceutically acceptable salt thereof, wherein,
$R^1$ is selected from —COOH, —COOR$^a$, —COR$^a$, and —CON(R$^b$)$_2$, wherein,
$R^a$ is selected from $C_{1-4}$ alkyl; and
each $R^b$ is independently selected from hydrogen, —OH, $C_{1-4}$ alkyl, and $C_{1-4}$ alkoxy;
$R^2$ is selected from hydrogen, halogen, $C_{1-6}$ alkyl, $C_{1-6}$ alkoxy;
n is selected from 1 and 2;
$R^3$ and $R^4$ are independently selected from a single bond ("—"), —NR$^c$—, —C(R$^c$)$_2$, —O—NR$^c$—, —NR$^c$—O—, —NR$^c$—C(R$^c$)$_2$—, —C(R$^c$)$_2$—NR$^c$—, —C(R$^c$)$_2$—O—NR$^c$—, and —NR$^c$—O—C(R$^c$)$_2$—, wherein each $R^c$ is independently selected from hydrogen, $C_{1-3}$ alkyl, and —S(O)$_p$—R$^4$—R$^5$;
p is selected from 0, 1, and 2; and
each $R^5$ is independently selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl.

A compound provided by the present disclosure can have the structure of Formula (2):

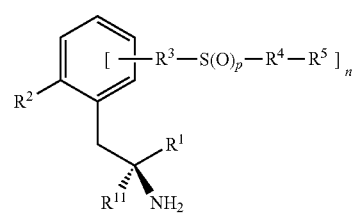

(2)

or a pharmaceutically acceptable salt thereof, wherein,
$R^1$ is selected from —COOH, —COOR$^a$, —COR$^a$, and —CON(R$^b$)$_2$, wherein,
$R^a$ is selected from $C_{1-4}$ alkyl; and each $R^b$ is independently selected from hydrogen, —OH, $C_{1-4}$ alkyl, and $C_{1-4}$ alkoxy;
$R^2$ is selected from hydrogen, halogen, $C_{1-6}$ alkyl, $C_{1-6}$ alkoxy, $C_{3-6}$ cycloalkyl, phenyl, and —R$^3$—S(O)$_p$—R$^4$—R$^5$;
n is selected from 0, 1, and 2;
$R^3$ and $R^4$ are independently selected from a single bond ("—"), —NR$^c$—, —C(R$^c$)$_2$—, —O—NR$^c$—, —NR$^c$—O—, —NR$^c$—C(R$^c$)$_2$—, —C(R$^c$)$_2$—NR$^c$—, —C(R$^c$)$_2$—O—NR$^c$—, and —NR$^c$—O—C(R$^c$)$_2$—, wherein each $R^c$ is independently selected from hydrogen, $C_{1-3}$ alkyl, and —S(O)$_p$—R$^4$—R$^5$;
each p is independently selected from 0, 1, and 2;
each $R^5$ is independently selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl; and
$R^{11}$ is selected from hydrogen and methyl.

A compound provided by the present disclosure can have the structure of Formula (1a), Formula (1b), or Formula (1c):

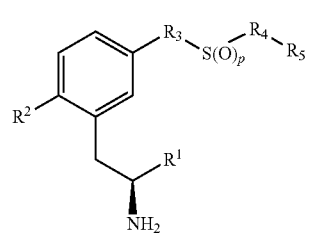

(1a)

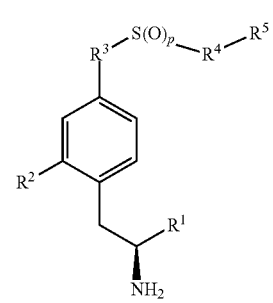

(1b)

-continued (1c)

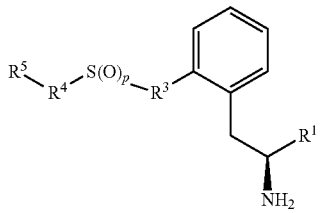

or a pharmaceutically acceptable salt thereof, wherein,
p is selected from 0, 1, and 2;
$R^1$ is selected from —COOH, —COOR$^a$, —COR$^a$ and —CON(R$^b$)$_2$, wherein,
$R^a$ is selected from $C_{1-4}$ alkyl; and
each $R^b$ is independently selected from hydrogen, —OH, $C_{1-4}$ alkyl, and $C_{1-4}$ alkoxy;
$R^2$ is selected from hydrogen, halogen, $C_{1-6}$ alkyl, $C_{1-6}$ alkoxy, $C_{3-6}$ cycloalkyl, phenyl, and —R$^3$—S(O)$_p$—R$^4$—R$^5$;
each of $R^3$ and $R^4$ is independently selected from a single bond ("—"), —NR$^c$—, C(R$^c$)$_2$, —O—NR$^c$—, —NR$^c$—O—, —NR$^c$—C(R$^c$)$_2$—, —C(R$^c$)$_2$—NR$^c$—, —C(R$^c$)$_2$—O—NR$^c$—, and —NR$^c$—O—C(R$^c$)$_2$—, wherein each $R^c$ is independently selected from hydrogen, $C_{1-3}$ alkyl, and —S(O)$_p$—R$^4$—R$^5$; and
$R^5$ is selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl.

A compound provided by the present disclosure can have the structure of Formula (1d), Formula (1e), or Formula (1f):

(1d)

(1e)

(1f)

or a pharmaceutically acceptable salt thereof, wherein,
p is selected from 0, 1, and 2;
$R^2$ is selected from hydrogen, halogen, $C_{1-3}$ alkyl, $C_{1-6}$ alkoxy, $C_{3-6}$ cycloalkyl, phenyl, and —R$^3$—S(O)$_p$—R$^4$—R$^5$; each of $R^3$ and $R^4$ is independently is selected from a single bond, —NH—, —N(—CH$_3$)—, and —CH$_2$—;
$R^5$ is selected from $C_{6-10}$ aryl, substituted $C_{6-10}$ aryl, $C_{5-6}$ cycloalkyl, $C_{1-4}$ alkyl, and benzyl; and
each substituent is independently selected from halogen, phenyl, —N(—R)$_2$, $C_{1-3}$ alkoxy, and $C_{1-3}$ alkyl, wherein each R is independently selected from hydrogen and methyl.

A compound provided by the present disclosure can have the structure of Formula (3):

(3)

or a pharmaceutically acceptable salt thereof, wherein,
$R^6$ is selected from —COOH, —COOR$^a$, —COR$^a$, and —CON(R$^b$)$_2$, wherein,
$R^a$ is $C_{1-4}$ alkyl; and
each $R^b$ is independently selected from hydrogen, —OH, $C_{1-4}$ alkyl, and $C_{1-4}$ alkoxy;
$R^7$ is selected from hydrogen and methyl;
$R^8$ is selected from hydrogen, halogen, $C_{1-3}$ alkyl, $C_{1-6}$ alkoxy, $C_{3-6}$ cycloalkyl, phenyl, and —R$^3$—S(O)$_p$—R$^4$—R$^5$; $R^9$ is selected from —S(O)$_2$—NR— and —NR—S(O)$_2$—, wherein R is selected from hydrogen and methyl;
$R^{10}$ is selected from $C_{6-10}$ aryl, substituted $C_{6-10}$ aryl, $C_{5-6}$ cycloalkyl, $C_{1-4}$ alkyl, and biphenyl; and
each substituent is independently selected from halogen, phenyl, —N(—R)$_2$, $C_{1-3}$ alkoxy, and $C_{1-3}$ alkyl.

A pharmaceutical composition provided by the present disclosure can comprise a compound provided by the present disclosure or a pharmaceutically acceptable salt thereof, and a pharmaceutically acceptable vehicle.

A method of treating organ transplant rejection in a patient comprising administering to a patient in need of such treatment a therapeutically effective amount of a compound provided by the present disclosure or a pharmaceutically acceptable salt thereof or a pharmaceutical composition provided by the present disclosure.

A method of treating an autoimmune disease in a patient comprising administering to a patient in need of such treatment a therapeutically effective amount of a compound provided by the present disclosure or a pharmaceutically acceptable salt thereof or a pharmaceutical composition provided by the present disclosure.

A method of treating a disease associated with T-cell activation, proliferation, metabolism, differentiation or a combination of any of the foregoing in a patient comprising administering to a patient in need of such treatment a therapeutically effective amount of a compound provided by the present disclosure or a pharmaceutically acceptable salt thereof or a pharmaceutical composition provided by the present disclosure.

A method of treating acute graft-vs-host-disease or chronic graft-vs-host-disease in a patient comprising administering to a patient in need of such treatment a therapeutically effective amount of a compound provided by the present disclosure or a pharmaceutically acceptable thereof or a pharmaceutical composition provided by the present disclosure.

A method of treating an inflammatory disease such as inflammatory bowel disease in a patient comprising administering to a patient in need of such treatment a therapeutically effective amount of a compound provided by the present disclosure or a pharmaceutically acceptable thereof or a pharmaceutical composition provided by the present disclosure.

DETAILED DESCRIPTION

Reference is now made to certain compounds and methods. The disclosed embodiments are not intended to be limiting of the claims. To the contrary, the claims are intended to cover all alternatives, modifications, and equivalents.

A dash ("—") that is not between two letters or symbols is used to indicate a point of attachment for a moiety or substituent. For example, —CONH$_2$ is attached through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, and but-3-yn-1-yl. The term "alkyl" is specifically intended to include groups having any degree or level of saturation, such as groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, in $C_{1-4}$ alkoxy, $C_{1-3}$ alkoxy, ethoxy or methoxy.

"Aryl" by itself or as part of another substituent refers to a monovalent aromatic hydrocarbon radical derived by the removal of one hydrogen atom from a single carbon atom of a parent aromatic ring system. Aryl encompasses 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. An aryl group can be $C_{6-10}$ aryl, $C_{6-9}$ aryl, $C_{6-8}$ aryl, or phenyl. Aryl, however, does not encompass or overlap with heteroaryl, separately defined herein.

"Compounds" disclosed herein include any specific compounds within these formulae. Compounds may be identified either by their chemical structure and/or chemical name. Compounds are named using the ChemDraw® Professional, Version 22.2.0.3300 (PerkinElmer Informatics, Inc.) or ChenDraw 23.1.2 (Revvity Signals, Waltham, MA, USA) nomenclature program. When the chemical structure and chemical name conflict, the chemical structure is determinative of the identity of the compound. The compounds described herein may comprise one or more stereogenic centers and/or double bonds, and conformationally (rotationally) restriction around single bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well-known to the skilled artisan.

Compounds disclosed herein include optical isomers of compounds of the compounds, racemates thereof, and other mixtures thereof. A single enantiomer may be obtained by asymmetric synthesis, enzymatic synthesis, the use of enantiomerically pure building blocks, or by resolution of the racemates. Resolution of the racemates may be accomplished, for example, by conventional methods such as crystallization in the presence of a resolving agent, or chromatography, using, for example a high-pressure liquid chromatography (HPLC) column with chiral stationary phases. In addition, compounds of Formula (1)-(3) include (Z)- and (E)-forms (or cis- and trans-forms) of compounds with double bonds either as single geometric isomers or mixtures thereof.

Compounds disclosed herein may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds disclosed herein include pharmaceutically acceptable salts thereof, or pharmaceutically acceptable solvates of the free acid form of any of the foregoing, as well as crystalline forms of any of the foregoing.

Compounds provided by the present disclosure include compounds of Formula (1), Formula (2), and Formula (3). Compounds of Formula (1) include compounds of Formula (1a), Formula (1b), Formula (1c), Formula (1d), Formula (1e), and Formula (1f).

Compounds of Formula (1)-(3) can comprise a mixture of compounds of Formula (1)-(3) wherein the mixture can comprise enantiomerically enriched mixtures in which the stereogenic center of the carbon atom bonded to the amine group of the compounds is in the pure (S) configuration or in the pure (R) configuration. A racemic mixture of compounds of Formula (1)-(3) can be a 50%/50% combination of compounds in the (S) configuration and the (R) configuration. A mixture of compounds of Formula (1)-(3) can comprise from 0% to 100% of compounds in which the stereogenic center of the carbon atom bonded to the amine group for the compounds is in the pure (S) configuration and from 100% to 0% of compounds in which the stereogenic center of the carbon atom bonded to the amine group is in the pure (R) configuration.

"Cycloalkyl" refers to a saturated or partially unsaturated cyclic alkyl radical. A cycloalkyl group can be $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, and cyclohexyl.

"Disease" refers to a disease, disorder, condition, or symptom of any of the foregoing.

"Halogen" refers, for example, to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in a heteroaryl group can be not more than two. In a heteroaryl, the heteroatomic group can be selected from —O—, —S—, —NH—, —N(—CH$_3$)—, —SO—, and —SO$_2$—; the heteroatomic group can be selected from —O— and —NH—, or the heteroatomic group can be —O— or —NH—. A heteroaryl group can be selected from $C_{5-10}$ heteroaryl, $C_{5-9}$ heteroaryl, $C_{5-8}$ heteroaryl, $C_{5-7}$ heteroaryl, $C_{5-6}$ heteroaryl, $C_5$ heteroaryl, and $C_6$ heteroaryl.

Examples of heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, pyrimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. A heteroaryl groups can be derived from thiophene, pyrrole, benzothiophene, benzofuran, indole, pyridine, quinoline, imidazole, oxazole, or pyrazine. For example, heteroaryl can be $C_5$ heteroaryl and is selected from furyl, thienyl, pyrrolyl, imidazolyl, pyrazolyl, isothiazolyl, or isoxazolyl. A heteroaryl can be $C_6$ heteroaryl, and can be selected from pyridinyl, pyrazinyl, pyrimidinyl, and pyridazinyl.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, and Si. Examples of heterocycloalkyl groups include groups derived from epoxides, azirines, thiiranes, imidazolidine, morpholine, piperazine, piperidine, pyrazolidine, pyrrolidine, quinuclidine, and the like. A heterocycloalkyl can be $C_5$ heterocycloalkyl and can be selected from pyrrolidinyl, tetrahydrothiophenyl, imidazolidinyl, oxazolidinyl, thiazolidinyl, doxolanyl, and dithiolanyl. A heterocycloalkyl can be $C_6$ heterocycloalkyl and can be selected from piperidinyl, piperizinyl, oxazinyl, dithianyl, and dioxanyl. A heterocycloalkyl group can be $C_{3-6}$ heterocycloalkyl, $C_{3-5}$ heterocycloalkyl, $C_{5-6}$ heterocycloalkyl, $C_5$ heterocycloalkyl or $C_6$ heterocycloalkyl. In a heterocycloalkyl, the heteroatomic group can be selected from —O—, —S—, —NH—, —N(—CH$_3$)—, —SO—, and —SO$_2$—, the heteroatomic group can be selected from —O— and —NH—, or the heteroatomic group can be —O— or —NH—.

In an expression such a "$R^1$ can be selected from a bond, —CH$_2$— etc." the term "a bond" refers to the variable $R^1$ being absent. For example, for a moiety —CH$_2$—$R^1$—NH—, wherein $R^1$ is a bond, the moiety has the structure —CH$_2$—NH—.

"Parent aromatic ring system" refers to an unsaturated cyclic or polycyclic ring system having a cyclic conjugated π (pi) electron system with 4n+2 electrons (Hückel rule). Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of π-electrons corresponding to the Hückel rule (4n+2). Examples of heteroatoms to replace the carbon atoms include N, P, O, S, and Si. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, and xanthene. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of inorganic acids include hydrochloric acid, hydrobromic acid, sulfuric acid, nitric acid, and phosphoric acid. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. A compound can have two or more ionizable groups, a pharmaceutically acceptable salt comprises one or more counterions, such as a di-salt, for example, a dihydrochloride salt, or a sodium salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound or a pharmaceutically acceptable salt thereof and at least one pharmaceutically acceptable vehicle, with which the compound or a pharmaceutically acceptable salt thereof is administered to a patient. Pharmaceutically acceptable vehicles are known in the art.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Substituted" refers to a group in which one or more hydrogen atoms are independently replaced with the same or different substituent(s). Each substituent can be independently selected from halogen, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl. Each substituent can be independently selected from halogen, —NH$_2$, —OH, C$_{1-3}$ alkoxy, and C$_{1-3}$ alkyl, trifluoromethoxy, and trifluoromethyl. Each substituent can be independently selected from —OH, methyl, ethyl, trifluoromethyl, methoxy, ethoxy, and trifluoromethoxy. Each substituent can be selected from C$_{1-3}$ alkyl, =O, C$_{1-3}$ alkyl, C$_{1-3}$ alkoxy, and phenyl. Each substituent can be selected from —OH, —NH$_2$, C$_{1-3}$ alkyl, and C$_{1-3}$ alkoxy.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also can refer to delaying the onset of the disease or at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to treat the disease or symptom thereof. A "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Zwitterion" refers to an internal salt of a compound wherein one or more protonizable functional group(s) can be protonated by one or more protogenic or proton-acidic functional group(s) within the same compound to form an internal salt typically resulting in a balanced or net zero ("0") overall charge. Examples include but are not limited to α-, β-, γ-, and δ-amino acids.

Reference is now made in detail to certain embodiments of compounds, compositions, and methods. The disclosed embodiments are not intended to be limiting of the claims. To the contrary, the claims are intended to cover all alternatives, modifications, and equivalents.

The GenBank accession number for human LAT1/4F2hc is NP_003477/NP_002385. Unless otherwise apparent from the context, reference to a transporter such as LAT1/4F2hc (as well as other transporters disclosed herein) includes the amino acid sequence described in or encoded by the GenBank reference number, and allelic, cognate and induced variants and fragments thereof retaining essentially the same transporter activity. Such variants can show at least 90% sequence identity to the exemplary Genbank nucleic acid or amino acid sequence. Allelic variants at the DNA level are the result of genetic variation between individuals of the same species. Some allelic variants at the DNA level that cause substitution, deletion or insertion of amino acids in proteins encoded by the DNA result in corresponding allelic variation at the protein level. Cognate forms of a gene refer to variation between structurally and functionally related genes between species. For example, the human gene showing the greatest sequence identity and closest functional relationship to a mouse gene is the human cognate form of the mouse gene.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. The sequence comparison algorithm enables calculation of the percent sequence identity for the test sequence(s) relative to the reference sequence, based on the designated program parameters. Optimal alignment of sequences for comparison may be conducted by methods known to those skilled in the art.

Allogeneic hematopoietic stem cell transplant (HSCT) is the only curative therapy for many malignant and non-malignant disorders of the blood, and over 20,000 HSCT procedures are completed worldwide each year. In the case of malignances, the therapeutic potential of HSCT is achieved through graft-versus-tumor (GVT) effects, which eradicate residual malignant cells long after traditional chemo- and radiotherapy has been delivered. Successful outcomes following HSCT, however, are limited by several life-threatening complications; graft-versus-host disease (GVHD) and malignant relapse are the two primary contributors to mortality. Despite advances in basic immunologic sciences, the prevention, diagnosis and treatment of GVHD has not changed significantly in the past 20 years; both acute and chronic forms of GVHD remain devastating complications to over 50% of HSCT recipients. Standard immunosuppressive therapy for GVHD is often therapeutically sub-optimal and predisposes patients to opportunistic infections and relapse of malignancy. Thus, the development of novel strategies that modulate immune dysregulation to reduce GVHD, preserve GVT activity, and facilitate immune reconstitution remains critical to enhancing survival after HSCT and are desperately needed.

Cells of the immune system undergo distinct metabolic reprogramming compared to somatic cells, and this reprogramming differs among the various immune cell populations. Therefore, targeting metabolic systems in specific T-cells involved in disease would allow for the selective regulation of those immune responses without affecting other normal cells. There are distinct immunologic and metabolic mechanisms that occur in GVHD and GVT after HSCT, including the involvement of different populations of T-cells. While memory T-cells primarily mediate GVT, GVHD is fundamentally dependent upon donor T-cell interactions with host antigen presenting cells. After engagement, these T-cells undergo clonal expansion and differentiate into distinct functional cell subsets including Th1, Th2, and Th17 cells. However, GVHD does not induce the formation of regulatory T-cells; in fact, regulatory T-cells have been shown to suppress GVHD without negatively affecting GVT. These T-cell subsets use distinct metabolic pathways. In GVHD, once naïve T-cells are activated by host antigens, they become heavily dependent on glycolytic metabolism to meet the bioenergetic needs required for their proliferation and differentiation to effector T-cells. On the other hand, regulatory (Treg) and memory T-cells (Teff) rely more heavily on lipid oxidation to generate energy. Because distinct T-cell subsets mediate GVHD and GVT, new therapeutics can be developed that target the discrete metabolic properties of these subsets to prevent or suppress GVHD without compromising GVT.

Activation, differentiation, and proliferation of T effector cells in GVHD requires both TCR engagement by host antigens and co-stimulation from the immune milieu. Many of the signals that lead to co-stimulation are integrated in the cell by activation of the mammalian target of rapamycin (mTOR) signaling pathway. Without co-stimulation, TCR engagement leads to antigen-induced cell death and anergy. However, when both signals are present, metabolic reprogramming of the activated T-cells occurs, leading to upregulate expression of various nutrient transporters to support the high energy requirements of differentiation and proliferation.

The mTOR signaling pathway has also been implicated in autoimmune diseases such as rheumatoid arthritis, Lupus, multiple sclerosis, and psoriasis, solid organ transplant rejection, inflammatory diseases such as inflammatory bowel disease including ulcerative colitis and Crohn's disease.

One of these transporters is the large neutral amino acid transporter type 1 (LAT1). LAT1 is comprised of two covalently linked subunits, a light chain (SLC7A5) and a heavy chain (CD98, SLC3A2, or 4F2hc). The light chain mediates the amino acid transport activity, while the heavy chain is required for appropriate cell surface expression of LAT1 and anchoring of the heterodimer as a functional transporter in the biomembrane. LAT1 facilitates uptake of neutral branched and neutral aromatic amino acids, such as leucine, isoleucine, and phenylalanine, and is important not only to provide the essential amino acids for protein synthesis, but also to stimulate cell growth via mTOR. LAT1 is highly expressed in the fetal organism to support rapid growth during development. In the adult, however, the expression of LAT1 is limited and is predominantly found on the endothelial cells that form the blood-brain barrier where LAT1 mediates amino acid transport into the brain, as well as in other specialized organs. However, in actively proliferating cells, such as activated T-cells and in a wide range of tumors, LAT1 expression is greatly increased. Recent studies have shown that LAT1 activity is essential for T-cell metabolism and function. Deletion of LAT1 prevents the metabolic reprogramming, proliferation, and effector function of CD4 and CD8 T cells without affecting the differentiation into regulatory T-cells. LAT1-negative cells do not transport sufficient leucine into the cell, cannot appropriately activate mTOR, and are therefore unable to induce mTOR-mediated metabolic processes.

A small molecule LAT1 inhibitor with improved drug-like properties has the potential to be a novel therapy for T-cell mediated diseases such as GVHD.

The development of inhibitors of LAT1 to treat GVHD has not been described. GVHD development after HSCT in mice is dependent on functional LAT1 expression. It has been demonstrated that T lymphocytes from mice lacking the LAT1 cofactor CD98 were unable to induce GVHD in recipient animals compared to cells from wild type mice, which prevented the mortality associated with disease progression.

We have demonstrated that the total numbers of LAT1 cofactor CD98 expressing allogeneic CD4 and CD8 splenic T-cells increases dramatically at 14 days following HSCT, while syngeneic or host-derived T-cell numbers do not significantly change. Moreover, on a per cell basis, the expression level of LAT1 (SLC7A5) was also significantly higher in allo-reactive T-cells compared to syngeneic or host T-cells. These data demonstrate that during HSCT, LAT1-positive T-cells significantly expand and LAT1 expression increases, suggesting that LAT1 activity is crucial for effector T-cell expansion and function during GVHD. This is consistent with the knockout mouse data demonstrating that LAT1-deficient T cells fail to induce GVHD. Therefore, blocking LAT1 function with a selective small molecule inhibitor could be a novel therapeutic approach for prevention or treatment of GVHD.

As provided in the present disclosure phenylalanine derivatives were synthesized and the ability of these derivatives to inhibit LAT1-mediated amino acid transport was evaluated. To analyze the potential of these compounds to inhibit LAT1-mediated amino acid transport, molecules were screened in a [$^3$H]-gabapentin uptake competition assay using LN229 cells constitutively expressing LAT1 (SLC7A5-CD98). From these results, a chemical scaffold with improved LAT1 inhibitory activity, improved synthetic tractability, and increased solubility was identified. These molecules are phenylalanine derivatives bearing: (i) lipophilic aromatic or aliphatic substituents (X) connected through sulfur-containing linkers (L) to the meta-position; and (ii) auxiliary substituents (R) in the ortho-position of the aromatic ring of the phenylalanine structure (see Table 1).

Compounds provided by the present disclosure are phenylalanine-based LAT1 inhibitors.

A compound provided by the present disclosure can have the structure of Formula (1):

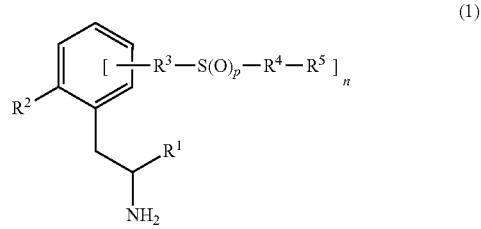

(1)

or a pharmaceutically acceptable salt thereof, wherein,
$R^1$ can be selected from —COOH, —COOR$^a$, —COR$^a$, and —CON(R$^b$)$_2$, wherein,
$R^a$ can be selected from $C_{1-4}$ alkyl; and
each $R^b$ can independently be selected from hydrogen, —OH, $C_{1-4}$ alkyl, and $C_{1-4}$ alkoxy;
$R^2$ can be selected from hydrogen, halogen, $C_{1-6}$ alkyl, and $C_{1-6}$ alkoxy;
n can be selected from 1 and 2;
$R^3$ and $R^4$ are independently selected from a single bond ("—"), —NR$^c$—, —C(R$^c$)$_2$—, —O—NR$^c$—, —NR$^c$—O—, —NR$^c$—C(R$^c$)$_2$—, —C(R$^c$)$_2$—NR$^c$—, —C(R$^c$)$_2$—O—NR$^c$—, and —NR$^c$—O—C(R$^c$)$_2$—, wherein each $R^c$ can be independently selected from hydrogen, $C_{1-3}$ alkyl, and —S(O)$_p$—R$^4$—R$^5$;
p can be selected from 0, 1, and 2; and
each $R^5$ can be independently selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl.

A compound provided by the present disclosure can have the structure of Formula (2):

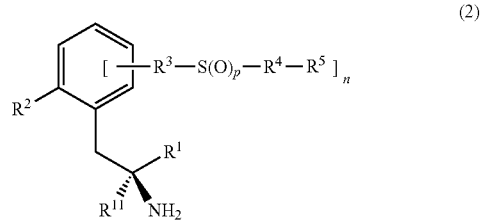

(2)

or a pharmaceutically acceptable salt thereof, wherein,
$R^1$ can be selected from —COOH, —COOR$^a$, —COR$^a$, and —CON(R$^b$)$_2$, wherein,
$R^a$ can be selected from $C_{1-4}$ alkyl; and
each $R^b$ can independently be selected from hydrogen, —OH, $C_{1-4}$ alkyl, and $C_{1-4}$ alkoxy;
$R^2$ can be selected from hydrogen, halogen, $C_{1-6}$ alkyl, $C_{1-6}$ alkoxy, $C_{3-6}$ cycloalkyl, phenyl, and —R$^3$—S(O)$_p$—R$^4$—R$^5$;

n can be selected from 0, 1 and 2;

$R^3$ and $R^4$ can independently be selected from a single bond ("—"), —$NR^c$—, —$C(R^c)_2$—, —O—$NR^c$—, —$NR^c$—O—, —$NR^c$—$C(R^c)_2$—, —$C(R^c)_2$—$NR^c$—, —$C(R^c)_2$—O—$NR^c$—, and —$NR^c$—O—$C(R^c)_2$—, wherein each $R^c$ can independently be selected from hydrogen, $C_{1-3}$ alkyl, and —$S(O)_p$—$R^4$—$R^5$;

each p can independently be selected from 0, 1, and 2;

each $R^5$ can be independently selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl; and $R^{11}$ can be selected from hydrogen and methyl.

In a compound of Formula (2), $R^{11}$ can be hydrogen.

In a compound of Formula (2), $R^{11}$ can be methyl.

In a compound of Formula (1) and Formula (2), each of the one or more substituent groups can be independently selected from halogen, $C_{1-6}$ alkyl, $C_{1-6}$ alkoxy, —$NH_2$, —$NR_2$, —$NO_2$, —NH—C(O)—R, —NR—$SO_2$—R, =O, —C(O)—OR, and —$CF_3$, wherein each R can be independently selected from hydrogen and $C_{1-3}$ alkyl.

In a compound of Formula (1) and Formula (2), each of the one or more substituent groups can be independently selected from halogen, $C_{1-6}$ alkyl, $C_{1-6}$ alkoxy, and —$NH_2$.

In a compound of Formula (1) and Formula (2), $R^1$ can be —COOH.

In a compound of Formula (1) and Formula (2), $R^1$ can be —$COOR^a$.

In a compound of Formula (1) and Formula (2), $R^1$ can be —$COOR^a$ and $R^a$ can be $C_{1-4}$ alkyl, such as methyl, ethyl, n-propyl, iso-propyl, or tert-butyl.

In a compound of Formula (1) and Formula (2), $R^1$ can be —$COR^a$.

In a compound of Formula (1) and Formula (2), $R^1$ can be —$COR^a$ and $R^a$ can be $C_{1-4}$ alkyl, such as methyl, ethyl, n-propyl, iso-propyl, or tert-butyl.

In a compound of Formula (1) and Formula (2), $R^1$ can be —$CON(R^b)_2$, wherein each $R^b$ can be hydrogen.

In a compound of Formula (1) and Formula (2), $R^1$ can be —$CON(R^b)_2$, wherein each $R^b$ can independently be $C_{1-4}$ alkyl.

In a compound of Formula (1) and Formula (2), $R^1$ can be —$CON(R^b)_2$, wherein each $R^b$ can independently be selected from hydrogen and $C_{1-4}$ alkyl.

In a compound of Formula (1) and Formula (2), $R^2$ can be hydrogen.

In a compound of Formula (1) and Formula (2), $R^2$ can be halogen.

In a compound of Formula (1) and Formula (2), $R^2$ can be Cl.

In a compound of Formula (1) and Formula (2), $R^2$ can be $C_{1-6}$ alkyl.

In a compound of Formula (1) and Formula (2), $R^2$ can be $C_{1-3}$ alkyl.

In a compound of Formula (1) and Formula (2), $R^2$ can be $C_{1-6}$ alkoxy.

In a compound of Formula (1) and Formula (2), $R^2$ can be $C_{1-3}$ alkoxy.

In a compound of Formula (2), $R^2$ can be $C_{3-6}$ cycloalkyl.

In a compound of Formula (2), $R^2$ can be cyclopentyl.

In a compound of Formula (2), $R^2$ can be cyclohexyl.

In a compound of Formula (2), $R^2$ can be phenyl.

In a compound of Formula (2), $R^2$ can be —$R^3$—$S(O)_p$—$R^4$—$R^5$.

In a compound of Formula (2), n can be 0.

In a compound of Formula (1) and Formula (2), n can be 1.

In a compound of Formula (1) and Formula (2), n can be 2.

In a compound of Formula (2), n can be 0, and $R^2$ can be —$R^3$—$S(O)_p$—$R^4$—$R^5$.

In a compound of Formula (1) and Formula (2), n can be 1 and —$R^3$—$S(O)_p$—$R^4$—$R^5$ can be bonded to the 3-position of the phenyl ring relative to the ethyl-2-amine moiety in ring position 1.

In a compound of Formula (1) and Formula (2), n can be 1 and —$R^3$—$S(O)_p$—$R^4$—$R^5$ can be bonded to the 4-position of the phenyl ring relative to the ethyl-2-amine moiety in ring position 1.

In a compound of Formula (1) and Formula (2), n can be 1 and —$R^3$—$S(O)_p$—$R^4$—$R^5$ can be bonded to the 5-position of the phenyl ring relative to the ethyl-2-amine moiety in ring position 1.

In a compound of Formula (1) and Formula (2), n can be 1 and —$R^3$—$S(O)_p$—$R^4$—$R^5$ can be bonded to the 6-position of the phenyl ring relative to the ethyl-2-amine moiety in ring position 1.

In a compound of Formula (1) and Formula (2), n can be 2 and a —$R^3$—$S(O)_p$—$R^4$—$R^5$ moiety can be bonded to the 3- and 4-positions of the phenyl ring relative to the ethyl-2-amine moiety in ring position 1.

In a compound of Formula (1) and Formula (2), n can be 2 and a —$R^3$—$S(O)_p$—$R^4$—$R^5$ moiety can be bonded to the 3 and 5 positions of the phenyl ring relative to the ethyl-2-amine moiety in ring position 1.

In a compound of Formula (1) and Formula (2), n can be 2 and a —$R^3$—$S(O)_p$—$R^4$—$R^5$ moiety can be bonded to the 3- and 6-positions of the phenyl ring relative to the ethyl-2-amine moiety in ring position 1.

In a compound of Formula (1) and Formula (2), n can be 2 and a —$R^3$—$S(O)_p$—$R^4$—$R^5$ moiety can be bonded to the 4- and 5-positions of the phenyl ring relative to the ethyl-2-amine moiety in ring position 1.

In a compound of Formula (1) and Formula (2), n can be 2 and a —$R^3$—$S(O)_p$—$R^4$—$R^5$ moiety can be bonded to the 4- and 6-positions of the phenyl ring relative to the ethyl-2-amine moiety in ring position 1.

In a compound of Formula (1) and Formula (2), n can be 2 and a —$R^3$—$S(O)_p$—$R^4$—$R^5$ moiety can be bonded to the 5- and 6-positions of the phenyl ring relative to the ethyl-2-amine moiety in ring position 1.

In a compound of Formula (1) and Formula (2), $R^3$ can be a single bond and $R^4$ can be —$NR^c$—.

In a compound of Formula (1) and Formula (2), $R^3$ can be —$NR^c$—. and $R^4$ can be a single bond.

In a compound of Formula (1) and Formula (2), $R^3$ can be a single bond and $R^4$ can be —$C(R^c)_2$—.

In a compound of Formula (1) and Formula (2), $R^3$ can be —$C(R^c)_2$— and $R^4$ can be a single bond.

In a compound of Formula (1) and Formula (2), $R^3$ can be —$NR^c$— and $R^4$ can be —$C(R^c)_2$—.

In a compound of Formula (1) and Formula (2), $R^3$ can be —$C(R^c)_2$— and $R^4$ can be —$NR^c$—.

In a compound of Formula (1) and Formula (2), $R^3$ can be —$C(R^c)_2$— and $R^4$ can be —$C(R^c)_2$—.

In a compound of Formula (1) and Formula (2), $R^3$ can be —$NR^c$— and $R^4$ can be —$NR^c$—.

In a compound of Formula (1) and Formula (2), each of $R^3$ and $R^4$ can be a single bond.

In a compound of Formula (1) and Formula (2), $R^3$ can be a single bond and $R^4$ can be —NH—.

In a compound of Formula (1) and Formula (2), $R^3$ can be —NH— and $R^4$ can be a single bond.

In a compound of Formula (1) and Formula (2), $R^3$ and/or $R^4$ can be —$NR^c$—$C(R^c)_2$—.

In a compound of Formula (1) and Formula (2), $R^3$ and/or $R^4$ can be —$C(R^c)_2$—$NR^c$—.

In a compound of Formula (1) and Formula (2), $R^3$ and/or $R^4$ can be —O—$NR^c$—

In a compound of Formula (1) and Formula (2), $R^3$ and/or $R^4$ can be —$NR^c$—O—, In a compound of Formula (1) and Formula (2), $R^3$ and/or $R^4$ can be —$C(R^c)_2$—O—$NR^c$—, In a compound of Formula (1) and Formula (2), $R^3$ and/or $R^4$ can be —$NR^c$—O—$C(R^c)_2$—, In a compound of Formula (1) and Formula (2), each $R^c$ can be hydrogen.

In a compound of Formula (1) and Formula (2), each $R^c$ can independently be selected from hydrogen and $C_{1-3}$ alkyl, such as methyl, ethyl, n-propyl, iso-propyl, and tert-butyl.

In a compound of Formula (1) and Formula (2), each $R^c$ can independently be selected from hydrogen and methyl.

In a compound of Formula (1) and Formula (2), $R^c$ can be —$S(O)_p$—$R^4$—$R^5$—.

In a compound of Formula (1) and Formula (2), p can be 0.

In a compound of Formula (1) and Formula (2), p can be 1.

In a compound of Formula (1) and Formula (2), p can be 2.

In a compound of Formula (1) and Formula (2), each $R^5$ can be hydrogen.

In a compound of Formula (1) and Formula (2), each $R^5$ can be $C_{1-6}$ alkyl.

In a compound of Formula (1) and Formula (2), each $R^5$ can independently be selected from $C_{6-12}$ aryl and substituted $C_{6-12}$ aryl.

In a compound of Formula (1) and Formula (2), each $R^5$ can independently be selected from $C_{5-12}$ heteroaryl and substituted $C_{5-12}$ heteroaryl.

In a compound of Formula (1) and Formula (2), each $R^5$ can independently be selected from $C_{3-12}$ cycloalkyl and substituted $C_{3-12}$ cycloalkyl.

In a compound of Formula (1) and Formula (2), each $R^5$ can independently be selected from $C_{3-12}$ heterocycloalkyl and substituted $C_{3-12}$ heterocycloalkyl.

In a compound of Formula (1) and Formula (2), each $R^5$ can independently be selected from phenyl and substituted phenyl.

In a compound of Formula (1) and Formula (2), each $R^5$ can independently selected from naphthyl and substituted naphthyl.

In a compound of Formula (1) and Formula (2), each $R^5$ can independently be selected from biphenyl and substituted biphenyl.

In a compound of Formula (1) and Formula (2), n can be 1, p can be 2, the moiety —$R^3$—S(O)—$R^4$—$R^5$ can be bonded to the 5-position of the phenyl ring relative to the ethyl-2-amine moiety in ring position 1, $R^3$ can be a single bond, and $R^4$ can be —NH—.

In a compound of Formula (1) and Formula (2), n can be 1, p can be 2, the moiety —$R^3$—S(O)—$R^4$—$R^5$ can be bonded to the 5-position of the phenyl ring relative to the ethyl-2-amine moiety in ring position 1, $R^3$ can be —NH— and $R^4$ can be a single bond.

In a compound of Formula (1) and Formula (2),
$R^1$ can be —COOH;
$R^2$ can be $C_{1-3}$ alkyl;
n can be 1;
—$R^3$—$S(O)_p$—$R^4$—$R^5$ can be bonded to the 5-position of the phenyl ring relative to the ethyl-2-amine moiety in ring position 1, and can be —$SO_2$—NH—; and
$R^5$ can be selected from phenyl, substituted phenyl, naphthyl, substituted naphthyl, biphenyl and substituted biphenyl;
wherein each of the one or more substituent groups can be independently selected from halogen, $C_{1-4}$ alkyl, $C_{1-4}$ alkoxy, and —$NR_2$, wherein each R can be independently selected from hydrogen and $C_{1-4}$ alkyl.

In a compound of Formula (1) and Formula (2),
$R^1$ can be —COOH;
$R^2$ can be $C_{1-3}$ alkyl;
n can be 1;
$R^3$—$S(O)_p$— $R^4$—$R^5$ can be bonded to the 5-position of the phenyl ring relative to the ethyl-2-amine moiety in ring position 1, and can be —NH—$SO_2$—; and
$R^5$ can be selected from phenyl, substituted phenyl, naphthyl, substituted naphthyl, biphenyl and substituted biphenyl;
wherein each of the one or more substituent groups can be independently selected from halogen, $C_{1-4}$ alkyl, $C_{1-4}$ alkoxy, and —$NR_2$, wherein each R can be independently selected from hydrogen and $C_{1-3}$ alkyl.

In a compound of Formula (1) and Formula (2) the stereogenic center of the carbon atom bonded to the amine group can be in the (S) configuration.

In a compound of Formula (1) and Formula (2) the stereogenic center of the carbon atom bonded to the amine group can be in the (R) configuration.

A compound of Formula (1) or Formula (2) can be selected from:

(S)-2-amino-3-(2-(methylsulfonamido)phenyl]propanoic acid (1);

(S)-2-amino-3-(5-((5-(dimethylamino)naphthalene)-1-sulfonamido)-2-methylphenyl)propanoic acid (2);

(S)-2-amino-3-(3-((5-(dimethylamino)naphthalene)-1-sulfonamido)phenyl)propanoic acid (3);

(S)-2-amino-3-(4-((5-(dimethylamino)naphthalene)-1-sulfonamido)phenyl)propanoic acid (4);

(S)-2-amino-3-(5-((5-(dimethylamino)naphthalene)-1-sulfonamido)-2-methoxyphenyl)propanoic acid (5);

(S)-2-amino-3-(2-methyl-5-(naphthalene-1-sulfonamido)phenyl)propanoic acid (6);

(S)-2-amino-3-(2-methyl-5-((4-methylphenyl)sulfonamido)phenyl)propanoic acid (7);

(S)-2-amino-3-(4-((5-(dimethylamino)naphthalene)-1-sulfonamido)-2-methoxyphenyl)propanoic acid (8);

(S)-2-amino-3-(2-methyl-5-(quinoline-5-sulfonamido)phenyl)propanoic acid (9);

(S)-2-amino-3-(2-methyl-5-(phenylsulfonamido)phenyl) propanoic acid (10);

(S)-2-amino-3-(2-methyl-5-(pyridine-3-sulfonamido)phenyl)propanoic acid (11);

(S)-2-amino-3-(2-methyl-5-((tetrahydro-2H-pyran)-4-sulfonamido)phenyl)propanoic acid (12);

(S)-3-(5-((4-acetamidonaphthalene)-1-sulfonamido)-2-methylphenyl)-2-aminopropanoic acid (13);

(S)-2-amino-3-(5-(cyclopropanesulfonamido)-2-methylphenyl)propanoic acid (14);

(S)-2-amino-3-(2-chloro-5-((5-(dimethylamino)naphthalene)-1-sulfonamido)phenyl)propanoic acid (15);

(S)-2-amino-3-(5-((5-(dimethylamino)-N-methylnaphthalene)-1-sulfonamido)-2-methylphenyl)propanoic acid (16);

(S)-3-(5-([1,1'-biphenyl]-4-sulfonamido)-2-methylphenyl)-2-aminopropanoic acid (17);
(S)-2-amino-3-(5-((1,2-dimethyl-1H-imidazole)-4-sulfonamido)-2-methylphenyl)propanoic acid (18);
(S)-2-amino-3-(2-((5-(dimethylamino)naphthalene)-1-sulfonamido)phenyl)propanoic acid (19);
(S)-2-amino-3-(2-methyl-5-((1-methylethyl)sulfonamido)phenyl)propanoic acid (20);
(S)-2-amino-3-(5-((5-(dimethylamino)naphthalene)-1-sulfonamido)-2-isopropylphenyl)propanoic acid (21);
(S)-2-amino-3-(5-((((1R,4R)-7,7-dimethyl-2-oxobicyclo[2.2.1]heptan-1-yl)methyl)sulfonamido)-2-methylphenyl)propanoic acid (22);
(S)-2-amino-3-(2-methyl-5-((phenylmethyl)sulfonamido)phenyl)propanoic acid (23);
(S)-2-amino-3-(5-((7-chlorobenzo[c][1,2,5]oxadiazole)-4-sulfonamido)-2-methylphenyl)propanoic acid (24);
(S)-2-amino-3-(5-(benzo[c][1,2,5]oxadiazole-4-sulfonamido)-2-methylphenyl)propanoic acid (25);
(S)-2-amino-3-(5-(cyclohexanesulfonamido)-2-methylphenyl)propanoic acid (26);
(S)-2-amino-3-(5-(benzo[b]thiophene-3-sulfonamido)-2-methylphenyl)propanoic acid (27);
(S)-2-amino-3-(5-((3-aminophenyl)sulfonamido)-2-methylphenyl)propanoic acid (28);
(S)-2-amino-3-(5-((3-bromophenyl)sulfonamido)-2-methylphenyl)propanoic acid (29);
(S)-2-amino-3-(5-(N-benzylsulfamoyl)-2-methylphenyl)propanoic acid (30);
(S)-3-(5-(1H-imidazole-4-sulfonamido)-2-methylphenyl)-2-aminopropanoic acid (31);
(S)-2-amino-3-(2-methyl-5-((3-((4-methylphenyl)sulfonamido)phenyl)sulfonamido)phenyl)propanoic acid (32);
(S)-2-amino-3-(2-methyl-5-((4-((4-methylphenyl)sulfonamido)phenyl)sulfonamido)phenyl)propanoic acid (33);
(R)-2-amino-3-(5-((5-(dimethylamino)naphthalene)-1-sulfonamido)-2-isopropylphenyl)propanoic acid (34);
(S)-2-amino-3-(2-methyl-5-(N-phenylsulfamoyl)phenyl)propanoic acid hydrochloride (35);
(S)-2-amino-3-(5-((2,6-dichloro-4-(trifluoromethyl)phenyl)sulfonamido)-2-methylphenyl)propanoic acid (36);
(S)-2-amino-3-(3-(phenylsulfonamido)phenyl)propanoic acid (37);
(S)-3-(5-([1,1'-biphenyl]-3-sulfonamido)-2-methylphenyl)-2-aminopropanoic acid (38);
(S)-2-amino-3-(2-methyl-5-(N-(naphthalen-1-yl)sulfamoyl)phenyl)propanoic acid (39);
(S)-3-(5-(N-([1,1'-biphenyl]-4-yl)sulfamoyl)-2-methylphenyl)-2-aminopropanoic acid (40);
(S)-2-amino-3-(5-(N-butylsulfamoyl)-2-methylphenyl)propanoic acid (41);
(S)-2-amino-3-(5-((2,6-dichlorophenyl)sulfonamido)-2-methylphenyl)propanoic acid (42);
(S)-2-amino-3-(5-((3,5-dichlorophenyl)sulfonamido)-2-methylphenyl)propanoic acid (43);
(S)-2-amino-3-(5-(N-(4-methoxyphenyl)sulfamoyl)-2-methylphenyl)propanoic acid (44); ((3-((S)-2-amino-2-carboxyethyl)-4-methylphenyl)sulfonyl)-D-proline (45);
(S)-2-amino-3-(5-(N-isobutylsulfamoyl)-2-methylphenyl)propanoic acid (46);
(S)-2-amino-3-(3,5-dichloro-4-(phenylsulfonamido)phenyl)propanoic acid (47);
(S)-2-amino-3-(2-methyl-5-((4-methyl-N-tosylphenyl)sulfonamido)phenyl)propanoic acid (48);
(S)-2-amino-3-(5-(N-(5-(dimethylamino)naphthalen-1-yl)sulfamoyl)-2-methylphenyl)propanoic acid (49);
(S)-2-amino-3-(2-methyl-5-(N-(quinolin-5-yl)sulfamoyl)phenyl)propanoic acid (50);
(R)-2-amino-3-(5-(N-(4-chlorophenyl)sulfamoyl)-2-methylphenyl)propanoic acid (51);
(S)-2-amino-3-(5-(N-(4-chlorophenyl)sulfamoyl)-2-methylphenyl)propanoic acid (52);
(S)-2-amino-3-(5-(N-cyclohexylsulfamoyl)-2-methylphenyl)propanoic acid (53);
(S)-2-amino-3-(2-methyl-5-(((phenylmethyl)sulfonamido)methyl)phenyl)propanoic acid (54);
(S)-2-amino-3-(5-((benzylthio)methyl)-2-methylphenyl)propanoic acid (55);
(S)-2-amino-3-(5-((benzylsulfonyl)methyl)-2-methylphenyl)propanoic acid (56);
(S)-2-amino-3-(5-((4-methoxyphenyl)sulfonamido)-2-methylphenyl)propanoic acid (57);
(S)-2-amino-3-(5-(butylsulfonamido)-2-methylphenyl)propanoic acid (58);
(S)-2-amino-3-(5-(benzylthio)-2-methylphenyl)propanoic acid (59); (2S)-2-amino-3-(5-((benzylsulfinyl)methyl)-2-methylphenyl)propanoic acid (60);
(S)-2-amino-3-(3,5-di(methylsulfonamido)phenyl)propanoic acid (61);
(S)-2-amino-3-(3,5-bis(phenylsulfonamido)phenyl)propanoic acid (62);
(S)-2-amino-3-(3,5-bis((4-methylphenyl)sulfonamido)phenyl)propanoic acid (63);
(2S)-2-amino-3-(5-(benzylsulfinyl)-2-methylphenyl)propanoic acid (64);
(S)-2-amino-3-(5-(benzylsulfonyl)-2-methylphenyl)propanoic acid (65);
(S)-2-amino-3-(2-methyl-5-(((4-methylphenyl)sulfonamido)methyl)phenyl)propanoic acid (66);
(S)-2-amino-3-(2-methyl-5-(methylsulfonamido)phenyl)propanoic acid (67);
(S)-2-amino-3-(3-(methylsulfonamido)phenyl)propanoic acid (68);
(S)-2-amino-3-(2-methyl-5-(phenylsulfonamidomethyl)phenyl)propanoic acid (69);
(S)-2-amino-3-(4-(methylsulfonamido)phenyl)propanoic acid (70);
(S)-2-amino-3-(3-sulfamoylphenyl)propanoic acid (71);
(S)-2-amino-3-(3-(N-methylsulfamoyl)phenyl)propanoic acid (72);
(S)-2-amino-3-(3-(N,N-dimethylsulfamoyl)phenyl)propanoic acid (73);
(S)-2-amino-3-(4-sulfamoylphenyl)propanoic acid (74);
(S)-2-amino-3-(5-(N-(2-bromophenyl)sulfamoyl)-2-methylphenyl)propanoic acid (75);
(S)-2-amino-3-(5-(N-(3-bromophenyl)sulfamoyl)-2-methylphenyl)propanoic acid (76);
(S)-2-amino-3-(5-(N-(4-bromophenyl)sulfamoyl)-2-methylphenyl)propanoic acid (77);
(S)-2-amino-3-(3-(piperidin-1-ylsulfonyl)phenyl)propanoic acid (78);
(S)-2-amino-3-(3-(N-(4-chlorophenyl)sulfamoyl)phenyl)propanoic acid (79);
(S)-2-amino-3-(4-(N-(4-fluorophenyl)sulfamoyl)phenyl)propanoic acid (80);
(S)-2-amino-3-(2-(N-(4-chlorophenyl)sulfamoyl)phenyl)propanoic acid (81);
tert-butyl (S)-2-amino-3-(5-(N-(4-chlorophenyl)sulfamoyl)-2-methylphenyl)propanoate (82);
(S)-2-amino-3-(5-(N-(3,4-dichlorophenyl)sulfamoyl)-2-methylphenyl)propanoic acid (83);
(S)-2-amino-3-(5-(N-(4-chlorophenyl)-N-methylsulfamoyl)-2-methylphenyl)propanoic acid (84);

(S)-2-amino-3-(4-(N-(4-chlorophenyl)sulfamoyl)-2-methylphenyl)propanoic acid (85);
(S)-2-amino-3-(5-(N-(4-chlorophenyl)sulfamoyl)-2-isopropylphenyl)propanoic acid (86);
(S)-2-amino-3-(5-((4-(tert-butyl)phenyl)sulfonamido)-2-methylphenyl)propanoic acid (87); and
(S)-2-amino-3-(5-((4-chlorophenyl)sulfonamido)-2-methylphenyl)propanoic acid (88);
or a pharmaceutically acceptable salt of any of the foregoing.

A compound of Formula (1) can be selected from:
(S)-2-amino-3-(5-(N-(4-chlorophenyl)sulfamoyl)-2-methylphenyl)propanoic acid (89);
(S)-2-amino-3-(5-(N-(4-chlorophenyl)sulfamoyl)-2-methylphenyl)-N-methylpropanamide (90);
(S)-2-amino-3-(5-(N-(4-chlorophenyl)sulfamoyl)-2-methylphenyl)-N,N-dimethylpropanamide (91);
(S)-2-amino-3-(5-(N-(4-chlorophenyl)sulfamoyl)-2-methylphenyl)-N-isopropylpropanamide (92);
(S)-2-amino-3-(5-(N-(4-chlorophenyl)sulfamoyl)-2-methylphenyl)-N-hydroxypropanamide (93);
(S)-2-amino-3-(5-(N-(4-chlorophenyl)sulfamoyl)-2-methylphenyl)-N-methoxy-N-methylpropanamide (94);
(S)-3-(2-amino-4-methyl-3-oxopentyl)-N-(4-chlorophenyl)-4-methylbenzenesulfonamide (95);
(2S)-2-amino-3-(2-methyl-5-((p-tolylsulfinyl)amino)phenyl)propanoic acid (96);
(2S)-2-amino-3-(5-(((4-chlorophenyl)amino)sulfinyl)-2-methylphenyl)propanoic acid (97);
(S)-2-amino-3-(5-(((4-chlorophenyl)sulfonamido)oxy)-2-methylphenyl)propanoic acid (98);
(S)-2-amino-3-(5-((N-(4-chlorophenyl)sulfamoyl)amino)-2-methylphenyl)propanoic acid (99);
methyl (S)-2-amino-3-(5-(N-(4-chlorophenyl)sulfamoyl)-2-methylphenyl)propanoate (100); and
ethyl (S)-2-amino-3-(5-(N-(4-chlorophenyl)sulfamoyl)-2-methylphenyl)propanoate (101);
or a pharmaceutically acceptable salt of any of the foregoing.

A compound provided by the present disclosure can have the structure of Formula (1a), Formula (1b), or Formula (1c):

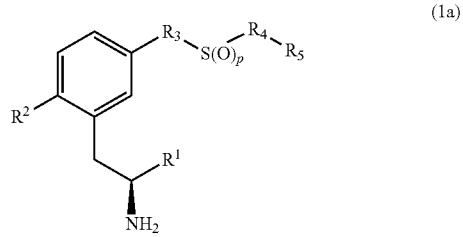
(1a)

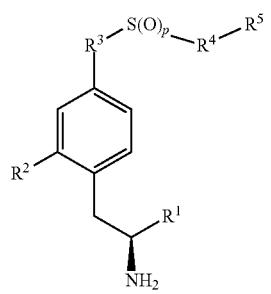
(1b)

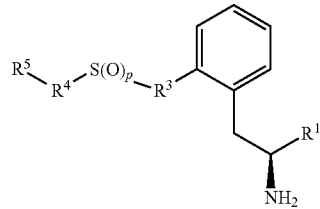
(1c)

or a pharmaceutically acceptable salt thereof, wherein,
p can be selected from 0, 1, and 2;
$R^1$ can be selected from —COOH, —COOR$^a$, —COR$^a$, and —CON(R$^b$)$_2$, wherein,
R$^a$ can be selected from $C_{1-4}$ alkyl; and
each R$^b$ can independently be selected from hydrogen, —OH, $C_{1-4}$ alkyl, and $C_{1-4}$ alkoxy;
$R^2$ can be selected from hydrogen, halogen, $C_{1-6}$ alkyl, $C_{1-6}$ alkoxy, $C_{3-6}$ cycloalkyl, and phenyl;
each of $R^3$ and $R^4$ can independently be selected from a single bond ("—"), —NR$^c$—, C(R$^c$)$_2$, —O—NR$^c$—, —NR$^c$—O—, —NR$^c$—C(R$^c$)$_2$—, —C(R$^c$)$_2$—NR$^c$—, —C(R$^c$)$_2$—O—NR$^c$—, and —NR$^c$—O—C(R$^c$)$_2$—, wherein each R$^c$ can independently be selected from hydrogen, $C_{1-3}$ alkyl, and —S(O)$_p$—R$^4$—R$^5$; and
each $R^5$ can independently be selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl.

A compound provided by the present disclosure can have the structure of Formula (1a).

A compound provided by the present disclosure can have the structure of Formula (1b).

A compound provided by the present disclosure can have the structure of Formula (1c).

In a compound of Formula (1a)-(1c), each of the one or more substituent groups can independently be selected from halogen, $C_{1-6}$ alkyl, $C_{1-6}$ alkoxy, —NH$_2$, —NR$_2$, —NO$_2$, —NH—C(O)—R, —NR—SO$_2$—R, =O, —C(O)—OR, and —CF$_3$, wherein each R can independently be selected from hydrogen and $C_{1-3}$ alkyl.

In a compound of Formula (1a)-(1c), $R^1$ can be —COOH.
In a compound of Formula (1a) and Formula (1b), $R^1$ can be —COOR$^a$, wherein R$^a$ can be selected from $C_{1-4}$ alkyl.
In a compound of Formula (1a)-(1c), $R^1$ can be —COR$^a$, wherein R$^a$ can be selected from $C_{1-4}$ alkyl.
In a compound of Formula (1a)-(1c), $R^1$ can be —CON(R$^b$)$_2$, wherein each R$^b$ can independently be selected from hydrogen, —OH, $C_{1-4}$ alkyl, and $C_{1-4}$ alkoxy.

A compound provided by the present disclosure can have the structure of Formula (1d), Formula (1e), or Formula (1f):

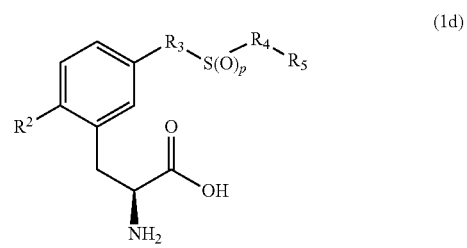
(1d)

(1e)

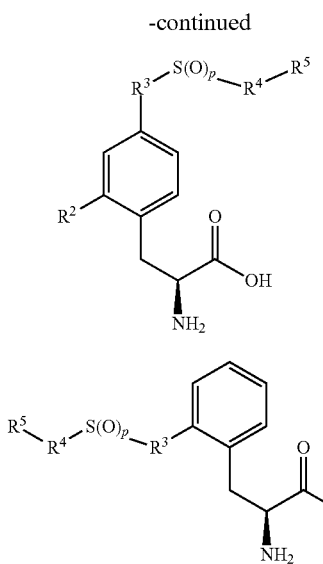

(1f)

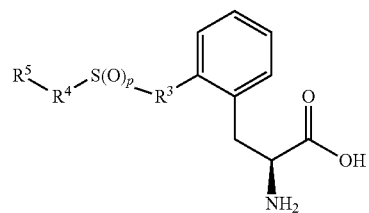

or a pharmaceutically acceptable salt thereof, wherein,
p can be selected from 0, 1, and 2;
R can be selected from hydrogen, halogen, $C_{1-3}$ alkyl, $C_{1-3}$ alkoxy, $C_{3-6}$ cycloalkyl, and phenyl;
each of $R^3$ and $R^4$ can independently be selected from a single bond, —NH—, —N(—$CH_3$)—, and —$CH_2$—;
$R^5$ can be selected from $C_{6-10}$ aryl, substituted $C_{6-10}$ aryl, $C_{5-6}$ cycloalkyl, $C_{1-4}$ alkyl, and benzyl; and
each substituent can independently be selected from halogen, phenyl, —N(—R)$_2$, $C_{1-3}$ alkoxy, and $C_{1-3}$ alkyl, wherein each R can independently be selected from hydrogen and methyl.

A compound provided by the present disclosure can have the structure of Formula (1d).
A compound provided by the present disclosure can have the structure of Formula (1e).
A compound provided by the present disclosure can have the structure of Formula (1f).
In a compound of Formula (1a)-(1f), p can be 0.
In a compound of Formula (1a)-(1f), p can be 1.
In a compound of Formula (1a)-(1f), p can be 2.
In a compound of Formula (1a), (1b), (1d) and (1e), $R^2$ can be hydrogen.
In a compound of Formula (1a), (1b), (1d) and (1e), $R^2$ can be halogen.
In a compound of Formula (1a), (1b), (1d) and (1e), $R^2$ can be $C_{1-3}$ alkyl.
In a compound of Formula (1a), (1b), (1d) and (1e), $R^2$ can be methyl.
In a compound of Formula (1a), (1b), (1d) and (1e), $R_2$ can be $C_{1-4}$ alkoxy.
In a compound of Formula (1a), (1b), (1d) and (1e), $R^2$ can be methoxy.
In a compound of Formula (1a), (1b), (1d) and (1e), $R^2$ can be $C_{3-6}$ cycloalkyl.
In a compound of Formula (1a), (1b), (1d) and (1e), $R^2$ can be cyclopentyl.
In a compound of Formula (1a), (1b), (1d) and (1e), $R^2$ can be cyclohexyl.
In a compound of Formula (1a), (1b), (1d) and (1e), $R^2$ can be phenyl.
In a compound of Formula (1d)-(1f), the moiety —$R^3$—$(S(O)_p)$—$R^4$— can be selected from —NH—$S(O)_2$—, —$S(O)_2$—NH—, —N(—$CH_3$)—$S(O)_2$—, —$S(O)_2$—N(—$CH_3$)—, —$CH_2$—S—$CH_2$—, —S—$CH_2$—, —$S(O)_2$—$CH_2$—, and —NH—$S(O)_2$—$CH_2$—.

In a compound of Formula (1a-(1f), the moiety —$R^3$—$(S(O)_p)$—$R^4$— can be —NH—$S(O)_2$—.
In a compound of Formula (1a)-(1f), the moiety —$R^3$—$(S(O)_p)$—$R^4$— can be —$S(O)_2$—NH—.
In a compound of Formula (1a)-(1f), the moiety —$R^3$—$(S(O)_p)$—$R^4$— can be —N(—$CH_3$)—$S(O)_2$—.
In a compound of Formula (1a)-(1f), the moiety —$R^3$—$(S(O)_p)$—$R^4$— can be —$S(O)_2$—N(—$CH_3$)—.
In a compound of Formula (1a)-(1f), the moiety —$R^3$—$(S(O)_p)$—$R^4$— can be —$CH_2$—S—$CH_2$—.
In a compound of Formula (1a)-(1f), the moiety —$R^3$—$(S(O)_p)$—$R^4$— can be —S—$CH_2$—.
In a compound of Formula (1a)-(1f), the moiety —$R^3$—$(S(O)_p)$—$R^4$— can be —$S(O)_2$—$CH_2$—.
In a compound of Formula (1a)-(1f), the moiety —$R^3$—$(S(O)_p)$—$R^4$— can be —NH—$S(O)_2$—$CH_2$—.
In a compound of Formula (1a)-(1f), $R^5$ can be $C_{6-10}$ aryl.
In a compound of Formula (1a)-(1f), $R^5$ can be substituted $C_{6-10}$ aryl; and each substituent can independently be selected from halogen, phenyl, —N(—R)$_2$, $C_{1-3}$ alkoxy, and $C_{1-3}$ alkyl.
In a compound of Formula (1a)-(1f), $R^5$ can be $C_{5-6}$ cycloalkyl.
In a compound of Formula (1a)-(1f), $R^5$ can be $C_{1-4}$ alkyl.
In a compound of Formula (1a)-(1f), each substituent can independently be selected from halogen, phenyl, —N(—R)$_2$, $C_{1-3}$ alkoxy, and $C_{1-3}$ alkyl.
In a compound of Formula (1a)-(1f), $R^5$ can be cyclohexyl.
In a compound of Formula (1a)-(1f), $R^5$ can be $C_{1-4}$ alkyl.
In a compound of Formula (1a)-(1f), $R^5$ can be phenyl.
In a compound of Formula (1a)-(1f), each substituent group can independently selected be from Cl, Br, $C_{1-3}$ alkyl, phenyl, and $C_{1-3}$ alkoxy.
In a compound of Formula (1a)-(1f), $R^5$ can be naphthyl.
In a compound of Formula (1a)-(1f), $R^5$ can be substituted naphthyl; and the substituent group can be selected from —$NH_2$, —NH(—$CH_3$), and —NH(—$CH_3$)$_2$.
In a compound of Formula (1a)-(1f), $R^5$ can be quinolinyl.
A compound provided by the present disclosure can have the structure of Formula (3):

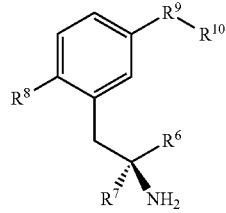

(3)

or a pharmaceutically acceptable salt thereof, wherein,
$R^6$ can be selected from —COOH, —COO$R^a$, —CO$R^a$, and —CON($R^b$)$_2$, wherein,
$R^a$ can be $C_{1-4}$ alkyl; and
each $R^b$ can independently be selected from hydrogen, —OH, $C_{1-4}$ alkyl, $C_{1-4}$ alkoxy;
$R^7$ can be selected from hydrogen and methyl;
$R^8$ can be selected from hydrogen, halogen, $C_{1-3}$ alkyl, $C_{1-3}$ alkoxy, $C_{3-6}$ cycloalkyl, and phenyl;

R$^9$ can be selected from —S(O)$_2$—NR— and —NR—S(O)$_2$—, wherein R is selected from hydrogen and methyl;

R$^{10}$ can be selected from C$_{6-10}$ aryl, substituted C$_{6-10}$ aryl, C$_{5-6}$ cycloalkyl, C$_{1-4}$ alkyl, and benzyl; and each substituent can independently be selected from halogen, phenyl, —N(—R)$_2$, C$_{1-3}$ alkoxy, and C$_{1-3}$ alkyl.

In a compound of Formula (3), R$^6$ can be —COOH.

In a compound of Formula (3), R$^7$ can be hydrogen.

In a compound of Formula (3), R$^7$ can be methyl.

In a compound of Formula (3), R$^8$ can be C$_{1-3}$ alkyl.

In a compound of Formula (3), R$^8$ can be methyl.

In a compound of Formula (3), R$^8$ can be C$_{1-4}$ alkoxy.

In a compound of Formula (3), R$^8$ can be methoxy.

In a compound of Formula (3), R$^8$ can be C$_{3-6}$ cycloalkyl.

In a compound of Formula (3), R$^8$ can be cyclopentyl.

In a compound of Formula (3), R$^8$ can be cyclohexyl.

In a compound of Formula (3), R$^8$ can be phenyl.

In a compound of Formula (3), R$^9$ can be —S(O)$_2$—NR—.

In a compound of Formula (3), R can be hydrogen.

In a compound of Formula (3), R can be methyl.

In a compound of Formula (3), R$^9$ can be —NR—S(O)$_2$—.

In a compound of Formula (3), R can be hydrogen.

In a compound of Formula (3), R can be methyl.

In a compound of Formula (3), R$^{10}$ can be selected from phenyl and substituted phenyl.

In a compound of Formula (3), the substituted phenyl can be 4-substituted phenyl.

In a compound of Formula (3), the substituted phenyl can be 3-substituted phenyl.

In a compound of Formula (3), the substituent can be selected from Cl, Br, methoxy, and phenyl.

In a compound of Formula (3), R$^{10}$ can be selected from naphthyl and substituted naphthyl.

In a compound of Formula (3), the substituent can be selected from —N(R)$_2$, wherein each R can independently be selected from hydrogen and methyl.

In a compound of Formula (3), R$^{10}$ can be benzyl.

In a compound of Formula (3), R$^{10}$ can be C$_{5-6}$ cycloalkyl.

In a compound of Formula (3), R$^{10}$ can be cyclohexyl.

In a compound of Formula (3), R$^{10}$ can be C$_{1-4}$ alkyl.

In a compound of Formula (3),
R$^6$ can be —COOH;
R$^7$ can be hydrogen;
R$^8$ can be methyl; and
R$^9$ can be from —S(O)$_2$—NH—.

In a compound of Formula (3),
R$^6$ can be —COOH;
R$^7$ can be hydrogen.
R$^8$ can be methyl; and
R$^9$ can be from —NH—S(O)$_2$—.

In a compound of Formula (3), R$^{10}$ can be C$_{6-10}$ aryl.

In a compound of Formula (3), R$^{10}$ can be substituted C$_{6-10}$ aryl.

In a compound of Formula (3), R$^{10}$ can be selected from phenyl and substituted phenyl.

In a compound of Formula (3), the substituted phenyl can be 4-substituted phenyl.

In a compound of Formula (3), the substituted phenyl can be 3-substituted phenyl.

In a compound of Formula (3), the substituent can be selected from Cl, Br, methoxy, and phenyl.

In a compound of Formula (3), R$^{10}$ can be selected from naphthyl and substituted naphthyl.

In a compound of Formula (3), the substituent can be —N(R)$_2$.

In a compound of Formula (3), each R can independently be selected from hydrogen and methyl.

In a compound of Formula (3), R$^{10}$ can be benzyl.

In a compound of Formula (3), R$^{10}$ can be C$_{5-6}$ cycloalkyl.

In a compound of Formula (3), R$^{10}$ can be cyclohexyl.

In a compound of Formula (3), R$^{10}$ can be C$_{1-4}$ alkyl.

In a compound of Formula (3), R$^{10}$ can be benzyl.

In a compound of Formula (3), R$^7$ can be —COOH.

In a compound of Formula (3), R$^7$ can be hydrogen.

In a compound of Formula (3), R$^8$ can be C$_{1-3}$ alkyl.

In a compound of Formula (3), R$^8$ can be methyl.

In a compound of Formula (3), R$^{10}$ can be selected from C$_{6-10}$ aryl, substituted C$_{6-10}$ aryl, C$_{1-6}$ alkyl, C$_{5-10}$ cycloalkyl, alkylarene, substituted alkylarene.

In a compound of Formula (3), R$^{10}$ can be selected from phenyl, 4-substituted phenyl, and 3-substituted phenyl.

In a compound of Formula (3), the substituent can be selected from halogen, —N(R)$_2$, C$_{1-3}$ alkyl, C$_{1-3}$ alkoxy, and benzyl.

A compound provided by the present disclosure can be selected from:
(S)-2-amino-3-(5-(N-benzylsulfamoyl)-2-methylphenyl)propanoic acid (30);
(S)-2-amino-3-(5-(N-(4-methoxyphenyl)sulfamoyl)-2-methylphenyl)propanoic acid (44);
(S)-2-amino-3-(5-(N-(4-chlorophenyl)sulfamoyl)-2-methylphenyl)propanoic acid (52);
(S)-2-amino-3-(5-(N-(3-bromophenyl)sulfamoyl)-2-methylphenyl)propanoic acid (76);
(S)-2-amino-3-(5-(N-(4-bromophenyl)sulfamoyl)-2-methylphenyl)propanoic acid (77); and
(S)-2-amino-3-(5-(N-(4-chlorophenyl)sulfamoyl)-2-isopropylphenyl)propanoic acid (86);
or a pharmaceutically acceptable salt of any of the foregoing.

A compound provided by the present disclosure can be selected from:
(S)-2-amino-3-(5-((5-(dimethylamino)naphthalene)-1-sulfonamido)-2-isopropylphenyl)propanoic acid (21);
(S)-2-amino-3-(5-((3-bromophenyl)sulfonamido)-2-methylphenyl)propanoic acid (29);
(S)-2-amino-3-(2-methyl-5-(N-phenylsulfamoyl)phenyl)propanoic acid hydrochloride (35);
(S)-3-(5-([1,1'-biphenyl]-3-sulfonamido)-2-methylphenyl)-2-aminopropanoic acid (38);
(S)-2-amino-3-(2-methyl-5-(N-(naphthalen-1-yl)sulfamoyl)phenyl)propanoic acid (39); and
(S)-3-(5-(N-([1,1'-biphenyl]-4-yl)sulfamoyl)-2-methylphenyl)-2-aminopropanoic acid (40);
or a pharmaceutically acceptable salt of any of the foregoing.

A compound provided by the present disclosure can be selected from:
(S)-2-amino-3-(2-methyl-5-(phenylsulfonamido)phenyl)propanoic acid (10);
(S)-2-amino-3-(5-(N-butylsulfamoyl)-2-methylphenyl)propanoic acid (41);
(S)-2-amino-3-(5-(N-(5-(dimethylamino)naphthalen-1-yl)sulfamoyl)-2-methylphenyl)propanoic acid (49);
(S)-2-amino-3-(5-(N-cyclohexylsulfamoyl)-2-methylphenyl)propanoic acid (53);
(S)-2-amino-3-(3-(N-(4-chlorophenyl)sulfamoyl)phenyl)propanoic acid (79);
tert-butyl (S)-2-amino-3-(5-(N-(4-chlorophenyl)sulfamoyl)-2-methylphenyl)propanoate (82);

(S)-2-amino-3-(5-(N-(4-chlorophenyl)-N-methylsulfamoyl)-2-methylphenyl)propanoic acid (84); and
(S)-2-amino-3-(5-((4-(tert-butyl)phenyl)sulfonamido)-2-methylphenyl)propanoic acid (87);
   or a pharmaceutically acceptable salt of any of the foregoing.

A compound provided by the present disclosure can be selected from:
(S)-2-amino-3-(5-((5-(dimethylamino)naphthalene)-1-sulfonamido)-2-methylphenyl)propanoic acid (2);
(S)-2-amino-3-(3-((5-(dimethylamino)naphthalene)-1-sulfonamido)phenyl)propanoic acid (3);
(S)-2-amino-3-(2-methyl-5-((4-methylphenyl)sulfonamido)phenyl)propanoic acid (7);
(S)-2-amino-3-(5-((3,5-dichlorophenyl)sulfonamido)-2-methylphenyl)propanoic acid (43);
(S)-2-amino-3-(5-(N-isobutylsulfamoyl)-2-methylphenyl)propanoic acid (46);
(S)-2-amino-3-(5-((benzylthio)methyl)-2-methylphenyl)propanoic acid (55);
(S)-2-amino-3-(5-(benzylsulfonyl)-2-methylphenyl)propanoic acid (65); and
(S)-2-amino-3-(5-(N-(2-bromophenyl)sulfamoyl)-2-methylphenyl)propanoic acid (75);
   or a pharmaceutically acceptable salt of any of the foregoing.

A compound provided by the present disclosure can be selected from:
(S)-2-amino-3-(2-methyl-5-(naphthalene-1-sulfonamido)phenyl)propanoic acid (6);
(S)-3-(5-([1,1'-biphenyl]-4-sulfonamido-2-methylphenyl)-2-aminopropanoic acid (17);
(S)-2-amino-3-(2-methyl-5-((phenylmethyl)sulfonamido)phenyl)propanoic acid (23);
(S)-2-amino-3-(2-methyl-5-(N-(quinolin-5-yl)sulfamoyl)phenyl)propanoic acid (50);
(S)-2-amino-3-(5-(benzylthio)-2-methylphenyl)propanoic acid (59); and
(S)-2-amino-3-(5-(N-(3,4-dichlorophenyl)sulfamoyl)-2-methylphenyl)propanoic acid (83);
   or a pharmaceutically acceptable salt of any of the foregoing.

A compound provided by the present disclosure can be selected from:
(S)-2-amino-3-(5-((5-(dimethylamino)-N-methylnaphthalene)-1-sulfonamido)-2-methylphenyl)propanoic acid (16);
(S)-2-amino-3-(5-(cyclohexanesulfonamido)-2-methylphenyl)propanoic acid (26);
(S)-2-amino-3-(5-(benzo[b]thiophene-3-sulfonamido)-2-methylphenyl)propanoic acid (27);
(S)-2-amino-3-(2-methyl-5-((3-((4-methylphenyl)sulfonamido)phenyl)sulfonamido)phenyl)propanoic acid (32);
(S)-2-amino-3-(2-methyl-5-((4-methyl-N-tosylphenyl)sulfonamido)phenyl)propanoic acid (48); and
(S)-2-amino-3-(5-((4-methoxyphenyl)sulfonamido)-2-methylphenyl)propanoic acid (57);
   or a pharmaceutically acceptable salt of any of the foregoing.

A compound provided by the present disclosure can be selected from:
(S)-2-amino-3-(2-chloro-5-((5-(dimethylamino)naphthalene)-1-sulfonamido)phenyl)propanoic acid (15);
(S)-2-amino-3-(5-((benzylsulfonyl)methyl)-2-methylphenyl)propanoic acid (56);
(S)-2-amino-3-(5-(butylsulfonamido)-2-methylphenyl)propanoic acid (58);
(S)-2-amino-3-(2-methyl-5-(phenylsulfonamidomethyl)phenyl)propanoic acid (69);
   or a pharmaceutically acceptable salt of any of the foregoing. <1000 nM A compound provided by the present disclosure can be selected from:
(S)-2-amino-3-(5-((5-(dimethylamino)naphthalene)-1-sulfonamido)-2-methoxyphenyl)propanoic (5);
(S)-2-amino-3-(2-((5-(dimethylamino)naphthalene)-1-sulfonamido)phenyl)propanoic acid (19);
(S)-2-amino-3-(5-((3-aminophenyl)sulfonamido)-2-methylphenyl)propanoic acid (28);
(S)-2-amino-3-(2-methyl-5-((4-((4-methylphenyl)sulfonamido)phenyl)sulfonamido)phenyl)propanoic acid (33);
(S)-2-amino-3-(3-(phenylsulfonamido)phenyl)propanoic acid (37);
(S)-2-amino-3-(5-((2,6-dichlorophenyl)sulfonamido)-2-methylphenyl)propanoic acid (42);
(2S)-2-amino-3-(5-((benzylsulfinyl)methyl)-2-methylphenyl)propanoic acid (60);
(S)-2-amino-3-(2-methyl-5-(((4-methylphenyl)sulfonamido)methyl)phenyl)propanoic acid (66); and
(S)-2-amino-3-(4-(N-(4-chlorophenyl)sulfamoyl)-2-methylphenyl)propanoic acid (85);
   or a pharmaceutically acceptable salt of any of the foregoing.

A compound provided by the present disclosure can be selected from:
(S)-2-amino-3-(4-((5-(dimethylamino)naphthalene)-1-sulfonamido)phenyl)propanoic acid (4);
(S)-2-amino-3-(4-((5-(dimethylamino)naphthalene)-1-sulfonamido)-2-methoxyphenyl)propanoic acid (8);
(S)-2-amino-3-(2-methyl-5-(quinoline-5-sulfonamido)phenyl)propanoic acid (9);
(S)-2-amino-3-(2-methyl-5-(pyridine-3-sulfonamido)phenyl)propanoic acid (11);
(S)-2-amino-3-(2-methyl-5-((tetrahydro-2H-pyran)-4-sulfonamido)phenyl)propanoic acid (12);
(S)-3-(5-((4-acetamidonaphthalene)-1-sulfonamido)-2-methylphenyl)-2-aminopropanoic acid (13);
(S)-2-amino-3-(5-(cyclopropanesulfonamido)-2-methylphenyl)propanoic acid (14);
(S)-2-amino-3-(2-methyl-5-((1-methylethyl)sulfonamido)phenyl)propanoic acid (20);
(S)-2-amino-3-(5-((((1R,4R)-7,7-dimethyl-2-oxobicyclo[2.2.1]heptan-1-yl)methyl)sulfonamido)-2-methylphenyl)propanoic acid (22);
(S)-2-amino-3-(5-((7-chlorobenzo[c][1,2,5]oxadiazole)-4-sulfonamido)-2-methylphenyl)propanoic acid (24);
(S)-2-amino-3-(5-(benzo[c][1,2,5]oxadiazole-4-sulfonamido)-2-methylphenyl)propanoic acid (25);
(R)-2-amino-3-(5-((5-(dimethylamino)naphthalene)-1-sulfonamido)-2-isopropylphenyl)propanoic acid (34);
(S)-2-amino-3-(5-((2,6-dichloro-4-(trifluoromethyl)phenyl)sulfonamido)-2-methylphenyl)propanoic acid (36);
(S)-2-amino-3-(2-methyl-5-(((phenylmethyl)sulfonamido)methyl)phenyl)propanoic acid (54);
(S)-2-amino-3-(3,5-bis((4-methylphenyl)sulfonamido)phenyl)propanoic acid (63);
(2S)-2-amino-3-(5-(benzylsulfinyl)-2-methylphenyl)propanoic acid (64);
(S)-2-amino-3-(3-(N,N-dimethylsulfamoyl)phenyl)propanoic acid (73);
(S)-2-amino-3-(3-(piperidin-1-ylsulfonyl)phenyl)propanoic acid (78);
(S)-2-amino-3-(4-(N-(4-fluorophenyl)sulfamoyl)phenyl)propanoic acid (80); and (S)-2-amino-3-(2-(N-(4-chlorophenyl)sulfamoyl)phenyl)propanoic acid (81);

or a pharmaceutically acceptable salt of any of the foregoing.

A compound provided by the present disclosure can be selected from:
(S)-2-amino-3-(2-(methylsulfonamido)phenyl]propanoic acid (1);
(S)-2-amino-3-(5-((1,2-dimethyl-1H-imidazole)-4-sulfonamido)-2-methylphenyl)propanoic acid (18);
(S)-3-(5-(1H-imidazole-4-sulfonamido)-2-methylphenyl)-2-aminopropanoic acid (31); ((3-((S)-2-amino-2-carboxyethyl)-4-methylphenyl)sulfonyl)-D-proline (45);
(S)-2-amino-3-(3,5-dichloro-4-(phenylsulfonamido)phenyl)propanoic acid (47);
(R)-2-amino-3-(5-(N-(4-chlorophenyl)sulfamoyl)-2-methylphenyl)propanoic acid (51);
(S)-2-amino-3-(3,5-di(methylsulfonamido)phenyl)propanoic acid (61);
(S)-2-amino-3-(3,5-bis(phenylsulfonamido)phenyl)propanoic acid (62);
(S)-2-amino-3-(2-methyl-5-(methylsulfonamido)phenyl)propanoic acid (67);
(S)-2-amino-3-(3-(methylsulfonamido)phenyl)propanoic acid (68);
(S)-2-amino-3-(4-(methylsulfonamido)phenyl)propanoic acid (70);
(S)-2-amino-3-(3-sulfamoylphenyl)propanoic acid (71);
(S)-2-amino-3-(3-(N-methylsulfamoyl)phenyl)propanoic acid (72);
(S)-2-amino-3-(4-sulfamoylphenyl)propanoic acid (74); and
(S)-2-amino-3-(5-((4-chlorophenyl)sulfonamido)-2-methylphenyl)propanoic acid (88);
or a pharmaceutically acceptable salt of any of the foregoing.

A compound provided by the present disclosure can exhibit an IC50 of less than 20 nM in the [$^3$H]-GP uptake inhibition assay described in Example 103.

A compound provided by the present disclosure can exhibit an IC50 of less than 50 nM in the [$^3$H]-GP uptake inhibition assay described in Example 103.

A compound provided by the present disclosure can exhibit an IC50 of less than 100 nM in the [$^3$H]-GP uptake inhibition assay described in Example 103.

A compound provided by the present disclosure can exhibit an IC50 of less than 200 nM in the [$^3$H]-GP uptake inhibition assay described in Example 103.

A compound provided by the present disclosure can exhibit an IC50 of less than 300 nM in the [$^3$H]-GP uptake inhibition assay described in Example 103.

A compound provided by the present disclosure can exhibit an IC50 of less than 400 nM in the [$^3$H]-GP uptake inhibition assay described in Example 103.

A compound provided by the present disclosure can exhibit an IC50 of less than 500 nM in the [$^3$H]-GP uptake inhibition assay described in Example 103.

A compound provided by the present disclosure can exhibit an IC50 of less than 1,000 nM in the [$^3$H]-GP uptake inhibition assay described in Example 103.

In certain embodiments, a compound provided by the present disclosure is not selected from and a subgenus of compounds provided by the present disclosure does not encompass the compounds:
(S)-2-amino-3-(4-(phenylsulfonamido)phenyl)propanoic acid;
(S)-2-amino-3-(4-((4-methoxyphenyl)sulfonamido)phenyl)propanoic acid;
(S)-2-amino-3-(4-((4-fluorophenyl)sulfonamido)phenyl)propanoic acid; and
(S)-2-amino-3-(4-((4-chlorophenyl)sulfonamido)phenyl)propanoic acid;
or a pharmaceutically acceptable salt thereof.

A pharmaceutical composition and use of a compound provided by the present disclosure can encompass (S)-2-amino-3-(4-(phenylsulfonamido)phenyl)propanoic acid;
(S)-2-amino-3-(4-((4-methoxyphenyl)sulfonamido)phenyl)propanoic acid;
(S)-2-amino-3-(4-((4-fluorophenyl)sulfonamido)phenyl)propanoic acid; and
(S)-2-amino-3-(4-((4-chlorophenyl)sulfonamido)phenyl)propanoic acid;
or a pharmaceutically acceptable salt thereof.

Compounds of Formula (1)-(3) provided by the present disclosure may be obtained via the general synthetic methods illustrated in Schemes 1-11. General synthetic methods useful in the synthesis of compounds, precursors, and starting materials described herein are available in the art. Starting materials useful for preparing compounds and intermediates thereof, and/or practicing methods described herein, are commercially available or may be prepared by well-known synthetic methods.

Additionally, as will be apparent to those skilled in the art, use of conventional protecting groups or protecting strategies may be necessary to prevent certain functional groups from undergoing undesired reactions. Suitable protecting groups for various functional groups as well as suitable conditions for protecting and deprotecting particular functional groups in the presence of other functional groups are well-known in the art. On the other hand, many methods for selective removal of protecting groups without affecting the desired molecular architecture or other functional groups are also well-known in the art.

It will be appreciated that where typical or preferred process conditions, e.g., reaction temperatures, reaction times, molar ratios of reactants, solvents, pressures, etc., are given other process conditions may also be used. Optimal reaction conditions may vary with the particular reactants, solvents, functional groups, and protecting groups used, but such conditions may be determined by one skilled in the art by routine optimization procedures.

Furthermore, certain compounds provided by the present disclosure may contain one or more stereogenic centers. Accordingly, and if desired, such compounds may be prepared or isolated as pure stereoisomers, e.g., as individual enantiomers, diastereomers, atropisomers, rotamers, or as stereoisomer enriched mixtures or racemates. All such stereoisomers are included within the scope of this disclosure. Pure stereoisomers or enriched mixtures thereof may be prepared using, for example, optically active starting materials, stereoselective reagents such as chiral catalysts and auxiliaries well-known in the art. Alternatively, racemic mixtures of such compounds may be separated or partially enriched using, for example, chromatographic methods with chiral stationary phases, and/or chiral resolving agents, also well-known in the art and easily adaptable to the particular compound to be separated.

Unnatural amino acids (UAAs) are members of a class of molecules with relevant impacts in the life sciences. The development of new methods for the stereocontrolled synthesis of nonproteinogenic α-amino acids continues to be an important area in modern organic chemistry. Therefore, there has been substantial interest in the synthesis of α-amino acids with various substitution patterns. Many methods for the synthesis of protected and unprotected α-amino acids with a wide variety of type and number of substituents either in racemic, enantio- or diastereomerically enriched or pure form from commercial or known starting materials are well-known in the art. Such methods were developed to serve the need for the broadest structural diversity for a broad variety of applications.

Unnatural α-amino acids are not only important building blocks for the synthesis of peptides, pharmaceutical molecules, and natural products, but may also exert biological and pharmaceutical properties by themselves.

An aromatic amino acid is an amino acid that contains at least one aromatic or one heteroaromatic ring system or a combination of any of the foregoing. Aromatic amino acids are frequently biological chemical precursors as well as metabolic intermediates in the biosynthesis of various neurotransmitters.

Examples of naturally occurring (essential) aromatic amino acids include phenylalanine (Phe), tryptophan (Trp), tyrosine (Tyr), and histidine (His). Other examples include thyroid hormones triiodothyronine (T3), thyroxine (T4), 5-hydroxytryptophan (5-HTP, oxitriptan), and 3,4-dihydroxyphenylalanine (L-DOPA).

Such derivatives may be used as convenient starting materials for the preparation of the target compounds provided by the present disclosure. Suitably functionalized protected and unprotected racemic or optically active α-amino acids, α-amino acids analogs, or α-amino acid carboxylic acid (bio)isosteres may be used as starting materials for the preparation of the target compounds provided by the present disclosure.

Starting materials may be used in their fully-protected form wherein the amino group or a synthetic equivalent or a precursor thereof and the carboxylic acid, phosphinic acid, sulfinic acid, carboxylic acid (bio)isosteres or synthetic equivalents or precursors of any of the foregoing can be appropriately protected.

Starting materials may be used in their hemi-protected form wherein the amino group or a synthetic equivalent or a precursor thereof is protected and the carboxylic acid group or the carboxylic acid (bio)isostere functional group or synthetic equivalents or precursors of any of the foregoing can be unprotected or free.

Starting materials may be used in their hemi-protected form wherein the amino group is unprotected or free and the carboxylic acid or the carboxylic acid (bio)isostere or synthetic equivalents or precursors of any of the foregoing can be appropriately protected.

Starting materials may be used in their full unprotected form wherein the amino group and the carboxylic acid or the free carboxylic acid (bio)isostere or synthetic equivalents or precursors of any of the foregoing can be unprotected.

Protected and unprotected α-substituted racemic or optically active α-amino acids, α-amino acids analogs, or α-amino acid carboxylic acid (bio)isosteres bear a group linking the α-carbon atom to an aromatic ring system. A linker can be a methylene group (1,1-methane-diyl) group (—CH$_2$—) and the protected and unprotected α-substituted racemic or optically active α-amino acids, α-amino acids analogs, or α-amino acid carboxylic acid (bio)isosteres can be a phenylalanine derivative.

An aromatic ring system can further be functionalized with an anchoring group to facilitate the introduction of additional substituents.

Methods for the synthetic manipulation and modification of the underlying protected or unprotected α-amino acid scaffold are well-known in the art. An underlying α-amino acid scaffold may be modified to allow for regio- and/or stereoselective incorporation of auxiliary molecular functionalities. Auxiliary molecular functionalities may, for example, be incorporated to modulate interaction with LAT1 transporter proteins, such as interactions involving efficiency of translocation through biological membranes, selectivity and affinity for binding to the LAT1-transporter protein and capacity or incapacity of LAT1-mediated transport, and/or aid the modulation of physiochemical parameters and pharmaceutical properties.

An aryl-ring may be modified to allow for regio- and/or stereo-selective incorporation of auxiliary molecular functionalities into the arene scaffold. Auxiliary molecular functionalities may, for example, be incorporated to modulate interaction with LAT1 transporter proteins, such as interactions involving efficiency of translocation through biological membranes, selectivity and affinity for binding to the LAT1-transporter protein and capacity or incapacity of LAT1-mediated transport, and/or aid the modulation of physiochemical parameters and pharmaceutical properties.

Synthetic methods for the preparation of appropriately functionalized or substituted, protected and unprotected α-substituted racemic or optically active α-amino acids, α-amino acids analogs, or α-amino acid carboxylic acid (bio)isosteres, derivatives or precursors of any of the foregoing from commercial or known starting materials and employing methods and protocols are either described herein, are described in the art, or will be readily apparent to the one skilled in the art. Accordingly, the methods presented in the schemes provided by the present disclosure are illustrative rather than comprehensive.

Accordingly, the methods and structures presented in the schemes provided by the present disclosure are illustrative rather than comprehensive.

Referring to Scheme 1, $R^2$, $R^4$, $R^5$, $R^f$, and p are defined as described herein; the aromatic ring carbon atom that is bound to the leaving group X is defined as being in position one (1); counting in a clockwise fashion from position one (1), $R^2$ is bound to the aromatic ring carbon atom in position two (2). In compounds of Formula (A) at least one of the aromatic ring carbon atoms in position three (3), four (4), five (5) or six (6) relative to the leaving group X in ring position one (1) is bonded to the group —$R^e$—$NR^f$—H. Each of the other remaining aromatic ring carbon atoms are bonded to a hydrogen; X is a suitable leaving group, e.g., iodo (—I) or bromo (—Br), or trifluoromethane sulfonate (—OSO$_2$CF$_3$); Z is a suitable leaving group, e.g., fluoro (—F), chloro (—Cl), bromo (—Br), azido (—N$_3$), or methoxy (—OMe).

Referring to Scheme 1, in compounds of Formula (A) the group —$R^e$—$NR^f$—H, wherein $R^e$ is a single bond ("—"), a (substituted) methylene group (—C($R^f$)$_2$—), an oxygen atom (—O—), or a (substituted) methyleneoxy group (—C($R^f$)$_2$—O—), the group —$R^e$—$NR^f$—H is equivalent to (a) a primary or secondary aromatic amino group (—$NR^f$—H), (b) a primary or secondary (substituted) aminomethyl group (—C($R^f$)$_2$—$NR^f$H) or aminoalkyl group (—C($R^f$)$_o$—$NR^f$H, where o is an integer from 1 to 4), (c) a primary or secondary O-aryl hydroxylamino group (—O—$NR^f$—H), or (d) a primary or secondary (substituted) O-methyl hydroxylamino group (—C($R^f$)$_2$—O—$NR^f$—H).

Referring to Scheme 1, in some embodiments, the aromatic ring carbon atom in position three (3) relative to the leaving group X in ring position one (1) in compounds of Formula (A) is bonded to the group —$R^e$—$NR^f$—H.

Referring to Scheme 1, in some embodiments, the aromatic ring carbon atom in position four (4) relative to the leaving group X in ring position one (1) in compounds of Formula (A) is bonded to the group —R$^e$—NR$^f$—H.

Referring to Scheme 1, in some embodiments, the aromatic ring carbon atom in position five (5) relative to the leaving group X in ring position one (1) in compounds of Formula (A) is bonded to the group —R$^e$—NR$^f$—H.

Referring to Scheme 1, in some embodiments, the aromatic ring carbon atom in position six (6) relative to the leaving group X in ring position one (1) in compounds of Formula (A) is bonded to the group —R$^e$—NR$^f$—H.

Referring to Scheme 1, in some embodiments, the aromatic ring carbon atoms in position three (3) and position five (5) relative to the leaving group X in ring position one (1) in compounds of Formula (A) are bonded to the group —R$^e$—NR$^f$—H.

Referring to Scheme 1, in compounds of Formula (A) the molecular unit consisting of R$^e$ together with —NR$^f$— constitutes R$^3$ is defined as described herein for compounds of Formula (A) in Scheme 1. Therefore, R$^3$ can be selected from —NR$^f$—, (b) —C(R$^f$)$_2$—NR$^f$—, (c) —O—NR$^f$—, or —C(R$^f$)$_2$—O—NR$^f$—.

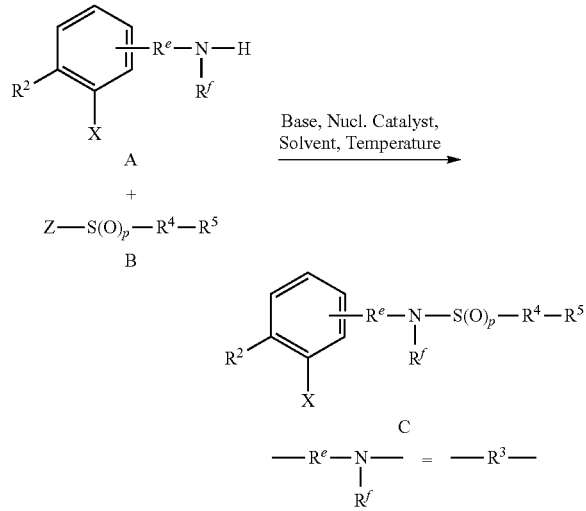

Scheme 1

Referring to Scheme 1, methods for the formation of N—S bonds as found in sulfenamides, sulfinamides, or sulfonamides from the corresponding sulfenyl halides, sulfinyl halides, or sulfonyl halides, azides or lower alkyl esters and primary and secondary amines or related derivatives thereof, e.g., hydroxylamines are well-known in the art.

Several activated sulfur compounds of Formula (B), e.g., aliphatic and aromatic sulfenyl halides, sulfinyl halides, sulfonyl halides, azides, or lower alkyl esters are either commercially available or can be prepared from readily available precursors.

Referring to Scheme 1, conversion of the primary or secondary amino group or primary or secondary hydroxylamine as in compounds of Formula (A) to the corresponding sulfenamide, sulfinamide, or sulfonamide as in compounds of Formula (C) can be accomplished by reacting the appropriate primary or secondary amine of Formula (A) in suitable inert organic solvents such as dichloromethane (DCM), chloroform (CHCl$_3$), tetrahydrofuran (THF), ethyl acetate (EtOAc), 1,4-dioxane or mixtures of any of the foregoing in the presence of a suitable organic base such as triethyl amine (Et$_3$N, TEA) or diisopropyl-ethyl amine (Hünig's-base, DIPEA) (about 1-5 equivalents) with a suitable sulfur halide or another activated sulfur compound as in compounds of Formula (B). The reaction can be carried out between 0° C. and 25° C. for 1-24 hours.

Sulfonyl halides, e.g., sulfonyl chlorides, of Formula (B) can be reacted with an appropriate primary or secondary amine or primary or secondary hydroxylamine of Formula (A) in pyridine (Pyr) which functions simultaneously as a solvent and as a base.

Optionally, nucleophilic catalysts, e.g., 4-N,N-dimethyl-aminopyridine (DMAP) (about 1-10 mol %; 0.01-0.1 equivalents) can be added to facilitate the rate of the N—S bond formation.

Referring to Scheme 2, where R$^2$, R$^3$, R$^5$, R$^f$, and p are defined herein; the aromatic ring carbon atom that is bound to the leaving group X is defined as being in position one (1); counting clockwise from position one (1), R$^2$ is bound to the aromatic ring carbon atom in position two (2). In compounds of Formula (D) at least one of the aromatic ring carbon atoms in position three (3), four (4), five (5) or six (6) relative to the leaving group X in ring position one (1) is bonded to the group —R$^3$—S(O)$_p$—Z. Each of the other remaining aromatic ring carbon atoms are bonded to hydrogen; X is a suitable leaving group, e.g., iodo (—I) or bromo (—Br), or trifluoromethane sulfonate (—OSO$_2$CF$_3$); Z is a suitable leaving group, e.g., fluoro (—F), chloro (—Cl), bromo (—Br), azido (—N$_3$), or methoxy (—OMe).

Referring to Scheme 2, in some embodiments, the aromatic ring carbon atom in position three (3) relative to the leaving group X in ring position one (1) in compounds of Formula (D) is bonded to the group —R$^3$—S(O)$_p$—Z.

Referring to Scheme 2, in some embodiments, the aromatic ring carbon atom in position four (4) relative to the leaving group X in ring position one (1) in compounds of Formula (D) is bonded to the group —R$^3$—S(O)$_p$—Z.

Referring to Scheme 2, in some embodiments, the aromatic ring carbon atom in position five (5) relative to the leaving group X in ring position one (1) in compounds of Formula (D) is bonded to the group —R$^3$—S(O)$_p$—Z.

Referring to Scheme 2, in some embodiments, the aromatic ring carbon atom in position six (6) relative to the leaving group X in ring position one (1) in compounds of Formula (D) is bonded to the group —R$^3$—S(O)$_p$—Z.

Referring to Scheme 2, in some embodiments, the aromatic ring carbon atoms in position three (3) and position five (5) relative to the leaving group X in ring position one (1) in compounds of Formula (D) are bonded to the group —R$^3$—S(O)$_p$—Z.

Referring to Scheme 2, in the group H—NR$^f$—R$^e$— in wherein R$^e$ is a single bond ("—"), a (substituted) methylene group (—C(R$^f$)$_2$—), an oxygen atom (—O—), or a (substituted) oxymethylene group (—O—C(R$^f$)$_2$—), the group H—NR$^f$—R$^e$— is equivalent to (a) a primary or secondary aromatic amino group (H—NR$^f$—) or aminoalkyl group (—C(R$^f$)$_o$—NR$^f$H, where o is an integer from 1 to 4), (b) a primary or secondary amino (substituted) methyl group (H—NR$^f$—C(R$^f$)$_2$—), c) a primary or secondary O-alkyl or O-aryl hydroxylamino group (H—NR$^f$—O—), or (d) a primary or secondary (substituted) hydroxylamino group (H—NR$^f$—O—C(R$^f$)$_2$—).

Referring to Scheme 2, the molecular unit consisting of R$^e$ together with —NR$^f$— constitutes R$^4$ and is defined as described herein for compounds of Formula (E) in Scheme 2. Therefore, R$^4$ is selected from (a) —NR$^f$—, (b) —NR$^f$—C(R$^f$)$_2$—, (c) —NR$^f$—O—, or (d) —NR$^f$—O—C(R$^f$)$_2$—.

Scheme 2

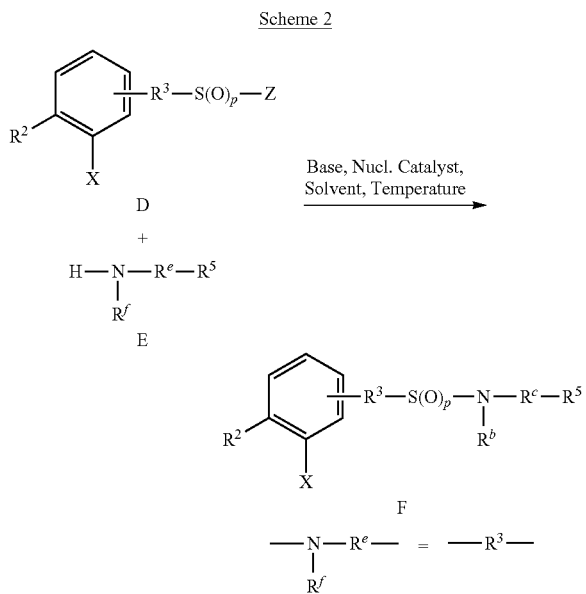

Referring to Scheme 2, methods for the formation of N—S bonds as found in sulfenamides, sulfinamides, or sulfonamides from the corresponding sulfenyl halides, sulfinyl halides, or sulfonyl halides, azides or lower alkyl esters and primary and secondary amines or related derivatives thereof, e.g., hydroxylamines are well-known in the art.

Referring to Scheme 2, a broad variety of activated sulfur compounds of Formula (D) (—$R^3$—$S(O)_p$—Z), e.g., aliphatic and aromatic sulfenyl halides, sulfinyl halides, or sulfonyl halides, azides, or lower alkyl esters, is either commercially available or can be readily prepared from available precursors following well-known literature procedures.

Referring to Scheme 2, the conversion of the primary or secondary amino group as in compounds of Formula (E) to the corresponding sulfenamide, sulfinamide, or sulfonamide as in compounds of Formula (F) may be accomplished by reacting a suitable sulfur halide or another activated sulfur compound such as a compound Formula (D) in an inert organic solvent such as dichloromethane (DCM), chloroform (CHCl$_3$), tetrahydrofuran (THF), ethyl acetate (EtOAc), 1,4-dioxane or mixtures of any of the foregoing in the presence of a suitable organic base such as triethyl amine (Et$_3$N, TEA), diisopropyl ethyl amine (Hünig's-base, DIPEA) (about 1-5 equivalents) with an appropriate primary or secondary amine or primary or secondary hydroxylamine of Formula (F). The reaction can be carried out between 0° C. and 25° C. for 1-24 hours.

Sulfonyl halides, e.g., sulfonyl chlorides, of Formula (D) are typically reacted with a primary or secondary amine or primary or secondary hydroxylamine of Formula (E) in pyridine (Pyr) which functions simultaneously as a solvent and as a base.

Optionally, nucleophilic catalysts, e.g., 4-N,N-dimethylaminopyridine (DMAP) (about 1-10 mol %; 0.01-0.1 equivalents) may be added to facilitate rate of the N—S bond formation.

The development of new methods for the stereo-controlled synthesis of nonproteinogenic α-amino acids either as biologically active entities or as building blocks for more complex molecular architectures continues to be an important area in modern organic chemistry. Many general approaches to α-amino acid syntheses exist, but one particular useful approach is to convert existing α-amino acids into more intricate structures with retention of the original configuration and preservation of optical purity.

The development of methods for the generation of zinc organometallics and their application to C—C bond forming reactions, including the Pd(0)-catalyzed Negishi-methodology, has become a powerful tool in amino acid synthesis.

Stereochemically pure, serine-derived zinc organometallics function as synthetic equivalents for the chiral "alanine β-anion" ("chiron"). Their application was used in the late 1980s for the synthesis of a wide range of highly functionalized enantiopure phenylalanine derivatives. The synthetic methodology distinguishes itself from other approaches due to its extraordinary tolerance toward a broad variety of functional groups within the coupling partners and exhibits excellent compatibility with common protecting group chemistry.

The starting materials are appropriately protected β-iodo alanines that are either commercially available in both enantiomeric forms or readily accessible from commercial enantiopure serine or suitable serine derivatives. Insertion of activated zinc (denoted as Zn*) into the carbon-iodine bond of an appropriately protected R-iodo alanine generates a chiral homo-enolate equivalent that can be coupled to various carbon electrophiles including aromatic halides, e.g., aromatic bromides or iodides, under Pd(0) catalysis (Negishi-coupling) to yield a desired phenylalanine derivative in good chemical yield and, importantly, without loss of enantiomeric purity. This method offers an extremely efficient route to large numbers of non-natural amino acids and in particular phenylalanines.

Referring to Scheme 3, $R^2$, $R^3$, $R^4$, $R^5$, and p are defined herein; the aromatic ring carbon atom that is bonded to the amino acid precursor group —$CH_2$—$CHQ$-$R^{20}$ in compounds of Formula (I) is defined as being in position one (1). The aromatic ring carbon atom that is bound to the leaving group X in compounds of Formula (G) is positionally equivalent to the aromatic ring carbon atom that is bonded to the amino acid precursor group —$CH_2$—$CHQ$-$R^{20}$ in compounds of Formula (I) and is also defined as being in position one (1). Counting clockwise from position one (1), $R^2$ is bound to the aromatic ring carbon atom in position two (2). In compounds of Formula (I), at least one of the aromatic ring carbon atoms in position three (3), four (4), five (5) or six (6) relative to the amino acid precursor group —$CH_2$—$CHQ$-$R^{20}$ in ring position one (1) is bonded to the group —$R^3$—$S(O)_p$—$R^4$—$R^5$. Each of the other remaining aromatic ring carbon atoms are bonded to hydrogen; X is a suitable leaving group, e.g., iodo (—I), bromo (—Br), or trifluoromethane sulfonate (—$OSO_2CF_3$).

Referring to Scheme 3, in some embodiments, the aromatic ring carbon atom in position three (3) relative to the amino acid precursor group —$CH_2$—$CHQ$-$R^{20}$ in ring position one (1) in compounds of Formula (I) is bonded to the group —$R^3$—$S(O)_p$—$R^4$—$R^5$.

Referring to Scheme 3, in some embodiments, the aromatic ring carbon atom in position four (4) relative to the amino acid precursor group —$CH_2$—$CHQ$-$R^{20}$ in ring position one (1) in compounds of Formula (I) is bonded to the group —$R^3$—$S(O)_p$—$R^4$—$R^5$.

Referring to Scheme 3, in some embodiments, the aromatic ring carbon atom in position five (5) relative to the amino acid precursor group —$CH_2$—$CHQ$-$R^{20}$ in ring position one (1) in compounds of Formula (I) is bonded to the group —$R^3$—$S(O)_p$—$R^4$—$R^5$.

Referring to Scheme 3, in some embodiments, the aromatic ring carbon atom in position six (6) relative to the amino acid precursor group —CH$_2$—CHQ-R$^{20}$ in ring position one (1) in compounds of Formula (I) is bonded to the group —R$^3$—S(O)$_p$—R$^4$—R$^5$.

Referring to Scheme 3, in some embodiments, the aromatic ring carbon atoms in position three (3) and position (5) relative to the amino acid precursor group —CH$_2$—CHQ-R$^{20}$ in ring position one (1) in compounds of Formula (I) are bonded to the group —R$^3$—S(O)$_p$—R$^4$—R$^5$.

Referring to Scheme 3, in certain embodiments R$^{20}$ in compounds of Formula (H) and of Formula (I) is a protected carboxyl group such as a lower alkyl ester of a carboxyl group, e.g., a methyl, an ethyl, or a tert-butyl ester, or a benzyl ester derivative, e.g., benzyl, pentamethylbenzyl, or (4-methoxy)benzyl.

In certain embodiments, R$^{20}$ in compounds of Formula (H) and of Formula (I) is a tert-butyl ester group (—CO$_2$tBu).

In certain embodiments, R$^{20}$ in compounds of Formula (H) and of Formula (I) is a methyl ester group (—CO$_2$Me).

In certain embodiments, R$^{20}$ in compounds of Formula (H) and of Formula (I) is a benzyl ester group (—CO$_2$Bn).

Referring to Scheme 3, in certain embodiments of compounds of Formula (H) and of Formula (I) Q is —N(H)—PG where PG is a suitable nitrogen protecting group, e.g., tert-butoxycarbonyl (Boc), allyloxycarbonyl (alloc), benzyloxycarbonyl (Cbz, Z), ethoxycarbonyl, methoxycarbonyl, (R/S)-1-phenyl-ethoxycarbonyl, (R)-1-phenyl-ethoxycarbonyl, (S)-1-phenyl-ethoxycarbonyl, 1-methyl-1-phenyl-ethoxycarbonyl, formyl, acetyl, trifluoroacetyl, benzoyl, triphenylmethyl (trityl), 4-methoxyphenyl-diphenylmethyl, di-(4-methoxyphenyl)-phenylmethyl, phenylmethyl (benzyl), or 4-methoxyphenylmethyl (PMB).

Referring to Scheme 3, in compounds of Formula (H) and Formula (I) PG can be tert-butoxycarbonyl (Boc) and Q can be —N(H)Boc (—N(H)CO$_2$tBu).

Referring to Scheme 3, in compounds of Formula (H) and Formula (I) PG can be benzyloxycarbonyl (Cbz, Z), and Q can be —N(H)—Cbz (—N(H)COOBn).

Referring to Scheme 3, in compounds of Formula (H) and Formula (I) PG can be trifluoroacetylacetyl and Q can be —N(H)-TFA (—N(H)COCF$_3$).

Referring to Scheme 3, in compounds of Formula (H) and Formula (I) Q can be N(PG)$_2$, where PG can be a nitrogen protecting group such as an imide-type protecting group, e.g., phthalyl, bis-tert-butoxycarbonyl (Boc), bis-benzyl (NBn$_2$) or bis-4-methoxybenzyl (N(PMB)$_2$).

Referring to Scheme 3, in compounds of Formula (H) and Formula (I) PG can be phthalyl and Q can be —N(phthalyl).

Referring to Scheme 3, in compounds of Formula (H) and Formula (I) PG can be di-tert-butoxycarbonyl and Q is —N(Boc)$_2$.

Referring to Scheme 3, in compounds of Formula (H) and of Formula (I) the protected amine functionality can be an imine where Q can be —N=CR$^{30}$R$^{31}$ and each of R$^{30}$ and R$^{31}$ can be independently selected from branched C$_{1-4}$ alkyl, non-branched C$_{1-4}$ alkyl, substituted aryl, non-substituted aryl, substituted heteroaryl, and non-substituted heteroaryl.

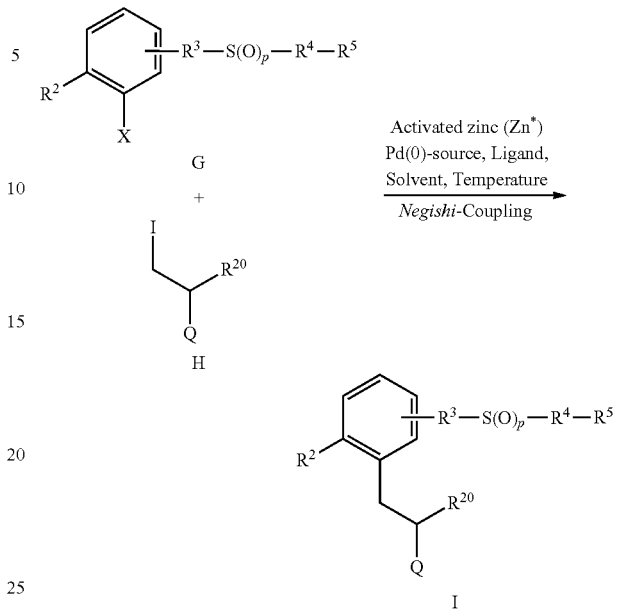

Scheme 3

Referring to Scheme 3, several appropriately protected (3-iodo alanines of Formula (H) are commercially available in both enantiomeric forms, e.g., N-Boc-(3-iodo-L-Ala-OMe, N-Boc-(3-iodo-D-Ala-OMe N-Boc-β-iodo-L-Ala-OtBu, N-Boc-(3-iodo-L-Ala-OBn, or N-Fmoc-β-iodo-L-Ala-OtBu. Alternatively and if specific protecting group combinations are required, they can be readily prepared from the corresponding commercial enantiopure serine or suitable derivative thereof, e.g., N-Boc-L-Ser-OMe, N-Boc-D-Ser-OMe, N-Boc-L-Ser-OtBu, H-L-Ser-OMe, H-D-Ser-OMe H-L-Ser-OtBu, etc., by using any of the many synthetic methods known in the art for amino acid esterification, amino acid N-protection.

Referring to Scheme 3, activated zinc dust is commercially available.

Referring to Scheme 3, commercial zinc dust (Zn) (about 3-12 equivalents) can be activated under an inert gas atmosphere (nitrogen or argon) in anhydrous degassed solvents, e.g., N,N-dimethylformamide (DMF), N,N-dimethyl acetamide (DMAc or DMA), tetrahydrofuran (THF), 2-methyltetrahydrofuran (2-Me-THF), or mixtures of any of the foregoing by addition of elemental iodine (I$_2$) (about 15-30 mol %), trimethyl silylchloride (MeSiCl, TMSCl) (about 15-30 mol %), 1,2-dibromoethane (about 15-30 mol %), or mixtures of any of the foregoing.

Referring to Scheme 3, in some embodiments zinc dust can be activated by removal of surface oxide layers through subsequent washings with dilute hydrochloric acid, e.g., 0.5 M HCl, distilled water, ethanol, and diethyl ether followed by rigorous drying.

Referring to Scheme 3, activated zinc can be inserted into the carbon-iodine bond of the appropriate iodo-compound, e.g., a protected R-iodo alanines of Formula (H). This reaction is exothermic and the reaction mixture can be optionally kept below about 40° C.

Referring to Scheme 3, in some embodiments, the zinc activation can be repeated with about the same amounts of activation agents during the zinc insertion as described herein.

Referring to Scheme 3, the intermediate functionalized zinc organic compound can be used directly in the subsequent Negishi cross-coupling reaction by addition of a solid mixture of the aryl halide or aryltrifluoromethanesulfonate of Formula (G) (about 1.0-1.5 equivalents) and a catalyst mixture consisting of tris(benzylideneacetone) dipalladium ($Pd_2(dba)_3$) (about 2.5 mol % to 10 mol %) and tris(o-tolyl) phosphine (P(o-tol)$_3$) (about 10 mol %) or SPhos (2-dicyclohexylphosphino-2',6'-dimethoxybiphenyl) (about 5 mol % to mol %) at 25° C. for 1-12 hours or heated under an inert gas atmosphere to about 40-60° C. for about 1-12 hours. The target compounds of Formula (I) can be isolated in conventional manner involving aqueous work-up and chromatographic purification.

Referring to Scheme 3, in some embodiments it can be advantageous to transfer the solution with intermediate functionalized zinc organic compound under an inert gas atmosphere to a solution of a mixture of the aryl halide of Formula (H) (about 1.0-1.5 equivalents), tris(benzylideneacetone) dipalladium ($Pd_2(dba)_3$) (about 2.5 mol % to 10 mol %) and tris(o-tolyl)phosphine (P(o-tol)$_3$) (about 10 mol %) or SPhos (2-dicyclohexylphosphino-2',6'-dimethoxybiphenyl) (about 5 mol % to 10 mol %) in the same solvent (mixture) as described herein. The remainder of the reaction can be carried out as described herein.

Referring to Scheme 4, where $R^2$, $R^{20}$, and Q are defined herein; the aromatic ring carbon atom that is bound to the amino acid precursor group —$CH_2$—$CHQ$-$R^{20}$ in compounds of Formula (L) is defined as being in position one (1). The aromatic ring carbon atom that is bonded to the leaving group X in compounds of Formula (J) is positionally equivalent to the aromatic ring carbon atom that is bound to the amino acid precursor group —$CH_2$—$CHQ$-$R^{20}$ in compounds of Formula (L) and is also defined as being in position one (1). Counting clockwise from position one (1), $R^2$ is bound to the aromatic ring carbon atom in position two (2). In compounds of Formula (L), at least one of the aromatic ring carbon atoms in position three (3), four (4), five (5) or six (6) relative to the amino acid precursor group —$CH_2$—$CHQ$-$R^{20}$ in ring position one (1) is bonded to a functional group -FG. Each of the other remaining aromatic ring carbon atoms are bonded to hydrogen; X is a suitable leaving group, e.g., iodo (—I). bromo (—Br), or trifluoromethane sulfonate (—$OSO_2CF_3$).

Referring to Scheme 4, the functional group -FG is described as any chemical group or functionality in compounds of Formula (J) and in compounds of Formula (L) that is useful for further modification of the intermediate compounds of Formula (L) that do not interfere with the Negishi-type cross-coupling between compounds of Formula (J) and compounds of Formula (K).

Useful functional groups (-FGs) include, for example, primary or secondary amino groups (—$NR^f$—H) wherein $R^f$ is defined herein, phenolic hydroxyl groups (—OH), (substituted) hydroxymethyl groups (—$C(R^f)_2$—OH) wherein $R^f$ is defined herein, (substituted) aminomethyl groups (—$C(R^f)_2$—$NR^fH$) wherein $R^f$ is defined herein, nitro groups (—$NO_2$), bromo (—Br) and other functional groups well-known in the art.

Referring to Scheme 4, in some embodiments, the aromatic ring carbon atom in position three (3) relative to the amino acid precursor group —$CH_2$—$CHQ$-$R^{20}$ in ring position one (1) in compounds of Formula (L) is bonded to the functional group -FG.

Referring to Scheme 4, in some embodiments, the aromatic ring carbon atom in position four (4) relative to the amino acid precursor group —$CH_2$—$CHQ$-$R^{20}$ in ring position one (1) in compounds of Formula (L) is bonded to the functional group -FG.

Referring to Scheme 4, in some embodiments, the aromatic ring carbon atom in position five (5) relative to the amino acid precursor group —$CH_2$—$CHQ$-$R^{20}$ in ring position one (1) in compounds of Formula (L) is bonded to the functional group -FG.

Referring to Scheme 4, in some embodiments, the aromatic ring carbon atom in position six (6) relative to the amino acid precursor group —$CH_2$—$CHQ$-$R^{20}$ in ring position one (1) in compounds of Formula (L) is bonded to the functional group -FG.

Referring to Scheme 4, in some embodiments, the aromatic ring carbon atoms in position three (3) and position (5) relative to the amino acid precursor group —$CH_2$—$CHQ$-$R^{20}$ in ring position one (1) in compounds of Formula (L) are bonded to the functional group -FG.

Scheme 4

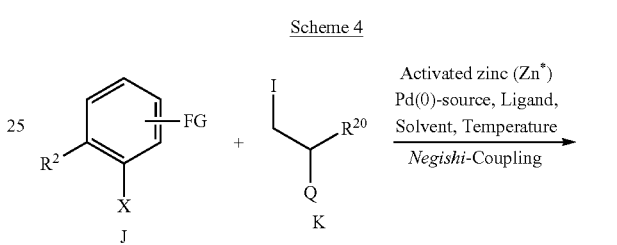

L

Referring to Scheme 4, several appropriately protected R-iodo alanines of Formula (K) are commercially available in both enantiomeric forms. Compounds of Formula (H) (Scheme 3) and compounds of Formula (K) (Scheme 4) are in essence identical. Alternatively, and if specific protecting group combinations are required, they can be prepared from the corresponding commercial enantiopure serine or suitable derivatives thereof by using any of the many synthetic methods for amino acid esterification, amino acid N-protection and Appel-type iodination of the primary hydroxyl group as described herein.

Referring to Scheme 4, appropriately functionalized and substituted aromatic halides or aryltrifluoromethanesulfonates of Formula (J) are commercially available or can be prepared from suitable precursors. For example, aromatic trifluoromethane sulfonates can be prepared from the corresponding phenol and trifluoromethanesulfonic anhydride (triflic anhydride, $(TfO)_2O$). Alternatively, when specific aromatic substituents, regiochemistry, or functional groups (-FGs) are required, appropriately functionalized and substituted aromatic halides of Formula (J) can be prepared using any of the many synthetic methods known in the art for such chemistry.

Referring to Scheme 4, coupling of appropriately protected R-iodo alanines of Formula (K) and appropriately functionalized and substituted aromatic halides of Formula (J) through the intermittent zinc organometallic insertion product can be performed under comparable if not identical reaction conditions and stoichiometries and Pd(0)-catalysis (Negishi-coupling) to produce the appropriately protected phenylalanine derivatives of Formula (L) as illustrated in Scheme 3. The protocol is an adaption of literature procedures.

Referring to Scheme 5, useful protected phenylalanine derivatives of Formula (L) (Scheme 4) include compounds of Formula (M), compounds of Formula (N), and compounds of Formula (O) wherein $R^2$, $R^3$, $R^4$, $R^5$, $R^{20}$, $R^f$, $R^e$, and Q are defined herein.

Referring to Scheme 5, appropriately protected phenylalanine derivatives of Formula (M), of Formula (N), and of Formula (O) can be used directly for further functionalization.

Referring to Scheme 5, appropriately protected phenylalanine derivatives of Formula (M), of Formula (N), and of Formula (O) can be further derivatized through functional group interconversions (FGIs) of the parent functional groups (-FGs).

Scheme 5

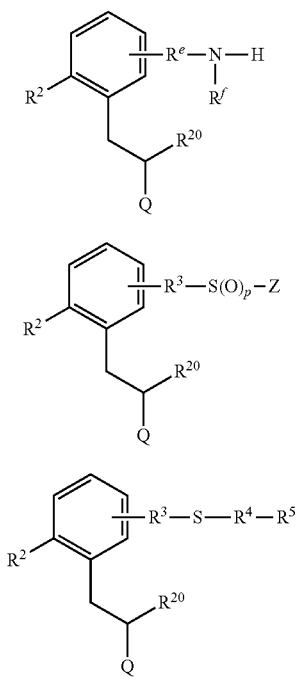

Referring to Scheme 4, the functional group (-FG) in compounds of Formula (L) can be a phenolic hydroxyl group (—OH) which can be converted to —$R^e$—$NR^f$—H wherein $R^e$ is an oxygen atom (—O—) so that —$R^e$—$NR^f$—H in compounds of Formula (M) (Scheme 5) is a primary or secondary hydroxylamine (—O—$NR^f$—H) using methods known in the art.

The phenolic hydroxyl groups can be coupled through a $H_2N$-transfer reaction using reagents such as mesitylenesulfonylhydroxylamine (mesitylenesulfonylhydroxylamine, 2,4,6-$Me_3$-$C_6H_2$—$SO_2O$—$NH_2$), (aminooxy)diphenylphosphine oxide ($Ph_2P(=O)O$—$NH_2$), O-(2,4-dinitrophenyl)hydroxylamine (2,4-di-$NO_2$—$C_6H_3O$—$NH_2$), or hydroxylamine-O-sulfonic acid ($HOSO_2O$—$NH_2$) or in the presence of bases such as potassium tert-butylate (potassium tert-butoxide, KOtBu) or sodium hydride (NaH) in solvents such as methanol, N,N-dimethylformamide (DMF), dichloromethane (DCM), diethyl ether ($Et_2O$), or mixtures of any of the foregoing at temperatures of about −20° C. to about 25° C. for about 1-12 hours.

Referring to Scheme 4, the functional group (-FG) in compounds of Formula (L) can be a (substituted) hydroxymethyl (—$C(R^f)_2$—OH) which can be converted to —$R^e$—$NR^f$—H wherein $R^e$ is a (substituted) oxymethylene group (—$C(R^f)_2$—O—) so that —$R^e$—$NR^f$—H in compounds of Formula (M) (Scheme 5) is a primary or secondary benzylic hydroxylamine (—$C(R^f)_2$—O—$NR^f$—H) using methods known in the art.

The benzylic hydroxyl groups can be coupled to N-hydroxyphthalimide under Mitsunobu-conditions with triphenylphosphine ($Ph_3P$) and diethylazodicarboxylate (DEAD) or diisopropylazodicarboxylate (DIAD) in ethereal solvents such as tetrahydrofuran (THF). The targeted O-benzyl hydroxylamine can be liberated through hydrazinolysis with hydrazine or its hydrate) ($H_2N$—$NH_2$/$H_2N$—$NH_2$·$H_2O$) or N-methyl hydrazine ($H_2N$—$NHCH_3$) in an alcoholic solvent, e.g., ethanol (EtOH) or methanol (MeOH) at 25° C. to about reflux temperature.

Referring to Scheme 4, the functional group (-FG) in compounds of Formula (L) can be a (substituted) hydroxymethyl (—$C(R^f)_2$—OH) which can be converted to —$R^e$—$NR^f$—H wherein $R^e$ is a (substituted) methylene group (—$C(R^f)_2$—) so that —$R^e$—$NR^f$—H in compounds of Formula (M) (Scheme 5) is a primary or secondary benzylic amine (—$C(R^f)_2$—$NR^f$—H) using methods known in the art.

The benzylic hydroxyl groups can be coupled to phthalimide under Mitsunobu-conditions with triphenylphosphine ($Ph_3P$) and diethylazodicarboxylate (DEAD) or diisopropylazodicarboxylate (DIAD) in ethereal solvents such as tetrahydrofuran (THF). The targeted benzylamine is liberated through hydrazinolysis with hydrazine or its hydrate) ($H_2N$—$NH_2$/$H_2N$—$NH_2$·$H_2O$) or N-methyl hydrazine ($H_2N$—$NHCH_3$) in alcoholic solvents, e.g., ethanol (EtOH) or methanol (MeOH) at 25° C. to about reflux temperature.

Many other synthetic methods for the conversion of benzyl alcohols to the corresponding benzylic amines are well-known in the art.

Referring to Scheme 4, the functional group (-FG) in compounds of Formula (L) can be a nitro group (—$NO_2$) which can be converted to —$R^e$—$NR^f$—H wherein $R^e$ is a single bond ("—") so that —$R^e$—$NR^f$—H in compounds of Formula (M) (Scheme 5) is a primary or secondary aromatic amine (—$NR^f$—H).

Using methods known in the art, e.g., catalytic hydrogenation over heterogenous metal catalysts, e.g., Raney-nickel in methanol (MeOH) or ethanol (EtOH) at about 25° C., palladium (palladium on carbon, Pd/C) in methanol (MeOH) or ethanol (EtOH) at about 25° C., ($Pd(OH)_2$), or platinum ($PtO_2$, Adams-catalyst) in methanol (MeOH) or ethanol (EtOH) at about 25° C.; stannous chloride dihydrate (tin(II) chloride dihydrate, $SnCl_2$—$H_2O$) in ethanol (EtOH) at about reflux temperature; iron (Fe) (Bechamp-reduction) or zinc (Zn) powder in protic solvents, e.g., acetic acid (AcOH), ethanol (EtOH) or mixtures of any of the foregoing at about reflux temperature and other methods and reducing agents well-known in the art can be used to provide compounds of Formula (M).

Referring to Scheme 4, the functional group (-FG) in compounds of Formula (L) can be bromo (—Br) which can be converted to —$R^3$—$S(O)_p$—$R^4$—$R^5$ wherein $R^3$, $R^4$, $R^5$, and p is zero (0) as defined herein using methods known in the art.

Palladium(0)-catalyzed coupling of the bromides with benzyl mercaptan (e.g., BnSH) in the presence of a catalyst system consisting of $Pd_2(dba)_3$, Xantphos, and diisopropylethylamine (DIPEA) in toluene at about reflux temperature affords the corresponding thioethers of Formula (O) (Scheme 5) that can be oxidized further.

Referring to Scheme 4, the functional group (-FG) in compounds of Formula (L) can be a (substituted) hydroxymethyl (—$C(R^f)_2$—OH) which can be converted to —$R^3$—S$(O)_p$—$R^4$—$R^5$ as in compounds of Formula (O) (Scheme 5) where $R^3$, $R^4$, and $R^5$ and p is zero (0) are defined herein using methods known in the art.

Halogenation of the benzylic alcohol under Appel-type reaction conditions using triphenylphosphine ($Ph_3P$) and tetrahalomethanes, e.g., tetrachlorocarbon ($CCl_4$) or tetrabromocarbon ($CBr_4$) yields a benzylic halide that can be further reacted with mercaptans, alkali salts thereof or in the presence of a suitable organic base, e.g., triethylamine ($Et_3N$, TEA) or diisopropylamine (DIPEA), in solvents such as tetrahydrofuran (THF) or dichloromethane (DCM) at about 0° C. to about 40° C. to provide the corresponding thioethers under well-known reaction conditions which can be oxidized further.

Referring to Scheme 4, the functional group (-FG) in compounds of Formula (L) can be a primary aromatic amine (aniline) (—$R^e$—$NR^f$—H) wherein $R^e$ is a single bond ("—") and $R^f$ is hydrogen (—H) which can be converted to —$S(O)_2$—Cl using methods known in the art to provide aromatic sulfonyl chlorides of Formula (N) (Scheme 5) wherein Z is chloro (—Cl).

The arylsulfonyl chlorides can be prepared under Sandmeyer-type conditions from anilines via their diazonium salts with sulfur dioxide ($SO_2$) in the presence of copper salts, preferably CuCl, together with thionyl chloride ($SOCl_2$) as the sulfur dioxide ($SO_2$) as a chlorine source in aqueous acidic conditions.

Alternative methods using tert-butylnitrite and sulfur dioxide ($SO_2$) or 1,4-diazabicyclo[2.2.2]octane bis-sulfur dioxide (DABSO) can also be used.

Referring to Scheme 4, the functional group (-FG) in compounds of Formula (L) can be bromo (—Br) which can be converted to aromatic sulfonyl chlorides (—$S(O)_2$—Cl) of Formula (N) (Scheme 5) using methods known in the art.

Palladium(0)-catalyzed coupling of the bromides with benzyl mercaptan (BnSH) in the presence of a catalyst system consisting of $Pd_2(dba)_3$, Xantphos, and diisopropylethylamine (DIPEA) in toluene at about reflux temperature affords the corresponding thioethers which can be further converted to the sulfonyl chloride through oxidative chlorination with N-chlorosuccinimide (NCS) in a mixture of acetic acid (HOAc) and water at temperatures from about 0° C. to about 25° C.

Several organosulfur compounds have been shown to having diverse biological activity such as antioxidant effects, anti-inflammatory properties, inhibition of platelet aggregation, reduction of systolic blood pressure, and reduction of cholesterol to name a few. As such organosulfur compounds, e.g., mercaptans/thiols, thioethers, sulfoxides, sulfones, and other sulfur-containing compounds have been attractive functional groups for the biopharmaceutical industry.

Therefore, development of chemoselective routes for the synthesis of sulfoxides as well as sulfones has remained a focal point for synthetic organic chemists. Among the vast array of existing methods used to synthesize sulfoxides or sulfones, oxidation of sulfides or oxidation of thioethers remains the most convenient preparative way.

Referring to Scheme 6, where $R^2$, $R^3$, $R^4$, $R^5$, $R^{20}$, and Q are defined herein; the aromatic ring carbon atom that is bonded to the amino acid precursor group —$CH_2$—CHQ-$R^{20}$ is defined as being in position one (1); counting clockwise from position one (1), $R^2$ is bound to the aromatic ring carbon atom in position two (2).

In compounds of Formula (P), at least one of the aromatic ring carbon atoms in position three (3), four (4), five (5) or six (6) relative to the amino acid precursor group —$CH_2$—CHQ-$R^{20}$ in ring position one (1) is bonded to a group —$R^3$—S—$R^4$—$R^5$. Each of the other remaining aromatic ring carbon atoms are bonded to hydrogen.

Referring to Scheme 6, the aromatic ring carbon atom in position three (3) relative to the amino acid precursor group —$CH_2$—CHQ-$R^{20}$ in ring position one (1) in compounds of Formula (P) can be bonded to a group —$R^3$—S—$R^4$—$R^5$.

Referring to Scheme 6, the aromatic ring carbon atom in position four (4) relative to the amino acid precursor group —$CH^2$—CHQ-$R^{20}$ in ring position one (1) in compounds of Formula (P) can be bonded to a group —$R^3$—S—$R^4$—$R^5$.

Referring to Scheme 6, the aromatic ring carbon atom in position five (5) relative to the amino acid precursor group —$CH_2$—CHQ-$R^{20}$ in ring position one (1) in compounds of Formula (P) can be bonded to a group —$R^3$—S—$R^4$—$R^5$.

Referring to Scheme 6, the aromatic ring carbon atom in position six (6) relative to the amino acid precursor group —$CH_2$—CHQ-$R^{20}$ in ring position one (1) in compounds of Formula (P) can be bonded to a group —$R^3$—S—$R^4$—$R^5$.

Referring to Scheme 6, the aromatic ring carbon atoms in position three (3) and position five (5) relative to the amino acid precursor group —$CH_2$—CHQ-$R^{20}$ in ring position one (1) in compounds of Formula (P) can be bonded to a group —$R^3$—S—$R^4$—$R^5$.

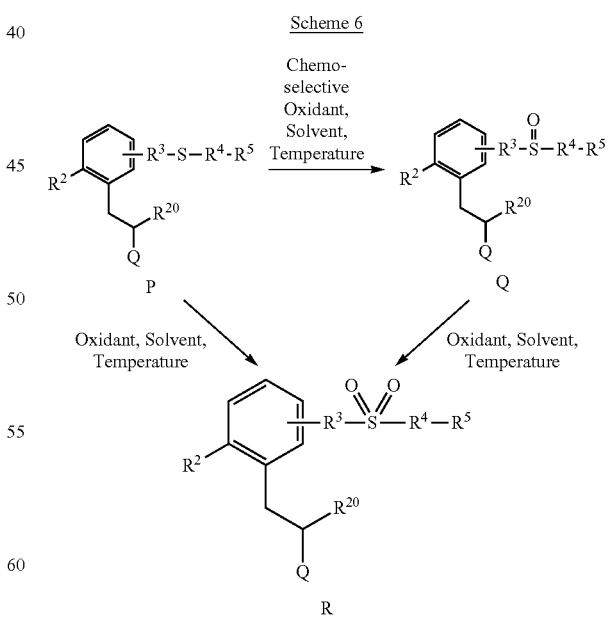

Scheme 6

Referring to Scheme 6, thioethers of Formula (P) can be treated with hydrogen peroxide ($H_2O_2$) in acetic acid (HOAc) as a solvent at about 0° C. to about 25° C. for about 1-12 hours to provide sulfoxides of Formula (Q).

Referring to Scheme 6, sulfoxides of Formula (Q) can be treated with commercial meta-chloroperbenzoic acid (MCPBA) in dichloromethane (DCM) as a solvent at about 0° C. to about 25° C. for about 12-24 hours to provide sulfones of Formula (R).

Referring to Scheme 6, there are also many synthetic methods known in the art for the direct oxidation of thioethers of Formula (P) to sulfones of Formula (R).

Referring to Scheme 7, where $R^2$, $R^4$, $R^5$, $R^{20}$, $R^f$, p, and Q are defined herein; the aromatic ring carbon atom that is bonded to the amino acid precursor group —$CH_2$—CHQ-$R^{20}$ is defined as being in position one (1); counting in a clockwise fashion from position one (1), $R^2$ is bound to the aromatic ring carbon atom in position two (2). In compounds of Formula (S) at least one of the aromatic ring carbon atoms in position three (3), four (4), five (5), or six (6) relative to the amino acid precursor group —$CH_2$—CHQ-$R^{20}$ in ring position one (1) are bonded to the group —$R^e$—$NR^f$—H. Each of the other remaining aromatic ring carbon atoms are bonded to hydrogen. Z is a suitable leaving group, e.g., fluoro (—F), chloro (—Cl), bromo (—Br), azido (—$N_3$), or methoxy (—OMe).

Referring to Scheme 7, in the group —$R^e$—$NR^f$—H, wherein $R^e$ is a single bond ("—"), a (substituted) methylene group (—$C(R^f)_2$—), an oxygen atom (—O—), or a substituted methyleneoxy group (—$C(R^f)_2$—O—), the group —$R^e$—$NR^f$—H is equivalent to (a) a primary or secondary aromatic amino group (—$NR^f$—H), (b) a primary or secondary (substituted) aminomethyl group (—$C(R^f)_2$—$NR^f$H), (c) a primary or secondary O-aryl hydroxylamino group (—O—$NR^f$—H), or (d) a primary or secondary (substituted) O-methyl hydroxylamino group (—$C(R^f)_2$—O—$NR^f$—H).

Referring to Scheme 7, the aromatic ring carbon atom in position three (3) relative to the amino acid precursor group —$CH_2$—CHQ-$R^{20}$ in ring position one (1) in compounds of Formula (S) can be bonded to the group —$R^e$—$NR^f$—H.

Referring to Scheme 7, the aromatic ring carbon atom in position four (4) relative to the amino acid precursor group —$CH_2$—CHQ-$R^{20}$ in ring position one (1) in compounds of Formula (S) can be bonded to the group —$R^e$—$NR^f$—H.

Referring to Scheme 7, the aromatic ring carbon atom in position five (5) relative to the amino acid precursor group —$CH_2$—CHQ-$R^{20}$ in ring position one (1) in compounds of Formula (S) can be bonded to the group —$R^e$—$NR^f$—H.

Referring to Scheme 7, the aromatic ring carbon atom in position six (6) relative to the amino acid precursor group —$CH_2$—CHQ-$R^{20}$ in ring position one (1) in compounds of Formula (S) can be bonded to the group —$R^e$—$NR^f$—H.

Referring to Scheme 7, the aromatic ring carbon atoms in position three (3) and position five (5) relative to the amino acid precursor group —$CH_2$—CHQ-$R^{20}$ in ring position one (1) in compounds of Formula (S) can be bonded to the group —$R^e$—$NR^f$—H.

Referring to Scheme 7, the molecular unit consisting of $R^e$ together with —$NR^f$— constitutes $R^3$ is defined as described herein for compounds of Formula (S) in Scheme 7. Therefore, $R^3$ is selected from —$NR^f$—, (b) —$C(R^f)_2$—$NR^f$—, (c) —O—$NR^f$—, or (d) —$C(R^f)_2$—O—$NR^f$—.

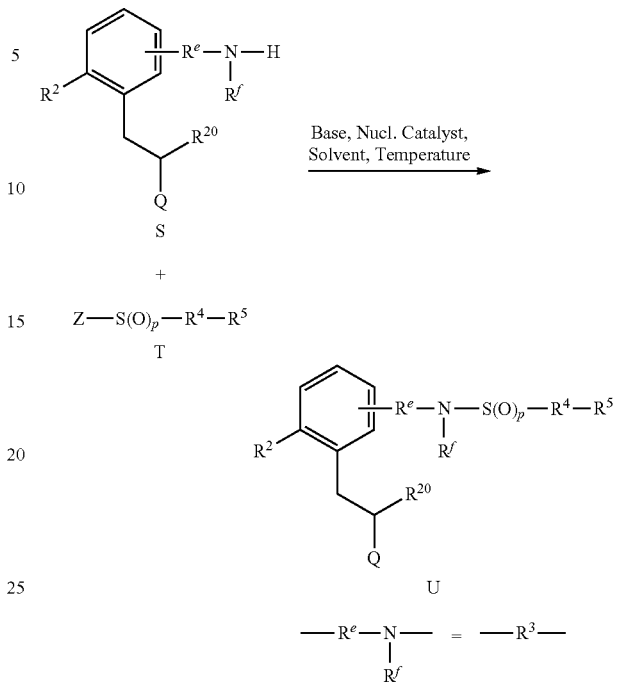

Scheme 7

Referring to Scheme 7, methods for the formation of N—S bonds as found in sulfenamides, sulfinamides, or sulfonamides from the corresponding sulfenyl halides, sulfinyl halides, or sulfonyl halides, azides or lower alkyl esters and primary and secondary amines or related derivatives thereof, e.g., hydroxylamines are well-known in the art.

Referring to Scheme 7, several activated sulfur compounds of Formula (T) (Z—$S(O)_p$—$R^4$—$R^5$), e.g., aliphatic and aromatic sulfenyl halides, sulfinyl halides, sulfonyl halides, azides, or lower alkyl esters are either commercially available or can be prepared from available precursors.

The conversion of the primary or secondary amino or primary or secondary hydroxylamino group as in compounds of Formula (S) to the corresponding sulfenamide, sulfinamide, or sulfonamide as in compounds of Formula (U) can be accomplished by reacting the appropriate primary or secondary amine or primary or secondary hydroxylamine of Formula (S) in suitable inert organic solvents such as dichloromethane (DCM), chloroform ($CHCl_3$), tetrahydrofuran (THF), ethyl acetate (EtOAc), 1,4-dioxane or mixtures of any of the foregoing in the presence of a suitable organic base such as triethyl amine ($Et_3N$, TEA) or diisopropyl ethyl amine (Hünig's-base, DIPEA) (about 1-5 equivalents) with a suitable sulfur halide or another activated sulfur compound as in compounds of Formula (T). The reaction can be carried out between 0° C. and 25° C. for 1-24 hours.

Sulfonyl halides, e.g., sulfonyl chlorides, of Formula (T) are typically reacted with an appropriate primary or secondary amine or primary or secondary hydroxylamine of Formula (S) in pyridine (Pyr) which functions simultaneously as a solvent and a base.

Optionally, nucleophilic catalysts, e.g., 4-N,N-dimethylaminopyridine (DMAP) (about 1-10 mol %; 0.01-0.1 equivalents) can be added to facilitate rate of the N—S bond formation.

Referring to Scheme 8, where $R^2$, $R^3$, $R^5$, $R^{20}$, $R^f$, and Q are defined herein; the aromatic ring carbon atom that is bonded to the amino acid precursor group —CH$_2$—CHQ-R$^{20}$ is defined as being in position one (1); counting clockwise from position one (1), R$^2$ is bound to the aromatic ring carbon atom in position two (2). In compounds of Formula (V) at least one of the aromatic ring carbon atoms in position three (3), four (4), five (5) or six (6) relative to the amino acid precursor group —CH$_2$—CHQ-R$^{20}$ in ring position one (1) is bonded to the group —R$^3$—S(O)$_p$—Z. Each of the other remaining aromatic ring carbon atoms are bonded to hydrogen; Z is a suitable leaving group, e.g., fluoro (—F), chloro (—Cl), bromo (—Br), azido (—N$_3$), or methoxy (—OMe).

Referring to Scheme 8, the aromatic ring carbon atom in position three (3) relative to the amino acid precursor group —CH$_2$—CHQ-R$^{20}$ in ring position one (1) in compounds of Formula (V) can be bonded to the group —R$^3$—S(O)$_p$—Z.

Referring to Scheme 8, the aromatic ring carbon atom in position four (4) relative to the amino acid precursor group —CH$_2$—CHQ-R$^{20}$ in ring position one (1) in compounds of Formula (V) can be bonded to the group —R$^3$—S(O)$_p$—Z.

Referring to Scheme 8, the aromatic ring carbon atom in position five (5) relative to the amino acid precursor group —CH$_2$—CHQ-R$^{20}$ in ring position one (1) in compounds of Formula (V) can be bonded to the group —R$^3$—S(O)$_p$—Z.

Referring to Scheme 8, the aromatic ring carbon atom in position six (6) relative to the amino acid precursor group —CH$_2$—CHQ-R$^{20}$ in ring position one (1) in compounds of Formula (V) can be bonded to the group —R$^3$—S(O)$_p$—Z.

Referring to Scheme 8, the aromatic ring carbon atoms in position three (3) and position five (5) relative to the amino acid precursor group —CH$_2$—CHQ-R$^{20}$ in ring position one (1) in compounds of Formula (V) can be bonded to the group —R$^3$—S(O)$_p$—Z.

Referring to Scheme 8, in the group H—NR$^f$—R$^e$—, wherein R$^e$ is a single bond ("—"), a (substituted) methylene group (—C(R$^f$)$_2$—), an oxygen atom (—O—), or a (substituted) oxymethylene group (—O—C(R$^f$)$_2$—), the group H—NR$^f$—R$^e$— is equivalent to (a) a primary or secondary aromatic amino group (H—NR$^f$—), (b) a primary or secondary amino (substituted) methyl group (H—NR$^f$—C(R$^f$)$_2$—), (c) a primary or secondary O-aryl hydroxylamino group (H—NR$^f$—O—), or (d) a primary or secondary (substituted) hydroxylamino group (H—NR$^f$—O—C(R$^f$)$_2$—).

Referring to Scheme 8, the molecular unit consisting of R$^e$ together with —NR$^f$— constitutes R$^4$ as defined as described herein for compounds of Formula (W) in Scheme 8. Therefore, R$^4$ is selected from —NR$^f$—, (b) —NR$^f$—C(R$^f$)$_2$—, (c) —NR$^f$—O—, or (d) —NR$^f$—O—C(R$^f$)$_2$—.

Scheme 8

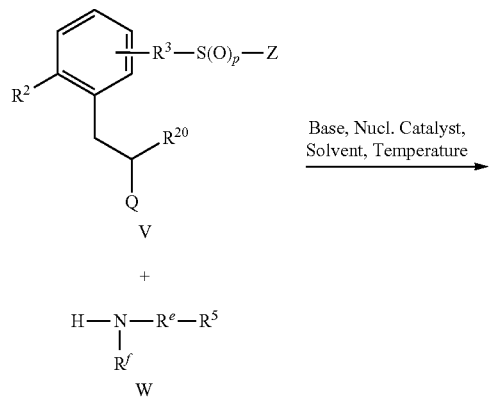

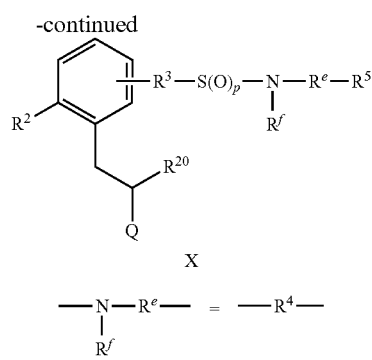

Referring to Scheme 8, methods for the formation of N—S bonds as found in sulfenamides, sulfinamides, or sulfonamides from the corresponding sulfenyl halides, sulfinyl halides, or sulfonyl halides, azides or lower alkyl esters and primary and secondary amines or related derivatives thereof, e.g., primary and secondary hydroxylamines are well-known in the art.

The conversion of the primary or secondary amino or primary or secondary hydroxylamino group as in compounds of Formula (W) to the corresponding sulfenamide, sulfinamide, or sulfonamide as in compounds of Formula (X) can be accomplished by reacting a suitable sulfur halide or another activated sulfur compound as in compounds of Formula (V) in suitable inert organic solvents such as dichloromethane (DCM), chloroform (CHCl$_3$), tetrahydrofuran (THF), ethyl acetate (EtOAc), 1,4-dioxane or mixtures of any of the foregoing in the presence of a suitable organic base such as triethyl amine (Et$_3$N, TEA), diisopropyl-ethylamine (Hünig's-base, DIPEA) (about 1-5 equivalents) with an appropriate primary or secondary amine or primary or secondary hydroxylamine of Formula (W). The reaction can be carried out between 0° C. and 25° C. for 1-24 h.

Sulfonyl halides, e.g., sulfonyl chlorides, of Formula (V) where Z is chloro (—Cl) can be reacted with an appropriate primary or secondary amine or a primary or secondary hydroxylamine of Formula (W) in pyridine (Pyr) which functions simultaneously as a solvent and a base.

Optionally, nucleophilic catalysts, e.g., 4-N,N-diemethylamino pyridine (DMAP) (about 1-10 mol %; 0.01-0.1 equivalents) can be added to facilitate rate of the N—S bond formation.

Referring to Scheme 9, where R$^1$, R$^2$, R$^3$, R$^4$, R$^5$, R$^{20}$, Q, and p are defined herein, where R$^{20}$ in compounds of Formula (Y) is a protected carboxyl group as defined herein, and Q in compounds of Formula (Y) is a protected amino group as defined herein.

The aromatic ring carbon atom that is bonded to the amino acid precursor group —CH$_2$—CHQ-R$^{20}$ in compounds of Formula (Y) is defined as being in position one (1); counting in a clockwise fashion from position one (1), R$^2$ is bound to the aromatic ring carbon atom in position two (2). In compounds of Formula (Y), at least one of the aromatic ring carbon atoms in position three (3), four (4), five (5) or six (6) relative to the amino acid precursor group —CH$_2$—CHQ-R$^{20}$ in ring position one (1) is bonded to the group —R$^3$—S(O)$_p$—R$^4$—R$^5$. Each of the other remaining aromatic ring carbon atoms are bonded to hydrogen.

Referring to Scheme 9, the aromatic ring carbon atom in position three (3) relative to the amino acid precursor group —CH$_2$—CHQ-R$^{20}$ in ring position one (1) in compounds of Formula (Y) can be bonded to the group —R$^3$—S(O)$_p$—R$^4$—R$^5$.

Referring to Scheme 9, the aromatic ring carbon atom in position four (4) relative to the amino acid precursor group —CH$_2$—CHQ-R$^{20}$ in ring position one (1) in compounds of Formula (Y) can be bonded to the group —R$^3$—S(O)$_p$—R$^4$-R$^5$.

Referring to Scheme 9, the aromatic ring carbon atom in position five (5) relative to the amino acid precursor group —CH$_2$—CHQ-R$^{20}$ in ring position one (1) in compounds of Formula (Y) can be bonded to the group —R$^3$—S(O)$_p$—R$^4$—R$^5$.

Referring to Scheme 9, the aromatic ring carbon atom in position six (6) relative to the amino acid precursor group —CH$_2$—CHQ-R$^{20}$ in ring position one (1) in compounds of Formula (Y) can be bonded to the group —R$^3$—S(O)$_p$—R$^4$—R$^5$.

Referring to Scheme 9, the aromatic ring carbon atoms in position three (3) and position (5) relative to the amino acid precursor group —CH$_2$—CHQ-R$^{20}$ in ring position one (1) in compounds of Formula (Y) can be bonded to the group —R$^3$—S(O)$_p$—R$^4$—R$^5$.

Referring to Scheme 9, liberation of fully unprotected phenyl alanine derivatives of Formula (AB) from their corresponding fully protected precursors of Formula (Y) may be conducted by global deprotection. The carboxylic acid protecting group and the amino protecting group can be cleaved simultaneously under the same reaction conditions and through the same cleaving agent.

Referring to Scheme 9, the protected carboxylic acid in compounds of Formula (Y) can be orthogonally or chemoselectively cleaved and without affecting the protected amino group Q to provide compounds of Formula (Z) which are either isolated by any of the known conventional methods or used directly for further derivatization or fully deprotection to provide compounds of Formula (AB) (stepwise or sequential deprotection).

Referring to Scheme 9, the protected amino group in compounds of Formula (Y) can be orthogonally or chemoselectively cleaved and without affecting the protected carboxylic acid group R$^{20}$ to provide compounds of Formula (AA) which are either isolated by any of the known conventional methods or used directly for further derivatization or fully deprotection to provide compounds of Formula (AB) (stepwise or sequential deprotection).

Protected phenylalanine derivatives of Formula (Y) bearing different combinations of suitable protecting groups can also be prepared. Different combinations of protecting groups may require specific reactants and reaction conditions for effective removal of a specific set of different protection groups to provide phenylalanine derivatives of Formula (AB). Accordingly, the methods and protecting group combinations presented in the schemes provided by the present disclosure are illustrative rather than comprehensive.

Reactions conditions for chemoselective removal of specific protecting groups of protected amino groups and protected carboxylic acids of phenylalanine derivatives of Formula (Y) to liberate unprotected phenyl alanine derivatives of Formula (AB) are well-known in the art.

Referring to Scheme 9, useful methods for the selective orthogonal cleavage of protected carboxylic acids, e.g., carboxylic acid lower alkyl esters, in the presence of N-protecting groups are well-known in the art. Selected deprotection conditions are known in the art to proceed without affecting the protected amino group Q and without compromising the stereochemical integrity of stereogenic center in compounds of Formula (Y) and in compounds of Formula (Z).

Referring to Scheme 9, particularly useful protecting group combinations for global and simultaneous deprotection of Q and R$^{20}$ of compounds of Formula (Y) under the same reaction conditions and through the same cleaving agent are, for example, where Q is —NHBoc and R$^{20}$ is —CO$_2$tBu, where Q is —NHTFA and R$^{20}$ is —CO$_2$Me, where Q is —NHCbz and R$^{20}$ is —CO$_2$Bn.

Referring to Scheme 9, particularly useful protecting group combinations for either orthogonal or chemoselective deprotection of Q and R$^{20}$ of compounds of Formula (Y) are, for example, where Q is —NHBoc and R$^{20}$ is —CO$_2$Me, where Q is —NHBoc and R$^{20}$ is —CO$_2$Bn, where Q is —NHCbz and R$^{20}$ is —CO$_2$Me, where Q is —NHCbz and R$^{20}$ is —CO$_2$tBu, where Q is —NHBoc and R$^{20}$ is —CO$_2$tBu, where Q is —NHTFA and R$^{20}$ is —CO$_2$tBu.

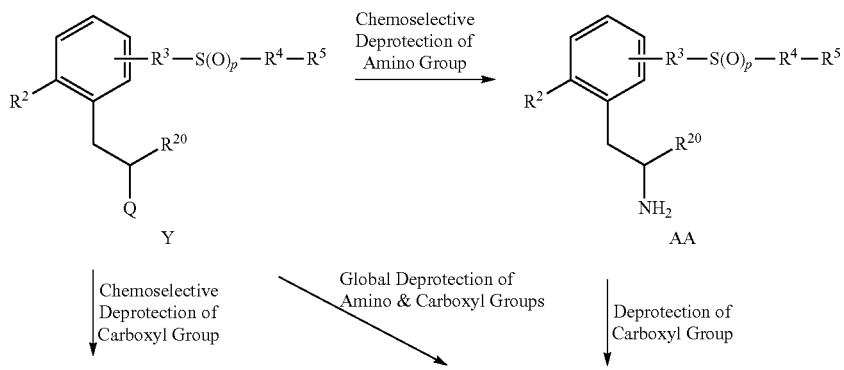

Scheme 9

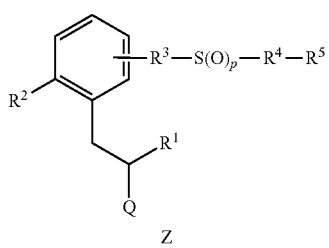

Z

-continued

Deprotection of Amino Group →

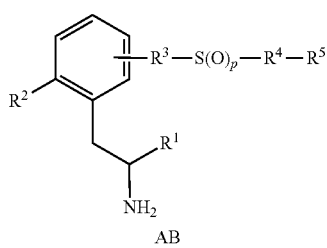

AB

Referring to Scheme 9, in compounds of Formula (Y) where Q is —NHBoc and $R^{20}$ is —CO$_2$tBu, fully deprotected phenylalanine derivatives of Formula (AB) can be prepared under anhydrous conditions through contacting fully protected phenylalanine derivatives of Formula (Y) with 10% to 100% trifluoroacetic acid (TFA) in solvents such as dichloromethane (DCM) at temperatures from about 0° C. to about 40° C. for about 1-12 hours.

Alternatively, fully protected phenylalanine derivatives of Formula (Y) where Q is —NHBoc and $R^{20}$ is —CO$_2$tBu can also be fully deprotected to compounds of Formula (AB) under anhydrous conditions through contact with hydrogen chloride (HCl) in organic solvents, e.g., commercial 1 M in ethyl acetate (EtOAc), 2 M HCl in diethyl ether (Et$_2$O), 4 M HCl in 1,4-dioxane, 6 M HCl in isopropyl alcohol (iPrOH) in the same solvents or mixtures of any of the foregoing at temperatures from about 0° C. to about 60° C. for about 1-12 hours.

Referring to Scheme 9, in compounds of Formula (Y) where Q is —NHCbz and $R^{20}$ is —CO$_2$Bn, fully deprotected phenylalanine derivatives of Formula (AB) can be deprotected under heterogenic hydrogenolytic conditions, e.g., catalytic hydrogenation over heterogenous metal catalysts, e.g., Raney-nickel in methanol (MeOH) or ethanol (EtOH) at about 25° C., palladium (palladium on carbon, Pd/C) in methanol (MeOH) or ethanol (EtOH) at about 25° C., palladium hydroxide (Pd(OH)$_2$) or platinum (PtO$_2$, Adams-catalyst) in methanol (MeOH), ethanol (EtOH), isopropanol (iPrOH) or mixtures of any of the forgoing at about 25° C. with hydrogen pressures ranging from about 1 atm to about 10 atm.

Referring to Scheme 9, in compounds of Formula (Y) where Q is —NHTFA and $R^{20}$ is —CO$_2$Me, fully deprotected phenylalanine derivatives of Formula (AB) can be deprotected by mild alkaline hydrolysis with alkaline hydroxides, e.g., lithium hydroxide hydrate (LiOH·H$_2$O) (about 1-5 equivalents), in solvents such as tetrahydrofuran (THF), methanol (MeOH), dichloromethane (DCM), water, and mixtures of any of the foregoing at about 25° C. or alkaline carbonates, e.g., potassium carbonate (K$_2$CO$_3$) in solvents such as tetrahydrofuran (THF), methanol (MeOH), water, and mixtures of any of the foregoing, or in the presence of hydrogen-bonding solvents, e.g., 0.1 N HCl in hexafluoroisopropanol or trifluoroethanol at about 25° C. to about 60° C.

Referring to Scheme 9, in compounds of Formula (Y) where $R^{20}$ is a carboxylic acid methyl ester (—CO$_2$Me) and Q is —NHBoc or —NHCbz, the carboxylic acid methyl ester can be selectively cleaved to the corresponding carboxylic acids of Formula (Z) wherein $R^1$ is —CO$_2$H by mild alkaline hydrolysis.

Referring to Scheme 9, in compounds of Formula (Y) where $R^{20}$ is a carboxylic acid benzyl ester (—CO$_2$Bn) and Q is —NHBoc or —NHTFA, the carboxylic acid methyl ester can be selectively cleaved to the corresponding carboxylic acids of Formula (Z) wherein $R^1$ is —CO$_2$H by heterogenous hydrogenolysis.

Referring to Scheme 9, in compounds of Formula (Y), where $R^{20}$ is a carboxylic acid tert-butyl ester (—CO$_2$tBu) and Q is —NHCbz or —NHTFA, the carboxylic acid tert-butyl ester can be selectively cleaved to the corresponding carboxylic acids of Formula (Y) wherein $R^1$ is —CO$_2$H by strong acids (HCl or TFA) under anhydrous conditions.

Referring to Scheme 9, in compounds of Formula (Y), where $R^{20}$ is a carboxylic acid tert-butyl ester (—CO$_2$tBu) and Q is —NHBoc, the carboxylic acid tert-butyl ester can be selectively cleaved to the corresponding carboxylic acid of Formula (Z) wherein $R^1$ is —CO$_2$H at reflux temperature in acetonitrile (MeCN) in the presence of about 1.3 equivalents of sodium iodide (NaI) and about 1.5 equivalents of cerium chloride heptahydrate (CeCl$_3$·7H$_2$O) within about 1-24 hours. Other selective cleavage methods known in the art employ zinc bromide (ZnBr$_2$) in dichloromethane (DCM).

Referring to Scheme 9, in compounds of Formula (Y), where $R^{20}$ is a carboxylic acid tert-butyl ester (—CO$_2$tBu) and Q is —NHBoc, the tert-butyloxycarbonyl protecting group can be selectively cleaved to the corresponding free amines of Formula (Z) by dilute strong acids (e.g., 1 vol % trifluoroacetic acid (TFA) in dichloromethane (DCM)) under anhydrous conditions.

Referring to Scheme 9, in compounds of Formula (Y), where $R^{20}$ is a carboxylic acid tert-butyl ester (—CO$_2$tBu) or methyl ester (—CO$_2$Me) and Q is —NHCbz, the benzyloxycarbonyl or trifluoroacetyl protecting groups can be selectively cleaved to the corresponding free amines of Formula (AA) by heterogenous hydrogenolysis.

Referring to Scheme 9, in compounds of Formula (Y), where $R^{20}$ is a carboxylic acid tert-butyl ester (—CO$_2$tBu) and Q is —NHTFA, the trifluoroacetyl protecting group can be selectively cleaved to the corresponding free amines of Formula (AA) by mild basic hydrolysis with dilute aqueous alkaline hydroxides, e.g., NaOH, KOH, or LiOH, aqueous alkaline carbonates, e.g., K$_2$CO$_3$, or in the presence of hydrogen-bonding solvents, e.g., 0.1 N HCl in hexafluoroisopropanol or trifluoroethanol.

Referring to Scheme 9, in compounds of Formula (Y), where $R^{20}$ is a carboxylic acid methyl ester (—CO$_2$Me) or carboxylic acid benzyl ester (—CO$_2$Bn) and Q is —NHBoc, the tert-butyloxycarbonyl protecting group can be selectively cleaved to the corresponding free amines of Formula (AA) by strong acids (HCl or TFA) under anhydrous conditions.

Referring to Scheme 9, separation of unprotected phenylalanine derivatives of Formula (AB) from unreacted starting materials, unwanted byproducts, and impurities can be accomplished using, for example, solid-phase extraction (SPE) techniques, e.g., with QMA® cartridges (Waters, USA), LiChrolut® cartridges (EMD Chemicals, USA), or Whatman® SAX cartridges (Whatman, USA), preparative normal or reverse phase TLC, reverse phase (RP) semi-preparative or preparative HPLC, crystallization, precipitation, or other suitable method.

Referring to Scheme 9, purified unprotected phenylalanine derivatives of Formula (AB) can be isolated in neat form using any suitable method. For example, such methods include removal of HPLC solvents (mobile phases) of the combined fractions containing the unprotected phenylalanine derivatives of Formula (AB) under reduced pressure with a rotary evaporator, or removal of frozen aqueous solvent mixtures by primary lyophilization.

Any suitable method can be used to produce acid addition salts or salts including pharmaceutically acceptable acid addition salts or salts of compounds of Formula (AB).

Referring to Scheme 9, the lyophilization may optionally be conducted in the presence of one or more equivalents of a mineral acid, optionally with a pharmaceutically acceptable counterion, to form (pharmaceutically acceptable) acid addition salts of compounds of Formula (AB). For example, one or more equivalents of hydrochloric acid (HCl) may be added prior to lyophilization to form mono-, di-, or polyhydrochloride salts of compounds of Formula (AB) or mixtures thereof.

Referring to Scheme 9, the lyophilization can optionally be conducted in the presence of one or more equivalents of a base, optionally with a pharmaceutically acceptable counterion, to form (pharmaceutically acceptable) salts of compounds of Formula (AB). For example, one or more equivalents of sodium hydrogen carbonate ($NaHCO_3$) may be added prior to lyophilization to form mono-, di-, or polysodium salts of compounds of Formula (AB) or mixtures thereof.

Referring to Scheme 10, besides the unprotected phenylalanine derivatives of Formula (AB) (Scheme 9) (α-amino acids) of the present disclosure it has been suggested that various esters, amides, and hydroxamic acid derivatives of Formula (AF) also interact with LAT1.

Referring to Scheme 10, a large variety of coupling methods is known in the art to facilitate the racemization free formation of amide bonds as in compounds of Formula (AE) from N-protected amino acids of Formula (AC).

Referring to Scheme 10, the carboxyl group of compounds of Formula (AC) can be activated as acyl halides including acyl fluorides, acyl azides, symmetrical or unsymmetrical carboxylic, carbonic, or boronic anhydrides, acyl imidazoles, activated esters such as acyl N-hydroxysuccinimides, N-hydroxyphthalimides, pentafluorophenol, 1-hydroxybenzotriazol, phosphonium salts, uronium salts, or ammonium salts followed by ammonolysis of the activated intermediate either after prior isolation or in situ with an appropriately functionalized amine or an acid addition salt thereof, e.g., a hydrochloride salt or a hydrobromide salt.

Referring to Scheme 10, where $R^2$, $R^3$, $R^4$, $R^5$, Q, and p are defined herein; $R^1$ in compounds of Formula (AC) can be a carboxylic acid (—$CO_2H$) and $R^1$ in compounds of Formula (AE) and of Formula (AE) can be a carboxylic amide derivative (—$CON(R^f)_2$) wherein each $R^f$ is independently selected from hydrogen, —OH and $C_{1-4}$ alkoxy.

Referring to Scheme 10, the aromatic ring carbon atom that is bonded to the amino acid amide group —$CH_2$—$CHNH_2$—$CON(R^b)_2$ in compounds of Formula (AF) is defined as being in position one (1); counting clockwise from position one (1), $R^2$ is bonded to the aromatic ring carbon atom in position two (2). In compounds of Formula (AF), at least one of the other aromatic ring carbon atoms in position three (3), four (4), five (5) or six (6) relative to the amino acid amide group —$CH_2$—$CHNH_2$—$CONR^xR^y$ in ring position one (1) is bonded to the group —$R^3$—$S(O)_p$—$R^4$—$R^5$. Each of the other remaining aromatic ring carbon atoms can be bonded to hydrogen.

Referring to Scheme 10, the aromatic ring carbon atom in position three (3) relative to the amino acid amide group —$CH_2$—$CHNH_2$—$CON(R^b)_2$ in ring position one (1) in compounds of Formula (AF) can be bonded to the group —$R^3$—$S(O)_p$—$R^4$—$R^5$.

Referring to Scheme 10, the aromatic ring carbon atom in position four (4) relative to the amino acid amide group —$CH_2$—$CHNH_2$—$CON(R^b)_2$ in ring position one (1) in compounds of Formula (AF) can be bonded to the group —$R^3$—$S(O)_p$—$R^4$—$R^5$.

Referring to Scheme 10, the aromatic ring carbon atom in position five (5) relative to the amino acid amide group —$CH_2$—$CHNH_2$—$CONR^xR^y$ in ring position one (1) in compounds of Formula (AF) can be bonded to the group —$R^3$—$S(O)_p$—$R^4$—$R^5$.

Referring to Scheme 10, the aromatic ring carbon atom in position six (6) relative to the amino acid amide group —$CH_2$—$CHNH_2$—$CON(R^b)_2$ in ring position one (1) in compounds of Formula (AF) can be bonded to the group —$R^3$—$S(O)_p$—$R^4$—$R^5$.

Referring to Scheme 10, the aromatic ring carbon atoms in position three (3) and position (5) relative to the amino acid amide group —$CH_2$—$CHNH_2$—$CON(R^b)_2$ in ring position one (1) in compounds of Formula (AF) can be bonded to the group —$R^3$—$S(O)_p$—$R^4$—$R^5$.

Referring to Scheme 10, in some embodiments an appropriately substituted amine of Formula (AD) is $HN(R^b)_2$ wherein each $R^b$ is independently selected from hydrogen, —OH, and $C_{1-4}$ alkoxy.

Scheme 10

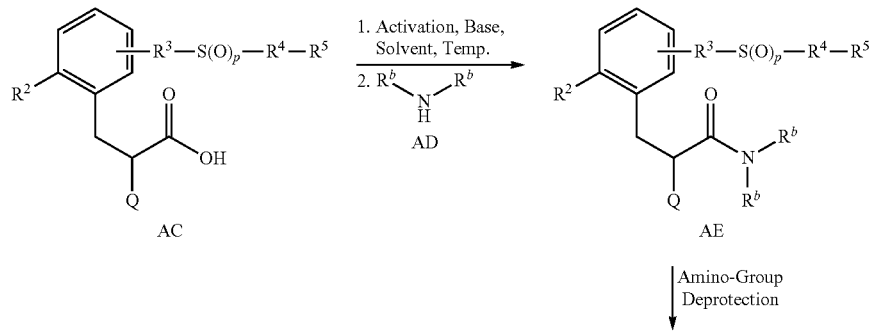

-continued

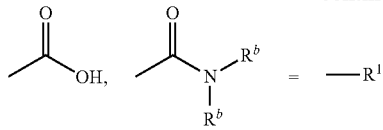 = —R¹

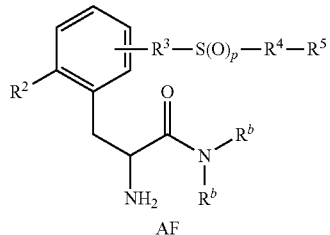

AF

Referring to Scheme 10, N-protected phenylalanine derivatives of Formula (AC) wherein $R^1$ is a carboxylic acid (—$CO_2H$) and Q is N(H)—PG or $NPG_2$ can be obtained through orthogonal deprotection of the protected carboxyl functionality $R^{20}$ of fully protected phenylalanine derivatives of Formula (Y) (Scheme 9). PG can be a suitable nitrogen protecting group as defined herein (Scheme 3 and Scheme 9).

Referring to Scheme 10, N-protected phenylalanine free carboxylic acids of Formula (AC) can be activated with isobutyl chloroformate (iBuOCOCl) or ethyl chloroformate (EtOCOCl) in the presence of bases such as 4-methyl-morpholine (NMM), diisopropylethylamine (DIPEA), or triethylamine ($Et_3N$, TEA) in solvents such as tetrahydrofuran (THF) at temperatures of about −40° C. to about 0° C. followed by amide bond formation with suitable amines $HN(R^b)_2$ of Formula (AD) or hydrochloride addition salts thereof ($HCl·HN(R^b)_2$) to provide compounds of Formula (AE).

Referring to Scheme 10, N-protected phenylalanine free carboxylic acids of Formula (AC) can be activated with dicyclohexylcarbodiimide (DCC), diisopropylcarbodiimide (DIC), 1-ethyl-(3-(3-dimethylamino)propyl)carbodiimide hydrochloride (EDC, EDAC, EDCI), or other carbodiimide reagents in the presence of N-hydroxysuccinimide (HOSu), 1-hydroxybenzotriazole (HOBT), pentafluorophenol, or others in the presence of bases such as 4-methyl-morpholine (NMM), diisopropylethylamine (DIPEA), 2,4,6-trimethylpyridine (2,4,6-collidine), or triethylamine ($Et_3N$, TEA), optionally in the presence of nucleophilic acylation catalysts, e.g., 4-N,N-dimethylpyridine (DMAP), in solvents such as tetrahydrofuran (THF), dichloromethane (DCM), acetonitrile (MeCN), ethyl acetate (EtOAc), or mixtures of any of the foregoing at temperatures of about −20° C. to about 20° C. followed by amide bond formation with suitable amines $HN(R^b)_2$ of Formula (AD) or hydrochloride addition salts thereof ($HCl·HN(R^b)_2$) to provide compounds of Formula (AE).

Referring to Scheme 10, N-protected phenylalanine free carboxylic acids of Formula (AC) can be activated with commercial O-(1H-benzotriazol-1-yl)-N,N,N',N'-tetramethyluronium hexafluorophosphate (HBTU), fluoro-N,N,N',N'-tetramethylformamidinium hexafluorophosphate (TFFH), 1-(bis(dimethylamino)methylene)-1H-1,2,3-triazolo(4,5-b)pyridinium 3-oxide hexafluorophosphate (HATU), (benzotriazol-1-yloxy)tris(dimethylamino)phosphonium hexafluorophosphate (BOP), or other commercial phosphonium salts, uronium salts, or ammonium salts, optionally in the presence of 1-hydroxybenzotriazole (HOBT), pentafluorophenol, or other additives such as nucleophilic acylation catalysts, e.g., 4-N,N-dimethylpyridine (DMAP), in the presence of bases such as 4-methyl-morpholine (NMM), diisopropylethylamine (DIPEA), or triethylamine ($Et_3N$, TEA), in solvents such as tetrahydrofuran (THF), dichloromethane (DCM), N,N-dimethylformamide (DMF) or mixtures of any of the foregoing at temperatures of about −20° C. to about 20° C. followed by amide bond formation with suitable amines $HN(R^b)_2$ of Formula (AD) or hydrochloride addition salts thereof ($HCl·HN(R^b)_2$) to provide compounds of Formula (AE).

Referring to Scheme 10, N-protected phenylalanine free carboxylic acids of Formula (AC) can be activated with agents such as 1,3,5-trichloro-2,4,6-triazine, 2,4,6-tripropyl-1,3,5,2,4,6-trioxaphosphinane-2,4,6-trioxide, ethyl 2-cyano-2-(4-nitrophenylsulfonyloxyimino)acetate, dimethylbromosulfonium bromide (BDMS), or others in the presence of bases such as 4-methyl-morpholine (NMM), diisopropylethylamine (DIPEA), 2,4,6-trimethylpyridine (2,4,6-collidine), or triethylamine ($Et_3N$, TEA), optionally in the presence of nucleophilic acylation catalysts, e.g., 4-N,N-dimethylpyridine (DMAP), in solvents such as tetrahydrofuran (THF), dichloromethane (DCM), acetonitrile (MeCN), ethyl acetate (EtOAc) or mixtures of any of the foregoing at temperatures of about −20° C. to about 20° C. followed by amide bond formation with either hydroxylamine (HNHOH), its hydrochloride addition salt (HNHOH·HCl), O-alkyl hydroxylamines ($HNHOR^z$ wherein $R^z$ is $C_{1-4}$ alkyl), or hydrochloride addition salts thereof ($HNHOR^z·HCl$ wherein $R^z$ is $C_{1-4}$ alkyl as defined herein) of Formula (AD) to provide compounds of Formula (AE).

Referring to Scheme 10, well-known peptide coupling reagents, combinations of any of the foregoing, variants, protocols, and reaction conditions exist in the art for the preparation of N-protected carboxylic amides of Formula (AE) from N-protected carboxylic acids of Formula (AC).

Referring to Scheme 10, in some embodiments wherein the protected amino group Q of compounds of Formula (AC) and of Formula (AE) is as described herein, protected α-amino acid amides of Formula (AE) can be further deprotected to provide unprotected compounds of Formula (AF) using comparable reaction conditions as described for compounds of Formula (AB) (Scheme 9).

Enantiomerically pure α-amino ketones are of great importance in natural product synthesis and pharmacological research.

The Weinreb-Nahm ketone synthesis is a practical synthetic method for the chemoselective conversion of carboxylic acids into a broad variety of the corresponding ketones including α-amino ketones derived from N-protected α-amino acids. The standard reaction conditions for the Weinreb-Nahm ketones synthesis are known to tolerate a wide variety of functional groups elsewhere in the molecule including sulfonamide groups and N-carbamoyl protection groups. The reaction of an intermittently activated carboxylic acid derivative with N,O-dimethylhydroxylamine (Me-NH—OMe) or preferentially its commercial hydrochloride salt (Me-NH—OMe·HCl) yields the Weinreb-Nahm amide (N'-methoxy-N'-methylamides, R—CO—NMe-OMe).

Moreover, some N'-methoxy-N'-methylamides of N-Boc-α-amino acids are commercially available.

Subsequent reaction of Weinreb-Nahm amides most commonly with (commercial) organometallic reagents such as organolithium or Grignard-reagents and a low temperature quench yield the corresponding ketones.

Referring to Scheme 11, $R^2$, $R^3$, $R^4$, $R^5$, and Q are defined as described herein; $R^1$ is a carboxylic acid; $R^1$ is lower alkyl, e.g., methyl (—$CH_3$), ethyl (—$CH_2CH_3$), isopropyl (—$CH(CH_3)_2$), or tert-butyl (—$C(CH_3)_3$); M is lithium ($Li^+$), magnesium (½ $Mg^{++}$), or a magnesium halide ($MgX^+$) wherein X is a halogenide ion, e.g., chloride ($Cl^-$) or bromide ($Br^-$).

Referring to Scheme 11, the aromatic ring carbon atom that is bonded to the α-amino ketone group —$CH_2$—$CHNH_2$—CO—$R^7$ in compounds of Formula (AK) is defined as being in position one (1); counting in a clockwise fashion from position one (1), $R^2$ is bonded to the aromatic ring carbon atom in position two (2). In compounds of Formula (AK), at least one of the other aromatic ring carbon atoms in position three (3), four (4), five (5) or six (6) relative to the α-amino ketone group —$CH_2$—$CHNH_2$—CO—$R^7$ in ring position one (1) is bonded to the group —$R^3$—$S(O)_p$—$R^4$—$R^5$. Each of the other remaining aromatic ring carbon atoms are bonded to hydrogen.

Referring to Scheme 11, the aromatic ring carbon atom in position three (3) relative to the α-amino ketone group —$CH_2$—$CHNH_2$—CO—$R^7$ in ring position one (1) in compounds of Formula (AK) can be bonded to the group —$R^3$—$S(O)_p$—$R^4$—$R^5$.

Referring to Scheme 11, the aromatic ring carbon atom in position four (4) relative to the α-amino ketone group —$CH_2$—$CHNH_2$—CO—$R^7$ in ring position one (1) in compounds of Formula (AK) can be bonded to the group —$R^3$—$S(O)_p$—$R^4$—$R^5$.

Referring to Scheme 11, the aromatic ring carbon atom in position five (5) relative to the α-amino ketone group —$CH_2$—$CHNH_2$—CO—$R^7$ in ring position one (1) in compounds of Formula (AK) can be bonded to the group —$R^3$—$S(O)_p$—$R^4$—$R^5$.

Referring to Scheme 11, the aromatic ring carbon atom in position six (6) relative to the α-amino ketone group —$CH_2$—$CHNH_2$—CO—$R^7$ in ring position one (1) in compounds of Formula (AK) can be bonded to the group —$R^3$—$S(O)_p$—$R^4$—$R^5$.

Referring to Scheme 11, the aromatic ring carbon atoms in position three (3) and position (5) relative to the α-amino ketone group —$CH_2$—$CHNH_2$—CO—$R^7$—$CH_2$—CHQ-$R^1$ in ring position one (1) in compounds of Formula (AK) can be bonded to the group —$R^3$—$S(O)_p$—$R^4$—$R^5$.

Scheme 11

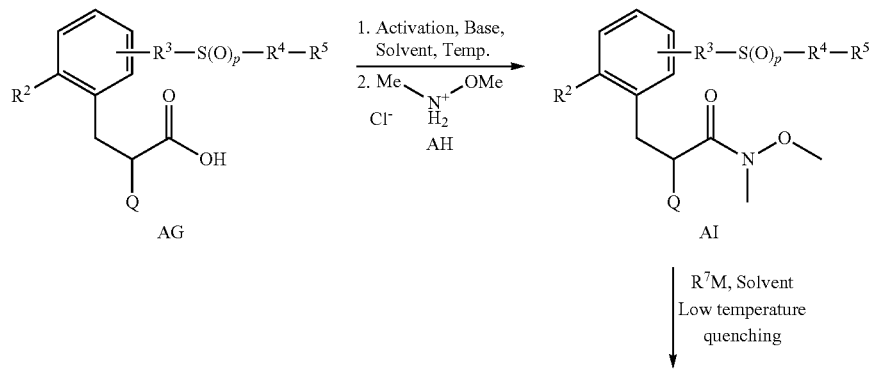

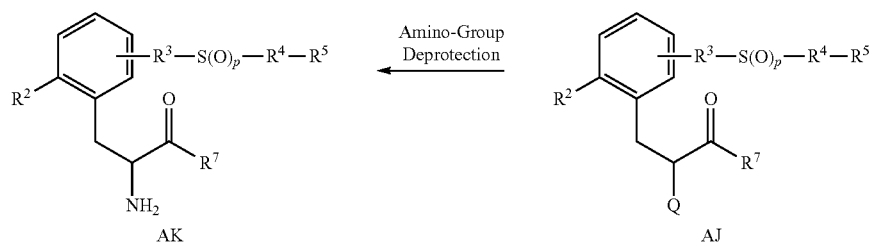

Referring to Scheme 11, N-protected phenylalanine derivatives of Formula (AG) where $R^1$ is a carboxylic acid (—$CO_2H$) and Q is N(H)—PG or $NPG_2$ can be readily accessible through orthogonal deprotection of the protected carboxyl functionality $R^{20}$ of fully protected phenylalanine derivatives of Formula (Y) (Scheme 9). PG can be a suitable nitrogen protecting group as described herein.

Referring to Scheme 11, several peptide coupling reagents can be used to prepare the intermediate Weinreb-Nahm amides from carboxylic acids of Formula (AG) and N-methyl-N-methoxy amine (HNMeOMe) or preferably its hydrogen chloride addition salt (HNMeOMe-HCl) of Formula (AH). However, various carbodiimide, hydroxybenzotriazole, (bis(2-methoxyethyl)amino) sulfur trifluoride (Deoxo-Fluor) and triphenylphosphine-based couplings have been developed specifically for this purpose.

Referring to Scheme 11, subsequent reaction of the Weinreb-Nahm amides of Formula (AI) with (commercial) organometallic reagents including organolithium, Grignard-reagents, or (functionalized) organo-zinc reagents (Knochel reagents) and a low temperature quench yield the corresponding ketones of Formula (AJ).

Referring to Scheme 11, in some embodiments the Weinreb-Nahm amides of Formula (AI) are treated with one (1) or more equivalent per H-acidic group of commercial lithium alkyls, e.g., methyl lithium (MeLi) in diethylether ($Et_2O$) or isopropyl lithium (iPrLi) in n-pentane) or a comparable Grignard reagents, e.g., methyl magnesium bromide (MeMgBr) in diethyl ether ($Et_2O$) or isopropyl magnesium chloride (iPrMgCl) in tetrahydrofuran (THF), at temperatures from about −78° C. to about −20° C. Low temperature quenching followed by conventional work-up and compound isolation provides the protected α-amino ketones of Formula (AJ).

Referring to Scheme 11, in some embodiments wherein the protected amino group Q of compounds of Formula (AG), of Formula (AI), and of Formula (AJ) is as described herein, protected α-amino ketones of Formula (AJ) are deprotected to provide unprotected α-amino ketones of Formula (AK) using comparable reaction conditions as described for compounds of Formula (AB) (Scheme 9).

Referring to Scheme 11, N-protected α-amino ketones of Formula (AJ) can be prepared directly by reaction of carboxylic acids of Formula (AG) with suitable alkyl or aryl carboxylic acid anhydrides $R^7$—CO—O—CO—$R^7$ in solvents such as pyridine and in the presence of nucleophilic acylation catalysts such as 4-N,N-dimethylamino pyridine (DMAP), 1-methylimidazole at temperatures from about 25° C. to about reflux temperature (Dankin-West ketone synthesis).

Referring to Scheme 11, in some embodiments wherein the protected amino group Q of compounds of Formula (AG), of Formula (AI), and of Formula (AJ) is as described herein, protected α-amino ketones of Formula (AJ) are deprotected to provide unprotected α-amino ketones of Formula (AK) using comparable reaction conditions as described for compounds of Formula (AB) (Scheme 9).

Compounds of Formula (1) are LAT1 transporter inhibitors.

Inhibitors of the LAT1 transporter can be useful in treating diseases or conditions in which modulation of the LAT1-mediated transport of amino acids including but not limited to amino acids such as leucine (Leu), isoleucine (Ileu), phenylalanine (Phe), Tyrosine (Tyr), tryptophan (Trp) is associated with the etiology of the disease or condition.

LAT1-mediated transport of amino acids including but not limited to amino acids such as leucine (Leu), isoleucine (Ileu), phenylalanine (Phe), Tyrosine (Tyr), tryptophan (Trp) is associated with diseases and conditions associated with the immune response such as an autoimmune disease, graft-versus-host disease, an inflammatory disease such as inflammatory bowel disease, and organ transplant rejection.

LAT1 transporter inhibitors can be useful in modulating the immune response and in modifying the immune response.

LAT1 transporter inhibitors can be useful in treating diseases associate with T-cell mediated immune responses.

LAT1 transporter inhibitors can be useful in modulating T-cell activation, modulating T-cell differentiation, T-cell metabolism, and/or T-cell proliferation and in treating diseases associated with the T-cell response.

Compounds of Formula (1)-(3) can be administered in combination with one or more additional compounds effective in treating a disease or condition.

Compounds of Formula (1)-(3) can be administered in combination with another LAT1 transporter inhibitor.

Compounds of Formula (1)-(3) or pharmaceutically acceptable salts thereof may be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, topical, or topical ophthalmic. Pharmaceutical compositions provided by the present disclosure can be injectable formulations. Pharmaceutical compositions provided by the present disclosure can be injectable intravenous formulations.

Pharmaceutical compositions provided by the present disclosure may comprise a therapeutically effective amount of a compound of Formula (1)-(3) or a pharmaceutically acceptable salt thereof together with a suitable amount of one or more pharmaceutically acceptable vehicles so as to provide a composition for proper administration to a patient. Suitable pharmaceutical vehicles and methods of preparing pharmaceutical compositions are described in the art.

A compound of Formula (1)-(3) and/or pharmaceutical composition thereof can generally be used in an amount effective to achieve the intended purpose. For use to treat a disease such as an autoimmune disease, graft-versus-host disease, an inflammatory disease such as inflammatory bowel disease, or organ transplant rejection, dry eye disease, a compound of Formula (1)-(3) and/or pharmaceutical compositions thereof, may be administered in a therapeutically effective amount.

The amount of a compound of Formula (1)-(3) and/or pharmaceutical composition thereof that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of a compound of Formula (1)-(3) and/or pharmaceutical composition thereof administered will depend on, among other factors, the patient being treated, the weight of the patient, the severity of the affliction, the manner of administration and the judgment of a prescribing physician.

A compound of Formula (1)-(3) may be assayed in vitro and in vivo, for the desired therapeutic activity, prior to use in humans. For example, in vitro assays may be used to determine whether administration of a specific compound or a combination of compounds is preferred. The compounds may also be demonstrated to be effective and safe using animal model systems.

A therapeutically effective dose of a compound of Formula (1)-(3) and/or pharmaceutical composition thereof can provide therapeutic benefit without causing substantial toxicity. Toxicity of compounds of Formula (1)-(3) and/or pharmaceutical compositions thereof may be determined using standard pharmaceutical procedures and may be readily ascertained by the skilled artisan. The dose ratio between toxic and therapeutic effect is the therapeutic index. A compound of Formula (1)-(3) and/or pharmaceutical composition thereof can exhibit a particularly high therapeutic index in treating disease and disorders. A dose of a compound of Formula (1)-(3) and/or pharmaceutical composition thereof can be within a range of circulating concentrations that include an effective dose with minimal toxicity.

A compound of Formula (1)-(3), a pharmaceutically acceptable salt thereof, or a pharmaceutical composition of any of the foregoing may be included in a kit that may be used to administer the compound to a patient for therapeutic purposes. A kit may include a pharmaceutical composition comprising a compound of Formula (1)-(3) suitable for administration to a patient and instructions for administering the pharmaceutical composition to the patient. A kit for use in treating a disease in a patient can comprise a compound of Formula (1)-(3) or a pharmaceutically acceptable salt thereof, a pharmaceutically acceptable vehicle for administering the compound, and instructions for administering the compound to a patient.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Compounds of Formula (1)-(3) and pharmaceutical compositions thereof may be administered to a patient to treat an autoimmune disease.

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Bechet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan's syndrome, cold agglutinin disease, congenital heart block, Coxsackie myocarditis, CREST syndrome, Crohn's disease (CD), dermatitis herpetiformis, dermatomyositis, Devic's disease, discoid lupus, Dressler's syndrome, (chronic) dry eye disease (DED), endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, acute and chronic graft vs. host disease (GVHD), Graves' disease, Guillain-Barre syndrome, Hashimoto' thyroiditis, hemolytic anemia, Henoch-Schonlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, intestinal bowel disease, inflammatory bowel disease, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha-Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, organ transplant rejection, sperm and testicular autoimmunity, stiff person syndrome, subacute bacterial endocarditis, Susac syndrome, sympathetic ophthalmia, Takayasu's arteritis, temporal arteritis, thrombocytopenic purpura, Tolosa-Hunt syndrome, transverse myelitis, type 1 diabetes, ulcerative colitis (UC), undifferentiated connective tissue disease, uveitis, vasculitis, vitiligo, and Wegener's granulomatosis.

Compounds of Formula (1)-(3) and pharmaceutical compositions thereof may be administered to a patient to treat acute or chronic graft-versus-host disease.

Compounds of Formula (1)-(3) and pharmaceutical compositions thereof may be administered to a patient to treat organ transplant rejection.

Compounds of Formula (1)-(3) and pharmaceutical compositions thereof may be administered to a patient to treat an inflammatory disease.

Compounds of Formula (1)-(3) and pharmaceutical compositions thereof may be administered to a patient to treat (chronic) dry eye disease (DED).

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

Compounds of Formula (1)-(3) and pharmaceutical compositions thereof may be administered to a patient to treat an inflammatory disease such as inflammatory bowel disease. Inflammatory bowel disease includes disorders involving chronic inflammation of the digestive tract such as ulcerative colitis, Crohn's disease.

Compounds of Formula (1)-(3) and pharmaceutical compositions thereof may be administered to a patient to treat a disease associated with the activation, proliferation, metabolism, and/or differentiation of T-cells.

A dose of compound of Formula (1)-(3) and appropriate dosing intervals may be selected to maintain a sustained therapeutically effective concentration of the compound of Formula (1)-(3) in the blood of a patient, and without exceeding a minimum adverse concentration.

Pharmaceutical compositions can comprise a compound of Formula (1)-(3) may be administered once per day, twice per day, or at intervals of more than once per day. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of compound of Formula (1)-(3) contained within each of the multiple dosage forms may be the same or different.

Suitable daily dosage ranges for administration may range from about 2 μg to about 20 mg of a compound of Formula (1)-(3) per kilogram body weight.

Suitable daily dosage ranges for administration may range from about 1 μg to about 50 mg of a compound of Formula (1)-(3) per square meter ($m^2$) of body surface.

A compound of Formula (1)-(3) may be administered to treat an inflammatory disease, an autoimmune disease graft-vs-host disease, organ transplant rejection or (chronic) dry eye disease, in a patient in an amount from about 1 mg to about 2,000 mg per day, from about 100 μg to about 1,500 mg per day, from about 20 μg to about 1,000 mg per day, or in any other appropriate daily dose.

Pharmaceutical compositions can comprise a compound of Formula (1)-(3) may be administered to treat an inflammatory disease, an autoimmune disease, graft-vs-host disease, or organ transplant rejection in a patient so as to provide a therapeutically effective concentration of a compound of Formula (1)-(3) in the blood or plasma of the patient. A therapeutically effective concentration of a compound of Formula (1)-(3) in the blood or plasma of a patient can be, for example, from about 1 g/mL to about 60 g/mL, from about 2 g/mL to about 50 g/mL, from about 5 g/mL to about 40 g/mL, from about 5 g/mL to about 20 g/mL, or from about 5 g/mL to about 10 g/mL. A therapeutically effective concentration of a compound of Formula (1)-(3) in the blood or plasma of a patient can be, for example, at least about 2 g/mL, at least about 5 g/mL, at least about 10 g/mL, at least about 15 g/mL, at least about 25 g/mL, or at least about 30 g/mL. A therapeutically effective concentration of a compound of Formula (1)-(3) in the blood or plasma of a patient can be less than an amount that causes unacceptable adverse effects including adverse effects to homeostasis. A therapeutically effective concentration of a compound of Formula (1)-(3) in the blood or plasma of a patient can be an amount sufficient to restore and/or maintain homeostasis in the patient.

Pharmaceutical compositions comprising a compound of Formula (1)-(3) may be administered to treat an inflammatory disease, an autoimmune disease, graft-vs-host disease, or organ transplant rejection in a patient so as to provide a therapeutically effective concentration of a compound of Formula (1)-(3) in the blood or plasma of a patient for an extended period of time such as, for example, for at least about 4 hours, for at least about 6 hours, for at least about 8 hours, for at least about 10 hours, or for at least about 12 hours.

The amount of a compound of Formula (1)-(3) administered may vary during a treatment regimen.

Pharmaceutical compositions provided by the present disclosure may further comprise one or more pharmaceutically active compounds in addition to a compound of Formula (1)-(3). Such compounds may be provided to treat an autoimmune disease, graft-versus-host disease, an inflammatory disease such as inflammatory bowel disease, or organ transplant rejection being treated with the compound of Formula (1)-(3) or to treat a disease, disorder, or condition other than the an autoimmune disease, graft-versus-host disease, an inflammatory disease such as inflammatory bowel disease, or organ transplant rejection being treated with the compound of Formula (1)-(3).

A compound of Formula (1)-(3) may be used in combination with at least one other therapeutic agent. A compound of Formula (1)-(3) may be administered to a patient together with another compound for treating an autoimmune disease, graft-versus-host disease, an inflammatory disease such as inflammatory bowel disease, or organ transplant rejection in the patient. The at least one other therapeutic agent may be a different compound of Formula (1)-(3). A compound of Formula (1)-(3) and the at least one other therapeutic agent may act additively or synergistically. The at least one additional therapeutic agent may be included in the same pharmaceutical composition or vehicle comprising the compound of Formula (1)-(3) or may be in a separate pharmaceutical composition or vehicle. Accordingly, methods provided by the present disclosure further include, in addition to administering a compound of Formula (1)-(3), administering one or more therapeutic agents effective for treating an autoimmune disease, graft-versus-host disease, an inflammatory disease such as inflammatory bowel disease, or organ transplant rejection or a different disease, disorder or condition than an autoimmune disease, graft-versus-host disease, an inflammatory disease such as inflammatory bowel disease, or organ transplant rejection. Methods provided by the present disclosure include administration of a compound of Formula (1)-(3) and one or more other therapeutic agents provided that the combined administration does not inhibit the therapeutic efficacy of a compound of Formula (1)-(3) and/or does not produce adverse combination effects.

Pharmaceutical compositions comprising a compound of Formula (1)-(3) may be administered concurrently with the administration of another therapeutic agent, which may be part of the same pharmaceutical composition as, or in a different pharmaceutical composition than that comprising a compound of Formula (1)-(3). A compound of Formula (1)-(3) may be administered prior or subsequent to administration of another therapeutic agent. In combination therapy, the combination therapy may comprise alternating between administering a compound of Formula (1)-(3) and a composition comprising another therapeutic agent, e.g., to minimize adverse drug effects associated with a particular drug. When a compound of Formula (1)-(3) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising a compound of Formula (1)-(3) may be administered with one or more substances to enhance, modulate and/or control release, bioavailability, therapeutic efficacy, therapeutic potency, stability, and the like of a compound of Formula (1)-(3). For example, to enhance the therapeutic efficacy of a compound of Formula (1)-(3), a compound of Formula (1)-(3) or a pharmaceutical composition comprising a compound of Formula (1)-(3) may be co-administered with one or more active agents to increase the absorption or diffusion of the compound of Formula (1)-(3) from the gastrointestinal tract to the systemic circulation, or to inhibit degradation of the compound of Formula (1)-(3) in the blood of a patient. A pharmaceutical composition comprising a compound of Formula (1)-(3) may be co-administered with an active agent having pharmacological effects that enhance the therapeutic efficacy of the compound of Formula (1)-(3).

A compound of Formula (1)-(3) or a pharmaceutical composition comprising a compound of Formula (1)-(3) may be administered in conjunction with an agent known or believed to be effective in treating an autoimmune disease, graft-versus-host disease, an inflammatory disease such as inflammatory bowel disease, or organ transplant rejection in a patient.

Methods provided by the present disclosure have use in animals, including mammals, such as humans.

A compound of Formula (1)-(3) or pharmaceutical composition thereof can be administered with a compound effective in treating an autoimmune disease.

Examples of compounds useful for treating autoimmune diseases include non-steroidal anti-inflammatory drugs such as non-selective NSAIDs including salicylic acid derivatives such as acetylsalicylic acid diflunisal and sulfasalazine; para-aminophenol derivatives such as acetaminophen; fenamates such as mefenamic acid, meclofenamate, and flufenamic acid; propionic acid derivatives such as ibuprofen, naproxen, fenoprofen, detoprofen, purbiprofen, and oxaprozin; enolic acid derivatives such as piroxicam and tenoxicam; selective COX-2 inhibitors; and selective COX-1 inhibitors; glucocorticoids; conventional disease-modifying anti-rheumatic drugs such as methotrexate, leflunomide, hydroxychloroquine, and sulfasalazine; and anti-Tnf biologics such as infliximab, etanercept, adalimumab, golimumab, and certolizumab pegol.

Examples of compounds useful for treating autoimmune diseases also include corticosteroids such as prednisone, budesonide, and prednisolone; Janus kinase inhibitors such as tofacitinib; calineurin inhibitors such as cyclosporine and tacrolimus; mTOR inhibitors such as sirolimus and everolimus; IMDH inhibitors such as azathioprine, leflunomide, and mycophenolate; biologics such as abatacept, adalimumab, anakinra, certolizumab, etanercept, golimumab, infliximab, ixekizumab, natalizumab, rituximab, secukinumab, tocilizumab ustekinumab, and vedolizumab; and m Monoclonal antibodies such as basiliximab and daclizumab.

A compound of Formula (1)-(3) or pharmaceutical composition thereof can be administered with a compound effective in treating acute or chronic graft-versus-host disease (GVHD).

Examples of suitable compounds for treating GVHD include glucocorticoids such as prednisone, calcineurin inhibitors such as cyclosporine and tacrolimus, mTOR inhibitors such as sirolimus and everolimus, tyrosine kinase inhibitors, pentostatin, etanercept, alemtuzumab, ibrutinib, alemtuzumab, etanercept, methotrexate, posaconazole, rituximab, infliximab, thalidomide, mycophenolate mofetil, pentostatin, and combinations of any of the foregoing.

Other examples of suitable compounds for treating GVHD include kinase inhibitors such as Janus kinase inhibitors, proteasome inhibitors such as bortezomib, cytokine modulators such as alpha-1 antitrypsin and interleukin-22, monoclonal antibodies such as natalizumab, vedolizumab, brentuximab, and vendotin, adaptive cell therapy using mesenchymal stromal cells, microbiome restoration, and combinations of any of the foregoing.

Examples of compounds useful for treating chronic GVHD include Janus kinase inhibitors such as ruxolitnib, ibrutinib, spleen tyrosine kinase inhibitor, and Rho kinase inhibitors; immune checkpoint blockade modulators such as cytotoxic T-lymphocyte associated protein-4; cytokine modulator such as interleukin-2; proteasome inhibitors such as bortezomib, carfilzomib, and ixazomib; anti-CD20 monoclonal antibodies such as ofatumumab and obinutzumab, adoptive cell therapy such as involving regulatory T cells and mesenchymal stromal cells; and combinations of any of the foregoing.

A compound of Formula (1)-(3) or pharmaceutical composition thereof can be administered with a compound effective in treating organ transplant rejection including solid organ transplant rejection.

Examples of compounds useful in treating organ transplant rejection include calcineurin inhibitors such as tacrolimus and cyclosporine; antiproliferation agents such as mycophenolate mofetil and azathioprine; mTOR inhibitors such as sirolimus; and steroids such as prednisone.

Other compounds useful in treating organ transplant rejection include belatacept, difetelio, everolimus, basiliximab, daclizumab, and muromonab-CD3.

A compound of Formula (1)-(3) or pharmaceutical composition thereof can be administered with a compound effective in treating an inflammatory bowel disease such as Crohn's disease and ulcerative colitis.

Examples of compounds useful in treating in treating inflammatory bowel disease include 5-aminosalicylates (5-ASA) such as mesalamine and sulfasalazine, antibiotics such as metronidazole and ciprofloxacin, corticosteroids such as hydrocortisone and prednisone, immunomodulators such as azathioprine, cyclosporine, and methotrexate, anti-TNF antibodies such as adalimumab, certolizumab, and infliximab, and anti-Integrin antibodies such as natalizumab.

A compound of Formula (1)-(3) or pharmaceutical composition thereof can be administered with a compound effective in treating (chronic) dry eye disease (DED).

Examples of compounds useful in treating in (chronic) dry eye disease (DED) include immunosuppressive agents (steroids) and immunomodulators (cyclosporine and lifitegrast).

A compound of Formula (1)-(3) can be used to inhibit the LAT1 transporter in cells expressing the LAT1 transporter in vivo and ex vivo. For example, methods provided by the present disclosure include contact cells expressing the LAT1 transporter with a compound of Formula (1)-(3) to inhibit the LAT1 transporter. The methods can be used, for example, to screen compounds for LAT1 transport activity.

ASPECTS OF THE INVENTION

The invention is further defined by one or more of the following aspects.

Aspect 1. A compound having the structure of Formula (1):

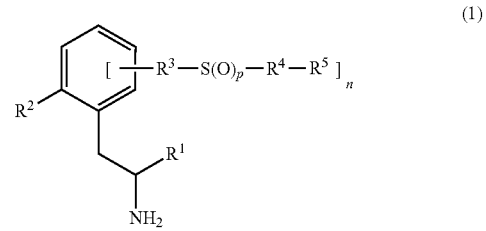

or a pharmaceutically acceptable salt thereof, wherein,
$R^1$ is selected from —COOH, —COOR$^a$, —COR$^a$, and —CON(R$^b$)$_2$, wherein,
  $R^a$ is selected from $C_{1-4}$ alkyl; and
  each R$^b$ is independently selected from hydrogen, —OH, $C_{1-4}$ alkyl, and $C_{1-4}$ alkoxy;
$R^2$ is selected from hydrogen, halogen, $C_{1-6}$ alkyl, and $C_{1-6}$ alkoxy;
n is selected from 1 and 2;
$R^3$ and $R^4$ are independently selected from a single bond ("—"), —NR$^c$—, C(R$^c$)$_2$, —O—NR$^c$—, —NR$^c$—O—, —NR$^c$—C(R$^c$)$_2$—, —C(R$^c$)$_2$—NR$^c$—, —C(R$^c$)$_2$—O—NR$^c$—, and —NR$^c$—O—C(R$^c$)$_2$—, wherein each R$^c$ is independently selected from hydrogen, $C_{1-3}$ alkyl, and —S(O)$_p$—R$^4$—R$^5$;
p is selected from 0, 1, and 2; and
each R$^5$ is independently selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl.

Aspect 2. A compound having the structure of Formula (2):

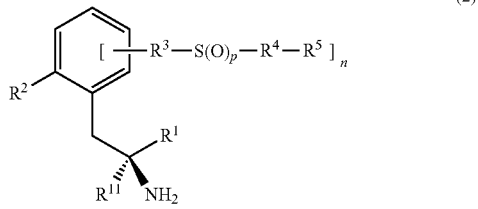

or a pharmaceutically acceptable salt thereof, wherein,
$R^1$ is selected from —COOH, —COOR$^a$, —COR$^a$, and —CON(R$^b$)$_2$, wherein,
  $R^a$ is selected from $C_{1-4}$ alkyl; and
  each R$^b$ is independently selected from hydrogen, —OH, $C_{1-4}$ alkyl, and $C_{1-4}$ alkoxy;
$R^2$ is selected from hydrogen, halogen, $C_{1-6}$ alkyl, $C_{3-6}$ cycloalkyl, phenyl, and —R$^3$—S(O)$_p$—R$^4$—R$^5$;
n is selected from 0, 1, and 2;
$R^3$ and $R^4$ are independently selected from a single bond ("—"), —NR$^c$—, —C(R$^c$)$_2$—, —O—NR$^c$—, —NR$^c$—O—, —NR$^c$—C(R$^c$)$_2$—, —C(R$^c$)$_2$—NR$^c$—, —C(R$^c$)$_2$—O—NR$^c$—, and —NR$^c$—O—C(R$^c$)$_2$—, wherein each R$^c$ is independently selected from hydrogen, $C_{1-3}$ alkyl, and —S(O)$_p$—R$^4$—R$^5$;
each p is independently selected from 0, 1, and 2;
each R$^5$ is independently selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl; and
$R^{11}$ is selected from hydrogen and methyl.

Aspect 3. The compound of aspect 2, wherein $R^{11}$ is hydrogen.

Aspect 4. The compound of aspect 2, wherein $R^{11}$ is methyl.

Aspect 5. The compound of any one of aspects 1 to 4, wherein each of the one or more substituent groups is independently selected from halogen, $C_{1-6}$ alkyl, $C_{1-6}$ alkoxy, —NH$_2$, —NR$_2$, —NO$_2$, —NH—C(O)—R, —NR—SO$_2$—R, =O, —C(O)—OR, and —CF$_3$, wherein each R is independently selected from hydrogen and $C_{1-3}$ alkyl.

Aspect 6. The compound of any one of aspects 1 to 4, wherein each of the one or more substituent groups is independently selected from halogen, $C_{1-6}$ alkyl, $C_{1-6}$ alkoxy, —NH$_2$, and —N(—CH$_3$)$_2$, wherein each R is independently selected from hydrogen and $C_{1-3}$ alkyl.

Aspect 7. The compound of any one of aspects 1 to 4, wherein each substituent is independently selected from $C_{1-3}$ alkyl, —N(—CH$_3$)$_2$, Cl, Br, and benzyl.

Aspect 8. The compound of any one of aspects 1 to 7, wherein $R^1$ is —COOH.

Aspect 9. The compound of any one of aspects 1 to 7, wherein $R^1$ is —COOR$^a$.

Aspect 10. The compound of aspect 9, wherein $R^a$ is $C_{1-4}$ alkyl.

Aspect 11. The compound of any one of aspects 1 to 7, wherein $R^1$ is —COR$^a$.

Aspect 12. The compound of aspect 11, wherein $R^a$ is $C_{1-4}$ alkyl.

Aspect 13. The compound of any one of aspects 1 to 12, wherein $R^2$ is hydrogen.

Aspect 14. The compound of any one of aspects 1 to 12, wherein $R^2$ is halogen.

Aspect 15. The compound of any one of aspects 1 to 12, wherein $R^2$ is $C_{1-6}$ alkyl.

Aspect 16. The compound of any one of aspects 1 to 12, wherein $R^2$ is $C_{1-3}$ alkyl.

Aspect 17. The compound of any one of aspects 1 to 12, wherein $R^2$ is methyl.

Aspect 18. The compound of any one of aspects 1 to 12, wherein $R^2$ is $C_{1-6}$ alkoxy.

Aspect 19. The compound of any one of aspects 1 to 12, wherein $R^2$ is $C_{1-3}$ alkoxy.

Aspect 20. The compound of any one of aspects 1 to 12, wherein $R^2$ is methoxy.

Aspect 21. The compound of any one of aspects 2 to 12, wherein $R^2$ is $C_{3-6}$ cycloalkyl.

Aspect 22. The compound of any one of aspects 2 to 12, wherein $R^2$ is cyclopentyl.

Aspect 23. The compound of any one of aspects 2 to 12, wherein $R^2$ is cyclohexyl.

Aspect 24. The compound of any one of aspects 2 to 12, wherein $R^2$ is phenyl.

Aspect 25. The compound of any one of aspects 2 to 12, wherein $R^2$ is —R$^3$—S(O)$_p$—R$^4$—R$^5$.

Aspect 26. The compound of any one of aspects 2 to 25, wherein n is 0.

Aspect 27. The compound of any one of aspects 2 to 25, wherein n is 0 and $R^2$ is —R$^3$—S(O)P—R$^4$—R$^5$.

Aspect 28. The compound of any one of aspects 1 to 25, wherein n is 1.

Aspect 29. The compound of any one of aspects 1 to 25, wherein n is 2.

Aspect 30. The compound of aspect 29, wherein n is 1 and the —R$^3$—S(O)$_p$—R$^4$—R$^5$ moiety is bonded to the 3-position of the phenyl ring relative to the ethyl-2-amine moiety in ring position 1.

Aspect 31. The compound of aspect 29, wherein n is 1 and the —R$^3$—S(O)$_p$—R$^4$—R$^5$ moiety is bonded to the 4-position of the phenyl ring relative to the ethyl-2-amine moiety in ring position 1.

Aspect 32. The compound of aspect 29, wherein n is 1 and the —R$^3$—S(O)$_p$—R$^4$—R$^5$ moiety is bonded to the 5-position of the phenyl ring relative to the ethyl-2-amine moiety in ring position 1.

Aspect 33. The compound of aspect 29, wherein n is 1 and the —$R^3$—$S(O)_p$—$R^4$—$R^5$ moiety is bonded to the 6-position of the phenyl ring relative to the ethyl-2-amine moiety in ring position 1.

Aspect 34. The compound of any one of aspects 1 to 25, wherein n is 2.

Aspect 35. The compound of aspect 34, wherein n is 2 and the —$R^3$—$S(O)_p$—$R^4$—$R^5$ moiety is bonded to the 3- and 4-positions of the phenyl ring relative to the ethyl-2-amine moiety in ring position 1.

Aspect 36. The compound of aspect 34, wherein n is 2 and the —$R^3$—$S(O)_p$—$R^4$—$R^5$ moiety is bonded to the 3- and 5-positions of the phenyl ring relative to the ethyl-2-amine moiety in ring position 1.

Aspect 37. The compound of aspect 34, wherein n is 2 and the —$R^3$—$S(O)_p$—$R^4$—$R^5$ moiety is bonded to the 3- and 6-positions of the phenyl ring relative to the ethyl-2-amine moiety in ring position 1.

Aspect 38. The compound of aspect 34, wherein n is 2 and the —$R^3$—$S(O)_p$—$R^4$—$R^5$ moiety is bonded to the 4- and 5-positions of the phenyl ring relative to the ethyl-2-amine moiety in ring position 1.

Aspect 39. The compound of aspect 34, wherein n is 2 and the —$R^3$—$S(O)_p$—$R^4$—$R^5$ moiety is bonded to the 4- and 6-positions of the phenyl ring relative to the ethyl-2-amine moiety in ring position 1.

Aspect 40. The compound of aspect 34, wherein n is 2 and the —$R^3$—$S(O)_p$—$R^4$—$R^5$ moiety is bonded to the 5- and 6-positions of the phenyl ring relative to the ethyl-2-amine moiety in ring position 1.

Aspect 41. The compound of any one of aspects 1 to 40, wherein $R^3$ is a single bond and $R^4$ is —$NR^c$—.

Aspect 42. The compound of any one of aspects 1 to 40, wherein $R^3$ is —$NR^c$— and $R^4$ is a single bond.

Aspect 43. The compound of any one of aspects 1 to 40, wherein $R^3$ is a single bond and $R^4$ is —$C(R^c)_2$—.

Aspect 44. The compound of any one of aspects 1 to 40, wherein $R^3$ is —$C(R^c)_2$— and $R^4$ is a single bond.

Aspect 45. The compound of any one of aspects 1 to 40, wherein $R^3$ is —$NR^c$— and $R^4$ is —$C(R^c)_2$—.

Aspect 46. The compound of any one of aspects 1 to 40, wherein $R^3$ is —$C(R^c)_2$— and $R^4$ is —$NR^c$—.

Aspect 47. The compound of any one of aspects 1 to 40, wherein each of $R^3$ and $R^4$ is —$C(R^c)_2$—.

Aspect 48. The compound of any one of aspects 1 to 40, wherein each of $R^3$ and $R^4$ is —$NR^c$—.

Aspect 49. The compound of any one of aspects 41 to 48, wherein each $R^c$ is hydrogen.

Aspect 50. The compound of any one of aspects 41 to 48, wherein each $R^c$ is independently selected from hydrogen and $C_{1-3}$ alkyl.

Aspect 51. The compound of any one of aspects 41 to 48, wherein each $R^c$ is independently selected from hydrogen and methyl.

Aspect 52. The compound of any one of aspects 1 to 40, wherein each of $R^3$ and $R^4$ is a single bond.

Aspect 53. The compound of any one of aspects 1 to 40, wherein $R^3$ is a single bond and $R^4$ is —NH—.

Aspect 54. The compound of any one of aspects 1 to 40, wherein $R^3$ is —NH— and $R^4$ is a single bond.

Aspect 55. The compound of any one of aspects 1 to 54, wherein p is 0.

Aspect 56. The compound of any one of aspects 1 to 54, wherein p is 1.

Aspect 57. The compound of any one of aspects 1 to 54, wherein p is 2.

Aspect 58. The compound of any one of aspects 1 to 57, wherein each $R^5$ is hydrogen.

Aspect 59. The compound of any one of aspects 1 to 57, wherein each $R^5$ is $C_{1-6}$ alkyl.

Aspect 60. The compound of any one of aspects 1 to 57, wherein each $R^5$ is independently selected from $C_{6-12}$ aryl and substituted $C_{6-12}$ aryl.

Aspect 61. The compound of any one of aspects 1 to 57, wherein each $R^5$ is independently selected from $C_{5-12}$ heteroaryl and substituted $C_{5-12}$ heteroaryl.

Aspect 62. The compound of any one of aspects 1 to 57, wherein each $R^5$ is independently selected from $C_{3-12}$ cycloalkyl and substituted $C_{3-12}$ cycloalkyl.

Aspect 63. The compound of any one of aspects 1 to 57, wherein each $R^5$ is independently selected from $C_{3-12}$ heterocycloalkyl and substituted $C_{3-12}$ heterocycloalkyl.

Aspect 64. The compound of any one of aspects 1 to 57, wherein each $R^5$ is independently selected from phenyl and substituted phenyl.

Aspect 65. The compound of any one of aspects 1 to 57, wherein each $R^5$ is independently selected from naphthyl and substituted naphthyl.

Aspect 66. The compound of any one of aspects 1 to 57, wherein each $R^5$ is independently selected from biphenyl and substituted biphenyl.

Aspect 67. The compound of aspect 1, wherein n is 1, p is 2, the moiety —$R^3$—$S(O)_p$—$R^4$—$R^5$ is bonded to the 5-position of the phenyl ring relative to the ethyl-2-amine moiety in ring position 1, $R^3$ is a single bond, and $R^4$ is —NH—.

Aspect 68. The compound of any one of aspects 1 to 25, wherein n is 1, p is 2, the moiety —$R^3$—$S(O)_p$—$R^4$—$R^5$ is bonded to the 5-position of the phenyl ring relative to the ethyl-2-amine moiety in ring position 1, $R^3$ is —NH— and $R^4$ is a single bond.

Aspect 69. The compound of aspect 1, wherein,
$R^1$ is —COOH;
$R^2$ is $C_{1-3}$ alkyl;
n is 1;
the moiety —$R^3$—$S(O)_p$—$R^4$— is bonded to the 5-position of the phenyl ring relative to the ethyl-2-amine moiety in ring position 1, and is —$SO_2$—NH—; and
$R^5$ is selected from phenyl, substituted phenyl, naphthyl, substituted naphthyl, biphenyl and substituted biphenyl;
wherein each of the one or more substituent groups is independently selected from halogen, $C_{1-4}$ alkyl, $C_{1-4}$ alkoxy, and —$NR_2$, wherein each R is independently selected from hydrogen and $C_{1-4}$ alkyl.

Aspect 70. The compound of any one of aspects 1 to 25, wherein,
$R^1$ is —COOH;
$R^2$ is $C_{1-3}$ alkyl;
n is 1;
the moiety-$R^3$—$S(O)_p$—$R^4$— is bonded to the 5-position of the phenyl ring relative to the ethyl-2-amine moiety in ring position 1, and is —NH—$SO_2$—; and
$R^5$ is selected from phenyl, substituted phenyl, naphthyl, substituted naphthyl, biphenyl and substituted biphenyl;
wherein each of the one or more substituent groups is independently selected from halogen, $C_{1-4}$ alkyl, $C_{1-4}$ alkoxy, and —$NR_2$, wherein each R is independently selected from hydrogen and $C_{1-3}$ alkyl.

Aspect 71. The compound of any one of aspects 1 to 70, wherein the stereogenic center of the carbon atom bonded to the amine group is in the (S) configuration.

Aspect 72. The compound of any one of aspects 1 to 70, wherein the stereogenic center of the carbon atom bonded to the amine group is in the (R) configuration.

Aspect 73. A compound of aspect 1, wherein the compound is selected from:

(S)-2-amino-3-(2-(methylsulfonamido)phenyl]propanoic acid (1);
(S)-2-amino-3-(5-((5-(dimethylamino)naphthalene)-1-sulfonamido)-2-methylphenyl)propanoic acid (2);
(S)-2-amino-3-(3-((5-(dimethylamino)naphthalene)-1-sulfonamido)phenyl)propanoic acid (3);
(S)-2-amino-3-(4-((5-(dimethylamino)naphthalene)-1-sulfonamido)phenyl)propanoic acid (4);
(S)-2-amino-3-(5-((5-(dimethylamino)naphthalene)-1-sulfonamido)-2-methoxyphenyl)propanoic acid (5);
(S)-2-amino-3-(2-methyl-5-(naphthalene-1-sulfonamido)phenyl)propanoic acid (6);
(S)-2-amino-3-(2-methyl-5-((4-methylphenyl)sulfonamido)phenyl)propanoic acid (7);
(S)-2-amino-3-(4-((5-(dimethylamino)naphthalene)-1-sulfonamido)-2-methoxyphenyl)propanoic acid (8);
(S)-2-amino-3-(2-methyl-5-(quinoline-5-sulfonamido)phenyl)propanoic acid (9);
(S)-2-amino-3-(2-methyl-5-(phenylsulfonamido)phenyl)propanoic acid (10);
(S)-2-amino-3-(2-methyl-5-(pyridine-3-sulfonamido)phenyl)propanoic acid (11);
(S)-2-amino-3-(2-methyl-5-((tetrahydro-2H-pyran)-4-sulfonamido)phenyl)propanoic acid (12);
(S)-3-(5-((4-acetamidonaphthalene)-1-sulfonamido)-2-methylphenyl)-2-aminopropanoic acid (13);
(S)-2-amino-3-(5-(cyclopropanesulfonamido)-2-methylphenyl)propanoic acid (14);
(S)-2-amino-3-(2-chloro-5-((5-(dimethylamino)naphthalene)-1-sulfonamido)phenyl)propanoic acid (15);
(S)-2-amino-3-(5-((5-(dimethylamino)-N-methylnaphthalene)-1-sulfonamido)-2-methylphenyl)propanoic acid (16);
(S)-3-(5-([1,1'-biphenyl]-4-sulfonamido)-2-methylphenyl)-2-aminopropanoic acid (17);
(S)-2-amino-3-(5-((1,2-dimethyl-1H-imidazole)-4-sulfonamido)-2-methylphenyl)propanoic acid (18);
(S)-2-amino-3-(2-((5-(dimethylamino)naphthalene)-1-sulfonamido)phenyl)propanoic acid (19);
(S)-2-amino-3-(2-methyl-5-((1-methylethyl)sulfonamido)phenyl)propanoic acid (20);
(S)-2-amino-3-(5-((5-(dimethylamino)naphthalene)-1-sulfonamido)-2-isopropylphenyl)propanoic acid (21);
(S)-2-amino-3-(5-((((1R,4R)-7,7-dimethyl-2-oxobicyclo[2.2.1]heptan-1-yl)methyl)sulfonamido)-2-methylphenyl)propanoic acid (22);
(S)-2-amino-3-(2-methyl-5-((phenylmethyl)sulfonamido)phenyl)propanoic acid (23);
(S)-2-amino-3-(5-((7-chlorobenzo[c][1,2,5]oxadiazole)-4-sulfonamido)-2-methylphenyl)propanoic acid (24);
(S)-2-amino-3-(5-(benzo[c][1,2,5]oxadiazole-4-sulfonamido)-2-methylphenyl)propanoic acid (25);
(S)-2-amino-3-(5-(cyclohexanesulfonamido)-2-methylphenyl)propanoic acid (26);
(S)-2-amino-3-(5-(benzo[b]thiophene-3-sulfonamido)-2-methylphenyl)propanoic acid (27);
(S)-2-amino-3-(5-((3-aminophenyl)sulfonamido)-2-methylphenyl)propanoic acid (28);
(S)-2-amino-3-(5-((3-bromophenyl)sulfonamido)-2-methylphenyl)propanoic acid (29);
(S)-2-amino-3-(5-(N-benzylsulfamoyl)-2-methylphenyl)propanoic acid (30);
(S)-3-(5-(1H-imidazole-4-sulfonamido)-2-methylphenyl)-2-aminopropanoic acid (31);
(S)-2-amino-3-(2-methyl-5-((3-((4-methylphenyl)sulfonamido)phenyl)sulfonamido)phenyl)propanoic acid (32);
(S)-2-amino-3-(2-methyl-5-((4-((4-methylphenyl)sulfonamido)phenyl)sulfonamido)phenyl)propanoic acid (33);
(R)-2-amino-3-(5-((5-(dimethylamino)naphthalene)-1-sulfonamido)-2-isopropylphenyl)propanoic acid (34);
(S)-2-amino-3-(2-methyl-5-(N-phenylsulfamoyl)phenyl)propanoic acid hydrochloride (35);
(S)-2-amino-3-(5-((2,6-dichloro-4-(trifluoromethyl)phenyl)sulfonamido)-2-methylphenyl)propanoic acid (36);
(S)-2-amino-3-(3-(phenylsulfonamido)phenyl)propanoic acid (37);
(S)-3-(5-([1,1'-biphenyl]-3-sulfonamido)-2-methylphenyl)-2-aminopropanoic acid (38);
(S)-2-amino-3-(2-methyl-5-(N-(naphthalen-1-yl)sulfamoyl)phenyl)propanoic acid (39);
(S)-3-(5-(N-([1,1'-biphenyl]-4-yl)sulfamoyl)-2-methylphenyl)-2-aminopropanoic acid (40);
(S)-2-amino-3-(5-(N-butylsulfamoyl)-2-methylphenyl)propanoic acid (41);
(S)-2-amino-3-(5-((2,6-dichlorophenyl)sulfonamido)-2-methylphenyl)propanoic acid (42);
(S)-2-amino-3-(5-((3,5-dichlorophenyl)sulfonamido)-2-methylphenyl)propanoic acid (43);
(S)-2-amino-3-(5-(N-(4-methoxyphenyl)sulfamoyl)-2-methylphenyl)propanoic acid (44); ((3-((S)-2-amino-2-carboxyethyl)-4-methylphenyl)sulfonyl)-D-proline (45);
(S)-2-amino-3-(5-(N-isobutylsulfamoyl)-2-methylphenyl)propanoic acid (46);
(S)-2-amino-3-(3,5-dichloro-4-(phenylsulfonamido)phenyl)propanoic acid (47);
(S)-2-amino-3-(2-methyl-5-((4-methyl-N-tosylphenyl)sulfonamido)phenyl)propanoic acid (48);
(S)-2-amino-3-(5-(N-(5-(dimethylamino)naphthalen-1-yl)sulfamoyl)-2-methylphenyl)propanoic acid (49);
(S)-2-amino-3-(2-methyl-5-(N-(quinolin-5-yl)sulfamoyl)phenyl)propanoic acid (50);
(R)-2-amino-3-(5-(N-(4-chlorophenyl)sulfamoyl)-2-methylphenyl)propanoic acid (51);
(S)-2-amino-3-(5-(N-(4-chlorophenyl)sulfamoyl)-2-methylphenyl)propanoic acid (52);
(S)-2-amino-3-(5-(N-cyclohexylsulfamoyl)-2-methylphenyl)propanoic acid (53);
(S)-2-amino-3-(2-methyl-5-(((phenylmethyl)sulfonamido)methyl)phenyl)propanoic acid (54);
(S)-2-amino-3-(5-((benzylthio)methyl)-2-methylphenyl)propanoic acid (55);
(S)-2-amino-3-(5-((benzylsulfonyl)methyl)-2-methylphenyl)propanoic acid (56);
(S)-2-amino-3-(5-((4-methoxyphenyl)sulfonamido)-2-methylphenyl)propanoic acid (57);
(S)-2-amino-3-(5-(butylsulfonamido)-2-methylphenyl)propanoic acid (58);
(S)-2-amino-3-(5-(benzylthio)-2-methylphenyl)propanoic acid (59);
(2S)-2-amino-3-(5-((benzylsulfinyl)methyl)-2-methylphenyl)propanoic acid (60);
(S)-2-amino-3-(3,5-di(methylsulfonamido)phenyl)propanoic acid (61);
(S)-2-amino-3-(3,5-bis(phenylsulfonamido)phenyl)propanoic acid (62);
(S)-2-amino-3-(3,5-bis((4-methylphenyl)sulfonamido)phenyl)propanoic acid (63);
(2S)-2-amino-3-(5-(benzylsulfinyl)-2-methylphenyl)propanoic acid (64);

(S)-2-amino-3-(5-(benzylsulfonyl)-2-methylphenyl)propanoic acid (65);
(S)-2-amino-3-(2-methyl-5-(methylsulfonamido)phenyl)propanoic acid (67);
(S)-2-amino-3-(3-(methylsulfonamido)phenyl)propanoic acid (68);
(S)-2-amino-3-(2-methyl-5-(phenylsulfonamidomethyl)phenyl)propanoic acid (69);
(S)-2-amino-3-(4-(methylsulfonamido)phenyl)propanoic acid (70);
(S)-2-amino-3-(3-sulfamoylphenyl)propanoic acid (71);
(S)-2-amino-3-(3-(N-methylsulfamoyl)phenyl)propanoic acid (72);
(S)-2-amino-3-(3-(N,N-dimethylsulfamoyl)phenyl)propanoic acid (73);
(S)-2-amino-3-(4-sulfamoylphenyl)propanoic acid (74);
(S)-2-amino-3-(5-(N-(2-bromophenyl)sulfamoyl)-2-methylphenyl)propanoic acid (75);
(S)-2-amino-3-(5-(N-(3-bromophenyl)sulfamoyl)-2-methylphenyl)propanoic acid (76);
(S)-2-amino-3-(5-(N-(4-bromophenyl)sulfamoyl)-2-methylphenyl)propanoic acid (77);
(S)-2-amino-3-(3-(piperidin-1-ylsulfonyl)phenyl)propanoic acid (78);
(S)-2-amino-3-(3-(N-(4-chlorophenyl)sulfamoyl)phenyl)propanoic acid (79);
(S)-2-amino-3-(4-(N-(4-fluorophenyl)sulfamoyl)phenyl)propanoic acid (80);
(S)-2-amino-3-(2-(N-(4-chlorophenyl)sulfamoyl)phenyl)propanoic acid (81);
tert-butyl (S)-2-amino-3-(5-(N-(4-chlorophenyl)sulfamoyl)-2-methylphenyl)propanoate (82);
(S)-2-amino-3-(5-(N-(3,4-dichlorophenyl)sulfamoyl)-2-methylphenyl)propanoic acid (83);
(S)-2-amino-3-(5-(N-(4-chlorophenyl)-N-methylsulfamoyl)-2-methylphenyl)propanoic acid (84);
(S)-2-amino-3-(4-(N-(4-chlorophenyl)sulfamoyl)-2-methylphenyl)propanoic acid (85);
(S)-2-amino-3-(5-(N-(4-chlorophenyl)sulfamoyl)-2-isopropylphenyl)propanoic acid (86); and
(S)-2-amino-3-(5-((4-(tert-butyl)phenyl)sulfonamido)-2-methylphenyl)propanoic acid (87),
or a pharmaceutically acceptable salt of any of the foregoing.

Aspect 74. A compound of aspect 1, wherein the compound is selected from:
(S)-2-amino-3-(5-((4-chlorophenyl)sulfonamido)-2-methylphenyl)propanoic acid (88);
(S)-2-amino-3-(5-(N-(4-chlorophenyl)sulfamoyl)-2-methylphenyl)propanoic acid (89);
(S)-2-amino-3-(5-(N-(4-chlorophenyl)sulfamoyl)-2-methylphenyl)-N-methylpropanamide (90);
(S)-2-amino-3-(5-(N-(4-chlorophenyl)sulfamoyl)-2-methylphenyl)-N,N-dimethylpropanamide (91);
(S)-2-amino-3-(5-(N-(4-chlorophenyl)sulfamoyl)-2-methylphenyl)-N-isopropylpropanamide (92);
(S)-2-amino-3-(5-(N-(4-chlorophenyl)sulfamoyl)-2-methylphenyl)-N-hydroxypropanamide (93);
(S)-2-amino-3-(5-(N-(4-chlorophenyl)sulfamoyl)-2-methylphenyl)-N-methoxy-N-methylpropanamide (94);
(S)-3-(2-amino-4-methyl-3-oxopentyl)-N-(4-chlorophenyl)-4-methylbenzenesulfonamide (95);
(2S)-2-amino-3-(2-methyl-5-((p-tolylsulfinyl)amino)phenyl)propanoic acid (96);
(2S)-2-amino-3-(5-(((4-chlorophenyl)amino)sulfinyl)-2-methylphenyl)propanoic acid (97);
(S)-2-amino-3-(5-(((4-chlorophenyl)sulfonamido)oxy)-2-methylphenyl)propanoic acid (98);
(S)-2-amino-3-(5-((N-(4-chlorophenyl)sulfamoyl)amino)-2-methylphenyl)propanoic acid (99); methyl (S)-2-amino-3-(5-(N-(4-chlorophenyl)sulfamoyl)-2-methylphenyl)propanoate (100); and ethyl (S)-2-amino-3-(5-(N-(4-chlorophenyl)sulfamoyl)-2-methylphenyl)propanoate (101);
or a pharmaceutically acceptable salt of any of the foregoing.

Aspect 75. A compound of aspect 2, wherein the compound has the structure of Formula (1a), Formula (1b), or Formula (1c):

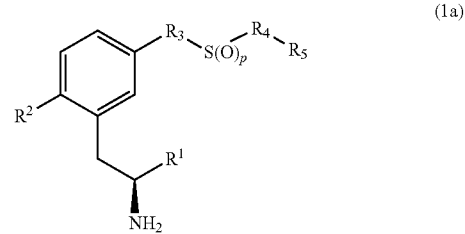

(1a)

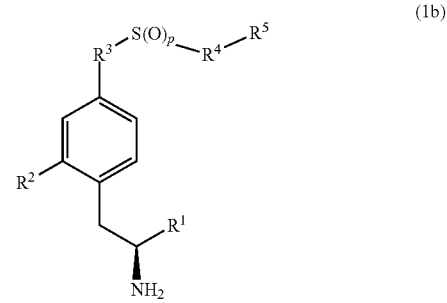

(1b)

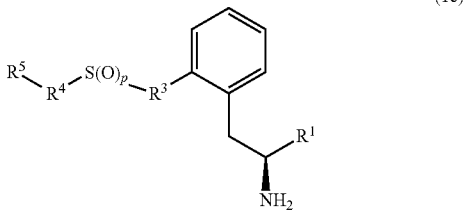

(1c)

or a pharmaceutically acceptable salt thereof, wherein,
p is selected from 0, 1, and 2;
$R^1$ is selected from —COOH, —COOR$^a$, —COR$^a$, and —CON(R$^b$)$_2$, wherein,
  $R^a$ is selected from $C_{1-4}$ alkyl; and
  each $R^b$ is independently selected from hydrogen, —OH, $C_{1-4}$ alkyl, and $C_{1-4}$ alkoxy;
$R^2$ is selected from hydrogen, halogen, $C_{1-6}$ alkyl, $C_{1-6}$ alkoxy, $C_{3-6}$ cycloalkyl, and phenyl;
each of $R^3$ and $R^4$ is independently selected from a single bond ("—"), —NR$^c$—, C(R$^c$)$_2$, —O—NR$^c$—, —NR$^c$—O—, —NR$^c$—C(R$^c$)$_2$—, —C(R$^c$)$_2$—NR$^c$—, —C(R$^c$)$_2$—O—NR$^c$—, and —NR$^c$—O—C(R$^c$)$_2$—, wherein each R$^c$ is independently selected from hydrogen, $C_{1-3}$ alkyl, and —S(O)$_p$—R$^4$—R$^5$; and
$R^5$ is selected from hydrogen, $C_{1-6}$ alkyl, $C_{6-12}$ aryl, substituted $C_{6-12}$ aryl, $C_{5-12}$ heteroaryl, substituted $C_{5-12}$ heteroaryl, $C_{3-12}$ cycloalkyl, substituted $C_{3-12}$ cycloalkyl, $C_{3-12}$ heterocycloalkyl, and substituted $C_{3-12}$ heterocycloalkyl.

Aspect 76. The compound of aspect 75, wherein the compound has the structure of Formula (1a).

Aspect 77. The compound of aspect 75, wherein the compound has the structure of Formula (1b).

Aspect 78. The compound of aspect 75, wherein the compound has the structure of Formula (1c).

Aspect 79. The compound of any one of aspects 75 to 78, wherein each of the one or more substituent groups is independently selected from halogen, $C_{1-6}$ alkyl, $C_{1-6}$ alkoxy, —$NH_2$, —$NR_2$, —$NO_2$, —NH—C(O)—R, —NR—$SO_2$—R, =O, —C(O)—OR, and —$CF_3$, wherein each R is independently selected from hydrogen and $C_{1-3}$ alkyl.

Aspect 80. The compound of any one of aspects 75 to 78, wherein each of the one or more substituent groups is independently selected from Cl, Br, $C_{1-3}$ alkyl, —N(—$CH_3$)$_2$, and benzyl.

Aspect 81. The compound of any one of aspects 75 to 80, wherein $R^1$ is —COOH.

Aspect 82. The compound of any one of aspects 75 to 80, wherein $R^1$ is —COO$R^a$, wherein $R^a$ is selected from $C_{1-4}$ alkyl.

Aspect 83. The compound of any one of aspects 75 to 80, wherein $R^1$ is —CO$R^a$, wherein $R^a$ is selected from $C_{1-4}$ alkyl.

Aspect 84. The compound of any one of aspects 75 to 80, wherein $R^1$ is —CON($R^b$)$_2$, wherein each $R^b$ is independently selected from hydrogen, —OH, $C_{1-4}$ alkyl, and $C_{1-4}$ alkoxy.

Aspect 85. A compound of aspect 2 wherein the compound has the structure of Formula (1d), Formula (1e), or Formula (1f):

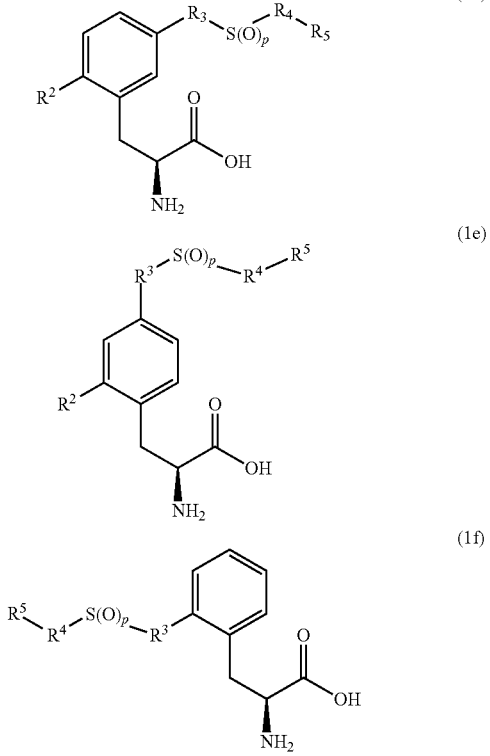

or a pharmaceutically acceptable salt thereof, wherein, p is selected from 0, 1, and 2;

$R^2$ is selected from hydrogen, halogen, $C_{1-3}$ alkyl, $C_{1-3}$ alkoxy, $C_{3-6}$ cycloalkyl, and phenyl;

each of $R^3$ and $R^4$ is independently is selected from a single bond, —NH—, —N(—$CH_3$)—, and —$CH_2$—;

$R^5$ is selected from $C_{6-10}$ aryl, substituted $C_{6-10}$ aryl, $C_{5-6}$ cycloalkyl, $C_{1-4}$ alkyl, and benzyl; and each substituent is independently selected from halogen, phenyl, —N(—R)$_2$, $C_{1-3}$ alkoxy, and $C_{1-3}$ alkyl, wherein each R is independently selected from hydrogen and methyl.

Aspect 86. The compound of aspect 85, wherein the compound has the structure of Formula (1d).

Aspect 87. The compound of aspect 85, wherein the compound has the structure of Formula (1e).

Aspect 88. The compound of aspect 85, wherein the compound has the structure of Formula (1f).

Aspect 89. The compound of any one of aspects 75 to 88, wherein p is 0.

Aspect 90. The compound of any one of aspects 75 to 88, wherein p is 1.

Aspect 91. The compound of any one of aspects 75 to 88, wherein p is 2.

Aspect 92. The compound of any one of aspects 75 to 91, wherein $R^2$ is hydrogen.

Aspect 93. The compound of any one of aspects 75 to 91, wherein $R^2$ is halogen.

Aspect 94. The compound of any one of aspects 75 to 91, wherein $R^2$ is $C_{1-3}$ alkyl.

Aspect 95. The compound of any one of aspects 75 to 91, wherein $R^2$ is methyl.

Aspect 96. The compound of any one of aspects 75 to 91, wherein $R_2$ is $C_{1-4}$ alkoxy.

Aspect 97. The compound of any one of aspects 75 to 91, wherein $R^2$ is methoxy.

Aspect 98. The compound of any one of aspects 75 to 91, wherein $R^2$ is $C_{3-6}$ alkyl.

Aspect 99. The compound of any one of aspects 75 to 91, wherein $R^2$ is cyclopentyl.

Aspect 100. The compound of any one of aspects 75 to 91, wherein $R^2$ is cyclohexyl.

Aspect 101. The compound of any one of aspects 75 to 91, wherein $R^2$ is phenyl.

Aspect 102. The compound of any one of aspects 75 to 101, wherein the moiety —$R^3$—(S(O)$_p$—$R^4$— is selected from —NH—S(O)$_2$—, —S(O)$_2$—NH—, —N(—$CH_3$)—S(O)$_2$—, —S(O)$_2$—N(—$CH_3$)—, —$CH_2$—S—$CH_2$—, —S—$CH_2$—, —S(O)$_2$—$CH_2$—, and —NH—S(O)$_2$—$CH_2$—.

Aspect 103. The compound of any one of aspects 75 to 101, wherein the moiety —$R^3$—(S(O)$_p$—$R^4$— is —NH—S(O)$_2$—.

Aspect 104. The compound of any one of aspects 75 to 101, wherein the moiety —$R^3$—(S(O)$_p$—$R^4$— is —S(O)$_2$—NH—.

Aspect 105. The compound of any one of aspects 75 to 101, wherein the moiety —$R^3$—(S(O)$_p$—$R^4$— is —N(—$CH_3$)—S(O)$_2$—.

Aspect 106. The compound of any one of aspects 75 to 101, wherein the moiety —$R^3$—(S(O)$_p$—$R^4$— is —S(O)$_2$—N(—$CH_3$)—.

Aspect 107. The compound of any one of aspects 75 to 101, wherein the moiety —$R^3$—(S(O)$_p$—$R^4$— is —$CH_2$—S—$CH_2$—.

Aspect 108. The compound of any one of aspects 75 to 101, wherein the moiety —$R^3$—(S(O)$_p$—$R^4$— is —S—$CH_2$—.

Aspect 109. The compound of any one of aspects 75 to 101, wherein the moiety —R³—(S(O)$_p$—R⁴— is —S(O)$_2$—CH$_2$—.

Aspect 110. The compound of any one of aspects 75 to 101, wherein the moiety —R³—(S(O)$_p$—R⁴— is —NH—S(O)$_2$—CH$_2$—.

Aspect 111. The compound of any one of aspects 75 to 110, wherein R⁵ is C$_{6-10}$ aryl.

Aspect 112. The compound of any one of aspects 75 to 110, wherein R⁵ is substituted C$_{6-10}$ aryl; and each substituent is independently selected from halogen, phenyl, —N(—R)$_2$, C$_{1-3}$ alkoxy, and C$_{1-3}$ alkyl.

Aspect 113. The compound of any one of aspects 75 to 110, wherein R⁵ is C$_{5-6}$ cycloalkyl.

Aspect 114. The compound of any one of aspects 75 to 110, wherein R⁵ is C$_{1-4}$ alkyl.

Aspect 115. The compound of any one of aspects 75 to 110, wherein each substituent is independently selected from halogen, phenyl, —N(—R)$_2$, C$_{1-3}$ alkoxy, and C$_{1-3}$ alkyl.

Aspect 116. The compound of any one of aspects 75 to 110, wherein R⁵ is cyclohexyl.

Aspect 117. The compound of any one of aspects 75 to 110, wherein R⁵ is C$_{1-4}$ alkyl.

Aspect 118. The compound of any one of aspects 75 to 110, wherein R⁵ is phenyl.

Aspect 119. The compound of aspect 118, wherein each substituent group is independently selected from Cl, Br, C$_{1-3}$ alkyl, phenyl, and C$_{1-3}$ alkoxy.

Aspect 120. The compound of any one of aspects 75 to 110, wherein R⁵ is naphthyl.

Aspect 121. The compound of aspect 120, wherein R⁵ is substituted naphthyl; and the substituent group is selected from —NH$_2$, —NH(—CH$_3$), and —NH(—CH$_3$)$_2$.

Aspect 122. The compound of any one of aspects 75 to 110, wherein R⁵ is quinolinyl.

Aspect 123. A compound having the structure of Formula (3):

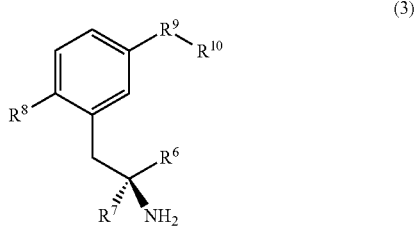

or a pharmaceutically acceptable salt thereof, wherein,
R⁶ is selected from —COOH, —COOR$^a$, —COR$^a$, and —CON(R$^b$)$_2$, wherein,
R$^a$ is C$_{1-4}$ alkyl; and
each R$^b$ is independently selected from hydrogen, —OH, C$_{1-4}$ alkyl, and C$_{1-4}$ alkoxy;
R⁷ is selected from hydrogen and methyl;
R⁸ is selected from hydrogen, halogen, C$_{1-3}$ alkyl, C$_{1-3}$ alkoxy, C$_{3-6}$ cycloalkyl, and phenyl;
R⁹ is selected from —S(O)$_2$—NR— and —NR—S(O)$_2$—, wherein R is selected from hydrogen and methyl;
R¹⁰ is selected from C$_{6-10}$ aryl, substituted C$_{6-10}$ aryl, C$_{5-6}$ cycloalkyl, C$_{1-4}$ alkyl, and biphenyl; and
each substituent is independently selected from halogen, phenyl, —N(—R)$_2$, C$_{1-3}$ alkoxy, and C$_{1-3}$ alkyl.

Aspect 124. The compound of aspect 123, wherein R⁶ is —COOH.

Aspect 125. The compound of any one of aspects 123 to 124, wherein R⁶ is —COOR$^a$.

Aspect 126. The compound of any one of aspects 123 to 124, wherein R⁶ is —COR$^a$.

Aspect 127. The compound of any one of aspects 123 to 124, wherein R⁶ is —CON(R$^b$)$_2$.

Aspect 128. The compound of any one of aspects 123 to 127, wherein R⁷ is hydrogen.

Aspect 129. The compound of any one of aspects 123 to 127, wherein R⁷ is methyl.

Aspect 130. The compound of any one of aspects 123 to 129, wherein R⁸ is hydrogen.

Aspect 131. The compound of any one of aspects 123 to 129, wherein R⁸ is halogen.

Aspect 132. The compound of any one of aspects 123 to 129, wherein R⁸ is C$_{1-3}$ alkyl.

Aspect 133. The compound of any one of aspects 123 to 129, wherein R⁸ is methyl.

Aspect 134. The compound of any one of aspects 123 to 129, wherein R$_2$ is C$_{1-4}$ alkoxy.

Aspect 135. The compound of any one of aspects 123 to 129, wherein R² is methoxy.

Aspect 136. The compound of any one of aspects 123 to 129, wherein R² is C$_{3-6}$ alkyl.

Aspect 137. The compound of any one of aspects 123 to 129, wherein R² is cyclopentyl.

Aspect 138. The compound of any one of aspects 123 to 129, wherein R² is cyclohexyl.

Aspect 139. The compound of any one of aspects 123 to 129, wherein R² is phenyl.

Aspect 140. The compound of any one of aspects 123 to 133, wherein R⁹ is —S(O)$_2$—NR—.

Aspect 141. The compound of any one of aspects 123 to 133, wherein R⁹ is —NR—S(O)$_2$—.

Aspect 142. The compound of any one of aspects 140 to 141, wherein R is hydrogen.

Aspect 143. The compound of any one of aspects 140 to 141, wherein R is methyl.

Aspect 144. The compound of any one of aspects 123 to 143, wherein R¹⁰ is selected from phenyl and substituted phenyl.

Aspect 145. The compound of aspect 144, wherein the substituted phenyl is 4-substituted phenyl.

Aspect 146. The compound of aspect 144, wherein the substituted phenyl is 3-substituted phenyl.

Aspect 147. The compound of any one of aspects 144 to 146, wherein the substituent is selected from Cl, Br, methoxy, and benzyl.

Aspect 148. The compound of any one of aspects 123 to 143, wherein R¹⁰ is selected from naphthyl and substituted naphthyl.

Aspect 149. The compound of aspect 148, wherein the substituent is selected from —N(R)$_2$, wherein each R is independently selected from hydrogen and methyl.

Aspect 150. The compound of any one of aspects 123 to 143, wherein R¹⁰ is biphenyl.

Aspect 151. The compound of any one of aspects 123 to 143, wherein R¹⁰ is C$_{5-6}$ cycloalkyl.

Aspect 152. The compound of any one of aspects 123 to 143, wherein R¹⁰ is cyclohexyl.

Aspect 153. The compound of any one of aspects 123 to 143, wherein R¹⁰ is C$_{1-4}$ alkyl.

Aspect 154. The compound of any one of aspects 123 to 143, wherein R¹⁰ is methyl.

Aspect 155. The compound of aspect 123, wherein
R⁶ is —COOH;
R⁷ is hydrogen;
R⁸ is methyl; and
R⁹ is from —S(O)₂—NH—.

Aspect 156. The compound of aspect 123, wherein
R⁶ is —COOH;
R⁷ is hydrogen.
R⁸ is methyl; and
R⁹ is from —NH—S(O)₂—.

Aspect 157. The compound of any one of aspects 123 to 156, wherein R¹⁰ is C₆₋₁₀ aryl.

Aspect 158. The compound of any one of aspects 123 to 156, wherein R¹⁰ is substituted C₆₋₁₀ aryl.

Aspect 159. The compound of any one of aspects 155 to 158, wherein R¹⁰ is selected from phenyl and substituted phenyl.

Aspect 160. The compound of any one of aspects 155 to 158, wherein the substituted phenyl is 4-substituted phenyl.

Aspect 161. The compound of any one of aspects 155 to 158, wherein the substituted phenyl is 3-substituted phenyl.

Aspect 162. The compound of any one of aspects 155 to 161, wherein the substituent is selected from Cl, Br, methoxy, and benzyl.

Aspect 163. The compound of any one of aspects 123 to 156, wherein R¹⁰ is selected from naphthyl and substituted naphthyl.

Aspect 164. The compound of aspect 163, wherein the substituent is selected from —N(R)₂.

Aspect 165. The compound of aspect 164, wherein each R is independently selected from hydrogen and methyl.

Aspect 166. The compound of aspect 1 or aspect 2, wherein the compound is selected from:
(S)-2-amino-3-(5-(N-benzylsulfamoyl)-2-methylphenyl)propanoic acid (30);
(S)-2-amino-3-(5-(N-(4-methoxyphenyl)sulfamoyl)-2-methylphenyl)propanoic acid (44);
(S)-2-amino-3-(5-(N-(4-chlorophenyl)sulfamoyl)-2-methylphenyl)propanoic acid (52);
(S)-2-amino-3-(5-(N-(3-bromophenyl)sulfamoyl)-2-methylphenyl)propanoic acid (76);
(S)-2-amino-3-(5-(N-(4-bromophenyl)sulfamoyl)-2-methylphenyl)propanoic acid (77); and
(S)-2-amino-3-(5-(N-(4-chlorophenyl)sulfamoyl)-2-isopropylphenyl)propanoic acid (86);
or a pharmaceutically acceptable salt of any of the foregoing.

Aspect 167. The compound of aspect 1 or aspect 2, wherein the compound is selected from:
(S)-2-amino-3-(5-((5-(dimethylamino)naphthalene)-1-sulfonamido)-2-isopropylphenyl)propanoic acid (21);
(S)-2-amino-3-(5-((3-bromophenyl)sulfonamido)-2-methylphenyl)propanoic acid (29);
(S)-2-amino-3-(2-methyl-5-(N-phenylsulfamoyl)phenyl)propanoic acid hydrochloride (35);
(S)-3-(5-([1,1'-biphenyl]-3-sulfonamido)-2-methylphenyl)-2-aminopropanoic acid (38);
(S)-2-amino-3-(2-methyl-5-(N-(naphthalen-1-yl)sulfamoyl)phenyl)propanoic acid (39); and
(S)-3-(5-(N-([1,1'-biphenyl]-4-yl)sulfamoyl)-2-methylphenyl)-2-aminopropanoic acid (40);
or a pharmaceutically acceptable salt of any of the foregoing.

Aspect 168. The compound of aspect 1 or aspect 2, wherein the compound is selected from:
(S)-2-amino-3-(2-methyl-5-(phenylsulfonamido)phenyl)propanoic acid (10)
(S)-2-amino-3-(5-(N-butylsulfamoyl)-2-methylphenyl)propanoic acid (41);
(S)-2-amino-3-(5-(N-(5-(dimethylamino)naphthalen-1-yl)sulfamoyl)-2-methylphenyl)propanoic acid (49);
(S)-2-amino-3-(5-(N-cyclohexylsulfamoyl)-2-methylphenyl)propanoic acid (53);
(S)-2-amino-3-(3-(N-(4-chlorophenyl)sulfamoyl)phenyl)propanoic acid (79);
tert-butyl (S)-2-amino-3-(5-(N-(4-chlorophenyl)sulfamoyl)-2-methylphenyl)propanoate (82);
(S)-2-amino-3-(5-(N-(4-chlorophenyl)-N-methylsulfamoyl)-2-methylphenyl)propanoic acid (84); and
(S)-2-amino-3-(5-((4-(tert-butyl)phenyl)sulfonamido)-2-methylphenyl)propanoic acid (87);
or a pharmaceutically acceptable salt of any of the foregoing.

Aspect 169. The compound of aspect 1 or aspect 2, wherein the compound is selected from:
(S)-2-amino-3-(5-((5-(dimethylamino)naphthalene)-1-sulfonamido)-2-methylphenyl)propanoic acid (2);
(S)-2-amino-3-(3-((5-(dimethylamino)naphthalene)-1-sulfonamido)phenyl)propanoic acid (3);
(S)-2-amino-3-(2-methyl-5-((4-methylphenyl)sulfonamido)phenyl)propanoic acid (7);
(S)-2-amino-3-(5-((3,5-dichlorophenyl)sulfonamido)-2-methylphenyl)propanoic acid (43);
(S)-2-amino-3-(5-(N-isobutylsulfamoyl)-2-methylphenyl)propanoic acid (46);
(S)-2-amino-3-(5-((benzylthio)methyl)-2-methylphenyl)propanoic acid (55);
(S)-2-amino-3-(5-(benzylsulfonyl)-2-methylphenyl)propanoic acid (65); and
(S)-2-amino-3-(5-(N-(2-bromophenyl)sulfamoyl)-2-methylphenyl)propanoic acid (75);
or a pharmaceutically acceptable salt of any of the foregoing.

Aspect 170. The compound of aspect 1 or aspect 2, wherein the compound is selected from:
(S)-2-amino-3-(2-methyl-5-(naphthalene-1-sulfonamido)phenyl)propanoic acid (6);
(S)-3-(5-([1,1'-biphenyl]-4-sulfonamido)-2-methylphenyl)-2-aminopropanoic acid (17);
(S)-2-amino-3-(2-methyl-5-((phenylmethyl)sulfonamido)phenyl)propanoic acid (23);
(S)-2-amino-3-(2-methyl-5-(N-(quinolin-5-yl)sulfamoyl)phenyl)propanoic acid (50);
(S)-2-amino-3-(5-(benzylthio)-2-methylphenyl)propanoic acid (59); and
(S)-2-amino-3-(5-(N-(3,4-dichlorophenyl)sulfamoyl)-2-methylphenyl)propanoic acid (83);
or a pharmaceutically acceptable salt of any of the foregoing.

Aspect 171. The compound of aspect 1 or aspect 2, wherein the compound is selected from:
(S)-2-amino-3-(5-((5-(dimethylamino)-N-methylnaphthalene)-1-sulfonamido)-2-methylphenyl)propanoic acid (16);
(S)-2-amino-3-(5-(cyclohexanesulfonamido)-2-methylphenyl)propanoic acid (26);
(S)-2-amino-3-(5-(benzo[b]thiophene-3-sulfonamido)-2-methylphenyl)propanoic acid (27);
(S)-2-amino-3-(2-methyl-5-((3-((4-methylphenyl)sulfonamido)phenyl)sulfonamido)phenyl)propanoic acid (32);
(S)-2-amino-3-(2-methyl-5-((4-methyl-N-tosylphenyl)sulfonamido)phenyl)propanoic acid (48); and (S)-2-amino-3-(5-((4-methoxyphenyl)sulfonamido)-2-methylphenyl)propanoic acid (57);
or a pharmaceutically acceptable salt of any of the foregoing.

Aspect 172. The compound of aspect 1 or aspect 2, wherein the compound is selected from:
(S)-2-amino-3-(2-chloro-5-((5-(dimethylamino)naphthalene)-1-sulfonamido)phenyl)propanoic acid (15);
(S)-2-amino-3-(5-((benzylsulfonyl)methyl)-2-methylphenyl)propanoic acid (56);
(S)-2-amino-3-(5-(butylsulfonamido)-2-methylphenyl)propanoic acid (58); and
(S)-2-amino-3-(2-methyl-5-(phenylsulfonamidomethyl)phenyl)propanoic acid (69);
or a pharmaceutically acceptable salt of any of the foregoing.

Aspect 173. The compound of aspect 1 or aspect 2, wherein the compound is selected from:
(S)-2-amino-3-(5-((5-(dimethylamino)naphthalene)-1-sulfonamido)-2-methoxyphenyl)propanoic (5);
(S)-2-amino-3-(2-((5-(dimethylamino)naphthalene)-1-sulfonamido)phenyl)propanoic acid (19);
(S)-2-amino-3-(5-((3-aminophenyl)sulfonamido)-2-methylphenyl)propanoic acid (28);
(S)-2-amino-3-(2-methyl-5-((4-((4-methylphenyl)sulfonamido)phenyl)sulfonamido)phenyl)propanoic acid (33);
(S)-2-amino-3-(3-(phenylsulfonamido)phenyl)propanoic acid (37);
(S)-2-amino-3-(5-((2,6-dichlorophenyl)sulfonamido)-2-methylphenyl)propanoic acid (42);
(2S)-2-amino-3-(5-((benzylsulfinyl)methyl)-2-methylphenyl)propanoic acid (60);
(S)-2-amino-3-(2-methyl-5-(((4-methylphenyl)sulfonamido)methyl)phenyl)propanoic acid (66); and
(S)-2-amino-3-(4-(N-(4-chlorophenyl)sulfamoyl)-2-methylphenyl)propanoic acid (85);
or a pharmaceutically acceptable salt of any of the foregoing.

Aspect 174. The compound of aspect 1 or aspect 2, wherein the compound is selected from:
(S)-2-amino-3-(4-((5-(dimethylamino)naphthalene)-1-sulfonamido)phenyl)propanoic acid (4);
(S)-2-amino-3-(4-((5-(dimethylamino)naphthalene)-1-sulfonamido)-2-methoxyphenyl)propanoic acid (8);
(S)-2-amino-3-(2-methyl-5-(quinoline-5-sulfonamido)phenyl)propanoic acid (9);
(S)-2-amino-3-(2-methyl-5-(pyridine-3-sulfonamido)phenyl)propanoic acid (11);
(S)-2-amino-3-(2-methyl-5-((tetrahydro-2H-pyran)-4-sulfonamido)phenyl)propanoic acid (12);
(S)-3-(5-((4-acetamidonaphthalene)-1-sulfonamido)-2-methylphenyl)-2-aminopropanoic acid (13);
(S)-2-amino-3-(5-(cyclopropanesulfonamido)-2-methylphenyl)propanoic acid (14);
(S)-2-amino-3-(2-methyl-5-((1-methylethyl)sulfonamido)phenyl)propanoic acid (20);
(S)-2-amino-3-(5-(((((1R,4R)-7,7-dimethyl-2-oxobicyclo[2.2.1]heptan-1-yl)methyl)sulfonamido)-2-methylphenyl)propanoic acid (22);
(S)-2-amino-3-(5-((7-chlorobenzo[c][1,2,5]oxadiazole)-4-sulfonamido)-2-methylphenyl)propanoic acid (24);
(S)-2-amino-3-(5-(benzo[c][1,2,5]oxadiazole-4-sulfonamido)-2-methylphenyl)propanoic acid (25);
(R)-2-amino-3-(5-((5-(dimethylamino)naphthalene)-1-sulfonamido)-2-isopropylphenyl)propanoic acid (34);
(S)-2-amino-3-(5-((2,6-dichloro-4-(trifluoromethyl)phenyl)sulfonamido)-2-methylphenyl)propanoic acid (36);
(S)-2-amino-3-(2-methyl-5-(((phenylmethyl)sulfonamido)methyl)phenyl)propanoic acid (54);
(S)-2-amino-3-(3,5-bis((4-methylphenyl)sulfonamido)phenyl)propanoic acid (63);
(2S)-2-amino-3-(5-(benzylsulfinyl)-2-methylphenyl)propanoic acid (64);
(S)-2-amino-3-(3-(N,N-dimethylsulfamoyl)phenyl)propanoic acid (73);
(S)-2-amino-3-(3-(piperidin-1-ylsulfonyl)phenyl)propanoic acid (78);
(S)-2-amino-3-(4-(N-(4-fluorophenyl)sulfamoyl)phenyl)propanoic acid (80); and
(S)-2-amino-3-(2-(N-(4-chlorophenyl)sulfamoyl)phenyl)propanoic acid (81);
or a pharmaceutically acceptable salt of any of the foregoing.

Aspect 175. The compound of aspect 1 or aspect 2, wherein the compound is selected from:
(S)-2-amino-3-(2-(methylsulfonamido)phenyl]propanoic acid (1);
(S)-2-amino-3-(5-((1,2-dimethyl-1H-imidazole)-4-sulfonamido)-2-methylphenyl)propanoic acid (18);
(S)-3-(5-(1H-imidazole-4-sulfonamido)-2-methylphenyl)-2-aminopropanoic acid (31); ((3-((S)-2-amino-2-carboxyethyl)-4-methylphenyl)sulfonyl)-D-proline (45);
(S)-2-amino-3-(3,5-dichloro-4-(phenylsulfonamido)phenyl)propanoic acid (47);
(R)-2-amino-3-(5-(N-(4-chlorophenyl)sulfamoyl)-2-methylphenyl)propanoic acid (51);
(S)-2-amino-3-(3,5-di(methylsulfonamido)phenyl)propanoic acid (61);
(S)-2-amino-3-(3,5-bis(phenylsulfonamido)phenyl)propanoic acid (62);
(S)-2-amino-3-(2-methyl-5-(methylsulfonamido)phenyl)propanoic acid (67);
(S)-2-amino-3-(3-(methylsulfonamido)phenyl)propanoic acid (68);
(S)-2-amino-3-(4-(methylsulfonamido)phenyl)propanoic acid (70);
(S)-2-amino-3-(3-sulfamoylphenyl)propanoic acid (71);
(S)-2-amino-3-(3-(N-methylsulfamoyl)phenyl)propanoic acid (72); and
(S)-2-amino-3-(4-sulfamoylphenyl)propanoic acid (74);
or a pharmaceutically acceptable salt of any of the foregoing.

Aspect 176. The compound of any one of aspects to 1 to 175, wherein the compound exhibits an IC50 of less than 50 nM in a [$^3$H]-GP uptake inhibition assay.

Aspect 177. The compound of any one of aspects to 1 to 175, wherein the compound exhibits an IC50 of less than 200 nM in a [$^3$H]-GP uptake inhibition assay.

Aspect 178. The compound of any one of aspects to 1 to 175, wherein the compound exhibits an IC50 of less than 400 nM in a [$^3$H]-GP uptake inhibition assay.

Aspect 179. The compound of any one of aspects to 1 to 175, wherein the compound exhibits an IC50 of less than 1,000 nM in a [$^3$H]-GP uptake inhibition assay.

Aspect 180. A pharmaceutical composition comprising the compound of any one of aspects 1 to 179 or a pharmaceutically acceptable salt thereof; and a pharmaceutically acceptable vehicle.

Aspect 181. A method of treating organ transplant rejection in a patient comprising administering to a patient in need of such treatment a therapeutically effective amount of the compound of any one of aspects 1 to 179 or a pharmaceutically acceptable salt thereof.

Aspect 182. A method of treating an autoimmune disease in a patient comprising administering to a patient in need of such treatment a therapeutically effective amount of the compound of any one of aspects 1 to 179 or a pharmaceutically acceptable salt thereof.

Aspect 183. A method of treating a disease associated with T-cell activation, proliferation, metabolism, differentiation or a combination of any of the foregoing in a patient comprising administering to a patient in need of such treatment a therapeutically effective amount of the compound of any one of aspects 1 to 179 or a pharmaceutically acceptable salt thereof.

Aspect 184. A method of treating acute graft-vs-host-disease or chronic graft-vs-host-disease in a patient comprising administering to a patient in need of such treatment a therapeutically effective amount of the compound of any one of aspects 1 to 179 or a pharmaceutically acceptable thereof.

Aspect 185. A method of treating an inflammatory disease such as inflammatory bowel disease in a patient comprising administering to a patient in need of such treatment a therapeutically effective amount of the compound of any one of aspects 1 to 179 or a pharmaceutically acceptable thereof.

Aspect 186. A method of treating an organ transplant rejection in a patient comprising administering to a patient in need of such treatment a therapeutically effective amount of the pharmaceutical composition of aspect 180.

Aspect 187. A method of treating an autoimmune disease in a patient comprising administering to a patient in need of such treatment a therapeutically effective amount of the pharmaceutical composition of aspect 180.

Aspect 188. A method of treating a disease associated with T-cell activation, proliferation, metabolism, differentiation or a combination of any of the foregoing in a patient comprising administering to a patient in need of such treatment a therapeutically effective amount of the pharmaceutical composition of aspect 180.

Aspect 189. A method of treating acute graft-vs-host-disease or chronic graft-vs-host-disease in a patient comprising administering to a patient in need of such treatment a therapeutically effective amount of the pharmaceutical composition of aspect 180.

Aspect 190. A method of treating an inflammatory disease such as inflammatory bowel disease in a patient comprising administering to a patient in need of such treatment a therapeutically effective amount of the pharmaceutical composition of aspect 180.

Aspect 191. Use of the compound of any one of aspects 1 to 179 or a pharmaceutically acceptable salt thereof in the manufacture of a medicament for treating an organ transplant rejection.

Aspect 192. Use of the compound of any one of aspects 1 to 179 or a pharmaceutically acceptable salt thereof, in the manufacture of a medicament for treating an autoimmune disease.

Aspect 193. Use of the compound of any one of aspects 1 to 179 or a pharmaceutically acceptable salt thereof in the manufacture of a medicament for treating a disease associated with T-cell activation, proliferation, metabolism, differentiation or a combination of any of the foregoing.

Aspect 194. Use of the compound of any one of aspects 1 to 179 or a pharmaceutically acceptable thereof in the manufacture of a medicament for treating acute graft-vs-host-disease or chronic graft-vs-host-disease.

Aspect 195. Use of the compound of any one of aspects 1 to 179 or a pharmaceutically acceptable thereof for treating an inflammatory disease such as inflammatory bowel disease.

Aspect 196. Use of the pharmaceutical composition of aspect 180 in the manufacture of a medicament for treating an organ transplant rejection.

Aspect 197. Use of the pharmaceutical composition of aspect 180 in the manufacture of a medicament for treating an autoimmune disease.

Aspect 198. Use of the pharmaceutical composition of aspect 180 in the manufacture of a medicament for treating a disease associated with T-cell activation, proliferation, metabolism, differentiation or a combination of any of the foregoing.

Aspect 199. Use of the pharmaceutical composition of aspect 180 in the manufacture of a medicament for treating acute graft-vs-host-disease or chronic graft-vs-host-disease.

Aspect 200. Use of the pharmaceutical composition of aspect 180 in the manufacture of a medicament for treating an inflammatory disease such as inflammatory bowel disease.

EXAMPLES

The following examples describe in detail the synthesis of compounds of Formula (1)-(3), characterization of compounds of Formula (1)-(3), and uses of compounds of Formula (1)-(3). It will be apparent to those skilled in the art that many modifications, both to materials and methods, may be practiced without departing from the scope of the disclosure.

General Experimental Protocols

All reagents and solvents were purchased from commercial suppliers and used without further purification or manipulation.

Proton NMR spectra were recorded on a Varian Mercury Plus300 Spectrometer (300 MHz) or a Varian VNMRS 400 Spectrometer (400 MHz). $CDCl_3$ (99.8% D), $CD_3OD$ (MeOH-$d_4$), deuteroxide ($D_2O$) (99.8+% D), or DMSO-$d_6$ ($D_3CSOCD_3$) were used as recording solvents unless otherwise noted. The $CHCl_3$, $CD_3OH$, HDO, DMSO-$d_5$ solvent signals or tetramethylsilane (TMS) were used for calibration of the individual spectra.

Analytical thin layer chromatography (TLC) was performed using EMD Millipore aluminum-backed TLC sheets (EMD5554-7) pre-coated with silica gel 60 F254 (200 μm thickness, 60 Å pore size) where F254 is a fluorescent indicator with a 254 nm excitation wavelength. An ENF-240C Spectroline® UV-lamp (Spectronics Corporation, USA) was used for TLC detection and visualization. Dyeing or staining reagents for TLC detection and visualization, e.g., an ethanolic ninhydrin solution or a 0.2 wt % aqueous potassium permanganate ($KMnO_4$) solution, were prepared according to methods known in the art.

Analytical LC/MS was performed on a Shimadzu LC/MS-2020 Prominence Series system (Shimadzu 228-45012-32), an SPD-20AV UV/VIS detector (Shimadzu 228-45004-32), a SIL-20AC autosampler (Shimadzu 228-45136-32), DGU-20A5 degasser (Shimadzu 228-45019-32), two LC-20AD XP HPLC pumps (Shimadzu 228-45137-32), an Agilent Zorbax 5 m XDB-C18 2.1×50 mm column (Agilent 960 967-902). Gradients of water (solvent A) (Arrowhead, Nestle North America, Inc.) and acetonitrile (MeCN; solvent B) (EMD AX0145-1 or Aldrich CHROMASOLV® 439134)

containing 0.075-0.1 vol % of formic acid (EMD FX0440-7) were used in analytical LC/MS/UV analyses.

Analytical LC/UV was performed on an Agilent 1100 Series system equipped with an Agilent 1100 Series degasser (Agilent G1379A), an Agilent 1100 Series quad pump (Agilent G1311A), an Agilent 1100 Series autosampler (ALS) (Agilent G1329A), an Agilent 1100 Series COLCOM (Agilent G1316A), a Phenomenex Gemini® C18, 5 µm 110 Å pore size 150 mm×4.6 mm HPLC column (Phenomenex OOF-4435-EO). Gradients of water (solvent A) (Arrowhead, Nestle North America, Inc.) and acetonitrile (MeCN; solvent B) (EMD AX0145-1 or Aldrich CHROMASOLV® 439134) containing 0.075-0.1 vol % of formic acid (EMD FX0440-7) or TFA (Oakwood Chemicals) were used in analytical LC/UV analyses.

Preparative HPLC was conducted with a Varian ProStar@Series system equipped with a Model 340 UV-C UV-VIS detector, a Model 210 solvent delivery module, a Hamilton PRP-112-20 µm, 100 Å 21.2 mm×250 mm preparative HPLC column (Hamilton 79428), a Phenomenex OOF-4633-PO-AX, Kinetex, 5-µm EVO C18 100A 150 mm×21.2 mm column (S/No. 761412-1), and a commercial desktop personal computer for data computation. Gradients of water (solvent A) (Arrowhead, Nestle North America, Inc.) and acetonitrile (MeCN; solvent B) (EMD AX0145-1 or Aldrich CHROMASOLV® 439134) containing 0.1 vol % of formic acid (EMD FX0440-7) were used for preparative HPLC purifications. For some preparative HPLC purifications and depending on the analyte, the additive was 0.1 vol-% TFA or 0.1 vol-% concentrated hydrochloric acid ($HCl_{aq}$), or no acidifying additives were used ("neutral conditions") for preparative HPLC purifications.

Preparative HPLC was also conducted with a Varian PrepStar® Series system SD1 equipped with a ProStar® Model 325 UV-VIS detector, SD1 solvent delivery modules (S/No. 05567 and S/No. 05567), a custom-packed preparative HPLC column (ca. 250 mm×50 mm) using Phenomenex Luna® C-18 Prep. C18(3) 100 Å (B15-001256) as a stationary phase. Gradients of water (solvent A) (Arrowhead, Nestle North America, Inc.) and acetonitrile (MeCN; solvent B) (EMD AX0145-1 or Aldrich CHROMASOLV® 439134) containing 0.1 vol % of formic acid (EMD FX0440-7), TFA, conc. HCl, or no acidifying additives were used ("neutral conditions") for preparative HPLC purifications.

Compound isolation from aqueous solvent mixtures, e.g., acetonitrile/water/0.1 vol % formic acid, was accomplished by primary lyophilization of pooled and frozen (after freeze drying) fractions under reduced pressure at 25° C. using manifold freeze dryers such as Heto Drywinner® DW 6-85-1, Heto FD4, or VIRTIS Freezemobile® 25 ES equipped with a high vacuum pump.

When the preparative HPLC eluents contained 0.1 vol-% formic acid additive, the compounds (typically amino acids) may be isolated initially as full internal salts (zwitterions), stoichiometric formate addition salts, partial formate addition salts, or mixtures of any of the forgoing. The presence of residual formate counterions can be readily determined by H NMR spectroscopy. If the full internal salt (zwitterion) of the isolate compound (typically amino acids) are needed, repeated dissolution/lyophilization cycles of the stoichiometric formate addition salts or partial formate addition salts using a "neutral" acetonitrile/water mixture (ca. 1:1, (v/v)) were employed until the $^1$H NMR signal of the repeatedly lyophilized isolated compound had no detectable residual formate counterion as evidenced by $^1$H NMR spectroscopic analysis of the lyophilization repeatedly lyophilized isolated compound.

Optionally, and if the isolated compound had ionizable functional groups such as an amino group or a carboxylic acid, the lyophilization process was conducted in the presence of either equimolar or an excess (about 1.1 to 5.0 equivalents) of 1.0 M hydrochloric acid (HCl) to yield the purified compound(s) as the corresponding hydrochloride salt (HCl-salt) and/or the corresponding protonated free carboxylic acid. Optionally, any of the compounds of the present disclosure can be converted into a desired (pharmaceutically acceptable) acid addition salt by this method or any other method well known in the art.

Filtrations were conducted using commercial Celite® 545 (EMD CX0574-1). The clay was compressed into glass Büchner-funnels to create a plug of 2 cm to 5 cm thickness. Reaction mixtures containing precipitated reaction side products or heterogenous catalyst residues were filtered off using standard techniques. Care must be taken filtering off activated catalysts or finely dispersed metals (ignition!).

Unless otherwise noted, aqueous work-up typically involved dilution of a crude reaction product, with or without residual reaction solvent, with 1.0 M hydrochloric acid (HCl) or a saturated aqueous solution of ammonium chloride ($NH_4Cl$), multiple extractions with an organic solvent, e.g., ethyl acetate (EtOAc), diethyl ether ($Et_2O$), or dichloromethane (DCM), washing with water, a saturated sodium sulfite ($Na_2SO_3$) or sodium hydrogen sulfite ($NaHSO_3$) solution, a saturated aqueous solution of sodium hydrogen carbonate ($NaHCO_3$), and brine (saturated aqueous solution of sodium chloride (NaCl)), drying of the organic phase (combined organic extracts) over anhydrous magnesium sulfate ($MgSO_4$) (EMD MX0075-1) or sodium sulfate ($Na_2SO_4$) (EMD SX0760E-3), filtration, washing of the filter residue, and evaporation of the combined filtrates under reduced pressure using a rotary evaporator at room or elevated temperature followed by compound purification e.g., silica gel column chromatography, preparative TLC (prep.-TLC), crystallization, or trituration.

Silica gel column chromatography was conducted with silica gel (about 100-200 mL silica gel per gram of compound) 600.04-0.063 mm (40-63 m, 230-400 mesh) (EMD Millipore EM1.09385.9026/EM1.09385.1033/EM1.09385.2503) using single solvents or mixtures of suitable solvents, e.g., ethyl acetate (EtOAc) and hexane or dichloromethane (DCM) and methanol (MeOH), as determined by TLC. Samples/fractions containing desired product detected by analytical TLC and/or analytical LC/MS, or LC/UV were pooled and the solvents were removed under reduced pressure using a Heidolph Laborota 4001 efficient rotary evaporator (Heidolph, Germany) (Heidolph 519-10000-01-5) equipped with a HB digit heating bath (Heidolph 517-01002-01-4), and a Rotavac valve control vacuum pump (Heidolph 591-00130-01-0).

Chemical names were generated using the ChemDraw® Professional 23.1.2.2.0.3300 (Revvity Signals Software, Inc. Waltham, MA, USA) nomenclature program.

Starting Materials

Starting Material 1
Methyl (R)-2-((tert-butoxycarbonyl)amino)-3-iodopropanoate (SM-1)

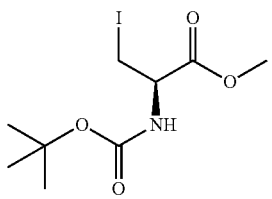

Starting material 1 (SM-1), methyl (R)-2-(tert-butoxycarbonylamino)-3-iodopropanoate, is commercially available [CAS No. 93267-04-0]. Starting material 1 (SM-1), methyl (R)-2-((tert-butoxycarbonyl)amino)-3-iodopropanoate [CAS No. 93267-04-0], can also be prepared from the corresponding commercial serine derivatives H—N-L-Ser-OH [CAS No. 56-45-1], H—N-L-Ser-OMe HCl [CAS No. 5680-80-8], or Boc-L-Ser-OMe [CAS No. 2766-43-0] following and adapting well-known literature procedures, e.g., procedures disclosed U.S. Pat. No. 9,783,487 and references cited therein (Scheme 3).

Starting material 1 (SM-1), methyl (R)-2-(tert-butoxycarbonylamino)-3-iodopropanoate [CAS No. 93267-04-0], was prepared through Appel-iodination of commercial methyl (tert-butoxycarbonyl)-L-serinate (H—N-L-Ser-OMe) [CAS No. 2766-43-0](21.9 g, 100 mmol) with elemental iodine ($I_2$) [CAS No. 7553-56-2](33.0 g, 130 mmol) in the presence of commercial triphenyl phosphine ($Ph_3P$) [CAS No. 603-35-0](34.1 g, 130 mmol) in the presence of commercial imidazole [CAS No. 288-32-4](10.2 g, 150 mmol) in DCM (500 mL) at room temperature for about 2 h. Reductive extractive workup including a saturated aqueous sodium sulfite ($Na_2SO_3$) solution and chromatographic purification on silica gel (hexane/ethyl acetate=4:1 (v/v)), yielded pure methyl (R)-2-((tert-butoxycarbonyl)amino)-3-iodopropanoate (SM-1) (29 g, 88% yield) as an oil that solidified upon standing at room temperature. TLC: Rf: 0.38 (hexane/ethyl acetate=4:1 (v/v)).

Starting Material 2
Methyl (S)-2-((tert-butoxycarbonyl)amino)-3-iodopropanoate (SM-2)

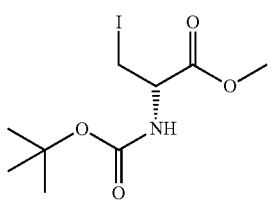

Starting material 2 (SM-2), methyl (S)-2-(tert-butoxycarbonylamino)-3-iodopropanoate, is commercially available [CAS No. 170848-34-7]. Starting material 2 (SM-2), methyl (S)-2-(tert-butoxycarbonylamino)-3-iodopropanoate, can also be prepared from the corresponding commercial serine derivatives H—N-D-Ser-OH [CAS No. 312-84-5], H—N-D-Ser-OMe HCl [CAS No. 5619-04-5], or Boc-D-Ser-OMe [CAS No. 95715-85-8] following and adapting well-known literature procedures, e.g., procedures disclosed in US patent publication U.S. Pat. No. 9,783,487 and references cited therein (Scheme 3).

Starting Material 3
tert-Butyl (R)-2-((tert-butoxycarbonyl)amino)-3-iodopropanoate (SM-3)

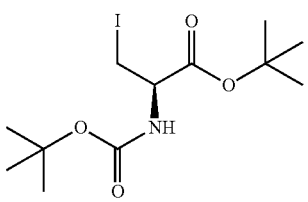

Starting material 3 (SM-3), tert-butyl (R)-2-((tert-butoxycarbonyl)amino)-3-iodopropanoate, is commercially available [CAS No. 1057341-65-7]. The starting material 3 (SM-3), tert-butyl (R)-2-((tert-butoxycarbonyl)amino)-3-iodopropanoate [CAS No. 1057341-65-7], can be prepared from the corresponding commercial serine derivatives H—N-L-Ser-OH [CAS No. 56-45-1], H—N-L-Ser-OtBu [CAS No. 106402-41-9], Boc-L-Ser-OH [CAS No. 3262-72-4], or Boc-L-Ser-OtBu [CAS No. 7738-22-9] following well-known literature procedures, e.g., procedures disclosed in U.S. Pat. No. 9,783,487 and references cited therein (Scheme 3).

Starting material 3 (SM-3), tert-butyl (R)-2-((tert-butoxycarbonyl)amino)-3-iodopropanoate (CAS No. 1057341-65-7], was prepared through Appel-iodination of commercial and synthetic tert-butyl (tert-butoxycarbonyl)-L-serinate (Boc-L-Ser-OtBu [CAS No. 7738-22-9](120 g, 459 mmol) with elemental iodine ($I_2$) [CAS No. 7553-56-2](152 g, 597 mmol) in the presence of commercial triphenyl phosphine ($Ph_3P$) [CAS No. 603-35-0](157 g, 597 mmol) in the presence of commercial imidazole [CAS No. 288-32-4](46.9 g, 689 mmol) in DCM (2.4 L+1.2 L) at room temperature for about 2 h. Extractive aqueous workup and chromatographic purification on silica gel (petroleum ether/ethyl acetate=100:1 to 10:1 (v/v)), yielded pure tert-butyl (R)-2-((tert-butoxycarbonyl)amino)-3-iodopropanoate SM-3) (114 g, 52% yield) as a white solid. TLC: Rf: 0.70 (petroleum ether/ethyl acetate=3:1, (v/v); LC/MS/UV: Rt: 2.444 min, calculated for $C_{12}H_{22}INO_4$ 371.06, found (ESI pos.) m/z=215.95 $[M-C_4H_8-CO_2-C_4H_8+H^+]^+$, ESI (neg.) m/z=370.00 $[M-H^+]^-$]; HPLC/UV: Rt: 5.001 min (100% AUC at 220 nm, 100% AUC at 254 nm); $^1H$ NMR (400 MHz, $CDCl_3$): δ 5.34 (d, J=7.2 Hz, 1H), 4.36-4.32 (m, 1H), 3.57-3.55 (m, 2H), 1.50 (s, 9H), 1.45 (s, 9H); Enantiomeric excess (e.e.): >99% (DAICEL Chiral AD-H, hexane/EtOH/TFA (90:10:0.01, (v/v/v)), 220 nm and 254 nm, 35° C.; Rt ((R)-isomer (SM-3))=4.511 min and Rt ((S)-isomer (SM-4))=4.894 min (not detectable).

Starting Material 4
tert-Butyl (S)-2-((tert-butoxycarbonyl)amino)-3-iodopropanoate (SM-4)

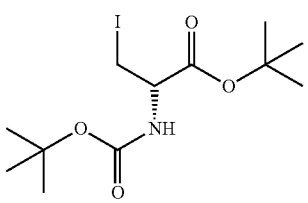

Starting material 4 (SM-4), tert-butyl (S)-2-(tert-butoxycarbonylamino)-3-iodopropanoate (SM-4) is commercially available [CAS No. 170848-34-7]. Starting material 4 (SM-4) can also be prepared from the corresponding commercial serine derivatives H—N-D-Ser-OH [CAS No. 312-84-5], H—N-D-Ser-OtBu [CAS No. 948296-15-9], Boc-D-Ser-OH [CAS No. 6368-20-3], or Boc-D-Ser-OtBu [CAS No. 71630-31-4] following well-known literature procedures, e.g., procedures disclosed in U.S. Pat. No. 9,783,487 and references cited therein (Scheme 3).

Starting material 4 (SM-4), tert-butyl (S)-2-((tert-butoxycarbonyl)amino)-3-iodopropanoate [CAS No. 170848-34-7], was prepared through Appel-iodination of commercial and synthetic tert-butyl (tert-butoxycarbonyl)-D-serinate (Boc-D-Ser-OtBu [CAS No. 71630-31-4](5.7 g, 21.8 mmol) with elemental iodine ($I_2$) [CAS No. 7553-56-2](8.3 g, 32.7 mmol) in the presence of commercial triphenyl phosphine ($Ph_3P$) [CAS No. 603-35-0](7.5 g, 28.3 mmol) in the presence of commercial imidazole [CAS No. 288-32-4](1.93 g, 28.3 mmol) in DCM (200 mL+500 mL) at room temperature for about 2 h. Extractive aqueous workup and chromatographic purification on silica gel (petroleum ether/ethyl acetate=100:1 to 10:1 (v/v)), yielded pure tert-butyl (S)-2-((tert-butoxycarbonyl)amino)-3-iodopropanoate (SM-4) (5.0 g, 61% yield) as a colorless (white) solid. TLC: Rf: 0.70 (petroleum ether/ethyl acetate=3:1, (v/v); $^1$H NMR (400 MHz, $CDCl_3$): δ 5.32 (d, J=7.2 Hz, 1H), 4.36-4.30 (m, 1H), 3.57-3.55 (m, 2H), 1.47 (s, 9H), 1.43 (s, 9H); Enantiomeric excess (e.e.): >99% (DAICEL Chiral AD-H, hexane/EtOH/TFA (90:10:0.01, (v/v/v)), 220 & 254 nm, 35° C.; Rt ((R)-isomer (SM-3))=4.511 min (not detectable) and Rt ((S)-isomer (SM-4))=4.894 min.

Starting Material 5
Methyl (S)-3-(5-amino-2-methylphenyl)-2-((tert-butoxycarbonyl)amino)propanoate (SM-5)

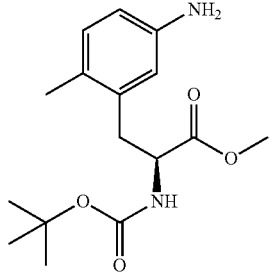

Starting material 5 (SM-5), methyl (S)-3-(5-amino-2-methylphenyl)-2-((tert-butoxycarbonyl)amino)propanoate, was prepared from starting material 1 (SM-1), methyl (R)-2-((tert-butoxycarbonyl)amino)-3-iodopropanoate [CAS No. 93267-04-0], and commercial 3-iodo-4-methylaniline [CAS No. 35944-64-0] following well-known literature procedures e.g., procedures disclosed in U.S. Pat. No. 9,783,487 and references cited therein or as described herein (Scheme 3 and Scheme 4).

Commercial 3-iodo-4-methylaniline [CAS No. 35944-64-0](5.0 g, 21.5 mol) and starting material 1 (SM-1), methyl (R)-2-((tert-butoxycarbonyl)amino)-3-iodopropanoate [CAS No. 1057341-65-7] (7.8 g, 24.0 mol) were cross-coupled through Pd(0)-catalyzed Negishi-coupling using tris(dibenzylideneacetone)dipalladium ($Pd_2(dba)_3$) [CAS No. 51364-51-3](492 mg, 0.54 mmol) and tri(o-tolyl) phosphine (P(o-Tol)$_3$) [CAS No. 6163-58-2](669 mg, 2.2 mmol) in the presence of an excess of zinc dust [CAS No. 7440-66-6](9.4 g, 144 mmol), pre-activated with elemental iodine ($I_2$) [CAS No. 7553-56-2](914 mg, 3.6 mmol) and trimethylchlorosilane (TMSCl) [CAS No. 75-77-4](457 μL, 391 mg, 3.6 mmol) in anhydrous DMF (10 mL+5 mL+5 mL) at 60° C. for overnight under a nitrogen atmosphere. Filtration over Celite®, extractive aqueous workup, and chromatographic purification over silica gel (hexane/ethyl acetate=1:1, (v/v)) yielded methyl (S)-3-(5-amino-2-methylphenyl)-2-((tert-butoxycarbonyl)amino)propanoate (SM-5) (5.3 g, 80% yield) as a brown oil. TLC: Rf: 0.42 (hexane/ethyl acetate=1:1 (v/v)).

Starting Material 6
tert-Butyl (S)-3-(5-amino-2-methylphenyl)-2-((tert-butoxycarbonyl)amino)propanoate (SM-6)

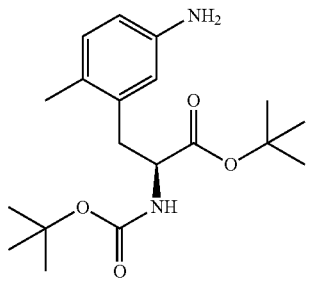

Starting material 6 (SM-6), tert-butyl (S)-3-(5-amino-2-methylphenyl)-2-((tert-butoxycarbonyl)amino)propanoate, was prepared from starting material 3 (SM-3), tert-butyl (R)-2-((tert-butoxycarbonyl)amino)-3-iodopropanoate [CAS No. 1057341-65-7], and commercial 3-iodo-4-methylaniline [CAS No. 35944-64-0] following and adapting well-known literature procedures, e.g., procedures disclosed in US patent publication U.S. Pat. No. 9,783,487 and references cited therein, and described herein (Scheme 3 and Scheme 4).

Commercial 3-iodo-4-methylaniline [CAS No. 35944-64-0](18.8 g, 80.8 mmol) and starting material 3 (SM-3), tert-butyl (R)-2-((tert-butoxycarbonyl)amino)-3-iodopropanoate [CAS No. 1057341-65-7](30.0 g, 80.8 mmol) were cross-coupled through Pd(0)-catalyzed Negishi-coupling using tris(dibenzylideneacetone)dipalladium ($Pd_2(dba)_3$) [CAS No. 51364-51-3](7.40 g, 8.08 mmol) and 2-dicyclohexylphosphino-2',6'-dimethoxybiphenyl (S-Phos) [CAS No. 657408-07-6](3.32 g, 8.08 mmol) in the presence of an excess of zinc dust [CAS No. 7440-66-6](63.4 g, 970 mmol), pre-activated with elemental iodine ($I_2$) [CAS No. 7553-56-2](3.08 g, 12.1 mmol) and trimethylchlorosilane (TMSCl) [CAS No. 75-77-4](1.54 mL, 1.32 g, 12.1 mol) in anhydrous DMF (300 mL+120 mL+100 mL) at 60° C. for overnight under a nitrogen atmosphere. Filtration over Celite®, extractive aqueous workup, and chromatographic purification over silica gel (petroleum ether/ethyl acetate=100:1 to 5:1, (v/v)) yielded tert-butyl (S)-3-(5-amino-2-methylphenyl)-2-((tert-butoxycarbonyl)amino)propanoate (21.0 g, 75%) as a brown oil. The Negishi cross-coupling reaction was repeated twice a) at the 30.0 g (80.8 mmol) scale and b) at the 20 g (53.9 mmol) scale with respect to starting material 3 (SM-3), tert-butyl (R)-2-((tert-butoxycarbonyl)amino)-3-iodopropanoate [CAS No. 1057341-65-7]. The three (3) batches of isolated pure starting material 6 (SM-6) were combined (47 g in total) and analytical data were produced from the combined material 6

(SM-6). TLC: Rf: 0.20 (petroleum ether/ethyl acetate=5:1 (v/v)); LC/MS/UV: Rt: 1.538 min, calculated for $C_{19}H_{30}N_2O_4$ 350.22, found ESI (pos.) m/z=195.15 [M−$C_4H_8$—$CO_2$—$C_4H_8$+H$^+$]$^+$, 701.55 [2M+H$^+$]$^+$; HPLC/UV: Rt: 5.401 min (97.5% AUC at 220 nm); $^1$H NMR (400 MHz, DMSO-$d_6$): δ 7.14 (d, J=8.0 Hz, 1H), 6.75 (d, J=8.0 Hz, 1H), 6.36 (br s, 1H, 6.32 (d, J=8.0 Hz, 1H), 4.70 (br s, 2H), 3.94-3.88 (m, 1H), 2.80-2.75 (m, 1H), 2.75-2.60 (m, 1H), 2.08 (s, 3H), 1.34 (s, 9H), 1.31 (s, 9H); $^1$H NMR (400 MHz, CDCl$_3$): δ 6.89 (d, J=8.0 Hz, 1H), (dd, J=8.8, 2.8 Hz, 1H), 6.44 (d, J=2.5 Hz, 1H), 5.00 (d, J=8.8 Hz, 1H), 4.37 (q, J=7.6 Hz, 1H), 3.27 (br s, 2H), 2.92 (dd, J=13.6, 6.4 Hz, 1H), 2.86 (dd, J=13.6, 7.6 Hz, 1H), 2.20 (s, 3H), 1.38 (s, 9H), 1.35 (s, 9H).

Starting Material 7
3-Iodo-4-isopropyl-aniline (SM-7)

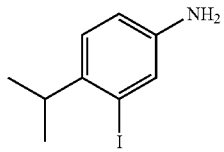

3-Iodo-4-isopropyl-aniline [CAS No. 1369814-96-9] is commercially available. Following a literature procedure, 3-iodo-4-isopropyl-aniline can also be prepared in two steps from commercial 1-isopropyl-4-nitrobenzene [CAS No. 1817-47-6].

The nitro compound, 1-isopropyl-4-nitrobenzene [CAS No. 1817-47-6](80.0 g, 484 mmol) was regioselectively iodinated with powered commercial elemental iodine ($I_2$) [CAS No. 7553-56-2](69.4 g, 273 mmol), commercial potassium iodide (KI) [CAS No. 7681-11-0](76.7 g, 462 mmol), and sodium periodate [CAS No. 7790-28-5](NaIO$_4$) (33.9 g, 159 mmol) in concentrated sulfuric acid ($H_2SO_4$) (~98 wt-%, 800 mL) for 1-2 h at 25° C.-30° C. Careful aqueous work-up in an ice/water mixture and filtration yielded 2-iodo-1-isopropyl-4-nitrobenzene [CAS No. 1100053-97-1](125 g, crude) as a yellow-viscous oil which was used without further isolation and purification procedures in the next step.

2-Iodo-1-isopropyl-4-nitrobenzene is also commercially available [CAS No. 1100053-97-1]. The nitro-group of 2-iodo-1-isopropyl-4-nitrobenzene (35.0 g, 120 mmol) was reduced with sodium borohydride (NaBH$_4$) [CAS No. 16940-66-2](27.3 g, 722 mmol) in the presence of nickel(II) acetate tetrahydrate (Ni(OAc)$_2$ 4H$_2$O) [CAS No. 6018-89-9](4.49 g, 18.0 mmol) in a mixture of MeCN/water (330 mL) (10:1 (v/v)) at 10° C. to room temperature for 2 h. Filtration over Celite®, extractive aqueous work-up, and chromatographic purification over silica gel (petroleum ether/ethyl acetate=50/1 to 5/1 (v/v)) yielded 3-iodo-4-isopropyl-aniline (SM-7) (20.0 g, 64% over two steps) as a yellow solid. TLC: Rf: 0.60 (petroleum ether/ethyl acetate=5:1 (v/v)); $^1$H NMR (400 MHz, CDCl$_3$): δ 7.18 (d, J=2.5 Hz, 1H), 6.98 (d, J=8.3 Hz, 1H), 6.65 (dd, J=8.3, 2.5 Hz, 1H), 3.06 (t, J=6.8 Hz, 1H), 1.16 (d, J=6.8 Hz, 6H).

Starting Material 8
tert-Butyl (S)-3-(5-amino-2-isopropylphenyl)-2-(tert-butoxycarbonylamino)propanoate (SM-8)

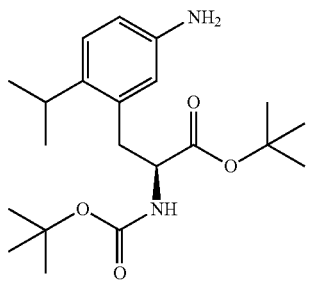

Starting material 8 (SM-8) was synthesized adapting methods well-known in the literature, e.g., procedures disclosed in U.S. Pat. No. 9,783,487 and references cited therein, and described herein (Scheme 4, Scheme 7, and Scheme 9).

Synthetic 3-iodo-4-isopropylaniline [CAS No. 1369814-96-9](45 g, 0.17 mol) and starting material (SM-3), tert-butyl (R)-2-((tert-butoxycarbonyl)amino)-3-iodopropanoate [CAS No. 1057341-65-7] (64.0 g, 0.17 mol) were cross-coupled through Pd(0)-catalyzed Negishi-coupling using tris(dibenzylideneacetone)dipalladium (Pd$_2$(dba)$_3$) [CAS No. 51364-51-3](15.8 g, 17 mmol) and 2-dicyclohexylphosphino-2,6-dimethoxybiphenyl (S-Phos) [CAS No. 657408-07-6](7.1 g, 17 mmol) in the presence of an excess of zinc dust [CAS No. 7440-66-6](135 g, 2.07 mol), pre-activated with powdered elemental iodine [CAS No. 7553-56-2](3.28 g, 26 mmol) and trimethylchlorosilane (TMSCl) [CAS No. 75-77-4](4.5 mL, 3.8 g, 35 mmol) in anhydrous DMF (2×300 mL, 1×200 mL) at 60° C. for overnight under a nitrogen atmosphere. Filtration over Celite®, extractive aqueous work-up, and chromatographic purification over silica gel (petroleum ether/ethyl acetate=100:1 to 10:1, (v/v)) yielded tert-butyl (S)-3-(5-amino-2-isopropylphenyl)-2-(tert-butoxycarbonylamino)propanoate (SM-8) (32 g, 49% yield) as a brown oil. TLC: Rf: 0.25 (petroleum ether/ethyl acetate=5:1, (v/v)); LC/MS/UV: Rt: 1.916 min, calculated for $C_{21}H_{34}N_2O_4$ 378.25, found ESI (pos.) m/z=379.25 [M+H$^+$]$^+$, 757.55 [2M+H$^+$]$^+$; HPLC/UV: Rt: 6.482 min (98.2% AUC at 220 nm, 92.5% at 254 nm); $^1$H NMR (400 MHz, CDCl$_3$): δ 7.05 (d, J=8.4 Hz, 1H), 6.60 (dd, J=8.4, 2.4 Hz, 1H), 6.45 (d, J=2.4 Hz, 1H), 4.97 (d, J=8.8 Hz, 1H), 4.37 (dd, J=15.6, 7.6 Hz, 1H), 3.14-3.04 (m, 1H), 3.00-2.80 (m, 2H), 1.41 (s, 9H), 1.37 (s, 9H), 1.20 (d, J=6.8 Hz, 6H). The $^1$H NMR signal of the aromatic amino group (anilino group) was not observed because of H-D exchange with the moisture in the NMR solvent.

Starting Material 9
tert-Butyl (S)-((tert-butoxycarbonyl)amino)-3-(5-chlorosulfonyl)-2-methylphenyl)propanoate (SM-9)

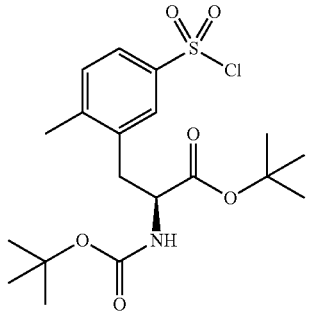

Starting material 9 (SM-9), tert-butyl (S)-2-((tert-butoxycarbonylamino)-3-(5-chlorosulfonyl)-2-methylphenyl)propanoate, was prepared from starting material 6 (SM-6), tert-butyl (S)-3-(5-amino-2-methylphenyl)-2-((tert-butoxycarbonyl)amino)propanoate, in three (3) synthetic steps following well-known literature procedures for the chlorosulfonation of anilines.

Starting material 6 (SM-6), tert-butyl (S)-3-(5-amino-2-methylphenyl)-2-((tert-butoxycarbonyl)amino)propanoate, (30.0 g, 85.6 mmol) was reacted with elemental iodine ($I_2$) [CAS No. 7553-56-2](26.1 g, 103 mmol) and commercial isoamyl nitrite [CAS No. 110-46-3](ONO—$CH_2$—$CH_2$—$CH(CH_3)_2$) (20.0 g, 171 mmol) in anhydrous toluene (300 mL) with warming from 0° C. to 25° C. for overnight. Reductive aqueous work up with a saturated aqueous sodium sulfite ($Na_2SO_3$) solution and chromatographic purification on silica gel (petroleum ether/ethyl acetate=100:1 to 30:1, (v/v)) yielded tert-butyl (S)-2-(tert-butoxycarbonylamino)-3-(5-iodo-2-methylphenyl)propanoate (30 g, crude) which was used without further isolation or purification procedures in the next step.

An aliquot of the material was further purified by chromatographic purification on silica gel (petroleum ether/ethyl acetate=4:1, (v/v)) (see Example 50 (compound (50))). TLC: Rf: 0.65 (petroleum ether/ethyl acetate=4:1, (v/v)); LC/MS: Calculated for $C_{19}H_{28}INO_4$ 461.11, found 375.30 [M−86]$^+$; $^1$H NMR (CDCl$_3$, 400 MHz): δ7.42 (d, J=8.0 Hz, 1H), 7.39 (s, 1H), 6.87 (d, J=8.0 Hz, 1H), 5.04 (d, J=8.5 Hz, 1H), 4.43-4.34 (m, 1H), 2.96-2.88 (2×dd, 2H, superimposed signals), 2.29 (s, 3H), 1.39 (s, 9H), 1.37 (s, 9H).

The aromatic iodide tert-butyl (S)-2-(tert-butoxycarbonylamino)-3-(5-iodo-2-methylphenyl)propanoate (30.0 g, 65.0 mmol) was reacted with commercial benzyl mercaptan (phenylmethanethiol, BnSH) [CAS No. 100-53-8](12.1 g, 98.0 mmol) under Pd(0)-catalysis using tris(dibenzylideneacetone)dipalladium(0) (Pd$_2$(dba)$_3$) [CAS No. 51364-51-3](5.95 g, 6.50 mmol) and 9,9-dimethyl-9H-xanthene-4,5-diyl)bis(diphenylphosphane) (Xantphos®) [CAS No. 161265-03-8](7.53 g, 13.0 mmol) in the presence of diisopropylethylamine (DIEA) [CAS No. 7087-68-5](34.0 mL, 25.2 g, 195 mmol) in toluene (300 mL) at 120° C. for overnight under an atmosphere of nitrogen. Filtration over Celite®, evaporation of volatiles, and chromatographic purification on silica gel (petroleum ether/ethyl acetate=100:1 to 50:1, (v/v)) yielded tert-butyl (S)-3-(5-(benzylthio)-2-methylphenyl)-2-((tert-butoxycarbonyl)amino)propanoate (13.0 g, 44% two steps) as a yellow solid. LC/MS: calculated for $C_{26}H_{35}NO_4S$ 457.23, found ESI (pos.) m/z=480.40 [M+Na$^+$]$^+$; $^1$H NMR (CDCl$_3$, 400 MHz): δ 7.26 (t, J=4.7 Hz, 4H), 7.24-7.19 (m, 1H), 7.06 (d, J=2.4 Hz, 2H), 7.02 (d, J=8.3 Hz, 1H), 4.98 (d, J=8.3 Hz, 1H), 4.39 (q, J=7.4 Hz, 1H), 4.04 (s, 2H), 2.99 (dd, J=14.0, 7.0 Hz, 1H), 2.89 (dd, J=13.9, 7.3 Hz, 1H), 2.30 (s, 3H), 1.37 (2×s, 2×9H).

The benzylic thioether tert-butyl (S)-3-(5-(benzylthio)-2-methylphenyl)-2-((tert-butoxycarbonyl)amino)propanoate (5.0 g, 10.9 mmol) was reacted with commercial chlorination agent 1,3-dichloro-5,5-dimethylhydantoin (Dichlorantin) [CAS No. 118-52-5](6.46 g, 32.8 mmol) in a mixture of MeCN/AcOH/H$_2$O (324 mL, 3:1:1, (v/v/v)) at 0° C. for 15 min. Extractive aqueous work-up with DCM and chromatographic purification on silica gel (petroleum ether/ethyl acetate=100:1 to 50:1 to 10:1, (v/v)) yielded the sulfonyl chloride tert-butyl (S)-2-((tert-butoxycarbonylamino)-3-(5-chlorosulfonyl)-2-methylphenyl)propanoate (SM-9) (3.07 g, 65% yield) as an off-white solid. HPLC/UV: Rt: 6.031 min (100% AUC at 220 nm, 100% AUC at 254 nm); LC/MS/UV: Rt: 2.613 min, calculated for $C_{19}H_{28}ClNO_6S$ 433.13, found ESI (pos.) m/z=451.25 [M+H$_2$O+H$^+$]$^+$, 867.60 [2M+H$^+$]$^+$, 889.55 [2M+Na$^+$]$^+$; $^1$H NMR (400 MHz, CDCl$_3$): δ 7.89 (dd, J=8.0, 2.0 Hz, 1H), 7.75 (br d, J=2.0 Hz, 1H), 7.38 (d, J=8.4 Hz, 1H), 5.12 (d, J=8.0 Hz, 1H), 4.47 (q, J=7.6 Hz, 1H), 3.19 (dd, J=14.0, 6.4 Hz, 1H), 3.01 (dd, J=14.0, 7.2 Hz, 1H), 2.49 (s, 3H), 1.39 (s, 9H), 1.36 (s, 9H).

Starting Material 10
tert-Butyl (S)-2-((tert-butoxycarbonyl)amino)-3-(5-(chlorosulfonly)-2-isopropylpheny)propanoate (SM-10)

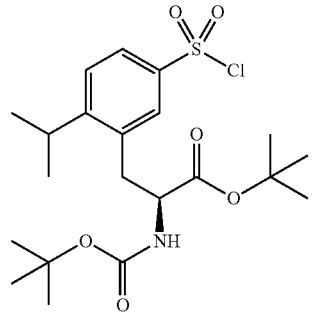

Starting material 10 (SM-10), tert-butyl (S)-2-((tert-butoxycarbonyl)amino)-3-(5-(chlorosulfonyl)-2-isopropylphenyl)propanoate, was prepared from starting material 8 (SM-8), tert-butyl (S)-3-(5-amino-2-isopropylphenyl)-2-(tert-butoxycarbonylamino)propanoate, in three (3) synthetic steps following well-known literature procedures.

Starting material 8 (SM-8), tert-butyl (S)-3-(5-amino-2-isopropylphenyl)-2-(tert-butoxycarbonylamino)propanoate, (29.3 g, 76.6 mmol) was reacted with commercial isoamyl nitrite (ONO—$CH_2$—$CH_2$—$CH(CH_3)_2$) [CAS No. 110-46-3](54.6 g, 460 mmol) in commercial diiodomethane (methylene iodide, $CH_2I2$) [CAS No. 75-11-6](124 g, 460 mmol) initially at 0° C. and then at 65° C. for 3 h. Evaporation of volatiles and chromatographic purification on silica gel (petroleum ether/ethyl acetate=100:1 to 20:1 (v/v)) yielded tert-butyl (S)-2-((tert-butoxycarbonyl)amino)-3-(5-iodo-2-isopropylphenyl)propanoate (20.5 g, 54% yield) as a yellow oil. TLC: Rf: 0.85 (petroleum ether/ethyl acetate=10:1, (v/v)); $^1$H NMR (CDCl$_3$, 400 MHz): δ 7.50 (d, J=8.2 Hz, 1H), 7.37 (d, J=1.9 Hz, 1H), 7.00 (d, J=8.3 Hz, 1H), 5.00 (s, 1H), 4.37 (m, 1H), 3.14 (m, 1H), 2.98 (m, 1H), 1.37 (2×s, 2×9H, superimposed), 1.20 (m, 6H).

The aromatic iodide tert-butyl (S)-2-((tert-butoxycarbonyl)amino)-3-(5-iodo-2-isopropylphenyl)propanoate (20.5 g, 41.9 mmol) was reacted with commercial benzyl mercaptan (phenylmethanethiol, BnSH) [CAS No. 100-53-8] (7.8 g, 63 mmol) under Pd(0)-catalysis using tris(dibenzylideneacetone)dipalladium(0) (Pd$_2$(dba)$_3$) [CAS No. 51364-51-3](3.84 g, 4.2 mmol) and 9,9-dimethyl-9H-xanthene-4,5-diyl)bis(diphenylphosphane (Xantphos®) [CAS No. 161265-03-8](4.85 g, 8.0 mmol) in the presence of N,N-diisopropylethylamine (DIEA) [CAS No. 7085-68-5] (22 mL, 16.3 g, 126 mmol) in toluene (200 mL) at 120° C. for overnight under a nitrogen atmosphere. Filtration over Celite® and chromatographic purification on silica gel (petroleum ether/ethyl acetate=100:1 to 50:1, (v/v)) yielded tert-butyl (S)-3-(5-(benzylthio)-2-isopropylphenyl)-2-((tert-butoxycarbonyl)amino)propanoate (16.2 g, 61% yield) as a yellow solid. LC/MS: calculated for C$_{28}$H$_{39}$NO$_4$S 485.26, found ESI (pos.) m/z=330.20 [M−2×C$_4$H$_8$—CO$_2$+H]$^+$.

The benzylic thioether tert-butyl (S)-3-(5-(benzylthio)-2-isopropylphenyl)-2-((tert-butoxycarbonyl)amino)propanoate (9.6 g, 19.8 mmol) was reacted with commercial chlorination agent 1,3-dichloro-5,5-dimethylhydantoin (Dichlorantin) [CAS No. 118-52-5](11.7 g, 59.3 mmol) in a mixture of MeCN/AcOH/H$_2$O (640 mL, 3:1:1 (v/v/v)) at 0° C. for 15 min. Extractive aqueous workup and chromatographic purification on silica gel (petroleum ether/ethyl acetate=100:1 to 50:1 to 10:1, (v/v)) yielded the sulfonyl chloride tert-butyl (S)-2-((tert-butoxycarbonyl)amino)-3-(5-(chlorosulfonyl)-2-isopropylphenyl)propanoate (SM-10) (7.26 g, 80% yield) as a light-yellow oil. LC/MS/UV: Rt: 2.779 min, calculated for C$_{21}$H$_{32}$ClNO$_6$S 461.16, found ESI (pos.) m/z=347.05 [M−2×C$_4$H$_8$—CO$_2$+MeCN+H]$^+$, 484.20 [M+Na$^+$]$^+$, 945.65 [2M+Na$^+$]$^+$. HPLC/UV: Rt: 6.807 min (100% AUC at 220 nm, 100% AUC at 254 nm); $^1$H NMR (CDCl$_3$, 400 MHz) δ 7.87 (dd, J=8.8, 2.4 Hz, 1H), 7.74 (d, J=2.4 Hz, 1H), 7.52 (dd, J=8.4, 2.0 Hz, 1H), 5.10 (d, J=8.0 Hz, 1H)), 4.45 (q, J=7.6 Hz, 1H), 3.36-3.29 (m, 1H), 3.22 (dd, J=14.0, 6.8 Hz, 1H), 3.12 (dd, J=14.0, 7.2 Hz, 1H), 1.39 (s, 9H), 1.36 (s, 9H), 1.33 (d, J=6.8 Hz, 3H), 1.28 (d, J=6.8 Hz, 3H).

Starting Material 11
3-Iodo-4-methylbenzenesulfonyl Chloride (SM-11)

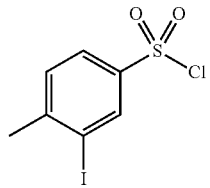

Starting material sulfonyl chloride 11 (SM-11), 3-iodo-4-methyl-benzenesulfonyl chloride (3-iodo-4-methylbenzene-1-sulfonyl chloride, 3-iodo-4-methylbenzenesulfonyl chloride) [CAS No. 953725-14-9] is commercially available.

3-Iodo-4-methyl-benzenesulfonyl chloride [CAS No. 953725-14-9], was also prepared from commercial 3-iodo-4-methylaniline [CAS No. 35944-64-0] under Sandmeyer-type reaction conditions using well-known reaction conditions for chlorosulfonation of anilines.

3-Iodo-4-methylbenzenesulfonyl chloride was also synthesized by reacting a solution of commercial 3-iodo-4-methylaniline [CAS No. 35944-64-0](1.0 g, 4.29 mmol) in a mixture of water (2 mL) and concentrated hydrochloric acid (HCl$_{aq}$) [CAS No. 7647-01-0](~37 wt-%, 12.5 mL) with an aqueous solution of sodium nitrite (NaNO$_2$) [CAS No. 7632-00-0](326 mg, 4.72 mmol) at 0° C. to 5° C. for 30 minutes. The diazonium chloride solution was then added to a suspension of copper(II) chloride (CuCl$_2$) [CAS No. 7447-39-4](29 mg, 0.22 mmol) and copper(I) chloride (CuCl) [CAS No. 7758-89-6](365 mg, 3.69 mmol) in a solution of sulfur dioxide (SO$_2$) in acetic acid (SO$_2$/HOAc) (2 M in HOAc, 10 mL, 20 mmol) at room temperature for 2 h. Extractive aqueous workup from an ice/water mixture and filtration yielded 3-iodo-4-methylbenzenesulfonyl chloride (914 mg, 68% yield) as a gray solid which was directly in subsequent steps without further isolation, purification or characterization. LC/MS/UV: Rt: 3.279 min, calculated for C$_7$H$_6$ClIO$_2$S 315.88, found ESI (pos.) 316.65 [M+H$^+$]$^+$.

Starting Material 12
(S)-2-((tert-Butoxycarbonyl)amino)-3-(5-(chlorophenyl)sulfamoly)-2-methylphenyl)propanoic Acid (SM-12)

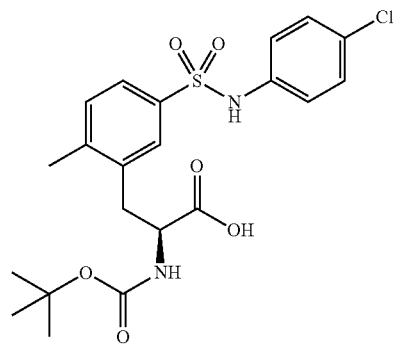

Starting material 12 (SM-12), (S)-2-((tert-butoxycarbonyl)amino)-3-(5-(N-(4-chlorophenyl)sulfamoyl)-2-methylphenyl)propanoic acid, can be prepared from Negishi cross-coupling of commercial starting material 1 (SM-1), methyl (R)-2-((tert-butoxycarbonyl)amino)-3-iodopropanoate [CAS No. 1057341-65-7] and synthetic 3-bromo-N-(4-chlorophenyl)-4-methylbenzenesulfonamide (see Example 51) followed by chemoselective hydrolysis of the methyl ester.

Synthetic 3-bromo-N-(4-chlorophenyl)-4-methylbenzenesulfonamide (see Example 51) (1.0 g, 2.8 mol) and starting material (SM-1), methyl (R)-2-((tert-butoxycarbonyl)amino)-3-iodopropanoate [CAS No. 1057341-65-7](1.1 g, 3.36 mol) were cross-coupled through Pd(0)-catalyzed Negishi-coupling using tris(dibenzylideneacetone)dipalladium (Pd$_2$(dba)$_3$) [CAS No. 51364-51-3](63 mg, 0.07 mmol) and tri(o-tolyl)phosphine (P(o-Tol)$_3$) [CAS No. 6163-58-2](85 mg, 0.28 mmol) in the presence of an excess of zinc dust [CAS No. 7440-66-6](1.3 g, 20.2 mmol), pre-activated with powdered elemental iodine [CAS No. 7553-56-2](128 mg, 0.5 mmol) and trimethylchlorosilane (TMSCl) [CAS No. 75-77-4](63 μL, 54 mg, 0.5 mmol) in DMF (8 mL+5 mL+5 mL) at 60° C. for overnight under a nitrogen atmosphere. Filtration over Celite®, extractive aqueous work-up, and chromatographic purification over silica gel (hexane/ethyl acetate=7:3, (v/v)) yielded methyl (S)-2-((tert-butoxycarbonyl)amino)-3-(5-(N-(4-chlorophenyl)sulfamoyl)-2-methylphenyl)propanoate (709 g, 52% yield) as colorless (white) sticky solid. A second reaction at the same scale yielded methyl (S)-2-((tert-butoxycarbonyl)amino)-3-(5-(N-(4-chlorophenyl)sulfamoyl)-2-methylphenyl)propanoate (800 mg, 59% yield). TLC: Rf: 0.40 (hexane/ethyl acetate=7:3, (v/v)).

The methyl ester group of synthetic methyl (S)-2-((tert-butoxycarbonyl)amino)-3-(5-(N-(4-chlorophenyl)sulfamoyl)-2-methylphenyl)propanoate (1.5 g, 3.3 mmol) was hydrolyzed off with lithium hydroxide monohydrate (LiOH H$_2$O) [CAS No. 1310-66-3] in a mixture of THF and water (20 mL, 3:2, (v/v)) at room temperature for 1 h. Acidic aqueous work-up and evaporation of volatiles yielded (S)-2-((tert-butoxycarbonyl)amino)-3-(5-(N-(4-chlorophenyl) sulfamoyl)-2-methylphenyl)propanoic acid (SM-12) (1.4 g, quant.) as a colorless (white) solid which was used directly in the next steps. Alternatively, starting material 12 (SM-12), (S)-2-((tert-butoxycarbonyl)amino)-3-(5-(N-(4-chlorophenyl)sulfamoyl)-2-methylphenyl)propanoic acid, can also be prepared from compound (52) (Example 52) through N-Boc protection with di-tert-butyl dicarbonate (Boc$_2$O) [CAS No. 24424-99-5] in a mixture of aqueous saturated sodium hydrogen carbonate (NaHCO$_3$)/acetonitrile at room temperature for one (1) to 24 h using reaction conditions well-known in the art.

Starting Material 13
tert-Butyl (R)-3-(5-amino-2-methylphenyl)-2-((tert-butoxycarbonyl) amino)propanoate (SM-13)

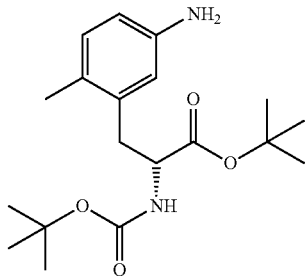

Starting material 13 (SM-13), tert-butyl (R)-3-(5-amino-2-methylphenyl)-2-((tert-butoxycarbonyl)amino)propanoate, was prepared from commercial starting material 4 (SM-4), tert-butyl (S)-2-((tert-butoxycarbonyl)amino)-3-iodopropanoate [CAS No. 170848-34-7], and commercial 3-iodo-4-methylaniline [CAS No. 35944-64-0] following and adapting well-known literature procedures, e.g., procedures disclosed in U.S. Pat. No. 9,783,487 and references cited therein, and described herein (Scheme 3 and Scheme 4).

Commercial 3-iodo-4-methylaniline [CAS No. 35944-64-0](10.0 g, 42.9 mmol) and starting material 4 (SM-4) tert-butyl (S)-2-((tert-butoxycarbonyl)amino)-3-iodopropanoate [CAS No. 170848-34-7] (64.0 g, 0.17 mol) were cross-coupled through Pd(0)-catalyzed Negishi-coupling using tris(dibenzylideneacetone)dipalladium (Pd$_2$(dba)$_3$) [CAS No. 51364-51-3](3.94 g, 4.29 mmol) and 2-dicyclohexylphosphino-2',6'-dimethoxybiphenyl (S-Phos) [CAS No. 657408-07-6](1.77 g, 4.29 mmol) in the presence of an excess of zinc dust [CAS No. 7440-66-6](33.7 g, 516 mmol), pre-activated with elemental iodine (I$_2$) [CAS No. 7553-56-2](820 mg, 6.46 mmol) and trimethylchlorosilane (TMSCl) [CAS No. 75-77-4](1.0 mL, 856 mg, 7.88 mmol) in anhydrous DMF (70 mL+100 mL+70 mL) at 60° C. for overnight under a nitrogen atmosphere. Filtration over Celite®, extractive aqueous workup, and chromatographic purification over silica gel (petroleum ether/ethyl acetate=50:1 to 5:1, (v/v)) yielded tert-butyl (S)-3-(5-amino-2-isopropylphenyl)-2-(tert-butoxycarbonylamino)propanoate (SM-13) (2.8 g, 26% yield) as a yellow oil. TLC: Rf: 0.25 (petroleum ether/ethyl acetate=4:1 (v/v)); LC/MS/UV: Rt: 1.598 min, calculated for C$_{19}$H$_{30}$N$_2$O$_4$ 350.22, found ESI (pos.) m/z=351.20 [M+H$^+$]$^+$, 701.50 [2M+H$^+$]$^+$; HPLC/UV: Rt: 6.924 min (100% AUC at 220 nm, 100% AUC at 254 nm); $^1$H NMR (400 MHz, CDCl$_3$): δ 6.93 (d, J=8.0 Hz, 1H), 6.63-6.38 (m, 2H), 4.99 (d, J=8.4 Hz, 1H), 4.40 (dd, J=7.6, 6.8 Hz, 1H), 2.95 (dd, J=14.0, 6.8 Hz, 1H), 2.87 (dd, J=14.0, 7.6 Hz, 1H), 2.24 (s, 3H). The $^1$H NMR signal of the aromatic amino group (aniline) was not observed because of H-D exchange with moisture in the NMR solvent.

Starting Material 14
tert-Butyl (R)-3-(5-amino-2-isopropylphenyl)-2-((tert-butoxycarbonyl) amino)propanoate (SM-14)

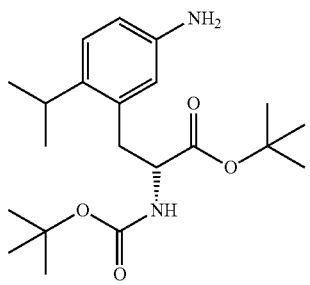

Synthetic starting material 7 (SM-7), 3-iodo-4-isopropylaniline, (366 mg, 1.40 mmol) and starting material 4 (SM-4), tert-butyl (S)-2-((tert-butoxycarbonyl)amino)-3-iodopropanoate [CAS No. 170848-34-7](520 mg, 1.40 mmol) were cross-coupled through Pd(0)-catalyzed Negishi-coupling using tris(dibenzylideneacetone)dipalladium (Pd$_2$(dba)$_3$) [CAS No. 51364-51-3](128 mg, 0.14 mmol) and tri(o-tolyl) phosphine (P(o-Tol)$_3$) [CAS No. 6163-58-2](43 mg, 0.14 mmol) in the presence of an excess of zinc dust [CAS No. 7440-66-6](1.09 g, 16.7 mmol), pre-activated with elemental iodine (I$_2$) [CAS No. 7553-56-2](27 mg, 0.11 mmol) and trimethylchlorosilane (TMSCl) [CAS No. 75-77-4](50 μL, 43 mg, 0.40 mmol) in DMF (10 mL+5 mL+10 mL) at 60° C. for overnight under a nitrogen atmosphere. Filtration over Celite®, evaporation of volatiles, extractive aqueous work-up, and chromatographic purification by prep.-TLC on silica gel (petroleum ether/ethyl acetate=4:1, (v/v)) yielded tert-butyl (R)-3-(5-amino-2-isopropylphenyl)-2-((tert-butoxycarbonyl)amino)propanoate (SM-14) (358 mg, 68% yield) as a yellow solid. TLC: Rf: 0.20 (hexane/ethyl acetate=4:1, (v/v)); LC/MS/UV: Rt: 2.298 min, calculated for C$_{21}$H$_{34}$N$_2$O$_4$ 378.25, found ESI (pos.) m/z=223.20 [M–C$_4$H$_8$—CO$_2$—C$_4$H$_8$+H$^+$]$^+$, 323.30 [M–C$_4$H$_8$+H$^+$]$^+$, 757.85 [2M+H$^+$]$^+$.

SYNTHETIC EXAMPLES

Example 1

(S)-2-Amino-3-(2-(methylsulfonamido)phenyl)propanoic Acid (1)

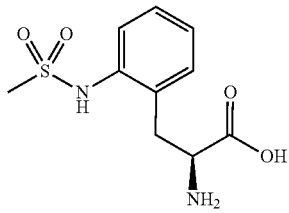

Compound (1) was synthesized by adapting methods described in Scheme 1, Scheme 3, and Scheme 9. Commercial 2-iodoaniline [CAS No. 615-43-0](500 mg, 2.28 mmol) was reacted with an excess of commercial methanesulfonyl chloride (MsCl) [CAS No. 124-63-0](213 μL, 315 mg, 2.74 mmol) in the presence of triethylamine ($Et_3N$, TEA) [CAS No. 121-44-8](476 μL, 346 mg, 3.42 mmol) and 4-N,N-dimethylaminopyridine (DMAP) [CAS No. 1122-58-3](28 mg, 0.23 mmol) in THF (10 mL) at 40° C. for overnight. Evaporation of volatiles, extractive aqueous work-up, and chromatographic purification on silica gel (hexane/ethyl acetate=1:1, (v/v) yielded the di-mesylated derivative N-(2-iodophenyl)-N-methylsulfonyl-methanesulfonamide (520 mg) as a solid. The isolated material contained small amounts of the mono-mesylated material N-(2-iodophenyl)methanesulfonamide [CAS No. 116547-92-3]. TLC: Rf: 0.63 (hexane/ethyl acetate=1:1, (v/v)).

N-(2-Iodophenyl)-N-methylsulfonyl-methanesulfonamide (500 mg, 1.33 mmol) and starting material 1 (SM-1), methyl (R)-2-((tert-butoxycarbonyl)amino)-3-iodopropanoate [CAS No. 93267-04-0](656 mg, 2.0 mmol) were cross-coupled through Pd(0)-catalyzed Negishi-coupling using tris(dibenzylideneacetone)dipalladium ($Pd_2(dba)_3$) [CAS No. 51364-51-3](31 mg, 0.033 mol) and tri(o-tolyl)phosphine [CAS No. 6163-58-2](40 mg, 0.133 mmol) in the presence of an excess of zinc dust [CAS No. 7440-66-6](780 mg, 12 mmol), pre-activated with elemental iodine ($I_2$) [CAS No. 7553-56-2](76 mg, 0.3 mmol) and trimethylchlorosilane (TMSCl) [CAS No. 75-77-4](38 μL, 33 mg, 0.3 mmol) in anhydrous DMF (5 mL+5 mL) at 60° C. for overnight under a nitrogen atmosphere. Filtration over Celite®, extractive aqueous work-up, and chromatographic purification over silica gel (hexane/ethyl acetate=1:1, (v/v)) yielded methyl (S)-2-((tert-butoxycarbonyl)amino)-3-(2-(N-(methylsulfonyl)methylsulfonamido)phenyl)propanoate (305 mg, 51% yield) as an oil. The isolated material contained small amounts of methyl (S)-2-((tert-butoxycarbonyl)amino)-3-(2-(methylsulfonamido)phenyl)propanoate. TLC: Rf: 0.63 (hexane/ethyl acetate=1:1, (v/v)). TLC: Rf: 0.63 (hexane/ethyl acetate=1:1, (v/v)).

The protecting groups of the sulfonamide were removed in two steps (Scheme 9). Chemoselective removal of the N-Boc-protection group of methyl (S)-2-((tert-butoxycarbonyl)amino)-3-(2-(N-(methylsulfonyl)methylsulfonamido)phenyl)propanoate (305 mg, 0.68 mmol) was conducted with 20 vol-% TFA in DCM (5 mL) at room temperature for 1 h. Evaporation of volatiles and hydrolysis of the methyl ester group with LiOH·$H_2O$ [CAS No. 1310-66-3](143 mg, 3.4 mmol) in a THF/water mixture (1:1, (v/v)) (10 mL) at room temperature for 4 h afforded crude compound (1). Evaporation of volatiles, purification by prep. HPLC, and removal of the solvents by lyophilization yielded compound (1) (78 mg, 34% yield) as a colorless (white) solid. LC/MS/UV: Rt: 0.348 min, calculated for $C_{10}H_{14}N_2O_4S$ 258.07, found ESI (pos.) m/z=259.10 $[M+H^+]^-$, ESI (neg.) m/z=256.85 $[M-H^+]^-$, 514.70 $[2M-H^+]^-$; HPLC/UV: Rt: 4.892 min (98.0% AUC at 220 nm, 96.0% AUC at 254 nm); $^1$H NMR (300 MHz, DMSO-$d_6$): δ 7.38-7.26 (m, 2H), 7.25-7.18 (m, 1H), 7.13-7.05 (m, 1H), 3.45 (br t, J=4.5 Hz, 1H), 3.16-3.02 (m, 2H), 2.95 (s, 3H). The $^1$H NMR signals of the amino-group, the N—H acidic group and the carboxyl group were not observed because of H-D exchange with moisture in the NMR solvent.

Example 2

(S)-2-Amino-3-(5-((5-dimethylamino)naphthalene)-1-sulfonamido)-2-methylphenyl)propanoic Acid (2)

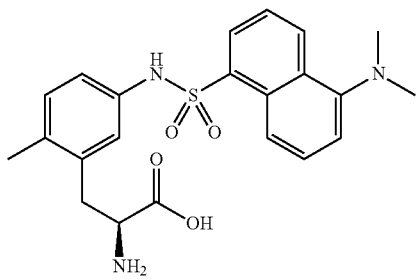

Compound (2) was synthesized by adapting methods described in Scheme 7 and Scheme 9. Commercial 5-(dimethylamino)naphthalene-1-sulfonyl chloride (dansyl chloride) [CAS No. 605-65-2](339 mg, 1.26 mmol) was reacted with aniline starting material 6 (SM-6), tert-butyl (S)-3-(5-amino-2-methylphenyl)-2-((tert-butoxycarbonyl)amino) propanoate, (440 mg, 1.26 mmol) in THF (10 mL) in the presence of triethylamine ($Et_3N$, TEA) [CAS No. 121-44-8](125 μL, 91 mg, 1.26 mmol) and 4-N,N-dimethylpyridine (DMAP) [CAS No. 1122-58-3](15 mg, 0.13 mmol) at room temperature for overnight. Extractive aqueous workup and chromatographic purification on silica gel (hexane/ethyl acetate=1:1, (v/v)) yielded tert-butyl (S)-2-((tert-butoxycarbonyl)amino)-3-(5-((5-(dimethylamino)naphthalene)-1-sulfonamido)-2-methylphenyl)propanoate (750 mg, quant.) as a yellow solid. TLC: R: 0.60 (hexane/ethyl acetate=1:1, (v/v)).

The protecting groups of the sulfonamide were removed in one step (Scheme 9). Global removal of the N-Boc-protecting group and the tert-butyl ester group of tert-butyl (S)-2-((tert-butoxycarbonyl)amino)-3-(5-((5-(dimethylamino)naphthalene)-1-sulfonamido)-2-methylphenyl)propanoate (750 mg, 1.28 mmol) in THF (2-5 mL) was conducted through reaction with commercial 4 M HCl in 1,4-dioxane [CAS No. 7647-01-0](10 mL, 40 mmol) at 40° C. for overnight. Evaporation of volatiles yielded the crude compound (2). Purification by prep. HPLC and removal of the solvents by lyophilization yielded compound (2) (300 mg, 55% yield) as a yellow solid. LC/MS/UV: Rt: 0.875 min, calculated for $C_{22}H_{25}N_3O_4S$ 427.16, ESI (pos.) m/z=428.00 $[M+H^+]^+$, 854.70 $[2M+H^+]^+$, ESI (neg.) m/z=425.95 $[M-H^+]^-$; HPLC/UV: Rt: 7.158 min (95.2% AUC at 254 nm); $^1$H NMR (300 MHz, $CD_3OD$): δ 8.47 (d, J=8.1 Hz, 1H), 8.41 (d, J=9.0 Hz, 1H), 8.18 (dd, J=6.9, 1.2 Hz, 1H), 7.57 (dd, J=8.7, 7.5 Hz, 1H), 7.46 (dd, J=8.7, 7.5

Hz, 1H), 7.22 (d, J=7.5 Hz, 1H), 6.98 (d, J=2.4 Hz, 1H), 6.91 (d, J=9.0 Hz, 1H), 6.75 (dd, J=8.1, 1.8 Hz, 1H), 3.79 (dd, J=9.3, 6.0 Hz, 1H), 3.23 (dd, J=14.7, 5.1 Hz, 1H), 2.84 (dd, J=14.7, 9.3 Hz, superimposed), 2.82 (s, 6H, superimposed), 2.19 (s, 3H). The $^1$H NMR signals of the amino-group, the N—H acidic group, and the carboxyl group were not observed because of H-D exchange with the NMR solvent.

Example 3

(S)-2-Amino-3-(3-((5-dimethylamino)naphthalene)-1-sulfonamido)phenyl)propanoic Acid (3)

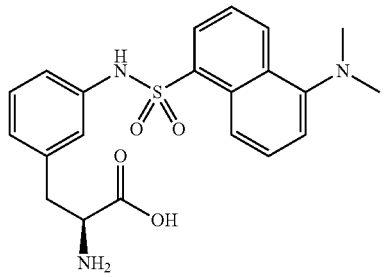

Compound (3) was synthesized by adapting methods described in Scheme 4, Scheme 7, and Scheme 9. Commercial 3-iodoaniline [CAS No. 626-01-7](1.0 g, 4.6 mmol) and starting material 3 (SM-3), tert-butyl (R)-2-((tert-butoxycarbonyl)amino)-3-iodopropanoate [CAS No. 1057341-65-7] (1.86 g, 5.0 mmol, 1.0 eq.) were cross-coupled through Pd(0)-catalyzed Negishi-coupling using tris(dibenzylideneacetone)dipalladium (Pd$_2$(dba)$_3$) [CAS No. 51364-51-3] (105 mg, 0.11 mol) and tri(o-tolyl)phosphine [CAS No. 6163-58-2](140 mg, 0.46 mmol) in the presence of an excess of zinc dust [CAS No. 7440-66-6](1.96 g, 30 mmol), pre-activated with elemental iodine (I$_2$) [CAS No. 7553-56-2] (191 mg, 0.75 mmol) and trimethylchlorosilane (TMSCl) [CAS No. 75-77-4](95 μL, 82 mg, 0.75 mmol) in anhydrous DMF (10 mL+5 mL) at 60° C. for overnight under a nitrogen atmosphere. Filtration over Celite®, extractive aqueous work-up, and chromatographic purification over silica gel (hexane/ethyl acetate=1:1, (v/v)) yielded tert-butyl (S)-3-(3-aminophenyl)-2-((tert-butoxycarbonyl)amino)propanoate (1.1 g, 71% yield). TLC: Rf: 0.66 (hexane/ethyl acetate=1:1, (v/v)).

Commercial 5-(dimethylamino)naphthalene-1-sulfonyl chloride (dansyl chloride) [CAS No. 605-65-2](80 mg, 0.3 mmol) was reacted with aniline coupling product tert-butyl (S)-3-(3-aminophenyl)-2-((tert-butoxycarbonyl)amino)propanoate (100 mg, 0.3 mmol, 1.0 eq.) in THF (5 mL) in the presence of triethylamine (Et$_3$N, TEA) [CAS No. 121-44-8](42 μL, 31 mg, 0.3 mmol, 1.0 eq.) and 4-N,N-dimethylpyridine (DMAP) [CAS No. 1122-58-3](4 mg, 0.03 mmol, 0.1 eq.) at room temperature for 4 h. Extractive aqueous workup and chromatographic purification on silica gel (hexane/ethyl acetate=7:3, (v/v)) yielded tert-butyl (S)-2-((tert-butoxycarbonyl)amino)-3-(3-((5-(dimethylamino) naphthalene)-1-sulfonamido)phenyl)propanoate (150 mg, 88% yield) as a yellow solid. TLC: R: 0.88 (hexane/ethyl acetate=1:1, (v/v)).

The protecting groups of the sulfonamide were removed in one step (Scheme 9). Global removal of the N-Boc-protecting group and the tert-butyl ester group of tert-butyl (S)-2-((tert-butoxycarbonyl)amino)-3-(3-((5-(dimethylamino)naphthalene)-1-sulfonamido)phenyl)propanoate (150 mg, 0.26 mmol) in a small amount of 1,4-dioxane was conducted through reaction with an excess of commercial 4 M HCl in 1,4-dioxane [CAS No. 7647-01-0] at 40° C. for overnight. Evaporation of volatiles yielded crude compound (3). Purification by prep. HPLC and removal of the solvents by lyophilization yielded compound (3) (75 mg, 69% yield) as a pale yellow solid. LC/MS/UV: Rt: 0.862 min, calculated for C$_{21}$H$_{23}$N$_3$O$_4$S 413.14, ESI (pos.): m/z=414.00 [M+H$^+$]$^+$, ESI (neg.) m/z=411.80 [M−H$^{+-}$; HPLC/UV: Rt: 6.840 min (93.4% AUC at 220, 97.3% AUC at 254 nm); $^1$H NMR (300 MHz, CD$_3$OD): δ 8.51 (d, J=8.1 Hz, 1H), 8.41 (d, J=8.7 Hz, 1H), 8.24 (d, J=7.2 Hz, 1H), 7.59 (t, J=7.5 Hz, 1H), 7.51 (t, J=8.1 Hz, 1H), 7.25 (d, J=7.2 Hz, 1H), 7.09 (t, J=7.8 Hz, 1H), 7.02 (br s, 1H), 6.95-6.86 (m, 2H), 3.75-3.65 (m, 1H), 3.16 (dd, J=14.7, 3.6 Hz, 1H), 2.92-2.80 (m, 2×3H, 1×1H, superimposed). The $^1$H NMR signal of the amino-group, the N—H acidic group and the carboxyl group were not observed because of H-D exchange with the NMR solvent.

Example 4

(S)-2-Amino-3-(4-((5-dimethylamino)naphthalene)-1-sulfonamido)phenyl)propanoic Acid (4)

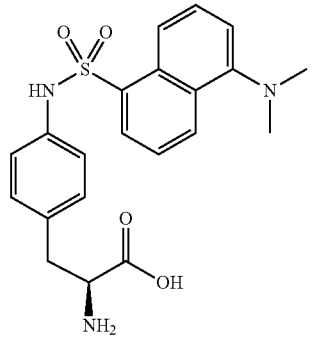

Compound (4) was synthesized by adapting methods described in Scheme 4, Scheme 7, and Scheme 9. Commercial 4-iodoaniline [CAS No. 540-37-4](220 mg, 1.0 mmol) and starting material 1 (SM-1), methyl (R)-2-(tert-butoxycarbonylamino)-3-iodopropanoate, [CAS No. 93267-04-0] (395 mg, 1.2 mmol, 1.0 eq.) were cross-coupled through Pd(0)-catalyzed Negishi-coupling using tris(dibenzylideneacetone)dipalladium (Pd$_2$(dba)$_3$) [CAS No. 51364-51-3] (23 mg, 0.025 mol) and tri(o-tolyl)phosphine [CAS No. 6163-58-2](30 mg, 0.1 mmol) in the presence of an excess of zinc dust [CAS No. 7440-66-6](468 mg, 7.2 mmol), pre-activated with elemental iodine (I$_2$) [CAS No. 7553-56-2](46 mg, 0.18 mmol) and trimethylchlorosilane (TMSCl) [CAS No. 75-77-4](23 μL, 20 mg, 0.18 mmol) in anhydrous DMF (5 mL+2 mL) at 60° C. for overnight under a nitrogen atmosphere. Filtration over Celite®, extractive aqueous work-up, and chromatographic purification over silica gel (hexane/ethyl acetate=1:1, (v/v)) yielded methyl (S)-3-(4-aminophenyl)-2-((tert-butoxycarbonyl)amino)propanoate (190 mg, 65% yield). TLC: Rf: 0.40 (hexane/ethyl acetate=1:1, (v/v)).

Commercial 5-(dimethylamino)naphthalene-1-sulfonyl chloride (dansyl chloride) [CAS No. 605-65-2](174 mg, 0.65 mmol) was reacted with aniline coupling product methyl (S)-3-(4-aminophenyl)-2-((tert-butoxycarbonyl) amino)propanoate (190 mg, 0.65 mmol) in THF (5 mL) in the presence of triethylamine (Et₃N, TEA) [CAS No. 121-44-8](90 µL, 65 mg, 0.65 mmol) and 4-N,N-dimethylpyridine (DMAP) [CAS No. 1122-58-3](8 mg, 0.07 mmol) at room temperature for 2 h. Extractive aqueous workup yielded crude methyl (S)-2-((tert-butoxycarbonyl)amino)-3-(4-((5-(dimethylamino)naphthalene)-1-sulfonamido)phenyl)propanoate (310 mg, crude) which was directly deprotected without further isolation and characterization.

The protecting groups of the sulfonamide were removed in two steps (Scheme 9). Chemoselective removal of the N-Boc-protection group of methyl (S)-2-((tert-butoxycarbonyl)amino)-3-(4-((5-(dimethylamino)naphthalene)-1-sulfonamido)phenyl)propanoate (310 mg crude, max. 0.59 mmol) was conducted with 20 vol-% TFA in DCM (5 mL) at room temperature for 1 h. Evaporation of volatiles and hydrolysis of the methyl ester group was conducted with lithium hydroxide hydrate (LiOH·H₂O) [CAS No. 1310-66-3](123 mg, 2.94 mmol) in a THF/water mixture (1:1, (v/v)) (10 mL) at room temperature for 2 h. Evaporation of volatiles afforded crude compound (4). Purification by prep. HPLC and removal of the solvents by lyophilization yielded compound (4) as a yellow solid (120 mg, 49% yield). LC/MS/UV: Rt: 0.847 min, calculated for $C_{21}H_{23}N_3O_4S$ 413.14, ESI (pos.) m/z=414.00 [M+H⁺]⁺, 826.75 [2M+H⁺]⁺, ESI (neg.) m/z=411.80 [M−H⁺]⁻, 824.55 [2M−H⁺]⁻; HPLC/UV: Rt: 7.134 min (93.6% AUC at 220 nm, 94.2% AUC at 254 nm); ¹H NMR (300 MHz, CD₃OD): δ 8.49 (d, J=8.7 Hz, 1H), 8.40 (d, J=9.0 Hz, 1H), 8.22 (dd, J=6.9, 1.2 Hz, 1H), 7.64-7.54 (m, 1H), 7.50-7.44 (m, 1H), 7.24 (d, J=7.8 Hz, 1H), 7.10-7.03 (m, 2H), 7.03-6.96 (m, 2H), 3.63 (dd, J=8.4, 4.2 Hz, 1H), 3.12 (dd, J=14.7, 4.2 Hz, 1H), 2.89-2.80 (m, 1H superimposed), 2.86-2.78 (br m, 6H, superimposed). The ¹H NMR signals of the amino-group, the N—H acidic group, and the carboxyl group were not observed because of H-D exchange with the NMR solvent.

Example 5

(S)-2-Amino-3-(5-((5-dimethylamino)naphthalene)-1-sulfonamido)-2-methoxyphenyl)propanoic Acid (5)

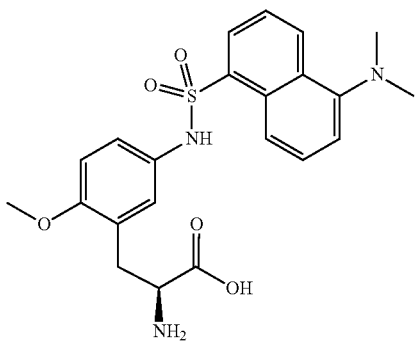

Compound (5) was synthesized by adapting methods described in Scheme 4, Scheme 7, and Scheme 9. Commercial 3-iodo-4-methoxy-aniline [CAS No. 74587-12-5](3.5 g, 14.2 mmol) and tert-butyl (R)-2-((tert-butoxycarbonyl)amino)-3-iodopropanoate (SM-3) [CAS No. 1057341-65-7] (5.0 g, 13.5 mmol) were cross-coupled through Pd(0)-catalyzed Negishi-coupling using tris(dibenzylideneacetone)dipalladium (Pd₂(dba)₃) [CAS No. 51364-51-3](618 mg, 0.68 mol) and tri(o-tolyl)phosphine [CAS No. 6163-58-2](410 mg, 1.35 mmol) in the presence of an excess of zinc dust [CAS No. 7440-66-6](5.3 g, 81 mmol), pre-activated with elemental iodine (I₂) [CAS No. 7553-56-2](510 mg, 2.0 mmol) and trimethylchlorosilane (TMSCl) [CAS No. 75-77-4](257 µL, 220 mg, 2.0 mmol) in anhydrous DMF (27 mL+10 mL+10 mL) at 60° C. for 1 h under a nitrogen atmosphere. Filtration over Celite® and extractive aqueous work-up yielded tert-butyl (S)-3-(5-amino-2-methoxyphenyl)-2-((tert-butoxycarbonyl)amino) propanoate (1.5 g, crude). Chromatographic purification by prep.-HPLC and removal of the solvents by lyophilization yielded the compound (780 mg, 16% yield) as a red brown oil. TLC: Rf: 0.30 (petroleum ether/ethyl acetate=3:1, (v/v)); LC/MS/UV: Rt: 1.450 min, calculated for $C_{19}H_{30}N_2O_5$ 366.22, found ESI (pos.) m/z=367.20 [M+H⁺]⁺, 733.55 [2M+H⁺]⁺; HPLC/UV: Rf: 5.554 min (94.6% AUC at 220 nm); ¹H NMR (400 MHz, DMSO-d₆): δ 6.96 (d, J=8.0 Hz, 1H), 6.63 (d, J=7.6 Hz, 1H), 6.38 (d, J=8.8 Hz, 1H), 6.35 (br s, 1H), 4.51 (br s, 2H), 4.01 (dd, J=7.2, 1.6 Hz, 1H), 3.64 (s, 3H), 2.75 (dd, J=14.0, 1.6 Hz, 1H), 2.63 (dd, J=14.0, 7.2 Hz, 1H), 1.33 (s, 9H, 1.27 (s, 9H).

The aniline starting material tert-butyl (S)-3-(5-amino-2-methoxyphenyl)-2-((tert-butoxycarbonyl)amino)propanoate (120 mg, 0.33 mmol) in THF (3 mL) was reacted with commercial 5-(dimethylamino)naphthalene-1-sulfonyl chloride (dansyl chloride) [CAS No. 605-65-2](132 mg, 0.82 mmol) in the presence of triethylamine (Et₃N, TEA) [CAS No. 121-44-8](91 µL, 66 mg, 0.65 mmol) and 4-N,N-dimethylaminopyridine (DMAP) [CAS No. 1122-58-3](4 mg, 0.03 mmol) at room temperature for overnight under a nitrogen atmosphere. Evaporation of volatiles and purification by prep-TLC on silica gel (petroleum ether/ethyl acetate=2:1, (v/v)) yielded tert-butyl (S)-2-((tert-butoxycarbonyl)amino)-3-(5-((5-(dimethylamino)naphthalene)-1-sulfonamido)-2-methoxyphenyl)propanoate (150 mg, 76% yield) as a yellow solid. TLC: Rf: 0.45 (petroleum ether/ethyl acetate=2:1, (v/v)); LC/MS/UV: Rt: 3.090 min, calculated for $C_{31}H_{41}N_3O_7S$ 599.27, found ESI (pos.) m/z=444.20 [M−C₄H₈−CO₂−C₄H₈+H⁺]⁺, 600.70 [M+H⁺]⁺, ESI (neg.) m/z=598.45 [M−H⁺]⁻.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-((5-(dimethylamino)naphthalene)-1-sulfonamido)-2-methoxyphenyl)propanoate (150 mg, 0.25 mmol) was conducted through reaction with 50 vol-% TFA in DCM (4 mL) at room temperature for overnight. Evaporation of volatiles afforded crude compound (5). Purification by prep. HPLC and removal of the solvents by lyophilization yielded compound (5) (64 mg, 58% yield) as a light yellow solid. LC/MS/UV: Rt: 1.972 min, calculated for $C_{22}H_{25}N_3O_5S$ 443.15, found ESI (pos.) m/z=444.20 [M+H⁺]⁺, 887.60 [2M+H⁺]⁺, ESI (neg.) m/z=442.10 [M−H⁺]⁻, 885.65 [2M−H⁺]⁻; HPLC/UV: Rt: 5.077 min (100% AUC at 220 nm, 100% AUC at 254 nm); ¹H NMR (400 MHz, CD₃OD): δ 9.02 (d, J=8.4 Hz, 1H), 8.61 (d, J=8.8 Hz, 1H), 8.35 (d, J=7.2 Hz, 1H), 8.17 (d, J=7.2 Hz, 1H), 7.91 (t, J=8.8 Hz, 1H), 7.84 (dd, J=8.8, 7.2 Hz, 1H), 7.07 (d, J=2.4 Hz, 1H), 6.80-6.71 (m, 2H), 5.14 (br. t, J=6.8 Hz, 1H), 3.76 (s, 3H), 3.52 (s, 6H), 3.21 (dd, J=14.0, 6.0 Hz, 1H), 2.99 (dd, J=14.0, 7.2 Hz, 1H). The ¹H NMR signals of the amino group, the N—H acidic group, and the carboxyl group were not observed because of H-D exchange with the NMR solvent.

Example 6

(S)-2-Amino-3-(2-methyl-5-(naphthalene-1-sulfonamido)phenyl)propanoic Acid (6)

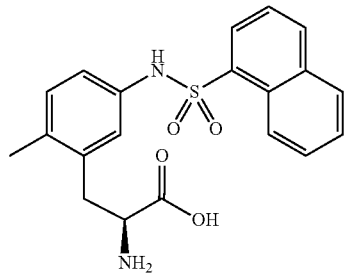

Compound (6) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (150 mg, 0.43 mmol) in DCM (3 mL) was reacted with commercial naphthalene-1-sulfonyl chloride [CAS No. 85-46-1](146 mg, 0.64 mmol) in the presence of triethylamine ($Et_3N$, TEA) [CAS No. 121-44-8](120 µL, 87 mg, 0.86 mmol) and 4-N,N-dimethylaminopyridine (DMAP) [CAS No. 1122-58-3](5 mg, 0.04 mmol) at room temperature for overnight under a nitrogen atmosphere. Evaporation of volatiles and purification by prep.-TLC on silica gel (petroleum ether/ethyl acetate=2:1, (v/v)) yielded tert-butyl (S)-2-((tert-butoxycarbonyl)amino)-3-(2-methyl-5-(naphthalene-1-sulfonamido)phenyl)propanoate (150 mg, 65% yield) as a yellow solid. TLC: Rf: 0.45 (petroleum ether/ethyl acetate=2:1, (v/v)); LC/MS/UV: Rt: 3.244 min, calculated for $C_{29}H_{36}N_2O_6S$ 540.23, found ESI (pos.) m/z=385.10 [M–$C_4H_8$—$CO_2$—$C_4H_8$+H$^+$]$^+$, 541.25 [M+H$^+$]$^+$, ESI (neg.) m/z=539.35 [M–H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(naphthalene-1-sulfonamido)phenyl)propanoate (150 mg, 0.28 mmol) was conducted through reaction with 50 vol-% TFA in DCM (4 mL) at room temperature for overnight. Evaporation of volatiles afforded crude compound (6). Purification by prep. HPLC and removal of the solvents by lyophilization yielded compound (6) (28 mg, 26% yield) as a light yellow solid. LC/MS/UV: Rt: 2.010 min, calculated for $C_{20}H_{20}N_2O_4S$ 384.11, found ESI (pos.) m/z=385.10 [M+H$^+$]$^+$, 767.55 [2M+H$^+$]$^+$, ESI (neg.) m/z=383.05 [M–H$^+$]$^-$, 767.55 [2M–H$^+$]$^-$; HPLC/UV: Rt: 5.744 min (99.4% AUC at 220 nm, 99.4% AUC at 254 nm); $^1$H NMR (400 MHz, $CD_3OD$): δ 8.73 (d, J=8.8 Hz, 1H), 8.17 (d, J=8.4 Hz, 1H), 8.08 (d, J=8.4 Hz, 1H), 7.96 (d, J=8.0 Hz, 1H), 7.69 (t, J=8.4 Hz, 1H), 7.60 (t, J=8.4 Hz, 1H), 7.49 (t, J=7.6 Hz, 1H), 7.00 (d, J=2.0 Hz, 1H), 6.92 (d, J=8.0 Hz, 1H), 6.71 (dd, J=8.0, 2.0 Hz, 1H), 3.97 (br t, J=8.0 Hz, 1H), 3.20 (dd, J=14.4, 6.4 Hz, 1H), 2.92 (dd, J=14.4, 8.4 Hz, 1H), 2.19 (s, 3H). The $^1$H NMR signals of the amino group, the N—H acidic group, and the carboxyl group were not observed because of H-D exchange with the NMR solvent.

Example 7

(S)-2-Amino-3-(2-methyl-5-((4-methylphenyl)sulfonamido)phenyl)propanoic Acid (7)

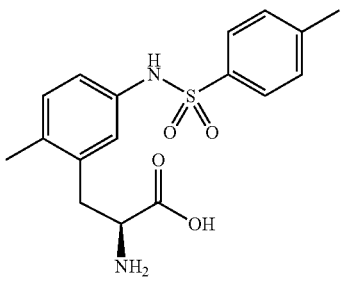

Compound (7) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (150 mg, 0.43 mmol) in DCM (3 mL) was reacted with commercial 4-methylbenzenesulfonyl chloride (tosylchloride, TsCl) [CAS No. 51419-59-1](122 mg, 0.64 mmol) in the presence of triethylamine ($Et_3N$, TEA) [CAS No. 121-44-8](120 µL, 87 mg, 0.86 mmol) and 4-N,N-dimethylaminopyridine (DMAP) [CAS No. 1122-58-3](5 mg, 0.04 mmol) at room temperature for overnight under a nitrogen atmosphere. Evaporation of volatiles and purification by prep-TLC on silica gel (petroleum ether/ethyl acetate=2:1, (v/v)) yielded tert-butyl (S)-2-((tert-butoxycarbonyl)amino)-3-(2-methyl-5-((4-methylphenyl)sulfonamido)phenyl)propanoate (90 mg, 42% yield) as a light yellow solid. TLC: Rf: 0.50 (petroleum ether/ethyl acetate=2:1, (v/v)); LC/MS/UV: Rt: 2.957 min, calculated for $C_{26}H_{36}N_2O_6S$ 504.23, found ESI (pos.) m/z=349.10 [M–$C_4H_8$—$CO_2$—$C_4H_8$+H$^+$]$^+$, 527.30 [M+Na$^+$]$^+$, ESI (neg.) m/z=503.25 [M–H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-((4-methylphenyl)sulfonamido)phenyl)propanoate (90 mg, 0.18 mmol) was conducted through reaction with 50 vol-% TFA in DCM (4 mL) at room temperature for overnight. Evaporation of volatiles afforded crude compound (7). Purification by prep. HPLC and removal of the solvents by lyophilization yielded compound (7) (18 mg, 29% yield) as a light yellow solid. LC/MS/UV: Rt: 1.984 min, calculated for $C_{17}H_{20}N_2O_4S$ 348.11, found ESI (pos.) m/z=349.10 [M+H$^+$]$^+$, 697.45 [2M+H$^+$]$^+$, ESI (neg.) m/z=347.05 [M–H$^+$]$^-$, 695.40 [2M–H$^+$]$^-$; HPLC/UV: Rt: 5.486 min (100% AUC at 220 nm, 100% AUC at 254 nm); $^1$H NMR (400 MHz, $CD_3OD$): δ 7.61 (d, J=8.4 Hz, 2H), 7.26 (d, J=8.0 Hz, 2H), 7.07 (d, J=2.0 Hz, 1H), 7.03 (d, J=8.4 Hz, 1H), 6.83 (dd, J=8.0, 2.4 Hz, 1H), 4.06 (br. t, J=6.8 Hz, 1H), 3.27 (dd, J=14.4, 6.8 Hz, 1H), 3.01 (dd, J=14.4, 8.4 Hz, 1H), 2.35 (s, 3H), 2.27 (s, 3H). The $^1$H NMR signals of the amino group, the N—H acidic group, and the carboxyl group were not observed because of H-D exchange with the NMR solvent.

Example 8

(S)-2-Amino-3-(4-((5-dimethylamino)naphthalene)-1-sulfonamido)-2-methoxyphenyl)propanoic Acid (8)

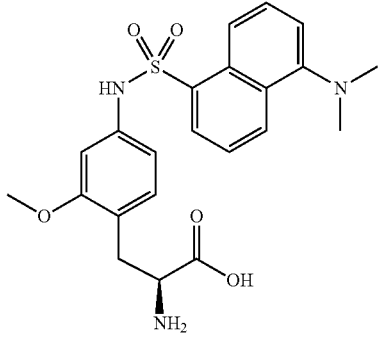

Compound (8) was synthesized by adapting methods described in Scheme 4, Scheme 7, and Scheme 9. Commercial 1-iodo-2-methoxy-4-nitrobenzene [CAS No. 5458-84-4](4.5 g, 16.1 mmol) and starting material 3 (SM-3), tert-butyl (R)-2-((tert-butoxycarbonyl)amino)-3-iodopropanoate, [CAS No. 1057341-65-7](5.7 g, 15.4 mmol) were cross-coupled through Pd(0)-catalyzed Negishi-coupling using tris(dibenzylideneacetone)dipalladium (Pd$_2$(dba)$_3$) [CAS No. 51364-51-3](703 mg, 0.77 mol) and tri(o-tolyl)phosphine [CAS No. 6163-58-2](469 mg, 1.54 mmol) in the presence of an excess of zinc dust [CAS No. 7440-66-6](6.02 g, 92 mmol), pre-activated with elemental iodine (I$_2$) [CAS No. 7553-56-2](585 mg, 2.3 mmol) and trimethylchlorosilane (TMSCl) [CAS No. 75-77-4](291 µL, 249 mg, 2.3 mmol) in anhydrous DMF (30 mL+10 mL+10 mL) at 60° C. for 1 h under a nitrogen atmosphere. Filtration over Celite®, extractive aqueous work-up, and chromatographic purification on silica gel (petroleum ether/ethyl acetate=5:1, (v/v)) yielded tert-butyl (S)-2-((tert-butoxycarbonyl)amino)-3-(2-methoxy-4-nitrophenyl)propanoate (2.4 g, 39% yield). TLC: Rf: 0.30 (hexane/ethyl acetate=5:1, (v/v)); $^1$H NMR (400 MHz, DMSO-d$_6$): δ 7.77 (dd, J=8.4, 2.4 Hz, 1H), 7.71 (d, J=2.0 Hz, 1H), 7.38 (d, J=8.0 Hz, 1H), 7.19 (d, J=8.4 Hz, 1H), 4.12 (dd, J=14.4, 9.2 Hz, 1H), 3.92 (s, 3H), 3.06 (dd, 1H), 2.84 (dd, 1H), 1.32 (s, 9H), 1.28 (s, 9H).

Following well-known synthetic procedures for the reduction of aromatic nitro groups to the corresponding aniline, tert-butyl (S)-2-((tert-butoxycarbonyl)amino)-3-(2-methoxy-4-nitrophenyl)propanoate (2.4 g, 6.06 mmol) in methanol (60 mL) was hydrogenated under a hydrogen atmosphere (15 psi) in the presence of palladium on carbon (Pd(C)) [CAS No. 7440-05-03](250 mg) at 40° C. for 4 h. Filtration over Celite®, evaporation of volatiles, and chromatographic purification on silica gel with petroleum ether/ethyl acetate mixtures yielded impure tert-butyl (S)-3-(4-amino-2-methoxyphenyl)-2-((tert-butoxycarbonyl)amino)propanoate. Further purification by prep.-HPLC and removal of the solvents by lyophilization yielded the aniline (580 mg, 26% yield) as a slightly yellow oil. LC/MS/UV: Rf: 1.644 min, calculated for C$_{19}$H$_{30}$N$_2$O$_5$ 366.22, found (ESI (pos.) 211.10 [M–C$_4$H$_8$–CO$_2$–C$_4$H$_8$+H$^+$]$^+$, 367.20 [M+H$^+$]$^+$; HPLC/UV: Rt: 6.994 min (97.9% AUC at 220 nm, 100% AUC at 254 nm); $^1$H NMR (400 MHz, DMSO-d$_6$): δ 6.88 (d, J=8.0 Hz, 1H), 6.70 (d, J=8.0 Hz, 1H), 6.16 (d, J=2.0 Hz, 1H), 6.00 (dd, J=8.8, 2.4 Hz, 1H), 4.92 (br s, 2H), 3.94 (dd, J=15.2, 7.6 Hz, 1H), 3.67 (s, 3H), 2.74 (dd, J=13.6, 6.4 Hz, 1H), 2.55 (dd, J=13.6, 8.8 Hz, 1H), 1.33 (s, 9H), 1.29 (s, 9H).

The aniline tert-butyl (S)-3-(4-amino-2-methoxyphenyl)-2-((tert-butoxycarbonyl)amino)propanoate (60 mg, 0.16 mmol) in DCM (2 mL) was reacted with commercial 5-(dimethylamino)naphthalene-1-sulfonyl chloride (dansyl chloride) [CAS No. 605-65-2](66 mg, 0.24 mmol) in the presence of triethylamine (Et$_3$N, TEA) [CAS No. 121-44-8](45 µL, 33 mg, 0.33 mmol) and 4-N,N-dimethylamino-pyridine (DMAP) [CAS No. 1122-58-3](2 mg, 0.02 mmol) at room temperature for overnight under a nitrogen atmosphere. Evaporation of volatiles and purification by prep-TLC on silica gel (petroleum ether/ethyl acetate=10:1, (v/v)) yielded tert-butyl (S)-2-((tert-butoxycarbonyl)amino)-3-(4-((5-(dimethylamino)naphthalene)-1-sulfonamido)-2-methoxyphenyl)propanoate (114 mg, impure) as a light yellow solid. TLC: Rf: 0.50 (petroleum ether/ethyl acetate=10:1, (v/v)); LC/MS/UV: Rt: 2.830 min, calculated for C$_{31}$H$_{41}$N$_3$O$_7$S 599.27, found ESI (pos.) m/z=600.65 [M+H$^+$]$^+$, ESI (neg.) m/z=598.70 [M–H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(4-((5-(dimethylamino)naphthalene)-1-sulfonamido)-2-methoxyphenyl)propanoate (110 mg impure, max. 0.18 mmol) was conducted through reaction with 50 vol-% TFA in DCM (4 mL) at room temperature for overnight. Evaporation of volatiles afforded crude compound (8). Purification by prep. HPLC and removal of the solvents by lyophilization yielded compound (8) (64 mg, 78% yield) as a light yellow solid. LC/MS/UV: Rt: 1.784 min, calculated for C$_{22}$H$_{25}$N$_3$O$_5$S 443.15, found ESI (pos.) m/z=444.25 [M+H$^+$]$^+$, 466.25 [M+Na$^+$]$^+$, 887.25 [2M+H$^+$]$^+$, ESI (neg.) m/z=442.25 [M–H$^+$]$^-$; HPLC/UV: Rt: 4.506 min (100% AUC at 220 nm, 100% AUC at 254 nm); H NMR (400 MHz, CD$_3$OD): δ 8.91 (d, J=8.4 Hz, 1H), 8.55 (d, J=8.8 Hz, 1H), 8.44 (d, J=8.4 Hz, 1H), 7.99 (d, J=7.6 Hz, 1H), 7.88-7.78 (m, 2H), 6.92 (d, J=8.4 Hz, 1H), 6.73 (d, J=2.0 Hz, 1H), 6.55 (dd, J=8.0, 2.0 Hz, 1H), 4.08 (dd, J=7.6, 5.6 Hz, 1H), 3.72 (s, 3H), 3.38 (s, 6H), 3.16 (dd, J=14.4, 5.6 Hz, 1H), 2.89 (d, J=14.4, 7.6 Hz, 1H). The $^1$H NMR signals of the amino group, the N—H acidic group, and the carboxyl group were not observed because of H-D exchange with the NMR solvent.

Example 9

(S)-2-Amino-3-(2-methyl-5-(quinoline-5-sulfonamido)phenyl)propanoic Acid (9)

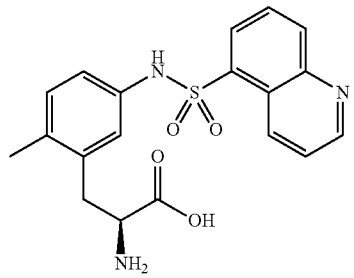

Quinoline-5-sulfonyl chloride was prepared from commercial 5-aminoquinoline under Sandmeyer-type reaction conditions using well-known reaction conditions for chlorosulfonation of anilines. 5-Aminoquinoline [CAS No. 611-34-7](1.0 g, 6.94 mmol) was converted to the corresponding diazonium chloride with an aqueous solution of sodium nitrite (NaNO$_2$) [CAS No. 7632-00-0](575 mg, 8.33 mmol) (0.5 mL) in a mixture of concentrated hydrochloric acid (HCl$_{aq}$) [CAS No. 7647-01-0] and water (25 mL) (1:1, v/v) at 0° C. for 30 min. A suspension of copper(II) chloride dihydrate (CuCl$_2$·2H$_2$O) [CAS No. 10125-13-0](590 mg, 3.47 mmol) and copper(I) chloride (CuCl) [CAS No. 7758-89-6](34 mg, 0.35 mmol) in SO$_2$/HOAc solution (3 M in HOAc, 10 mL, 30 mmol) was added to the diazonium salt and the reaction mixture was stirred for 2 h at room temperature. Filtration and evaporation of volatiles yielded crude quinoline-5-sulfonyl chloride which was directly used in the next step without further isolation and characterization. Quinoline-5-sulfonyl chloride is also commercially available [CAS No. 102878-84-2]. LC/MS/UV: Rt: 2.252 min, calculated for C$_9$H$_6$ClNO$_2$S 226.98, found ESI (pos.) m/z=228.05 [M+H$^+$]$^+$.

Compound (9) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (150 mg, 0.43 mmol) in DCM (2 mL) was reacted with synthetic quinoline-5-sulfonyl chloride [CAS No. 102878-84-2](117 mg, 0.51 mmol) in the presence of triethylamine (Et$_3$N, TEA) [CAS No. 121-44-8](120 µL, 87 mg, 0.86 mmol) and 4-N,N-dimethylaminopyridine (DMAP) [CAS No. 1122-58-3](5 mg, 0.04 mmol) at room temperature for overnight under a nitrogen atmosphere. Evaporation of volatiles and purification by prep-TLC on silica gel (petroleum ether/ethyl acetate=2:1, (v/v)) yielded tert-butyl (S)-2-((tert-butoxycarbonyl)amino)-3-(2-methyl-5-(quinoline-5-sulfonamido)phenyl)propanoate (100 mg, 43% yield) as a yellow solid. TLC: Rf: 0.45 (petroleum ether/ethyl acetate=2:1, (v/v)); LC/MS/UV: Rt: 2.672 min, calculated for C$_{28}$H$_{35}$N$_3$O$_6$S 541.22, found ESI (pos.) m/z=542.30 [M+H$^+$]$^+$, ESI (neg.) m/z=540.2 [M−H$^+$]$^−$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(quinoline-5-sulfonamido)phenyl)propanoate (100 mg, 0.18 mmol, 1.0 eq.) was conducted through reaction with 50 vol-% TFA in DCM (4 mL) at room temperature for overnight. Evaporation of volatiles afforded crude compound (9). Purification by prep. HPLC and removal of the solvents by lyophilization yielded compound (9) (51 mg, 82% yield) as a yellow solid. LC/MS/UV: Rt: 1.630 min, calculated for C$_{19}$H$_{19}$N$_3$O$_4$S 385.11, found ESI (pos.) m/z=386.10 [M+H$^+$]$^+$ ESI (neg.) m/z=384.05 [M−H$^+$]$^−$, 769.55 [2M−H$^+$]$^−$; HPLC/UV: Rt: 4.347 min (100% AUC at 220 nm, 100% AUC at 254 nm); $^1$H NMR (400 MHz, CD$_3$OD): δ 9.16 (d, J=7.6 Hz, 1H), 8.95 (dd, J=4.4, 1.6 Hz, 1H), 8.30-8.15 (m, H), 7.78 (dd, J=8.8, 7.6 Hz, 1H), 7.66 (dd, J=8.8, 4.4 Hz, 1H), 7.03 (d, J=2.4 Hz, 1H), 6.93 (d, J=8.4 Hz, 1H), 6.65 (dd, J=8.0, 2.4 Hz, 1H), 3.92 (dd, J=8.0, 7.2 Hz, 1H), 3.14 (dd, J=14.4, 7.2 Hz, 1H), 2.88 (dd, J=14.4, 7.6 Hz, 1H), 2.14 (s, 3H). The $^1$H NMR signals of the amino group, the N—H acidic group, and the carboxyl group were not observed because of H-D exchange with the NMR solvent.

Example 10

(S)-2-Amino-3-(2-methyl-5-(phenylsulfonamido)phenyl)propanoic Acid (10)

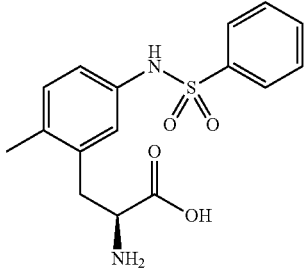

Compound (10) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (150 mg, 0.43 mmol) in DCM (2 mL) was reacted with commercial benzenesulfonyl chloride [CAS No. 98-09-9](83 mg, 0.47 mmol) in the presence of pyridine (69 µL, 68 mg, 0.86 mmol) for overnight at room temperature under a nitrogen atmosphere. Extractive aqueous workup and purification by prep.-TLC on silica gel (petroleum ether/ethyl acetate=2:1, (v/v)) yielded tert-butyl (S)-2-((tert-butoxycarbonyl)amino)-3-(2-methyl-5-(phenylsulfonamido)phenyl)propanoate (110 mg, 52% yield) as a yellow solid. TLC: Rf: 0.42 (petroleum ether/ethyl acetate=2:1, (v/v)); LC/MS/UV: Rt: 2.652 min, calculated for C$_{25}$H$_{34}$N$_2$O$_6$S 490.21, found ESI (pos.) m/z=513.55 [M+Na$^+$]$^+$, ESI (neg.) m/z=489.45 [M−H$^+$]$^−$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(phenylsulfonamido)phenyl)propanoate (110 mg, 0.22 mmol) was conducted through reaction with 50 vol-% TFA in DCM (4 mL) at room temperature for overnight. Evaporation of volatiles afforded crude compound (10). Purification by prep. HPLC and removal of the solvents by lyophilization yielded compound (10) (35 mg, 48% yield) as a colorless (white) solid. LC/MS/UV: Rt: 1.728 min, calculated for C$_{16}$H$_{18}$N$_2$O$_4$S 334.10, found ESI (pos.) m/z=335.15 [M+H$^+$]$^+$, 376.20 [M+H++MeCN]$^+$, 669.50 [2M+H$^+$]$^+$, ESI (neg.) m/z=333.05 [M−H$^+$]$^−$, 667.35 [2M−H$^+$]$^−$; HPLC/UV: Rt: 5.288 min (100% AUC at 220 nm, 100% AUC at 254 nm); $^1$H NMR (400 MHz, DMSO-d$_6$): δ 7.78-7.72 (m, 2H), 7.62-7.58 (m, 1H), 7.56-7.45 (m, 2H), 7.06-7.00 (br m, 1H), 6.96 (d, J=8.4 Hz, 1H), 6.82-6.76 (br m, 1H), 3.31 (dd, J=6.0, 4.4 Hz, 1H), 3.09 (dd, J=14.4, 5.2 Hz, 1H), 2.68 (dd, J=14.0, 8.0 Hz, 1H), 2.17 (s, 3H). The $^1$H NMR signals of the amino group, the N—H acidic group, and the carboxyl group were not observed because of H-D exchange with moisture in the NMR solvent.

Example 11

(S)-2-Amino-3-(2-methyl-5-(pyridine-3-sulfonamido)phenyl)propanoic Acid (11)

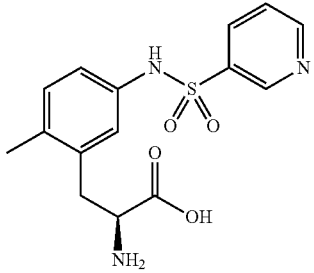

Compound (11) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (200 mg, 0.57 mmol) in THF (3 mL) was reacted with commercial pyridine-3-sulfonyl chloride [CAS No. 16133-25-8](152 mg, 0.86 mmol) in the presence of triethylamine ($Et_3N$, TEA) [CAS No. 121-44-8](158 μL, 115 mg, 1.14 mmol) and 4-N,N-dimethylaminopyridine (DMAP) [CAS No. 1122-58-3](6 mg, 0.06 mmol) at room temperature for overnight under a nitrogen atmosphere. Evaporation of volatiles and purification by prep.-TLC on silica gel (petroleum ether/ethyl acetate=2:1, (v/v)) yielded tert-butyl (S)-2-((tert-butoxycarbonyl)amino)-3-(2-methyl-5-(pyridine-3-sulfonamido)phenyl)propanoate (160 mg, 71% yield) as a yellow solid. TLC: Rf: 0.45 (petroleum ether/ethyl acetate=2:1, (v/v)); LC/MS/UV: Rt: 2.904 min, calculated for $C_{24}H_{33}N_3O_6S$ 491.21, found ESI (pos.) m/z=492.25 $[M+H^+]^+$, ESI (neg.) m/z=490.20 $[M-H^+]^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(pyridine-3-sulfonamido)phenyl)propanoate (160 mg, 0.32 mmol) was conducted through reaction with 50 vol-% TFA in DCM (4 mL) at room temperature for overnight. Evaporation of volatiles afforded crude compound (11). Purification by prep. HPLC and removal of the solvents by lyophilization yielded compound (11) (51 mg, 46% yield) as a light yellow solid. LC/MS/UV: Rt: 1.471 min, calculated for $C_{15}H_{17}N_3O_4S$ 335.09, found ESI (pos.) m/z=336.10 $[M+H^+]^+$, ESI (neg.) m/z=334.00 $[M-H^+]^-$, 669.35 $[2M-H^+]^-$; HPLC/UV: Rt: 4.084 min (100% AUC at 220 nm, 100% AUC at 254 nm); $^1H$ NMR (400 MHz, $CD_3OD$): δ 9.10 (d, J=2.4 Hz, 1H), 8.98 (d, J=5.6 Hz, 1H), 8.66 (ddd, J=8.0 Hz, 2.4, 1.6 Hz, 1H), 8.07 (ddd, J=8.4, 5.6, 0.8 Hz, 1H), 7.16 (d, J=2.0 Hz, 1H), 7.13 (d, J=8.0 Hz, 1H), 4.09 (t, J=7.2 Hz, 1H), 3.26 (dd, J=14.4, 7.6 Hz, 1H), 3.10 (dd, J=14.4, 7.6 Hz, 1H), 2.30 (s, 3H). The $^1H$ NMR signals of the amino group, the N—H acidic group, and the carboxyl group were not observed because of H-D exchange with the NMR solvent.

Example 12

(S)-2-Amino-3-(2-methyl-5-((tetrahydro-2H-pyran)-4-sulfonamido)phenyl)propanoic Acid (12)

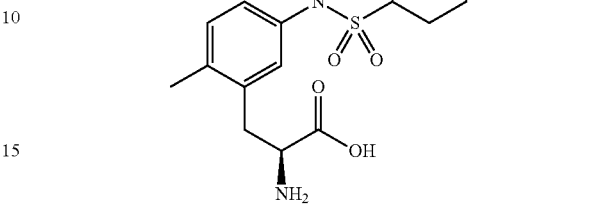

Compound (12) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (150 mg, 0.43 mmol) in DCM (6 mL) was reacted with commercial tetrahydro-2H-pyran-4-sulfonyl chloride [CAS No. 338453-21-7](135 mg, 0.73 mmol) in the presence of pyridine [CAS No. 110-86-1](78 μL, 77 mg, 0.97 mmol) at room temperature for overnight under a nitrogen atmosphere. Evaporation of volatiles and purification by prep.-TLC on silica gel (petroleum ether/ethyl acetate=3:1, (v/v)) yielded tert-butyl (S)-2-((tert-butoxycarbonyl)amino)-3-(2-methyl-5-((tetrahydro-2H-pyran)-4-sulfonamido)phenyl)propanoate (120 mg, 56% yield) as a yellow solid. TLC: Rf: 0.20 (petroleum ether/ethyl acetate=2:1, (v/v)); LC/MS/UV: Rt: 2.700 min, calculated for $C_{24}H_{38}N_2O_7S$ 498.24, found ESI (pos.) m/z=499.25 $[M+H^+]^+$, ESI (neg.) m/z=497.25 $[M-H^+]^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-((tetrahydro-2H-pyran)-4-sulfonamido)phenyl)propanoate (120 mg, 0.24 mmol, 1.0 eq.) was conducted through reaction with 50 vol-% TFA in DCM (8 mL) at room temperature for 5 h. Evaporation of volatiles afforded crude compound (12). Purification by prep. HPLC and removal of the solvents by lyophilization yielded compound (12) (13 mg, 15% yield) as a yellow solid. LC/MS/UV: Rt: 1.397 min, calculated for $C_{15}H_{22}N_2O_5S$ 342.12, found ESI (pos.) m/z=343.10 $[M+H^+]^+$, 684.45 $[2M+H^+]^+$, ESI (neg.) m/z=341.05 $[M-H^+]^-$, 683.45 $[2M-H^+]^-$; HPLC/UV: Rt: 4.748 min (100% AUC at 220 nm, 100% AUC at 254 nm); $^1H$ NMR (400 MHz, $CD_3OD$): δ 7.17 (d, J=2.4 Hz, 1H), 7.16 (br s, 1H), 7.07 (dd, J=8.4, 2.4 Hz, 1H), 4.04 (dd, J=8.0, 6.4 Hz, 1H), 3.97 (br dd, J=12.0, 3.2 Hz, 2H), 3.38-3.29 (m, 3H, superimposed with $^1H$ NMR signal of NMR solvent), 3.27-3.25 (m, 1H, superimposed with H NMR signal of NMR solvent), 3.03 (dd, J=14.4, 8.0 Hz, 1H), 2.33 (s, 3H), 1.96-1.90 (m, 2H), 1.88-1.75 (m, 2H). The $^1H$ NMR signals of the amino group, the N—H acidic group, and the carboxyl group were not observed because of H-D exchange with the NMR solvent.

Example 13

(S)-3-(5-((4-Acetamidonaphthalene)-1-sulfonamido)-2-methylphenyl)-2-aminopropanoic Acid (13)

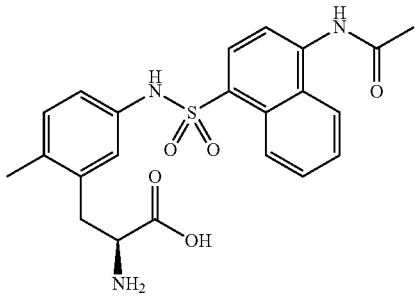

4-Acetamidonaphthalene-1-sulfonyl chloride [CAS No. 5690-20-4] is commercially available. Following well-known literature procedures, 4-acetamidonaphthalene-1-sulfonyl chloride was prepared from commercial 4-aminonaphthalene-1-sulfonic acid [CAS No. 84-86-5](500 mg, 8.96 mmol). The sulfonic acid in methanol (7 mL) was converted to its sodium salt with sodium methanolate (sodium methoxide, NaOMe) [CAS No. 124-41-4](484 mg, 8.96 mmol, in MeOH (0.45 mL)) at room temperature with sonication for 2 h. Filtration and subsequent N-acetylation with an excess of acetic anhydride ($Ac_2O$) [CAS No. 108-24-7](10 mL) at 110° C. for 2 h yielded crude sodium 4-acetamidonaphthalene-1-sulfonate. Evaporation of volatiles yielded crude 4-acetamidonaphthalene-1-sulfonic acid (500 mg) as a colorless (white) solid that was used directly in the next step. LC/MS/UV: Rt: 1.074, calculated for $C_{12}H_{11}NO_4S$ 265.04, found ESI (pos.) m/z=266.00 $[M+H^+]^+$, 531.15 $[2M+H^+]^+$, ESI (neg.) m/z=264.00 $[M-H^+]^-$, 529.00 $[2M-H^+]^-$.

4-Acetamidonaphthalene-1-sulfonic acid (500 mg, 1.88 mmol) in chlorosulfonic acid ($HClO_3S$) [CAS No. 7790-94-5](2.5 mL) was reacted for 0.5 h at 0° C. and 2 h at room temperature. Aqueous workup with ice-water, filtration, and removal of residual solvent under reduced pressure yielded crude 4-acetamidonaphthalene-1-sulfonyl chloride (300 mg) as a colorless (white) solid which was used directly in the next step. LC/MS/UV: Rt: min, calculated for $C_{12}H_{10}ClNO_3S$ 283.01, found ESI (pos.) m/z=325.00 $[M+MeCN+H^+]^+$, ESI (neg.)=281.95 $[M-H^+]^-$.

Compound (13) was synthesized by adapting methods described in Scheme 7 and Scheme 9. Starting material 6 (SM-6), tert-butyl (S)-3-(5-amino-2-methylphenyl)-2-((tert-butoxycarbonyl)amino)propanoate, (150 mg, 0.43 mmol) in THF (3 mL) was reacted with synthetic crude 4-acetamidonaphthalene-1-sulfonyl chloride (145 mg, 0.51 mmol) in the presence of triethylamine ($Et_3N$, TEA) [CAS No. 121-44-8](119 µL, 86 m, 0.86 mmol) at room temperature for overnight. Evaporation of volatiles and purification by prep.-TLC on silica gel (petroleum ether/ethyl acetate=2:1, (v/v)) yielded tert-butyl (S)-3-(5-((4-acetamidonaphthalene)-1-sulfonamido)-2-methylphenyl)-2-((tert-butoxycarbonyl)amino)propanoate (200 mg, 79% yield) as a yellow solid. TLC: Rf: 0.50 (petroleum ether/ethyl acetate=2:1, (v/v)); LC/MS/UV: Rt: 2.604 min, calculated for $C_{31}H_{39}N_3O_7S$ 597.25, found ESI (pos.) m/z=598.35 $[M+H^+]^+$, ESI (neg.) m/z=596.45 $[M-H^+]^-$.

The protecting groups of the sulfonamide were removed in one step (Scheme 9). Global removal of the N-Boc-protection group and the tert-butyl ester group of tert-butyl (S)-3-(5-((4-acetamidonaphthalene)-1-sulfonamido)-2-methylphenyl)-2-((tert-butoxycarbonyl)amino)propanoate (200 mg, 0.33 mmol) was conducted through reaction with 50 vol-% TFA in DCM (4 mL) at room temperature for overnight. Evaporation of volatiles afforded crude compound (13). Purification by prep. HPLC and removal of the solvents by lyophilization yielded compound (13) (81 mg, 56% yield) as a colorless (white) solid. LC/MS/UV: Rt: 1.650 min, calculated for $C_{22}H_{23}N_3O_5S$ 441.14, found ESI (pos.) m/z=442.20 $[M+H^+]^+$, 883.60 $[2M+H^+]^+$, ESI (neg.) m/z=440.10 $[M-H^+]^-$, 881.70 $[2M-H^+]^-$; HPLC/UV: Rt: 5.273 min (100% AUC at 220 nm, 100% AUC at 254 nm); $^1$H NMR (400 MHz, DMSO-$d_6$): δ 10.52 (br s, 1H), 10.20 (s, 1H), 8.73 (d, J=8.0 Hz, 1H), 8.28 (d, J=8.0 Hz, 1H), 8.17 (d, J=7.6 Hz, 1H), 7.92 (d, J=8.0 Hz, 1H), 7.70-7.64 (m, 2H), 6.99 (d, J=2.0 Hz, 1H), 6.90 (d, J=8.4 Hz, 1H), 6.73 (dd, J=8.4, 2.4 Hz, 1H), 3.72 (br t, J=7.6 Hz, 1H), 3.34 (br. s, 2H), 2.99 (dd, J=14.0, 7.2 Hz, 1H), 2.81 (dd, J=14.4, 7.6 Hz, 1H), 2.12 (s, 3H), 2.10 (s, 3H). The $^1$H NMR signal the carboxyl group was not observed because of H-D exchange with moisture in the NMR solvent.

Example 14

(S)-2-Amino-3-(5-(cyclopropanesulfonamido)-2-methylphenyl)propanoic Acid (14)

Compound (14) was synthesized by adapting methods described in Scheme 7 and Scheme 9. The aniline starting material 6 (SM-6) tert-butyl (S)-3-(5-amino-2-methylphenyl)-2-((tert-butoxycarbonyl)amino)propanoate, (150 mg, 0.43 mmol) in DCM (3 mL) was reacted with commercial cyclopropanesulfonyl chloride [CAS No. 139631-62-2](66 mg, 0.47 mmol) in the presence of triethylamine ($Et_3N$, TEA) [CAS No. 121-44-8](117 µL, 87 mg, 0.86 mmol) at room temperature for 3 d under a nitrogen atmosphere. Evaporation of volatiles and purification by prep.-TLC on silica gel (petroleum ether/ethyl acetate=2:1, (v/v)) yielded tert-butyl (S)-2-((tert-butoxycarbonyl)amino)-3-(5-(cyclopropanesulfonamido)-2-methylphenyl)propanoate (90 mg, 46% yield) as a light yellow solid. TLC: Rf: 0.38 (petroleum ether/ethyl acetate=2:1, (v/v)); LC/MS/UV: Rt: 2.700 min, calculated for $C_{22}H_{34}N_2O_6S$ 454.21, found ESI (pos.) m/z=456.40 $[M+2^+]^+$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(cyclopropanesulfonamido)-2-methylphenyl)propanoate (90 mg, 0.20 mmol) was conducted through reaction with 50 vol-% TFA in DCM (4 mL) at room temperature for overnight. Evaporation of volatiles afforded crude compound (14). Purification by prep. HPLC and removal of the solvents by lyophilization yielded compound (14) (26 mg, 44% yield) as a yellow solid. LC/MS/UV: Rt: 1.376 min, calculated for $C_{13}H_{18}N_2O_4S$ 298.10, found ESI (pos.) m/z=299.10 [M+H$^+$]$^+$; ESI (neg.) m/z=297.00 [M–H$^+$]$^-$, 595.30 [2M–H$^+$]$^-$; HPLC/UV: Rt: 4.735 min (100% AUC at 220 nm, 100% AUC at 254 nm); $^1$H NMR (400 MHz, DMSO-d$_6$): δ 9.54 (s, 1H), 7.15-7.05 (m, 2H), 7.01 (dd, J=8.0, 2.0 Hz, 1H), 3.86 (t, J=7.2 Hz, 1H), 3.50-3.25 (br s, 2H), 3.08 (dd, J=14.4, 7.2 Hz, 1H), 2.95 (dd, J=14.4, 7.6 Hz, 1H), 2.58 (quintet, J=6.4 Hz, 1H), 2.25 (s, 3H), 0.94-0.85 (m, 4H). The $^1$H NMR signal of the carboxyl group was not observed because of H-D exchange with (moisture in) the NMR solvent.

Example 15

(S)-2-Amino-3-(2-chloro-5-((5-(dimethylamino)naphthalene)-1-sulfonamido)phenyl)propanoic Acid (15)

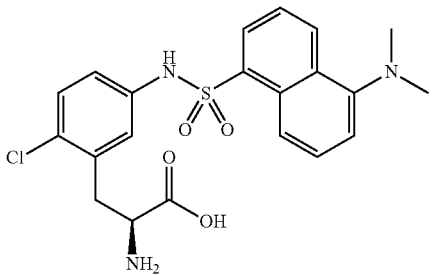

Compound (15) was synthesized by adapting methods described in Scheme 4, Scheme 7, and Scheme 9. Commercial 4-chloro-3-iodoaniline [CAS No. 573764-31-5](1.9 g, 7.5 mmol) and starting material 1 (SM-1), methyl (R)-2-((tert-butoxycarbonyl)amino)-3-iodopropanoate [CAS No. 93267-04-0](2.0 g, 6.0 mmol) were cross-coupled through Pd(0)-catalyzed Negishi-coupling using tris(dibenzylideneacetone)dipalladium (Pd$_2$(dba)$_3$) [CAS No. 51364-51-3] (556 mg, 0.6 mol) and tri(o-tolyl)phosphine [CAS No. 6163-58-2](250 mg, 0.82 mmol) in the presence of an excess of zinc dust [CAS No. 7440-66-6](4.76 g, 72.8 mmol), pre-activated with elemental iodine (I$_2$) [CAS No. 7553-56-2](106 mg, 0.42 mmol) and trimethylchlorosilane (TMSCl) [CAS No. 75-77-4](58 µL, 50 mg, 0.46 mmol) in DMF (20 mL+10 mL+10 mL) at 60° C. for overnight. Filtration over Celite®, extractive aqueous work-up, and chromatographic purification over silica gel (petroleum ether/ethyl acetate=100:1 to 5:1, (v/v)) yielded methyl (S)-3-(5-amino-2-chlorophenyl)-2-((tert-butoxycarbonyl)amino)propanoate (690 mg, 36% yield) as a colorless (white) solid. TLC: Rf: 0.30 (petroleum ether/ethyl acetate=3:1, (v/v)); LC/MS: calculated for $C_{15}H_{21}ClN_2O_4$ 328.12, found ESI (pos.) m/z=229.10 [M–C$_4$H$_8$—CO$_2$+H$^+$]$^+$.

Commercial 5-(dimethylamino)naphthalene-1-sulfonyl chloride (dansyl chloride) [CAS No. 605-65-2](812 mg, 3.02 mmol) was reacted with synthesized aniline methyl (S)-3-(5-amino-2-chlorophenyl)-2-((tert-butoxycarbonyl) amino)propanoate (660 mg, 2.01 mmol) in DCM (5 mL) in the presence of triethylamine (Et$_3$N, TEA) [CAS No. 121-44-8](560 µL, 406 mg, 4.02 mmol) and 4-N,N-dimethylpyridine (DMAP) [CAS No. 1122-58-3](44 mg, 0.3 mmol) at room temperature for overnight. Evaporation of volatiles, extractive aqueous workup, and chromatographic purification on silica gel (petroleum ether/ethyl acetate=3:1, (v/v)) yielded methyl (S)-2-((tert-butoxycarbonyl)amino)-3-(2-chloro-5-((5-(dimethylamino)naphthalene)-1-sulfonamido)phenyl)propanoate (380 mg, 34% yield) as a colorless (white) solid. TLC: R: 0.25 (petroleum ether/ethyl acetate=2:1, (v/v)).

The protecting groups of the sulfonamide were removed in two steps (Scheme 9). Chemoselective removal of the N-Boc-protection group of methyl (S)-2-((tert-butoxycarbonyl)amino)-3-(2-chloro-5-((5-(dimethylamino)naphthalene)-1-sulfonamido)phenyl)propanoate (380 mg, 0.68 mmol) was conducted with 50 vol-% TFA in DCM (32 mL) at room temperature for 2 h. Evaporation of volatiles yielded methyl (S)-2-amino-3-(2-chloro-5-((5-(dimethylamino) naphthalene)-1-sulfonamido)phenyl)propanoate (500 mg, crude) as a yellow solid which was used directly in the next step. Hydrolysis of the methyl ester group of methyl (S)-2-amino-3-(2-chloro-5-((5-(dimethylamino)naphthalene)-1-sulfonamido)phenyl)propanoate (500 mg, crude) was conducted with a 5 wt-% aq. solution of LiOH·H$_2$O [CAS No. 1310-66-3](10 mL) in THF (14 mL) at room temperature for 2 h. Extractive acidic aqueous workup and evaporation of volatiles yielded crude compound (15). Purification by prep. HPLC and removal of the solvents by lyophilization yielded pure compound (15) as a yellow solid (16 mg, 3% yield). LC/MS/UV: Rt: 1.751 min, calculated for $C_{21}H_{22}ClN_3O_4S$ 447.10, ESI (pos.) m/z=470.10 [M+Na$^+$]$^+$, ESI (neg.) m/z=446.05 [M–H$^+$]$^-$, 895.20 [2M–H$^+$]$^-$; HPLC/UV: Rt: 5.288 min (100% AUC at 220 nm, 100% AUC at 254 nm); $^1$H NMR (400 MHz, CD$_3$OD): δ 8.50 (d, J=8.4 Hz, 1H), 8.38 (d, J=8.4 Hz, 1H), 8.21 (dd, J=6.8, 1.2 Hz, 1H), 7.59 (dd, J=8.4, 7.6 Hz, 1H), 7.50 (dd, J=8.4, 7.2 Hz, 1H), 7.27 (d, J=7.6 Hz, 1H), 7.16 (dd, J=4.8, 2.4 Hz, 2H), 6.83 (dd, J=8.8, 2.8 Hz, 1H), 4.09 (dd, J=7.6, 6.8 Hz, 1H), 3.36-3.26 (m, 1H, superimposed with $^1$H NMR signal of the NMR solvent), 3.04 (dd, J=14.0, 8.0 Hz, 1H), 2.86 (s, 6H). The $^1$H NMR signals of the amino-group, the N—H-acidic group, and the carboxyl group were not observed because of H-D exchange with the NMR solvent.

Example 16

(S)-2-Amino-3-(5-((5-(dimethylamino)-N-methylnaphthalene)-1-sulfonamido)-2-methylphenyl)propanoic Acid (16)

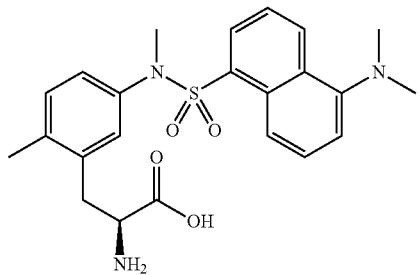

3-Iodo-N,4-dimethylaniline [CAS No. 1260814-07-0] is commercially available. Following well-known literature procedures, 3-iodo-N,4-dimethylaniline was prepared from commercial 3-iodo-4-methylaniline [CAS No. 35944-64-0] through N-monomethylation of 3-iodo-4-methylaniline (3.0 g, 12.9 mmol, 1.0 eq.) with iodomethane (methyliodide, MeI) [CAS No. 74-88-4](1.83 g, 12.9 mmol) in the presence of potassium carbonate (K$_2$CO$_3$) [CAS No. 584-08-7](3.5 g, 25.7 mmol) at 50° C. for 8 h in anhydrous DMF. Filtration, evaporation of volatiles, and chromatographic purification on silica gel (petroleum ether/ethyl acetate=50:1 to 20:1, (v/v)) yielded 3-iodo-N,4-dimethylaniline (1.13 g, 35% yield) as a yellow oil. TLC: Rf=0.50 (petroleum ether/ethyl acetate=10:1, (v/v)); LC/MS/UV: Rt: 2.163 min, calculated for $C_8H_{10}IN$ 246.99, found ESI (pos.) m/z=248.05 $[M+H^+]^+$; $^1H$ NMR (400 MHz, $CDCl_3$): δ 7.10-7.07 (m, 1H), 7.01 (dd, J=8.0, 1.6 Hz, 1H), 6.56-6.50 (m, 1H), 2.78 (s, 3H), 2.32 (s, 3H).

Synthetic 3-iodo-N,4-dimethylaniline [CAS No. 1260814-07-0](976 mg, 3.03 mmol) and starting material 1 (SM-1), methyl (R)-2-((tert-butoxycarbonyl)amino)-3-iodo-propanoate [CAS No. 93267-04-0](1.0 g, 3.03 mmol) were cross-coupled through Pd(0)-catalyzed Negishi-coupling using tris(dibenzylideneacetone)dipalladium ($Pd_2(dba)_3$) [CAS No. 51364-51-3](278 mg, 0.3 mmol) and tri(o-tolyl) phosphine [CAS No. 6163-58-2](93 mg, 0.30 mmol) in the presence of an excess of zinc dust [CAS No. 7440-66-6] (2.38 g, 36.4 mmol), pre-activated with elemental iodine ($I_2$) [CAS No. 7553-56-2](58 mg, 0.23 mmol) and trimethyl-chlorosilane (TMSCl) [CAS No. 75-77-4](100 μL, 86 mg, 0.79 mmol) in anhydrous DMF (10 mL+5 mL+10 mL) at 60° C. for overnight under a nitrogen atmosphere. Filtration over Celite®, extractive aqueous work-up, and chromatographic purification over silica gel (petroleum ether/ethyl acetate=10:1 to 4:1, (v/v)) yielded methyl (S)-2-((tert-butoxycarbonyl)amino)-3-(2-methyl-5-(methylamino)phenyl) propanoate (608 mg, 62% yield) as a colorless (white) solid. TLC: Rf: 0.20 (petroleum ether/ethyl acetate=4:1, (v/v)); LC/MS/UV: Rt: 1.740 min, calculated for $C_{17}H_{26}N_2O_4$ 322.19, found ESI (pos.) m/z=323.40 $[M+H^+]^+$, 645.45 $[2M+H^+]^+$; $^1H$ NMR (400 MHz, $CDCl_3$): δ 6.97 (d, J=8.0 Hz, 1H), 6.45 (dd, J=8.0, 2.4 Hz, 1H), 6.35 (d, J=2.4 Hz, 1H), 4.98 (d, J=8.4 Hz, 1H), 4.54 (dd, J=14.4, 7.6 Hz, 1H), 3.70 (s, 3H), 3.06 (dd, J=14.0, 6.0 Hz, 1H), 2.95-2.83 (m, 1H), 2.80 (s, 3H), 2.21 (s, 3H), 1.40 (s, 9H). The $^1H$ NMR signal of one of the N—H acidic groups was not observed because of H-D exchange with the moisture in the NMR solvent.

Commercial 5-(dimethylamino)naphthalene-1-sulfonyl chloride (dansyl chloride) [CAS No. 605-65-2](600 mg, 2.23 mmol) was reacted with synthesized aniline methyl (S)-2-((tert-butoxycarbonyl)amino)-3-(2-methyl-5-(methyl-amino)phenyl)propanoate (480 mg, 1.49 mmol) in THF (10 mL) in the presence of triethylamine ($Et_3N$, TEA) [CAS No. 121-44-8](413 μL, 300 mg, 2.98 mmol) and 4-N,N-dimethylpyridine (DMAP) [CAS No. 1122-58-3](20 mg, 0.16 mmol) at room temperature for overnight. Evaporation of volatiles and purification by prep.-TLC on silica gel (petroleum ether/ethyl acetate=4:1, (v/v)) yielded methyl (S)-2-((tert-butoxycarbonyl)amino)-3-(5-((5-(dimethylamino)-N-methylnaphthalene)-1-sulfonamido)-2-methylphenyl) propanoate (685 mg, 45% yield) as a light yellow-blue solid. TLC: Rf: 0.30 (petroleum ether/ethyl acetate=4:1, (v/v)); LC/MS/UV: Rt: 2.856 min, calculated for $C_{29}H_{37}N_3O_6S$ 555.24, found ESI (pos.) m/z=556.50 $[M+H^+]^+$; $^1H$ NMR (400 MHz, $CDCl_3$): δ 8.54 (br d, J=8.4 Hz, 1H), 8.11-8.06 (m, 2H), 7.48 (t, J=8.0 Hz, 1H), 7.38 (dd, J=8.8, 7.6 Hz, 1H), 7.14 (br d, J=7.6 Hz, 1H), 7.01 (d, J=8.0 Hz, 1H), 6.90 (br s, 1H), 6.80 (br d, J=7.6 Hz, 1H), 4.98 (d, J=8.4 Hz, 1H), 4.47 (dd, J=15.2, 7.2 Hz, 1H), 3.68 (s, 3H), 3.18 (s, 3H), 3.05 (dd, J=14.0, 6.4 Hz, 1H), 3.00-2.84 (m, 1H+6H, superimposed), 2.30 (s, 3H), 1.39 (s, 9H). The $^1H$ NMR signal of one of the N—H acidic groups was not observed because of H-D exchange with the moisture in the NMR solvent.

The protecting groups of the sulfonamide were removed in two steps (Scheme 9). Chemoselective removal of the N-Boc-protection group of methyl (S)-2-((tert-butoxycarbonyl)amino)-3-(5-((5-(dimethylamino)-N-methylnaphtha-lene)-1-sulfonamido)-2-methylphenyl)propanoate (680 mg, 1.22 mmol) was conducted with 60 vol-% TFA in DCM (5 mL) at room temperature for 2 h. Evaporation of volatiles yielded methyl (S)-2-amino-3-(5-((5-(dimethylamino)-N-methylnaphthalene)-1-sulfonamido)-2-methylphenyl)propanoate (600 mg, crude) which was used directly in the next step. LC/MS: calculated for $C_{24}H_{29}N_3O_4S$ 455.19, found ESI (pos.) m/z=456.40 $[M+H^+]^+$. Hydrolysis of the methyl ester group of methyl (S)-2-amino-3-(5-((5-(dimethyl-amino)-N-methylnaphthalene)-1-sulfonamido)-2-methylphenyl)propanoate (600 mg, crude) was conducted with a 5 wt-% aq. solution of lithium hydroxide monohydrate ($LiOH \cdot H_2O$) [CAS No. 1310-66-3](63 mg, 2.64 mmol) in THF (6 mL) at room temperature for 2 h. Extractive acidic aqueous workup yielded an aqueous solution of the crude compound (16). Direct purification of the aqueous solution by prep. HPLC and removal of the solvents by lyophilization yielded pure compound (16) (167 mg, 28%, two steps) as a colorless (white) solid. LC/MS/UV: Rt: 1.880 min, calculated for $C_{23}H_{27}N_3O_4S$ 441.17, ESI (pos.) m/z=442.30 $[M+H^+]^+$, 883.70 $[2M+H^+]^+$, ESI (neg.) m/z=440.30 $[M-H^+]^-$, 881.70 $[2M-H^+]^-$; HPLC/UV: Rt: 4.770 min (100% AUC at 220 nm, 100% AUC at 254 nm); $^1H$ NMR (400 MHz, $CD_3OD$): δ 8.75-8.60 (m, 1H), 8.55-8.39 (m, 1H), 8.38-8.30 (m, 1H), 8.13-7.85 (m, 1H), 7.85-7.78 (m, 1H), 7.7.63-7.55 (m, 1H), 7.18-7.05 (m, 2H), 6.88-6.75 (m, 1H), 4.15-4.05 (m, 1H), 3.46 (b s, 6H), 3.35-3.25 (m, 1H, superimposed), 3.21 (s, 3H), 3.02 (dd, J=15.2, 8.4 Hz, 1H), 2.37 (s, 3H). The $^1H$ NMR signals of the amino-group, the N—H-acidic group, and the carboxyl group were not observed because of H-D exchange with the NMR solvent.

Example 17

(S)-3-(5-([1,1'-Biphenyl]-4-sulfonamido)-2-methylphenyl)-2-aminopropanoic Acid (17)

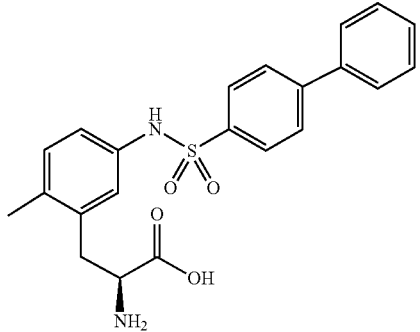

Compound (17) was synthesized by adapting methods described in Scheme 7 and Scheme 9. Commercial [1,1'-biphenyl]-4-sulfonyl chloride (4-phenylbenzenesulfonyl chloride) [CAS No. 1623-93-4] (245 mg, 0.97 mmol) was reacted with aniline starting material 5 (SM-5), methyl (S)-3-(5-amino-2-methylphenyl)-2-((tert-butoxycarbonyl) amino)propanoate, (200 mg, 0.65 mmol) in THF (3 mL) in the presence of triethylamine ($Et_3N$, TEA) [CAS No. 121-44-8](180 μL, 131 mg, 1.3 mmol) at room temperature for overnight under a nitrogen atmosphere. Evaporation of volatiles and purification by prep.-TLC on silica gel (petroleum ether/ethyl acetate=2:1, (v/v)) yielded methyl (S)-3-(5-([1,1'-biphenyl]-4-sulfonamido)-2-methylphenyl)-2-((tert-butoxycarbonyl)amino)propanoate (180 mg, 49% yield) as a colorless (white) solid. TLC: Rf: 0.55 (petroleum ether/ethyl acetate=2:1, (v/v)); LC/MS: calculated for $C_{28}H_{32}N_2O_6S$ 524.20, found ESI (pos.) 525.20 $[M+H^+]^+$.

The protecting groups of the sulfonamide were removed in two steps (Scheme 9). Chemoselective removal of the N-Boc-protection group of methyl (S)-3-(5-([1,1'-biphenyl]-4-sulfonamido)-2-methylphenyl)-2-((tert-butoxycarbonyl)amino)propanoate (180 mg, 0.34 mmol) was conducted with 50 vol-% TFA in DCM (4 mL) at room temperature for overnight. Evaporation of volatiles yielded crude methyl (S)-3-(5-([1,1'-biphenyl]-4-sulfonamido)-2-methylphenyl)-2-aminopropanoate. Purification by prep. HPLC and removal of the solvents by lyophilization yielded the pure intermediate methyl (S)-3-(5-([1,1'-biphenyl]-4-sulfonamido)-2-methylphenyl)-2-aminopropanoate (120 mg, 83% yield) as a colorless (white) solid. LC/MS: calculated for $C_{23}H_{24}N_2O_4S$ 424.15, found ESI (pos.) 425.20 $[M+H^+]^+$. Hydrolysis of the methyl ester group of methyl (S)-3-(5-([1,1'-biphenyl]-4-sulfonamido)-2-methylphenyl)-2-aminopropanoate (120 mg, 0.28 mmol) was conducted with a 5 wt-% aqueous solution of lithium hydroxide monohydrate (LiOH·H$_2$O) [CAS No. 1310-66-3](2 mL) in THF (2 mL) at room temperature for overnight. Evaporation of volatiles yielded crude compound (17). Purification by prep. HPLC and removal of the solvents by lyophilization yielded pure compound (17) (43 mg, 37%, two steps) as a colorless (white) solid. LC/MS/UV: Rt: 1.850 min, calculated for $C_{22}H_{22}N_2O_4S$ 410.13, ESI (pos.) m/z=411.20 $[M+H^+]^+$, 821.55 $[2M+H^+]^+$; ESI (neg.) m/z=409.10 $[M-H^+]^-$, 819.65 $[2M-H^+]^-$; HPLC/UV: Rt: 5.453 min (100% AUC at 220 nm, 100% AUC at 254 nm); $^1$H NMR (400 MHz, CD$_3$OD): δ 7.83-7.78 (m, 2H), 7.75-7.66 (m, 2H), 7.64-7.57 (m, 2H), 7.48-7.41 (m, 2H), 7.41-7.35 (m, 1H), 7.14 (d, J=2.4 Hz, 1H), 7.05 (d, J=8.4 Hz, 1H), 6.86 (dd, J=8.0, 2.4 Hz, 1H), 4.06 (br t, J=7.6 Hz, 1H), 3.35-3.25 (m, 1H, superimposed with $^1$H NMR signal of NMR solvent), 3.01 (dd, J=14.4, 8.0 Hz, 1H), 2.27 (s, 3H). The $^1$H NMR signals of the amino-group, the N—H-acidic group, and the carboxyl group were not observed because of H-D exchange with the NMR solvent.

Example 18

(S)-2-Amino-3-(5-((1,2-dimethyl-1H-imidazole)-4-sulfonamido)-2-methylphenyl)propanoic Acid (18)

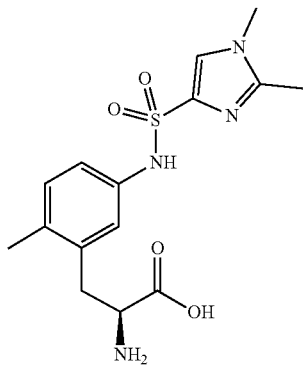

Compound (18) was synthesized by adapting methods described in Scheme 7 and Scheme 9. 1,2-Dimethylimidazole-4-sulfonyl chloride is commercially available [CAS No. 137049-02-6]. Following well-known literature procedures, 1,2-dimethylimidazole-4-sulfonyl chloride was also prepared from commercial 1,2-dimethylimidazole [CAS No. 1739-84-0](3.0 g, 31.2 mmol) in chlorosulfonic acid (sulfurochloridic acid, ClSO$_3$H) [CAS No. 7790-94-5](6 mL) at 150° C. for 3 h followed by heating with thionyl chloride (SOCl$_2$) [CAS No. 7719-09-7](4 mL) at 100° C. for 4 h. Aqueous workup from ice water, collection of the precipitate by filtration, filtration of a solution of the collected filter residue in chloroform (CHCl$_3$), and recrystallization of the crude compound yielded 1,2-dimethylimidazole-4-sulfonyl chloride (270 mg, 4% yield) as a grey-white solid. LC/MS/UV: Rt: 1.505 min, calculated for $C_5H_7ClN_2O_2S$ 193.99, found ESI (pos.) m/z=195.05 $[M+H^+]^+$; $^1$H NMR (400 MHz, CDCl$_3$): δ 7.59 (s, 1H), 3.69 (s, 3H), 2.47 (s, 3H).

Synthetic 1,2-dimethylimidazole-4-sulfonyl chloride [CAS No. 137049-02-6](214 mg, 0.87 mmol) was reacted with aniline starting material 5 (SM-5), methyl (S)-3-(5-amino-2-methylphenyl)-2-((tert-butoxycarbonyl)amino)propanoate, (226 mg, 0.73 mmol) in DCM (2 mL) in the presence of triethylamine (Et$_3$N, TEA) (CAS No. 121-44-8](205 µL, 149 mg, 1.46 mmol) at room temperature for overnight under a nitrogen atmosphere. Evaporation of volatiles and purification by prep.-TLC on silica gel (petroleum ether/ethyl acetate=4:1, (v/v)) yielded methyl (S)-2-((tert-butoxycarbonyl)amino)-3-(5-((1,2-dimethyl-1H-imidazole)-4-sulfonamido)-2-methylphenyl)propanoate (346 mg, 45% yield) as a light yellow-blue solid. TLC: Rf: 0.40 (petroleum ether/ethyl acetate=4:1, (v/v)); LC/MS/UV: Rt: 2.083 min; calculated for $C_{21}H_{30}N_4O_6S$ 466.19, found ESI (pos.) 467.30 $[M+H^+]^+$, 932.75 $[2M+H^+]^+$, 465.20 $[M-H^+]^-$, 931.85 $[2M-H^+]^-$; $^1$H NMR (400 MHz, CD$_3$OD) δ 7.48 (s, 1H), 7.05-6.94 (m, 2H), 6.93-6.82 (m, 2H), 4.32-4.18 (m, 1H), 3.61 (s, 3H), 3.58 (s, 3H), 3.02 (dd, J=14.0, 6.8 Hz, 1H), 2.85 (dd, J=14.0, 8.0 Hz, 1H), 2.33 (s, 3H), 2.23 (s, 3H), 1.39 (s, 9H).

The protecting groups of the sulfonamide were removed in two steps (Scheme 9). Chemoselective removal of the N-Boc-protection group of methyl (S)-2-((tert-butoxycarbonyl)amino)-3-(5-((1,2-dimethyl-1H-imidazole)-4-sulfonamido)-2-methylphenyl)propanoate (340 mg, 0.73 mmol) was conducted with 50 vol-% TFA in DCM (4 mL) at room temperature for 2 h. Evaporation of volatiles yielded crude methyl (S)-2-amino-3-(5-((1,2-dimethyl-1H-imidazole)-4-sulfonamido)-2-methylphenyl)propanoate (615 mg, crude) that was used directly in the next step. LC/MS/UV: Rt: 1.303 min, calculated for $C_{16}H_{22}N_4O_4S$ 366.14, found ESI (pos.) m/z=367.15 $[M+H^+]^+$.

Hydrolysis of the methyl ester group of methyl (S)-2-amino-3-(5-((1,2-dimethyl-1H-imidazole)-4-sulfonamido)-2-methylphenyl)propanoate (615 mg crude, 1.68 mmol, 1.0 eq.) was conducted with a 5 wt-% aqueous solution of lithium hydroxide monohydrate (LiOH·H$_2$O) [CAS No. 1310-66-3](80 mg, 3.36 mmol) in THF (6 mL) at room temperature for 2 h. Extractive workup yielded an acidified aqueous phase containing the crude compound (18). Purification by prep. HPLC and removal of the solvents by lyophilization yielded pure compound (18) (205 mg, 66%, two steps) as a colorless (white) solid. LC/MS/UV: Rt: 1.293 min, calculated for $C_{15}H_{20}N_4O_4S$ 352.12, ESI (pos.) m/z=353.10 $[M+H^+]^+$, 705.25 $[2M+H^+]^+$, ESI (neg.) m/z=351.05 $[M-H^+]^-$, 703.35 $[2M-H^+]^-$; HPLC/UV: Rt: 3.461 min (100% AUC at 220 nm, 100% AUC at 254 nm); $^1$H NMR (400 MHz, CD$_3$OD): δ 7.94 (s, 1H), 7.19 (d, J=8.4 Hz, 1H), 7.16 (d, J=2.4 Hz, 1H), 7.06 (dd, J=8.0, 2.4 Hz, 1H), 4.14 (brt, J=7.6 Hz, 1H), 3.78 (s, 3H), 3.35-3.25 (m, 1H, superimposed with $^1$H NMR signal of NMR solvent), 3.13 (dd, J=14.4, 7.6 Hz, 1H), 2.62 (s, 3H), 2.34 (s, 3H). The $^1$H NMR signals of the amino-group, the N—H-acidic group, and the carboxyl group were not observed because of H-D exchange with the NMR solvent.

Example 19

(S)-2-Amino-3-(2-((5-(dimethylamino)naphthalene)-1-sulfonamido)phenyl)propanoic Acid (19)

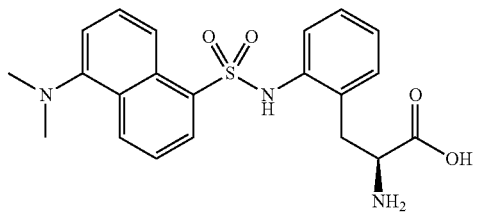

Compound (19) was synthesized by adapting methods described in Scheme 4, Scheme 7, and Scheme 9. Commercial 2-iodoaniline [CAS No. 615-43-0](767 mg, 3.5 mmol) and tert-butyl (R)-2-((tert-butoxycarbonyl)amino)-3-iodo-propanoate [CAS No. 1057341-65-7](1.0 g, 2.69 mmol, 1.0 eq.) were cross-coupled through Pd(0)-catalyzed Negishi-coupling using tris(dibenzylideneacetone)dipalladium (Pd$_2$(dba)$_3$) [CAS No. 51364-51-3](246 mg, 0.27 mol) and 2-dicyclohexylphosphino-2',6'-dimethoxybiphenyl (S-Phos) [CAS No. 657408-07-6](110 mg, 0.27 mmol) in the presence of an excess of zinc dust [CAS No. 7440-66-6](2.1 g, 32.3 mmol), pre-activated with elemental iodine (I$_2$) [CAS No. 7553-56-2](51 mg, 0.40 mmol) and trimethylchlorosilane (TMSCl) [CAS No. 75-77-4](100 µL, 86 mg, 0.79 mmol) in anhydrous DMF (10 mL+5 mL+10 mL) at 60° C. for 1 h under a nitrogen atmosphere. Filtration over Celite®, evaporation of volatiles, and chromatographic purification on silica gel (petroleum ether/ethyl acetate=50:1 to 5:1, (v/v)) yielded tert-butyl (S)-3-(2-aminophenyl)-2-((tert-butoxycarbonyl)amino)propanoate (400 mg, 57% yield) as a colorless (white) solid. TLC: Rf: 0.35 (petroleum ether/ethyl acetate=3:1, (v/v)); LC/MS/UV: Rt: 2.404 min C$_{18}$H$_{28}$N$_2$O$_4$ 336.20, found ESI (pos.) m/z=337.25 [M+H$^+$]$^+$, 673.50 [2M+H$^+$]$^+$.

The aniline tert-butyl (S)-3-(2-aminophenyl)-2-((tert-butoxycarbonyl)amino)propanoate (200 mg, 0.59 mmol) in THF (3 mL) was reacted with commercial 5-(dimethylamino)naphthalene-1-sulfonyl chloride (dansyl chloride) [CAS No. 605-65-2](240 mg, 0.89 mmol) in the presence of triethylamine (Et$_3$N, TEA) [CAS No. 121-44-8](165 µL, 120 mg, 1.19 mmol) at room temperature for overnight under a nitrogen atmosphere. Evaporation of volatiles and purification by prep.-TLC on silica gel (petroleum ether/ethyl acetate=2:1, (v/v)) yielded tert-butyl (S)-2-((tert-butoxycarbonyl)amino)-3-(2-((5-(dimethylamino)naphthalene)-1-sulfonamido)phenyl)propanoate (150 mg, 76% yield) as a colorless (white) solid. TLC: Rf: 0.45 (petroleum ether/ethyl acetate=3:1, (v/v)); LC/MS/UV: Rt: 2.867 min, calculated for C$_{30}$H$_{39}$N$_3$O$_6$S 569.26, found ESI (pos.) m/z=414.15 [M−C$_4$H$_8$—CO$_2$—C$_4$H$_8$+H$^+$]$^+$, 570.35 [M+H$^+$]$^+$, ESI (neg.) m/z=568.45 [M−H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-((5-(dimethylamino)naphthalene)-1-sulfonamido)phenyl)propanoate (150 mg, 0.26 mmol) was conducted through reaction with 50 vol-% TFA in DCM (4 mL) at room temperature for overnight. Evaporation of volatiles afforded crude compound (19). Purification by prep. HPLC and removal of the solvents by lyophilization yielded compound (19) (38 mg, 34% yield) as a colorless (white) solid. LC/MS/UV: Rt: 1.713 min, calculated for C$_{21}$H$_{23}$N$_3$O$_4$S 413.14, found ESI (pos.) m/z=414.10 [M+H$^+$]$^+$, ESI (neg.) m/z=412.05 [M−H$^+$]$^-$, 825.60 [2M−H$^+$]$^-$; HPLC/UV: Rt: 4.154 min (100% AUC at 220 nm, 100% AUC at 254 nm); $^1$H NMR (400 MHz, CD$_3$OD): δ 8.93 (d, J=8.8 Hz, 1H), 8.68 (d, J=8.4 Hz, 1H), 8.21 (d, J=7.2 Hz, 1H), 8.13 (d, J=8.0 Hz, 1H), 7.82-7.78 (m, 2H), 7.33 (d, J=7.6 Hz, 1H), 7.22 (brt, J=7.6 Hz, 1H), 6.92 (t, J=8.0 Hz, 1H), 6.26 (d, J=0.8 Hz, 1H), 4.42 (dd, J=8.8, 6.4 Hz, 1H), 3.58 (dd, J=14.8, 6.4 Hz, 1H), 3.50 (br s, 6H), 3.26 (dd, J=14.4, 8.8 Hz, 1H). The $^1$H NMR signals of the amino group, the N—H acidic group, and the carboxyl group were not observed because of H-D exchange with the NMR solvent.

Example 20

(S)-2-Amino-3-(2-methyl-5-((1-methylethyl)sulfonamido)phenyl)propanoic Acid (20)

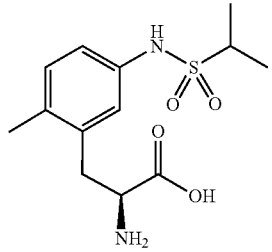

Compound (20) was synthesized by adapting methods described in Scheme 7 and Scheme 9.

The aniline starting material 5 (SM-5) methyl (S)-3-(5-amino-2-methylphenyl)-2-((tert-butoxycarbonyl)amino)propanoate, (500 mg, 1.62 mmol) was reacted with commercial 1-methylethylsulfonyl chloride (2-propanesulfonyl chloride, isopropylsulfonyl chloride) [CAS No. 10147-37-2](460 mg, 3.24 mmol) in DCM (5 mL) in the presence of pyridine (320 mg, 4.05 mmol) and 4-N,N-dimethylaminopyridine (DMAP) [CAS No. 1122-58-3](20 mg, 0.16 mmol) at 45° C. for 36 h under a nitrogen atmosphere. Evaporation of volatiles and purification by prep-TLC on silica gel (petroleum ether/ethyl acetate=2:1, (v/v)) yielded methyl (S)-2-((tert-butoxycarbonyl)amino)-3-(2-methyl-5-((1-methylethyl)sulfonamido)phenyl)propanoate (300 mg, 45% yield) as a light yellow solid. TLC: Rf: 0.47 (petroleum ether/ethyl acetate=2:1, (v/v)); LC/MS: calculated for C$_{19}$H$_{30}$N$_2$O$_6$S 418.18, found ESI (pos.) m/z=315.10 [M−C$_4$H$_8$—CO$_2$+H$^+$]$^+$.

The protecting groups of the sulfonamide were removed in two steps (Scheme 9). Chemoselective removal of the N-Boc-protection group of methyl (S)-2-((tert-butoxycarbonyl)amino)-3-(2-methyl-5-((1-methylethyl)sulfonamido)phenyl)propanoate (300 mg, 0.72 mmol) was conducted with 50 vol-% TFA in DCM (4 mL) at room temperature for 2 h. Evaporation of volatiles yielded crude intermediate methyl (S)-2-amino-3-(2-methyl-5-((1-methylethyl)sulfonamido)phenyl)propanoate (350 mg, crude). LC/MS: calculated for $C_{14}H_{22}N_2O_4S$ 314.13, found ESI (pos.) m/z=315.20 $[M-C_4H_8-CO_2+H^+]^+$.

Hydrolysis of the methyl ester group of the intermediate methyl (S)-2-amino-3-(2-methyl-5-((1-methylethyl)sulfonamido)phenyl)propanoate (350 mg, crude) in methanol (3 mL) with a 5 wt-% aqueous solution of lithium hydroxide monohydrate (LiOH·H₂O) [CAS No. 1310-66-3](0.75 mL) at room temperature for 2 h afforded crude compound (20). Evaporation of volatiles, purification by prep. HPLC, and removal of the solvents by lyophilization yielded compound (20) (42 mg, 19% yield) as a colorless (white) solid. LC/MS/UV: Rt: 1.357 min, calculated for $C_{13}H_{20}N_2O_4S$ 300.11, found ESI (pos.) m/z=301.10 $[M+H^+]^+$, ESI (neg.) m/z=299.05 $[M-H^+]^-$, 599.35 $[2M-H^+]^-$; HPLC/UV: Rt: 3.951 min (100% AUC at 220 nm, 100% AUC at 254 nm); $^1$H NMR (400 MHz, CD₃OD): δ 7.18-7.14 (m, 2H), 7.04 (dd, J=8.4 2.4 Hz, 1H), 4.07 (dd, J=8.4, 6.4H, 1H), 3.32 (dd, J=14.4, 6.4 Hz, 1H, superimposed with $^1$H NMR signal from NMR solvent), 3.24 (septet, J=8 Hz, 1H, superimposed with $^1$H NMR signal from NMR solvent), 3.03 (dd, J=14.8, 8.8 Hz, 1H), 2.32, (s, 3H), 1.30 (d, J=6.8 Hz, 6H). The H NMR signals of the amino group, the N—H acidic group, and the carboxyl group were not observed because of H-D exchange with the NMR solvent.

Example 21

(S)-2-Amino-3-(5-((5-(dimethylamino)naphthalene)-1-(sulfonamido)-2-isopropylphenyl)proponoic Acid (21)

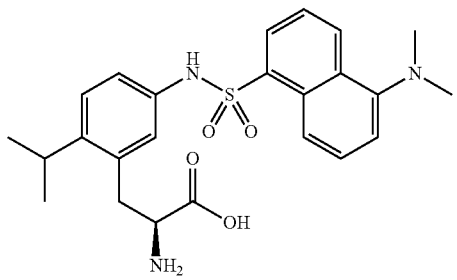

The aniline starting material 8 (SM-8) tert-butyl (S)-3-(5-amino-2-isopropylphenyl)-2-(tert-butoxycarbonylamino)propanoate, (300 mg, 0.8 mmol) was reacted with commercial 5-(dimethylamino)naphthalene-1-sulfonyl chloride (dansyl chloride, SNSCl) [CAS No. 605-65-2](235 mg, 0.87 mmol) in DCM (30 mL) in the presence of pyridine [CAS No. 110-86-1](22 µL, 21 mg, 0.16 mmol) eq.) at room temperature for overnight. Evaporation of volatiles and chromatographic purification by prep.-TLC on silica gel (petroleum ether/ethyl acetate 5:1, (v/v)) yielded tert-butyl (2S)-2-(tert-butoxycarbonylamino)-3-(5-((5-dimethylamino-1-naphthyl)sulfonylamino)-2-isopropyl-phenyl)propanoate (480 mg, 98% yield) as a light yellow solid. TLC: Rf: 0.50 (petroleum ether/ethyl acetate 4:1, (v/v)); LC/MS/UV: Rt: 3.469 min, calculated for $C_{33}H_{45}N_3O_6S$ 611.30, found ESI (pos.) m/z=556.60 $[M-C_4H_8+H^+]^+$, ESI (neg.) m/z=610.55 $[M-H^+]^-$; $^1$H NMR (400 MHz, CDCl₃): δ 8.55 (s, 1H), 8.32 (d, J=8.6 Hz, 1H), 8.20 (m, 1H), 7.60-7.52 (m, 1H), 7.47 (t, J=8.0 Hz, 1H), 7.20 (d, J=7.5 Hz, 1H), 7.02 (d, J=8.4 Hz, 1H), 6.77 (d, J=8.5 Hz, 1H), 6.73-6.60 (m, 2H), 4.91 (d, J=8.5 Hz, 1H), 4.35-4.19 (m, 1H), 3.07 (m, 1H), 2.90 (s, 6H), 1.39 (s, 9H), 1.26 (s, 9H), 1.16-1.10 (m, 6H).

Global removal of the N-Boc-protection group and the tert-butyl ester group of tert-butyl (2S)-2-(tert-butoxycarbonylamino)-3-(5-((5-dimethylamino-1-naphthyl)sulfonylamino)-2-isopropyl-phenyl)propanoate (480 mg, 0.78 mmol) was conducted through reaction with 50 vol-% TFA in DCM (4 mL) at room temperature for overnight. Evaporation of volatiles afforded crude compound (21). Purification by prep. HPLC and removal of the solvents by lyophilization yielded compound (21) (60 mg, 16% yield) as a colorless (white) solid. LC/MS/UV: Rt: 2.067 min, calculated for $C_{24}H_{29}N_3O_4S$ 455.19, found ESI (pos.) m/z=456.35 $[M+H^+]^+$, ESI (neg.) m/z=454.25 $[M-H^+]^-$, 909.85 $[2M-H^+]^-$; HPLC/UV: Rt: 5.538 min (99.6% AUC at 220 nm, 100% AUC at 254 nm); $^1$H NMR (400 MHz, CD₃OD): δ 8.93 (d, J=8.8 Hz, 1H), 8.58 (d, J=8.4 Hz, 1H), 8.40 (d, J=7.2 Hz, 1H), 8.08 (d, J=7.6 Hz, 1H), 7.88-7.78 (m, 2H), 7.07 (d, J=8.0 Hz, 1H), 7.02 (d, J=2.0 Hz, 1H), 6.79 (dd, J=8.0, 2.0 Hz, 1H), 3.92 (t, J=7.6 Hz, 1H), 3.45 (s, 6H), 3.22 (dd, J=14.4, 7.6 Hz, 1H), 3.06-2.94 (m, 2H), 1.12 (t, J=6.8 Hz, 6H). The H NMR signals of the amino group, the N—H acidic group, and the carboxyl group were not observed because of H-D exchange with the NMR solvent.

Example 22

(S)-2-Amino-3-(5-((((1R,4R)-7,7-dimethyl-2-oxobicyclo[2.2.1]hetptan-1-yl)methyl)sulfonamido)-2-methylphenyl)propanoic Acid (22)

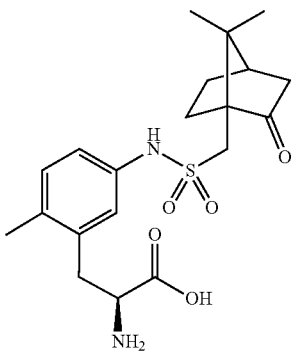

Compound (22) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (200 mg, 0.57 mmol) was reacted with commercial ((1R,4R)-7,7-dimethyl-2-oxobicyclo[2.2.1]heptan-1-yl)methanesulfonyl chloride [CAS No. 39262-22-1](172 mg, 0.68 mmol) in pyridine (4 mL) at room temperature under a nitrogen atmosphere. Extractive aqueous workup and purification by prep.-TLC on silica gel (petroleum ether/ethyl acetate=2:1, (v/v)) yielded tert-butyl (S)-2-((tert-butoxycarbonyl)amino)-3-(5-((((1R,4R)-7,7-dimethyl-2-oxobicyclo[2.2.1]heptan-1-yl)methyl)sulfonamido)-2-methylphenyl)propanoate (140 mg, 44% yield) as a yellow solid. TLC: Rf: 0.45 (petroleum ether/ethyl acetate=2:1, (v/v)); LC/MS/UV: Rt: 2.814 min, calculated for $C_{29}H_{44}N_2O_7S$ 564.29, found ESI (pos.) m/z=409.25 $[M-C_4H_8-CO_2-C_4H_8+H^+]^+$, 565.45 $[M+H^+]^+$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-((((1R,4R)-7,7-dimethyl-2-oxobicyclo[2.2.1]heptan-1-yl)methyl)sulfonamido)-2-methylphenyl)propanoate (140 mg, 0.25 mmol) was conducted through reaction with 50 vol-% TFA in DCM (4 mL) at room temperature for overnight. Evaporation of volatiles afforded crude compound (22). Purification by prep. HPLC and removal of the solvents by lyophilization yielded compound (22) (33 mg, 32% yield) as a colorless (white) solid. LC/MS/UV: Rt: 1.545 min, calculated for $C_{20}H_{28}N_2O_5S$ 408.17, found ESI (pos.) m/z=409.25 [M+H$^+$]$^+$, 818.05 [2M+H$^+$]$^+$, ESI (neg.) m/z=407.20 [M–H$^+$]$^-$, 815.60 [2M–H$^+$]$^-$; HPLC/UV: Rt: 5.593 min (100% AUC at 220 nm, 100% AUC at 254 nm); $^1$H NMR (400 MHz, CD$_3$OD): δ 7.25 (d, J=2.4 Hz, 1H), 7.18 (d, J=8.4 Hz, 1H), 7.05 (dd, J=8.4, 2.4 Hz, 1H), 4.18-4.05 (m, 1H), 3.50-3.40 m, 1H), 3.40-3.25 (dd, 1H), 3.15-2.95 (m, 2H), 2.45-2.25 (m, 5H), 2.15-2.00 (m, 2H), 1.95-1.88 (m, 1H), 1.75-1.65 (m, 1H), 1.50-1.32 (m, 1H) 1.06 (s, 3H), 0.83 (s, 3H). The $^1$H NMR signals of the amino group, the N—H acidic group, and the carboxyl group were not observed because of H-D exchange with the NMR solvent.

Example 23

(S)-2-Amino-3-(2-methyl-5-((phenylmethyl)sulfonamido)phenyl) propanoic Acid (23)

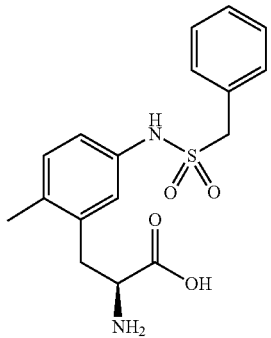

Compound (23) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (200 mg, 0.57 mmol, 1.0 eq.) was reacted with commercial phenylmethanesulfonyl chloride [CAS No. 1939-99-7](109 mg, 0.57 mmol, 1.0 eq.) in pyridine (4 mL) at room temperature under a nitrogen atmosphere. Extractive aqueous workup and purification by prep-TLC on silica gel (petroleum ether/ethyl acetate=2:1, (v/v)) yielded tert-butyl (S)-2-((tert-butoxycarbonyl)amino)-3-(2-methyl-5-((phenylmethyl)sulfonamido)phenyl)propanoate (140 mg, 48% yield) as a yellow solid. TLC: Rf: 0.70 (petroleum ether/ethyl acetate=2:1, (v/v)); LC/MS/UV: Rt: 2.700 min, calculated for $C_{26}H_{36}N_2O_6S$ 504.23, found ESI (pos.) m/z=349.10 [M–C$_4$H$_8$—CO$_2$—C$_4$H$_8$+H$^+$]$^+$, 505.30 [M+H$^+$]$^+$, ESI (neg.) m/z=503.25 [M–H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-((phenylmethyl)sulfonamido)phenyl)propanoate (140 mg, 0.27 mmol) was conducted through reaction with 50 vol-% TFA in DCM (4 mL) at room temperature for overnight. Evaporation of volatiles afforded crude compound (23). Purification by prep. HPLC and removal of the solvents by lyophilization yielded compound (23) (61 mg, 65% yield) as a colorless (white) solid. LC/MS/UV: Rt: 1.455 min, calculated for $C_{17}H_{20}N_2O_4S$ 348.11, found ESI (pos.) m/z=349.15 [M+H$^+$]$^+$, 697.30 [2M+H$^+$]$^+$, ESI (neg.) m/z=347.05 [M–H$^+$]$^-$, 695.50 [2M–H$^+$]$^-$; HPLC/UV: Rt: 5.386 min (100% AUC at 220 nm, 100% AUC at 254 nm); $^1$H NMR (400 MHz, CD$_3$OD): δ 7.35-7.25 (m, 5H), 7.18 (d, J=8.4 Hz, 1H), 7.13 (d, J=2.4 Hz, 1H), 6.95 (dd, J=8.4, 2.4 Hz, 1H), 4.38 (s, 2H), 4.11 (dd, J=6.4, 6.0 Hz, 1H), 3.33 (dd, J=14.4, 6.8 Hz, 1H), 3.06 (dd, J=14.4, 8.4 Hz, 1H), 2.34 (s, 3H). The $^1$H NMR signal of the amino group, the N—H acidic group, and the carboxyl group were not observed because of H-D exchange with the NMR solvent.

Example 24

(S)-2-Amino-3-(5-((7-chlorobenzo[c][1,2,5]oxadiazole-4-sulfonamido)-2-methylphenyl)propanoic Acid (24)

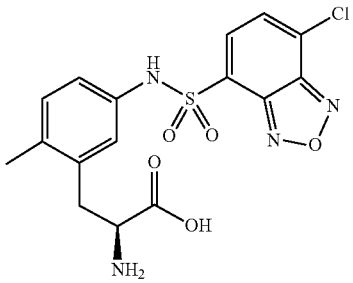

Compound (24) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (200 mg, 0.57 mmol) was reacted with commercial 7-chlorobenzo[c][1,2,5]oxadiazole-4-sulfonyl chloride [CAS No. 71125-38-7](217 mg, 0.89 mmol) in pyridine (2 mL) at 0° C. to room temperature under a nitrogen atmosphere. Extractive aqueous workup and purification by prep.-TLC on silica gel (petroleum ether/ethyl acetate=2:1, (v/v)) yielded tert-butyl (S)-2-((tert-butoxycarbonyl)amino)-3-(5-((7-chlorobenzo[c][1,2,5]oxadiazole)-4-sulfonamido)-2-methylphenyl)propanoate (160 mg, 49% yield) as a yellow solid. TLC: Rf: 0.50 (petroleum ether/ethyl acetate=2:1, (v/v)); LC/MS/UV: Rt: 2.612 min, calculated for $C_{25}H_{31}ClN_4O_7S$ 566.16, found ESI (pos.) m/z=411.10 [M–C$_4$H$_8$—CO$_2$-C$_4$H$_8$+H$^+$]$^+$, 589.20 [M+Na$^+$]$^+$, ESI (neg.) m/z=565.20 [M–H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-((7-chlorobenzo[c][1,2,5]oxadiazole)-4-sulfonamido)-2-methylphenyl)propanoate (160 mg, 0.28 mmol) was conducted through reaction with 50 vol-% TFA in DCM (4 mL) at room temperature for overnight. Evaporation of volatiles afforded crude compound (24). Purification by prep. HPLC and removal of the solvents by lyophilization yielded compound (24) (24 mg, 20% yield) as a yellow solid. LC/MS/UV: Rt: 1.460 min, calculated for $C_{16}H_{15}ClN_4O_5S$ 410.05, found ESI (pos.) m/z=411.00 [M+H$^+$]$^+$; ESI (neg.) m/z=409.00 [M–H$^+$]$^-$, 819.35 [2M–H$^+$]$^-$; HPLC/UV: Rt: 5.737 min (100% AUC at 220 nm, 100% AUC at 254 nm); $^1$H NMR (400 MHz, CD$_3$OD): δ 8.03 (d, J=7.6 Hz, 1H), 7.67 (d, J=7.2 Hz, 1H), 7.11 (d, J=2.4 Hz, 1H), 7.00 (d, J=8.4 Hz, 1H), 6.82 (dd, J=8.4, 2.4 Hz, 1H), 3.87 (dd, J=8.8, 6.0 Hz, 1H), 3.27 (dd, J=14.8, 6.4 Hz, 1H), 2.91 (dd, J=14.4, 8.8 Hz, 1H), 2.24 (s, 3H). The $^1$H NMR signals of the amino group, the N—H acidic group, and the carboxyl group were not observed because of H-D exchange with the NMR solvent.

Example 25

(S)-2-Amino-3-(5-(benzo[c][1,2,5]oxadiazole-4-sulfonamido)-2-methylphenyl)propanoic Acid (25)

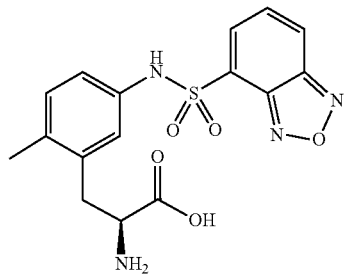

Compound (25) was synthesized by adapting methods described in Scheme 7 and Scheme 9. The aniline starting material 6 (SM-6) tert-butyl (S)-3-(5-amino-2-methylphenyl)-2-((tert-butoxycarbonyl)amino)propanoate, (200 mg, 0.57 mmol) was reacted with commercial benzo[c][1,2,5]oxadiazole-4-sulfonyl chloride [CAS No. 114322-14-4](150 mg, 0.69 mmol) in pyridine (2 mL) at 0° C. to room temperature under a nitrogen atmosphere. Extractive aqueous workup and purification by prep.-TLC on silica gel (petroleum ether/ethyl acetate=2:1, (v/v)) yielded tert-butyl (S)-3-(5-(benzo[c][1,2,5]oxadiazole-4-sulfonamido)-2-methylphenyl)-2-((tert-butoxycarbonyl)amino)propanoate (180 mg, 59% yield) as a yellow solid. TLC: Rf: 0.50 (petroleum ether/ethyl acetate=2:1, (v/v)); LC/MS/UV: Rt: 2.483 min, calculated for $C_{25}H_{32}N_4O_7S$ 532.20, found ESI (pos.) m/z=377.15 [M–$C_4H_8$—$CO_2$–$C_4H_8$+H$^+$]$^+$.

The protecting groups of the sulfonamide were removed in one step (Scheme 9). Global removal of the N-Boc-protection group and the tert-butyl ester group of tert-butyl (S)-3-(5-(benzo[c][1,2,5]oxadiazole-4-sulfonamido)-2-methylphenyl)-2-((tert-butoxycarbonyl)amino)propanoate (180 mg, 0.34 mmol) was conducted through reaction with 50 vol-% TFA in DCM (4 mL) at room temperature for overnight. Evaporation of volatiles afforded crude compound (25). Purification by prep. HPLC and removal of the solvents by lyophilization yielded compound (25) (43 mg, 33% yield) as a yellow solid. LC/MS/UV: Rt: 1.366 min, calculated for $C_{16}H_{16}N_4O_5S$ 376.08, found ESI (pos.) m/z=377.20 [M+H$^+$]$^+$, 753.45 [2M+H$^+$]$^+$, ESI (neg.) m/z=375.15 [M–H$^+$]$^-$, 751.65 [2M–H$^+$]$^-$; HPLC/UV: Rt: 5.308 min (100% AUC at 220 nm, 100% AUC at 254 nm); $^1$H NMR (400 MHz, CD$_3$OD): δ 8.08 (dd, J=8.8, 0.8 Hz, 2H), 7.53 (dd, J=9.2, 1.2 Hz, 1H), 7.06 (dd, J=2.4 Hz, 1H), 6.93 (d, J=8.0 Hz, 7.76 (dd, J=8.0, 2.4 Hz), 3.87 (dd, J=8.4, 6.0 Hz, 1H), 3.22 (dd, J=14.4, 6.0 Hz, 1H), 2.87 (dd, J=14.4, 8.8 Hz, 1H), 2.18 (s, 3H). The $^1$H NMR signals of the amino group, the N—H acidic group, and the carboxyl group were not observed because of H-D exchange with the NMR solvent.

Example 26

(S)-2-Amino-3-(5-(cyclohexanesulfonamido)-2-methylphenyl)propanoic Acid (26)

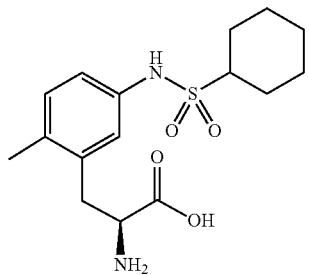

Compound (26) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (300 mg, 0.86 mmol) was reacted with commercial cyclohexanesulfonyl chloride [CAS No. 4837-38-1](781 mg, 4.28 mmol) in pyridine (2 mL) at room temperature and then heated at 80° C. for overnight under a nitrogen atmosphere. Dilution with MTBE, extractive aqueous workup, and purification by prep.-TLC on silica gel (petroleum ether/ethyl acetate=2:1, (v/v)) yielded tert-butyl (S)-2-((tert-butoxycarbonyl)amino)-3-(5-(cyclohexanesulfonamido)-2-methylphenyl)propanoate (114 mg, 27% yield) as a yellow solid. TLC: Rf: 0.35 (petroleum ether/ethyl acetate=2:1, (v/v)); LC/MS/UV: Rt: 2.570 min, calculated for $C_{25}H_{40}N_2O_6S$ 496.26, found ESI (pos.) m/z=341.2 [M–$C_4H_8$—$CO_2$—$C_4H_8$+H$^+$]$^+$, 497.45 [M+H$^+$]$^+$, ESI (neg.) m/z=495.40 [M–H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(cyclohexanesulfonamido)-2-methylphenyl)propanoate (114 mg, 0.23 mmol) was conducted through reaction with 50 vol % TFA in DCM (4 mL) at room temperature for overnight. Evaporation of volatiles afforded crude compound (26). Purification by prep. HPLC and removal of the solvents by lyophilization yielded compound (26) (27 mg, 34% yield) as a colorless (white) solid. LC/MS/UV: Rt: 1.378 min, calculated for $C_{16}H_{24}N_2O_4S$ 340.15, found ESI (pos.) m/z=341.20 [M+H$^+$]$^+$, 681.50 [2M+H$^+$]$^+$, ESI (neg.) m/z=679.60 [2M–H$^+$]$^-$; HPLC/UV: Rt: 5.449 min (99.9% AUC at 220 nm, 100% AUC at 254 nm); $^1$H NMR (400 MHz, CD$_3$OD): δ 7.22-7.14 (m, 2H), 7.05 (dd, J=8.4, 2.8 Hz, 1H), 4.11 (dd, J=8.4, 6.4 Hz, 1H), 3.35 (dd, J=14.8, 6.8 Hz, 1H), 3.05 (dd, J=14.4, 8.8 Hz, 1H, superimposed), 3.02-2.82 (m, 1H), 2.34 (s, 3H), 2.13-2.10 (m, 2H), 1.86-1.83 (m, 2H), 1.70-1.63 (m, 1H), 1.57-1.45 (m, 2H), 1.30-1.20 (m, 3H). The $^1$H NMR signals of the amino group, the N—H acidic group, and the carboxyl group were not observed because of H-D exchange with the NMR solvent.

Example 27

(S)-2-Amino-3-(5-(benzo[b]thiophene-sulfonamido)-2-methylphenyl)propanoic Acid (27)

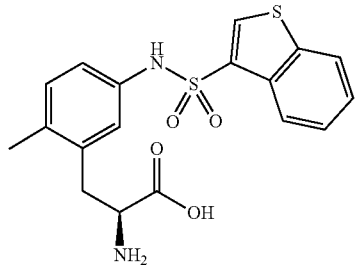

Compound (27) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (200 mg, 0.57 mmol) was reacted with commercial benzo[b]thiophene-3-sulfonyl chloride [CAS No. 18494-87-6](199 mg, 0.86 mmol) in pyridine (2 mL) at 0° C. to room temperature for overnight. Evaporation of volatiles, extractive aqueous workup, and purification by prep.-TLC on silica gel (petroleum ether/ethyl acetate=2:1, (v/v)) yielded tert-butyl (S)-3-(5-(benzo[b]thiophene-3-sulfonamido)-2-methylphenyl)-2-((tert-butoxycarbonyl)amino)propanoate (250 mg, 80% yield) as a yellow solid. TLC: Rf: 0.50 (petroleum ether/ethyl acetate=2:1, (v/v)); LC/MS/UV: Rt: 2.564 min, calculated for $C_{27}H_{34}N_2O_6S_2$ 546.19, found ESI (pos.) m/z=391.10 [M–$C_4H_8$–$CO_2$–$C_4H_8$+$H^+$]$^+$, 547.30 [M+$H^+$]$^+$.

The protecting groups of the sulfonamide were removed in one step (Scheme 9). Global removal of the N-Boc-protection group and the tert-butyl ester group of tert-butyl (S)-3-(5-(benzo[b]thiophene-3-sulfonamido)-2-methylphenyl)-2-((tert-butoxycarbonyl)amino)propanoate (250 mg, 0.46 mmol) was conducted through reaction with 50 vol-% TFA in DCM (6 mL) at room temperature for overnight. Evaporation of volatiles afforded crude compound (27). Purification by prep. HPLC and removal of the solvents by lyophilization yielded compound (27) (117 mg, 65% yield) as a colorless (white) solid. LC/MS/UV: Rt: 1.491 min, calculated for $C_{18}H_{18}N_2O_4S_2$ 390.07, found ESI (pos.) m/z=391.10 [M+$H^+$]$^+$, 781.40 [2M+$H^+$]$^+$, ESI (neg.) m/z=389.00 [M–$H^+$]$^-$, 779.55 [2M–$H^+$]$^-$; HPLC/UV: Rt: 5.730 min (99.7% AUC at 220 nm, 99.6% AUC at 254 nm); $^1$H NMR (400 MHz, CD$_3$OD): δ 8.29 (s, 1H), 8.25-8.17 (m, 1H), 7.96-7.89 (m, 1H), 7.52-7.40 (m, 2H), 7.06 (d, J=2.3 Hz, 1H), 6.99 (d, J=8.3 Hz, 1H), 6.78 (dd, J=8.2, 2.3 Hz, 1H), 3.85 (dd, J=8.8, 5.9 Hz, 1H), 3.25 (dd, J=14.4, 6.0 Hz, 1H), 2.90 (dd, J=14.5, 8.9 Hz, 1H), 2.24 (s, 3H). The $^1$H NMR signals of the amino group, the N—H acidic group, and the carboxyl group were not observed because of H-D exchange with the NMR solvent.

Example 28

(S)-2-Amino-3-(5-((3-aminophenyl)sulfonamido)-2-methylphenyl)propanoic Acid (28)

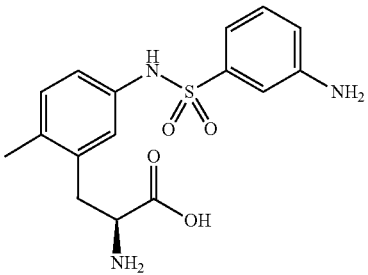

Compound (28) was synthesized by adapting methods described in Scheme 4, Scheme 7, and Scheme 9. The aniline starting material 6 (SM-6), tert-butyl (S)-3-(5-amino-2-methylphenyl)-2-((tert-butoxycarbonyl)amino)propanoate, (400 mg, 1.14 mmol) was reacted with commercial 3-nitrobenzenesulfonyl chloride [CAS No. 121-51-7](304 mg, 1.37 mmol) in pyridine (4 mL) at 0° C. to room temperature for overnight. Evaporation of volatiles, extractive aqueous workup, and purification by prep.-TLC on silica gel (petroleum ether/ethyl acetate=2:1, (v/v)) yielded tert-butyl (5)-2-((tert-butoxycarbonyl)amino)-3-(2-methyl-5-((3-nitrophenyl)sulfonamido)phenyl)propanoate (300 mg, 49% yield) as a yellow solid. TLC: Rf: 0.55 (petroleum ether/ethyl acetate=2:1, (v/v)); LC/MS/UV: Rt: 2.452 min, calculated for $C_{25}H_{33}N_3O_8S$ 535.20, found ESI (pos.) m/z=380.15 [M–$C_4H_8$–$CO_2$–$C_4H_8$+$H^+$]$^+$, 536.35 [M+$H^+$]$^+$, ESI (neg.) m/z=534.30 ([M–$H^+$]$^-$.

Following well-known literature procedures, the nitro-group of the sulfonamide tert-butyl (S)-2-((tert-butoxycarbonyl)amino)-3-(2-methyl-5-((3-nitrophenyl)sulfonamido)phenyl)propanoate (300 mg, 0.56 mmol) was reduced to the corresponding aniline using zinc [CAS No. 7440-66-6](364 mg, 5.6 mmol) in a mixture of EtOH and HOAc (1:1, (v/v)) at 85° C. for overnight. Evaporation of volatiles and chromatographic purification by prep.-TLC on silica gel (petroleum ether/ethyl acetate=2:1, (v/v)) yielded tert-butyl (S)-3-(5-((3-aminophenyl)sulfonamido)-2-methylphenyl)-2-((tert-butoxycarbonyl)amino)propanoate (200 mg, 70% yield) as a yellow solid. TLC: Rf: 0.45 (petroleum ether/ethyl acetate=2:1, (v/v)); LC/MS: calculated for $C_{25}H_{35}N_3O_6S$ 505.22, found ESI (pos.) m/z=506.35 [M+$H^+$]$^+$.

The protecting groups of the sulfonamide were removed in one step (Scheme 9). Global removal of the N-Boc-protection group and the tert-butyl ester group of tert-butyl (S)-3-(5-((3-aminophenyl)sulfonamido)-2-methylphenyl)-2-((tert-butoxycarbonyl)amino)propanoate (150 mg, 0.30 mmol) was conducted through reaction with 50 vol-% TFA in DCM (4 mL) at room temperature for overnight. Evaporation of volatiles afforded crude compound (28). Purification by prep. HPLC and removal of the solvents by lyophilization yielded compound (28) (22 mg, 21% yield) as a colorless (white) solid. LC/MS/UV: Rt: 1.212 min, calculated for $C_{16}H_{19}N_3O_4S$. 349.11, ESI (pos.) m/z=350.05 [M+$H^+$]$^+$, ESI (neg.) m/z=348.00 [M–$H^+$]$^-$, 697.20 [2M–$H^+$]$^-$; HPLC/UV: Rt: 4.663 min (99.9% AUC at 220 nm, 100% AUC at 254 nm); $^1$H NMR (400 MHz, CD$_3$OD): δ 7.20 (t, J=7.6 Hz, 1H), 7.12 (t, J=2.0 Hz, 1H), 7.09-7.06 (m, 2H), 7.05 (br s, 1H), 6.90 (ddd, J=8.4, 2.4, 1.2 Hz, 1H), 6.83 (dd, J=8.0, 2.0H, 1H), 4.06 (dd, J=8.4, 6.8 Hz, 1H), 3.27 (dd, J=14.4, 6.8 Hz, 1H), 3.01 (dd, J=14.4 8.4 Hz, 1H), 2.28 (s, 3H). The $^1$H NMR signals of the amino group, the anilino group, the N—H acidic group, and the carboxyl group were not observed because of H-D exchange with the NMR solvent.

Example 29

(S)-2-Amino-3-(5)-((3-bromophenyl)sulfonamido)-2-methylphenyl) propanoic Acid (29)

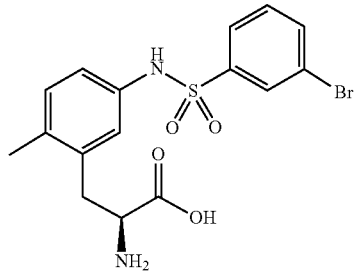

Compound (29) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (200 mg, 0.57 mmol) was reacted with commercial 3-bromobenzenesulfonyl chloride [CAS No. 2905-24-0](146 mg, 0.86 mmol) in pyridine (2 mL) at room temperature for overnight. Evaporation of volatiles, extractive aqueous workup, and purification by prep.-TLC on silica gel (petroleum ether/ethyl acetate=2:1, (v/v)) yielded tert-butyl (5)-3-(5-((3-bromophenyl)sulfonamido)-2-methylphenyl)-2-((tert-butoxycarbonyl)amino)propanoate (230 mg, 70% yield) as a yellow solid. TLC: Rf: 0.55 (petroleum ether/ethyl acetate=2:1, (v/v)); LC/MS/UV: Rt: 2.570 min, calculated for $C_{25}H_{33}BrN_2O_6S$ 568.12, found ESI (pos.) m/z=571.15 [M+H$^+$]$^+$; $^1$H NMR (400 MHz, CDCl$_3$): δ 7.90 (s, 1H), 7.66-7.60 (m, 2H), 7.29 (t, J=7.6 Hz, 1H), 7.01 (d, J=8.4 Hz, 1H), 6.87-6.79 (m, 2H), 6.57 (br s, 1H), 5.10-4.91 (m, 1H), 4.39-4.27 (m, 1H), 2.97 (dd, J=14.0, 6.4 Hz, 1H), 2.85 (dd, J=14.0, 11.2 Hz, 1H), 2.27 (s, 3H), 1.37 (s, 9H), 1.34 (s, 9H).

The protecting groups of the sulfonamide were removed in one step (Scheme 9). Global removal of the N-Boc-protection group and the tert-butyl ester group of tert-butyl (5)-3-(5-((3-bromophenyl)sulfonamido)-2-methylphenyl)-2-((tert-butoxycarbonyl)amino)propanoate (230 mg, 0.40 mmol) was conducted through reaction with 50 vol-% TFA in DCM (6 mL) at room temperature for overnight. Evaporation of volatiles afforded crude compound (29). Purification by prep. HPLC and removal of the solvents by lyophilization yielded compound (29) (86 mg, 52% yield) as a colorless (white) solid. LC/MS/UV: Rt: 1.487 min, calculated for $C_{16}H_{17}BrN_2O_4S$ 413.01, ESI (pos.) m/z=414.95 [M+H$^+$]$^+$, 827.15 [2M+H$^+$]$^+$, ESI (neg.) m/z=412.90 [M-H$^+$]$^-$, 825.15 [2M-H$^+$]$^-$; HPLC/UV: Rt: 5.700 min (99.9% AUC at 220 nm, 99.9% AUC at 254 nm); $^1$H NMR (400 MHz, CD$_3$OD): δ 7.88 (t, J=1.8 Hz, 1H), 7.73-7.69 (m, 1H), 7.76-7.65 (m, 1H), 7.31 (t, J=8.0 Hz, 1H), 7.08-7.04 (m, 2H), 6.82 (dd, J=8.0, 2.0 Hz, 1H), 3.59 (dd, J=8.8, 6.0 Hz, 1H), 3.29 (dd, J=14.8, 5.6 Hz, 1H, superimposed with NMR solvent signal), 2.94 (dd, J=14.8, 8.8 Hz, 1H), 2.28 (s, 3H). The $^1$H NMR signals of the amino group, the N—H acidic group, and the carboxyl group were not observed because of H-D exchange with the NMR solvent.

Example 30

(S)-2-Amino-3-(5-(N-benzylsulfamoyl)-2-methylphenyl)propanoic Acid (30)

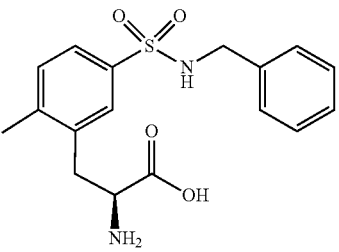

Synthetic sulfonyl chloride starting material 11 (SM-11), 3-iodo-4-methylbenzenesulfonyl chloride, (500 mg, 1.58 mmol) was reacted with commercial benzylamine [CAS No. 100-46-9](172 μL, 169 mg, 1.58 mmol) in DCM (5 mL) in the presence of pyridine [CAS No. 110-86-1](255 μL, 250 mg, 3.16 mmol) at room temperature for overnight. Evaporation of volatiles and chromatographic purification by prep.-TLC on silica gel (petroleum ether/ethyl acetate=4:1, (v/v)) yielded N-benzyl-3-iodo-4-methylbenzenesulfonamide [CAS No. 111633-88-2](339 mg, 55% yield) as a yellow solid. TLC: Rf: 0.10 (petroleum ether/ethyl acetate=4:1, (v/v)); LC/MS/UV: Rt: 3.207 min, calculated for $C_{14}H_{14}INO_2S$ 386.98, found ESI (pos.) m/z=410.15 [M+Na$^+$]$^+$, ESI (neg.) 385.95 [M-H$^+$]$^-$; $^1$H NMR (400 MHz, CDCl$_3$): δ 8.25 (d, J=2.0 Hz, 1H), 7.72 (dd, J=8.0, 2.0 Hz, 1H), 7.34 (d, J=7.9 Hz, 1H), 7.31-7.26 (m, 3H), 7.24-7.16 (m, 2H), 4.71 (s, 1H), 4.15 (d, J=6.0 Hz, 2H), 2.50 (s, 3H).

Synthetic N-benzyl-3-iodo-4-methylbenzenesulfonamide [CAS No. 111633-88-2](330 mg, 0.85 mmol) and starting material 3 (SM-3), tert-butyl (R)-2-((tert-butoxycarbonyl)amino)-3-iodopropanoate [CAS No. 1057341-65-7](317 mg, 0.85 mmol) were cross-coupled through Pd(0)-catalyzed Negishi-coupling using tris(dibenzylideneacetone)dipalladium (Pd$_2$(dba)$_3$) [CAS No. 51364-51-3](78 mg, 0.08 mol) and tri(o-tolyl)phosphine [CAS No. 6163-58-2](26 mg, 0.08 mmol) in the presence of an excess of zinc dust [CAS No. 7440-66-6](668 mg, 10.2 mmol), pre-activated with elemental iodine (I$_2$) [CAS No. 7553-56-2](16 mg, 0.13 mmol) and trimethylchlorosilane (TMSCl) [CAS No. 75-77-4](50 μL, 43 mg, 0.13 mmol) in anhydrous DMF (10 mL+5 mL) at 60° C. for overnight under a nitrogen atmosphere. Filtration over Celite®, extractive aqueous work-up, and chromatographic purification by prep.-TLC on silica gel (petroleum ether/ethyl acetate=1:1, (v/v)) yielded tert-butyl (S)-3-(5-(N-benzylsulfamoyl)-2-methylphenyl)-2-((tert-butoxycarbonyl)amino)propanoate (303 mg, 70% yield) as a yellow solid. TLC: Rf: 0.10 (petroleum ether/ethyl acetate=1:1, (v/v)); LC/MS/UV: Rt: 3.284 min, calculated for $C_{26}H_{36}N_2O_6S$ 504.23, found ESI (pos.) m/z=349.30 [M-C$_4$H$_8$—CO$_2$—C$_4$H$_8$+H$^+$]$^+$, 527.30 [M+Na$^+$]$^+$.

The protecting groups of the sulfonamide were removed in one step (Scheme 9). Global removal of the N-Boc-protection group and the tert-butyl ester group of tert-butyl (S)-3-(5-(N-benzylsulfamoyl)-2-methylphenyl)-2-((tert-butoxycarbonyl)amino)propanoate (280 mg, 0.55 mmol) was conducted through reaction with 50 vol-% TFA in DCM (6 mL) at room temperature for overnight. Evaporation of volatiles afforded crude compound (30). Purification by prep. HPLC and removal of the solvents by lyophilization yielded compound (30) (26 mg, 14% yield) as a colorless (white) solid. LC/MS/UV: Rt: 1.401 min, calculated for $C_{17}H_{20}N_2O_4S$ 348.11, ESI (pos.) m/z=349.10 [M+H$^+$]$^+$; ESI (neg.) m/z=347.05 [M–H$^+$]$^-$, 695.45 [2M–H$^+$]$^-$; HPLC/UV: Rt: 5.481 min (99.9% AUC at 220 nm, 100% AUC at 254 nm); $^1$H NMR (400 MHz, CD$_3$OD): δ 7.68-7.64 (m, 2H), 7.39 (br d, J=8.4 Hz, 1H), 7.26-7.17 (m, 5H), 4.17 (br t, J=7.6 Hz, 1H), 4.03 (s, 2H), 3.37 (dd, J=14.4, 7.2 Hz, 1H), 3.14 (dd, J=14.4, 8.0 Hz, 1H), 2.44 (s, 3H). The $^1$H NMR signals of the amino group, the N—H acidic group, and the carboxyl group were not observed because of H-D exchange with the NMR solvent.

Example 31

(S)-3-(5-(1H-imidazole-4-sulfonamide)-2-methylphenyl)-2-aminopropanoic Acid (31)

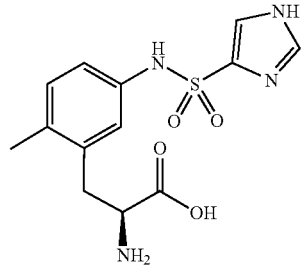

Compound (31) was synthesized by adapting methods described in Scheme 7 and Scheme 9. The aniline starting material 6 (SM-6), tert-butyl (S)-3-(5-amino-2-methylphenyl)-2-((tert-butoxycarbonyl)amino)propanoate, (200 mg, 0.57 mmol) was reacted with commercial 1H-imidazole-4-sulfonyl chloride [CAS No. 58767-51-4](95 mg, 0.57 mmol) in pyridine (2 mL) in a sealed tube at 80° C. for overnight (ca. 20 h). Extractive aqueous workup and purification by prep.-TLC on silica gel (petroleum ether/ethyl acetate=1:1, (v/v)) yielded tert-butyl (S)-3-(5-(1H-imidazole-4-sulfonamido)-2-methylphenyl)-2-((tert-butoxycarbonyl)amino)propanoate (158 mg, 57% yield, impure) as a light yellow oil. TLC: Rf: 0.40 (petroleum ether/ethyl acetate=1:1, (v/v)); LC/MS/UV: Rt: 3.486 min, calculated for $C_{22}H_{32}N_4O_6S$ 480.20, found ESI (pos.) m/z=481.40 [M+H$^+$]$^+$, 962.80 [2M+H$^+$]$^+$, ESI (neg.) m/z=489.35 [M–H$^+$]$^-$.

The protecting groups of the sulfonamide were removed in one step (Scheme 9). Global removal of the N-Boc-protection group and the tert-butyl ester group of tert-butyl (S)-3-(5-(1H-imidazole-4-sulfonamido)-2-methylphenyl)-2-((tert-butoxycarbonyl)amino)propanoate (150 mg, 0.31 mmol, 1.0 eq.) was conducted through reaction with 50 vol-% TFA in DCM (4 mL) at room temperature for overnight. Evaporation of volatiles afforded crude compound (31). Purification by prep. HPLC and removal of the solvents by lyophilization yielded compound (31) (37 mg, 40% yield) as a colorless (white) solid. LC/MS/UV: Rt: 1.035 min, calculated for $C_{13}H_{16}N_4O_4S$ 324.09, ESI (pos.) m/z=325.05 [M+H$^+$]$^+$; ESI (neg.): m/z=323.05 [M–H$^+$]$^-$, 647.25 [2M–H$^+$]$^-$; HPLC/UV: Rt: 4.265 min (99.6% AUC at 220 nm, 100% AUC at 254 nm); $^1$H NMR (400 MHz, CD$_3$OD): δ 8.86 (s, 1H), 7.95 (d, J=1.6 Hz, 1H), 7.19-7.14 (m, 2H), 6.99 (dd, J=8.4, 2.4 Hz, 1H), 4.13 (brt, J=6.8 Hz, 1H), 3.36-3.30 (m, 1H, superimposed with $^1$H NMR signal of NMR solvent), 3.10 (dd, J=14.4, 8.0 Hz, 1H), 2.32 (s, 3H). The $^1$H NMR signals of the amino group, the N—H acidic group, and the carboxyl group were not observed because of H-D exchange with the NMR solvent.

Example 32

(S)-2-Amino-3-(2-methyl-5-((3-((4-methylphenyl)sulfonamido)phenyl)sulfonamido)phenyl)propanoic Acid (32)

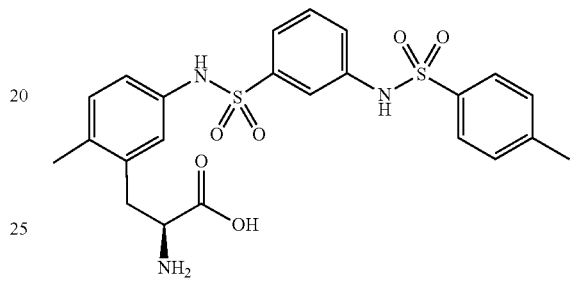

Compound (32) was synthesized by adapting methods described in Scheme 7 and Scheme 9. The aniline reduction product tert-butyl (S)-3-(5-((3-aminophenyl)sulfonamido)-2-methylphenyl)-2-((tert-butoxycarbonyl)amino)propanoate from the synthesis of compound (28) (Example 28) (200 mg, 0.57 mmol) in pyridine (2 mL) was reacted with commercial 4-methylbenzenesulfonyl chloride (tosylchloride, TsCl) [CAS No. 51419-59-1](131 mg, 0.69 mmol) at room temperature for overnight. Acidic aqueous extractive workup and chromatographic purification by prep.-TLC on silica gel (petroleum ether/ethyl acetate=1:1, (v/v)) yielded tert-butyl (S)-2-((tert-butoxycarbonyl)amino)-3-(2-methyl-5-((3-((4-methylphenyl)sulfonamido)phenyl)sulfonamido)phenyl)propanoate (150 mg, 40% yield) as a yellow solid. TLC: Rf: 0.65 (petroleum ether/ethyl acetate=1:1, (v/v)).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-((3-((4-methylphenyl)sulfonamido)phenyl)sulfonamido)phenyl)propanoate (150 mg, 0.23 mmol) was conducted through reaction with 50 vol-% TFA in DCM (4 mL) at room temperature for overnight. Evaporation of volatiles afforded crude compound (32). Purification by prep. HPLC and removal of the solvents by lyophilization yielded compound (32) (46 mg, 39% yield) as a yellow solid. LC/MS/UV: Rt: 1.539 min, calculated for $C_{23}H_{25}N_3O_6S_2$ 503.12, ESI (pos) m/z=504.30 [M+H$^+$]$^+$, ESI (neg.) m/z=502.30 [M–H$^+$]$^-$; HPLC/UV: Rt: 5.888 min (99.7% AUC at 220 nm, 99.8% AUC at 254 nm); $^1$H NMR (400 MHz, CD$_3$OD): δ 7.67 (t, J=2.0 Hz, 1H), 7.48-7.35 (m, 2H), 7.35-7.38 (m, 1H), 7.26 (t, J=8.0 Hz, 1H), 7.19 (dd, J=8.8, 0.8 Hz, 2H), 7.16 (d, J=2.4 Hz, 1H), 7.08-7.03 (m, 2H), 6.75 (dd, J=8.0, 2.4 Hz, 1H), 4.06 (dd, J=8.4, 6.4 Hz, 1H), 3.36-3.30 (m, 1H, superimposed by $^1$H NMR signal of NMR solvent), 3.00 (dd, J=14.4, 8.4 Hz, 1H), 2.35 (s, 3H), 2.28 (s, 3H). The $^1$H NMR signals of the amino group, the N—H acidic group, and the carboxyl group were not observed because of H-D exchange with the NMR solvent.

Example 33

(S)-2-Amino-3-(2-methyl-5-((4-((4-methylphenyl)sulfonamido)phenyl) propanoic Acid (33)

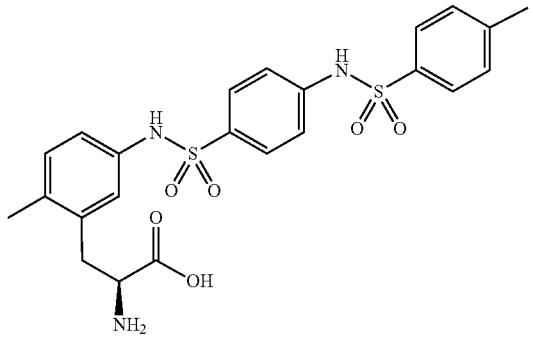

Compound (33) was synthesized by adapting methods described in Scheme 4, Scheme 7, and Scheme 9. The aniline starting material 6 (SM-6), tert-butyl (S)-3-(5-amino-2-methylphenyl)-2-((tert-butoxycarbonyl)amino)propanoate, (400 mg, 1.14 mmol) was reacted with commercial 4-nitrobenzenesulfonyl chloride [CAS No. 98-74-8](379 mg, 1.71 mmol) in pyridine (2 mL) at room temperature for overnight under a nitrogen atmosphere. Extractive aqueous workup and purification by prep.-TLC on silica gel (petroleum ether/ethyl acetate=2:1, (v/v)) yielded tert-butyl (S)-2-((tert-butoxycarbonyl)amino)-3-(2-methyl-5-((4-nitrophenyl)sulfonamido)phenyl)propanoate (400 mg, 66% yield) as a yellow solid. TLC: Rf: 0.65 (petroleum ether/ethyl acetate=3:1, (v/v)); LC/MS/UV: Rt: 2.459 min, calculated for $C_{25}H_{33}N_3O_8S$ 535.20, found ESI (pos.) m/z=380.10 $[M-C_4H_8—CO_2-C_4H_8+H^+]^+$, 536.25 $[M+H^+]^+$, ESI (neg.) m/z=534.30 $([M-H^+]^-$.

Following well-known literature procedures, the nitro-group of the sulfonamide tert-butyl (S)-2-((tert-butoxycarbonyl)amino)-3-(2-methyl-5-((4-nitrophenyl)sulfonamido)phenyl)propanoate (400 mg, 0.75 mmol) was reduced to the corresponding aniline through hydrogenation ($H_2$-balloon, 15 psi) over palladium on carbon (Pd(C)) [CAS No. 7440-05-3](40 mg) in MeOH (4 mL) at room temperature for overnight. Filtration through Celite®, evaporation of volatiles, and chromatographic purification by prep.-TLC on silica gel (petroleum ether/ethyl acetate=3:1, (v/v)) yielded tert-butyl (S)-3-(5-((4-aminophenyl)sulfonamido)-2-methylphenyl)-2-((tert-butoxycarbonyl)amino)propanoate (300 mg, 77% yield) as a colorless (white) solid. TLC: Rf: 0.25 (petroleum ether/ethyl acetate=3:1, (v/v)); LC/MS/UV: Rt: 2.615 min, calculated for $C_{25}H_{35}N_3O_6S$ 505.22, found ESI (pos.) m/z=350.25 $[M-C_4H_8—CO_2—C_4H_8+H^+]^+$, ESI (neg.) m/z=504.45 $[M-H^+]^-$.

The reduction product tert-butyl (S)-3-(5-((4-aminophenyl)sulfonamido)-2-methylphenyl)-2-((tert-butoxycarbonyl)amino)propanoate (300 mg, 0.59 mmol) in pyridine (3 mL) was reacted with commercial 4-methylbenzenesulfonyl chloride (tosylchloride, TsCl) [CAS No. 51419-59-1](170 mg, 0.89 mmol) at room temperature for overnight under a nitrogen atmosphere. Acidic aqueous extractive workup and chromatographic purification by prep.-TLC on silica gel (petroleum ether/ethyl acetate=2:1, (v/v)) yielded tert-butyl (S)-2-((tert-butoxycarbonyl)amino)-3-(2-methyl-5-((4-((4-methylphenyl)sulfonamido)phenyl)sulfonamido)phenyl) propanoate (100 mg, 25% yield) as a yellow solid. TLC: Rf: 0.55 (petroleum ether/ethyl acetate=1:1, (v/v)); LC/MS/UV: Rt: 2.896 min, calculated for $C_{32}H_{41}N_3O_8S_2$ 659.23, found ESI (pos.) 504.45 $[M-C_4H_8—CO_2—C_4H_8+H^+]^+$, ESI (neg.) m/z=658.55 $[M-H^+]^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-((4-((4-methylphenyl)sulfonamido)phenyl)sulfonamido)phenyl) propanoate (100 mg, 0.15 mmol) was conducted through reaction with 50 vol-% TFA in DCM (2 mL) at room temperature for overnight. Evaporation of volatiles afforded crude compound (33). Purification by prep. HPLC and removal of the solvents by lyophilization yielded compound (33) (17 mg, 26% yield) as a colorless (white) solid. LC/MS/UV: Rt: 1.544 min, calculated for $C_{23}H_{25}N_3O_6S_2$ 503.12, ESI (pos.) m/z=504.20 $[M+H^+]^+$, ESI (neg.) m/z=502.10 $[M-H^+]^-$; HPLC/UV: Rt: 5.242 min (99.2% AUC at 220 nm, 99.5% AUC at 254 nm); $^1$H NMR (400 MHz, CD$_3$OD): δ 7.66 (d, J=8.4 Hz, 2H), 7.55 (d, J=8.8 Hz, 2H), 7.28 (d, J=8.4 Hz, 2H), 7.14 (d, J=8.8 Hz, 2H), 7.04 (d, J=2.4 Hz, 1H), 7.01 (d, J=8.4 Hz, 1H), 6.72 (dd, J=8.0, 2.0 Hz, 1H), 3.91 (dd, J=8.8, 5.6 Hz, 1H), 3.28 (dd, J=14.4, 5.6 Hz, 1H, superimposed with $^1$H NMR signal of NMR solvent), 2.93 (dd, J=14.4, 8.8 Hz, 1H), 2.34 (s, 3H), 2.28 (s, 3H). The $^1$H NMR signals of the amino group, the N—H acidic groups, and the carboxyl group were not observed because of H-D exchange with the NMR solvent.

Example 34

(R)-2-Amino-3-(5-((5-(dimethylamino)naphthalene)-1-(sulfonamide)-2-isopropylphenyl) proponoic Acid (34)

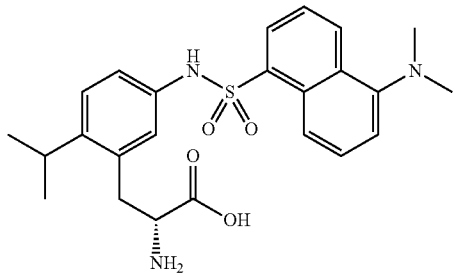

Compound (34) was synthesized by adapting methods described in Scheme 7 and Scheme 9. The aniline starting material 14 (SM-14), tert-butyl (R)-3-(5-amino-2-isopropylphenyl)-2-((tert-butoxycarbonyl)amino)propanoate, (300 mg, 0.79 mmol) was reacted with commercial 5-(dimethylamino)naphthalene-1-sulfonyl chloride (dansyl chloride) [CAS No. 605-65-2](235 mg, 0.87 mmol) in DCM (5 mL) in the presence of pyridine [CAS No. 110-86-1](64 µL, 63 mg, 1.58 mmol) at room temperature for overnight under a nitrogen atmosphere. Evaporation of volatiles and chromatographic purification on silica gel (petroleum ether/ethyl acetate=4:1, (v/v)) yielded tert-butyl (R)-2-((tert-butoxycarbonyl)amino)-3-(5-((5-(dimethylamino)naphthalene)-1-sulfonamido)-2-isopropylphenyl)propanoate (370 mg, 76% yield) as a yellow solid. TLC: Rf: 0.40 (petroleum ether/ethyl acetate=4:1, (v/v)); LC/MS/UV: Rt: 3.218 min, calculated for $C_{33}H_{45}N_3O_6S$ 611.30, found ESI (pos.)

m/z=556.55 [M−C₄H₈+H⁺]⁺, 612.60 [M+H⁺]⁺; ¹H NMR (400 MHz, CDCl₃): δ 8.54 (d, J=5.3 Hz, 1H), 8.32 (d, J=7.7 Hz, 1H), 8.20 (d, J=8.1 Hz, 1H), 7.55 (t, J=7.8 Hz, 1H), 7.50-7.42 (m, 1H), 7.20 (d, J=6.7 Hz, 1H), 7.02 (d, J=7.9 Hz, 1H), 6.78 (d, J=10.7 Hz, 2H), 6.67 (s, 1H), 4.90 (dd, J=8.4, 6.0 Hz, 1H), 4.28-4.21 (m, 1H), 3.04 (p, J=6.8 Hz, 1H), 2.97-2.91 (m, 1H), 2.90 (s, 6H), 1.39 (s, 9H), 1.26 (s, 9H), 1.13 (d, J=6.6 Hz, 6H).

The protecting groups of the sulfonamide were removed in one step (Scheme 9). Global removal of the N-Boc-protection group and the tert-butyl ester group of tert-butyl (R)-2-((tert-butoxycarbonyl)amino)-3-(5-((5-(dimethyl-amino)naphthalene)-1-sulfonamido)-2-isopropylphenyl)propanoate (400 mg, 0.65 mmol) was conducted through reaction with 50 vol-% TFA in DCM (6 mL) at room temperature for overnight. Evaporation of volatiles afforded crude compound (34). Purification by prep. HPLC and removal of the solvents by lyophilization yielded compound (34) (197 mg, 27% yield) as a colorless (white) solid. LC/MS/UV: Rt: 1.601 min, calculated for $C_{24}H_{29}N_3O_4S$ 455.19, ESI (pos.) m/z=456.20 [M+H⁺]⁺, ESI (neg.) m/z=454.15 [M−H⁺]⁻, 909.85 [2M−H⁺]⁻; HPLC/UV: Rt: 5.518 min (99.8% AUC at 220 nm, 99.6% AUC at 254 nm); ¹H NMR (400 MHz, DMSO-d₆): δ 10.68 (s, 1H), 8.64-8.37 (m, 5H), 8.27 (d, J=7.4 Hz, 1H), 7.66 (t, J=8.0 Hz, 2H), 7.47 (br s, 1H), 7.07 (d, J=8.4 Hz, 1H), 6.97 (d, J=2.4 Hz, 1H), 6.86 (dd, J=8.8, 2.3 Hz, 1H), 3.72-3.68 (m, 1H), 3.15-2.80 (br m, 2H+1H+6H, superimposed ¹H NMR signals), 1.04 (d, J=6.7 Hz, 6H).

Example 35

(S)-2-Amino-3-(2-methyl-5-(N-phenylsulfamoyl)phenyl)propanoic Acid Hydrochloride (35) ((S)-1-Carboxy-2-(2-methyl-5-(N-phenylsulfamoyl)phenyl)ethan-1-aminium Chloride)

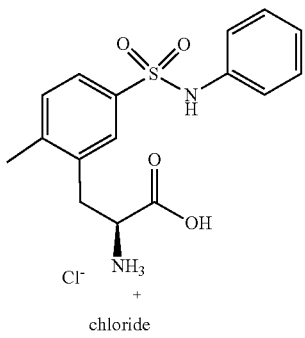

Compound (35) was synthesized by adapting methods described in Scheme 2, Scheme 3, and Scheme 9. Synthetic sulfonyl chloride starting material 11 (SM-11), 3-iodo-4-methyl-benzenesulfonyl chloride [CAS No. 953725-14-9] (500 mg, 1.58 mmol) in DCM (5 mL) was reacted with commercial aniline [CAS No. 62-53-3](93 mg, 1.58 mmol) in the presence of pyridine [CAS No. 110-86-1] at room temperature for overnight under a nitrogen atmosphere. Extractive aqueous workup and chromatographic purification on silica gel (petroleum ether/ethyl acetate=100:1 to 20:1, (v/v)) yielded 3-iodo-4-methyl-N-phenylbenzene-sulfonamide (522 mg, 88% yield) as a yellow solid. TLC: Rf: 0.40 (petroleum ether/ethyl acetate=5:1, (v/v)); LC/MS/UV: Rt: 3.067 min, calculated for $C_{13}H_{12}INO_2S$ 372.96, found ESI (pos.) m/z=396.05 [M+Na⁺]⁺, 769.35 [2M+Na⁺]⁺, ESI (neg.) m/z=372.05 [M−H⁺]⁻.

Synthetic 3-iodo-4-methyl-N-phenylbenzenesulfonamide (520 mg, 1.40 mmol) and starting material 3 (SM-3), tert-butyl (R)-2-((tert-butoxycarbonyl)amino)-3-iodopropanoate [CAS No. 1057341-65-7](517 mg, 1.40 mmol) were cross-coupled through Pd(0)-catalyzed Negishi-coupling using tris(dibenzylideneacetone)dipalladium (Pd₂(dba)₃) [CAS No. 51364-51-3](128 mg, 0.14 mmol) and tri-o-tolylphos-phine (P(o-tol)₃) [CAS No. 6163-58-2](42 mg, 0.14 mmol) in the presence of an excess of zinc dust [CAS No. 7440-66-6](1.09 g, 16.7 mmol), pre-activated with elemental iodine (I₂) [CAS No. 7553-56-2](27 mg, 0.11 mmol) and trimethylchlorosilane (TMSCl) [CAS No. 75-77-4](50 μL, 43 mg, 0.39 mmol) in anhydrous DMF (10 mL+5 mL+10 mL) at 60° C. for overnight under a nitrogen atmosphere. Filtration over Celite®, evaporation of volatiles, and chromatographic purification on silica gel (petroleum ether/ethyl acetate=20:1 to 1:1, (v/v)) yielded tert-butyl (S)-2-((tert-butoxycarbonyl)amino)-3-(2-methyl-5-(N-phenylsulfa-moyl)phenyl)propanoate (376 mg, 55% yield) as a yellow solid. TLC: Rf 0.20 (petroleum ether/ethyl acetate=4:1, (v/v)); LC/MS/UV: Rt: 3.096 min, calculated for $C_{25}H_{34}N_2O_6S$ 490.21, found ESI (pos.) m/z=335.20 [M−C₄H₈−CO₂−C₄H₈+H⁺]⁺, ESI (neg.) m/z=489.45 [M−H⁺]⁻.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(N-phe-nylsulfamoyl)phenyl)propanoate (320 mg, 0.64 mmol) was conducted through reaction with 50 vol-% TFA in DCM (4 mL) at room temperature for overnight. Evaporation of volatiles afforded crude compound (35). Purification by prep. HPLC with eluents A and B containing 0.1 vol-% of concentrated hydrochloric acid and removal of the solvents by lyophilization yielded compound (35) (104 mg, 41% yield) as a colorless (white) solid as a hydrochloride salt. LC/MS/UV: Rt: 1.344 min, calculated for $C_{16}H_{18}N_2O_4S$ 334.10 (free amino acid), ESI (pos.) m/z=335.10 [M+H⁺]⁺, 669.25 [2M+H⁺]⁺, ESI (neg.) m/z=333.05 [M−H⁺]⁻, 667.40 [2M−H⁺]⁻; HPLC/UV: Rt: 6.303 min (99.6% AUC at 220 nm, 99.8% AUC at 254 nm); ¹H NMR (400 MHz, CD₃OD): δ 7.63 (d, J=2.0 Hz, 1H), 7.54 (dd, J=8.0, 2.0 Hz, 1H), 7.32 (d, J=8.4 Hz, 1H), 7.25-7.16 (m, 2H), 7.12-7.02 (m, 3H), 3.94 (dd, J=8.0, 6.8 Hz, 1H), 3.34 (dd, J=14.4, 6.8 Hz, 1H), 3.07 (dd, J=14.4, 8.0 Hz, 1H), 2.40 (s, 3H). The ¹H NMR signals of the amino group, the N—H acidic group, and the carboxyl group were not observed because of H-D exchange with the NMR solvent.

Example 36

(S)-2-Amino-3-(5-((2,6-dichloro-4-(trifluoromethyl)phenyl)sulfonamido)-2-methylphenyl) propanoic Acid

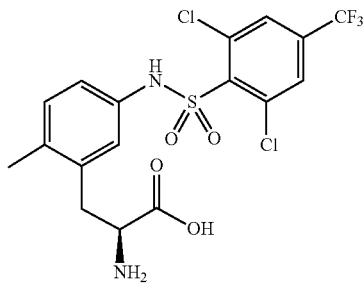

Compound (36) was synthesized by adapting methods described in Scheme 4, Scheme 7, and Scheme 9. 2,6-Dichloro-4-(trifluoromethyl)benzenesulfonyl chloride was prepared from commercial 2,6-dichloro-4-(trifluoromethyl)aniline under Sandmeyer-type reaction conditions using well-known reaction conditions for chlorosulfonation of anilines.

Commercial 2,6-dichloro-4-(trifluoromethyl)aniline [CAS No. 24279-39-8](1.0 g, 4.34 mmol) in a mixture of concentrated hydrochloric acid ($HCl_{aq}$) (~37 wt-%, ~12 M) and water (4 mL, 1:1, (v/v)) was converted to the corresponding diazonium chloride with sodium nitrite ($NaNO_2$) [CAS No. 7632-00-0](449 mg, 6.52 mmol dissolved in water (0.5 mL)) at 0° C. for 30 min. A suspension of copper(II) chloride dihydrate ($CuCl_2 \cdot 2H_2O$) [CAS No. 10125-13-0](370 mg, 2.17 mmol) and copper(I) chloride CuCl [CAS No. 7758-89-6](22 mg, 0.22 mmol) in $SO_2$/HOAc (3 M in HOAc, 5 mL, 15 mmol) was added to the diazonium salt, and the reaction mixture was stirred at 0° C. for 10 min and at room temperature for 2 h. Extractive aqueous workup from an ice/water mixture yielded crude 2,6-dichloro-4-(trifluoromethyl)benzenesulfonyl chloride (410 mg, crude) as a brown solid. The isolated product was used directly in the next step. 2,6-Dichloro-4-(trifluoromethyl)benzenesulfonyl chloride is also commercially available [CAS No. 175205-76-2]. TLC: Rf: 0.60 (petroleum ether/ethyl acetate=5:1, (v/v)).

The aniline starting material 6 (SM-6) tert-butyl (S)-3-(5-amino-2-methylphenyl)-2-((tert-butoxycarbonyl)amino)propanoate, (200 mg, 0.57 mmol) was reacted with synthetic 2,6-dichloro-4-(trifluoromethyl)benzenesulfonyl chloride [CAS No. 175205-76-2](179 mg, 0.57 mmol) in DCM (2 mL) in the presence of pyridine [CAS No. 110-86-1](92 µL, 90 mg, 1.14 mmol) at room temperature for overnight under a nitrogen atmosphere. Extractive aqueous workup and purification by prep.-TLC on silica gel (petroleum ether/ethyl acetate=2:1, (v/v)) yielded tert-butyl (S)-2-((tert-butoxycarbonyl)amino)-3-(5-((2,6-dichloro-4-(trifluoromethyl)phenyl)sulfonamido)-2-methylphenyl)propanoate (150 mg, 42% yield) as a yellow solid. TLC: Rf: 0.45 (petroleum ether/ethyl acetate=2:1, (v/v)); LC/MS/UV: Rt: 2.679 min, calculated for $C_{26}H_{31}Cl_2F_3N_2O_6S$ 626.12, found ESI (pos.) m/z=471.10 [M–$C_4H_8$—$CO_2$—$C_4H_8$+H$^+$]$^+$, 649.25 [M+Na$^+$]$^+$, ESI (neg.) m/z=625.25 [M–H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-((2,6-dichloro-4-(trifluoromethyl)phenyl)sulfonamido)-2-methylphenyl)propanoate (140 mg, 0.22 mmol) was conducted through reaction with HCl in 1,4-dioxane (4 M in 1,4 dioxane, 2 mL, 8 mmol) at 60° C. for overnight. Evaporation of volatiles afforded crude compound (36). Purification by prep. HPLC and removal of the solvents by lyophilization yielded compound (36) (33 mg, 32% yield) as a colorless (white) solid. LC/MS/UV: Rt: 1.608 min, calculated for $C_{17}H_{15}Cl_2F3N_2O_4S$ 470.01, ESI (pos.) m/z=471.00 [M+H$^+$]$^+$, 943.15 [2M+H$^+$]$^+$, ESI (neg.) m/z=468.95 [M–H$^+$]$^-$, 941.20 [2M–H$^+$]$^-$; HPLC/UV: Rt: 5.718 min (99.4% AUC at 220 nm, 100% AUC at 254 nm); $^1$H NMR (400 MHz, CD$_3$OD): δ 7.85 (s, 2H), 7.11 (d, J=2.4 Hz, 1H), 7.05 (d, J=8.0 Hz, 1H), 6.95 (dd, J=8.0, 2.4 Hz, 1H), 3.67 (dd, J=10.0, 4.8 Hz, 1H), 3.30 (dd, J=14.4, 5.2 Hz, 1H, superimposed with the $^1$H NMR signal of the NMR solvent), 2.83 (dd, J=14.4, 9.6 Hz, 1H), 2.26 (s, 3H). The $^1$H NMR signals of the amino group, the N—H acidic group, and the carboxyl group were not observed because of H-D exchange with the NMR solvent.

Example 37

(S)-2-Amino-3-(3-(phenylsulfonamido)phenyl)propanoic Acid (37)

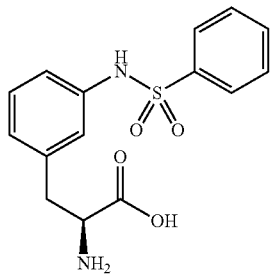

Compound (37) was synthesized by adapting methods described in Scheme 4, Scheme 7, and Scheme 9. Commercial 3-iodoaniline [CAS No. 626-01-7](1.0 g, 4.6 mmol) and tert-butyl (R)-2-((tert-butoxycarbonyl)amino)-3-iodopropanoate (SM-3) [CAS No. 1057341-65-7](1.86 g, 5.0 mmol) were cross-coupled through Pd(0)-catalyzed Negishi-coupling using tris(dibenzylideneacetone)dipalladium (Pd$_2$(dba)$_3$) [CAS No. 51364-51-3](105 mg, 0.11 mmol) and tri(o-tolyl)phosphine (P(o-Tol)$_3$) [CAS No. 6163-58-2](140 mg, 0.46 mmol) in the presence of an excess of zinc dust [CAS No. 7440-66-6](1.96 g, 30.0 mmol), pre-activated with elemental iodine (I$_2$) [CAS No. 7553-56-2](191 mg, 0.75 mmol) and trimethylchlorosilane (TMSCl) [CAS No. 75-77-4](95 µL, 81 mg, 0.75 mmol) in anhydrous DMF (10 mL+5 mL+10 mL) at 60° C. for overnight under a nitrogen atmosphere. Filtration over Celite®, evaporation of volatiles, extractive aqueous work-up, and chromatographic purification on silica gel (hexane/ethyl acetate=1:1, (v/v)) yielded tert-butyl (S)-3-(3-aminophenyl)-2-((tert-butoxycarbonyl)amino)propanoate (1.1 g, 71% yield). TLC: Rf: 0.67 (hexane/ethyl acetate=1:1, (v/v)).

The aniline starting material tert-butyl (S)-3-(3-aminophenyl)-2-((tert-butoxycarbonyl)amino)propanoate (128 mg, 0.38 mmol) was reacted with commercial benzenesulfonyl chloride [CAS No. 98-09-9](74 mg, 0.42 mmol) in THF (5 mL) in the presence of triethylamine (Et$_3$N, TEA) [CAS No. 121-44-8](79 µL, 57 mg, 0.57 mmol) and 4-N,N- dimethylaminopyridine (DMAP) [CAS No. 1122-58-3](5 mg, 0.04 mmol) at 50° C. for 2 h under a nitrogen atmosphere. Extractive aqueous workup and chromatographic purification on silica gel (hexane/ethyl acetate=1:1, (v/v)) yielded (impure) tert-butyl (S)-2-((tert-butoxycarbonyl)amino)-3-(3-(phenylsulfonamido)phenyl)propanoate (150 mg, 83% yield) as a solid. TLC: Rf: 0.73 (hexane/ethyl acetate=1:1, (v/v)).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(3-(phenylsulfonamido)phenyl)propanoate (150 mg, 0.3 mmol) was conducted through reaction with HCl in 1,4-dioxane (4 M in 1,4-dioxane, 5 mL, 20 mmol) at 40° C. for 3 h. Evaporation of volatiles afforded crude compound (37). Purification by prep. HPLC and removal of the solvents by lyophilization yielded compound (37) (30 mg, 30% yield) as a colorless (white) solid. LC/MS/UV: Rt: 0.751 min, calculated for $C_{15}H_{16}N_2O_4S$ 320.08, ESI (pos.) m/z=321.00.15 $[M+H^+]^+$, 640.80 $[2M+H^+]^+$, ESI (neg.) m/z=318.80 $[M-H^+]^-$, 638.60 $[2M-H^+]^-$; HPLC/UV: Rt: 7.010 min (96.6% AUC at 220 nm, 94.4% AUC at 254 nm); $^1$H NMR (300 MHz, CD$_3$OD): δ 7.80 (d, J=7.2 Hz, 2H), 7.60-7.52 (m, 1H), 7.52-7.43 (m, 2H), 7.19 (t, J=7.8 Hz, 1H), 7.07 (br s, 1H), 7.04-6.96 (m, 2H), 3.71 (dd, J=9.6, 5.4 Hz, 1H), 3.22, dd, J=14.7, 3.9 Hz, 1H), 2.89 (dd, J=14.7, 8.7 Hz, 1H). The $^1$H NMR signals of the amino group, the N—H acidic group, and the carboxyl group were not observed because of H-D exchange with the NMR solvent.

Example 38

(S)-3-(5-([1,1'-Biphenyl]-3-sulfonamido)-2-methylphenyl)-2-aminopropanoic Acid (38)

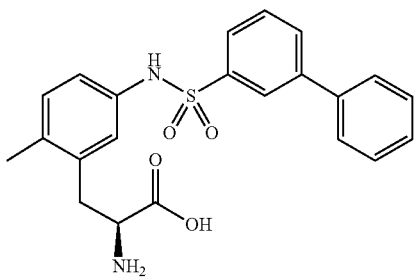

[1,1'-Biphenyl]-3-sulfonyl chloride [CAS No. 65685-01-0] was prepared from commercial [1,1'-biphenyl]-3-amine under Sandmeyer-type reaction conditions using well-known reaction conditions for chlorosulfonation of anilines.

Commercial [1,1'-biphenyl]-3-amine (3-aminobiphenyl) [CAS No. 2243-47-2](500 mg, 2.95 mmol) in a mixture of concentrated hydrochloric acid (HCl$_{aq}$) (~37 wt-%, ~12 M) and water (2 mL, 1:1, (v/v)) was converted to the corresponding diazonium chloride with sodium nitrite (NaNO$_2$) [CAS No. 7632-00-0](305 mg, 4.42 mmol, dissolved in water (0.5 mL)) at 0° C. for 30 min. A suspension of copper(II) chloride dihydrate (CuCl$_2$·2H$_2$O) [CAS No. 10125-13-0](251 mg, 1.47 mmol) and copper(I) chloride CuCl [CAS No. 7758-89-6](15 mg, 0.147 mmol) in SO$_2$/HOAc (3 M in HOAc, 2.5 mL, 7.5 mmol) was added to the diazonium salt, and the reaction mixture was stirred at room temperature for 2 h. Extractive aqueous workup from an ice/water mixture yielded crude [1,1'-biphenyl]-3-sulfonyl chloride (300 mg, crude) as a yellow solid. The isolated product was used directly in the next step. [1,1'-Biphenyl]-3-sulfonyl chloride is also commercially available [CAS No. 65685-01-0].

The aniline starting material 6 (SM-6), tert-butyl (S)-3-(5-amino-2-methylphenyl)-2-((tert-butoxycarbonyl)amino)propanoate, (300 mg, 0.86 mmol) was reacted with synthetic [1,1'-biphenyl]-3-sulfonyl chloride [CAS No. 65685-01-0] (238 mg, 0.94 mmol) in DCM (2 mL) in the presence of pyridine [CAS No. 110-86-1](139 µL, 136 mg, 0.94 mmol) at room temperature for overnight under a nitrogen atmosphere. Extractive aqueous workup and purification by prep.-TLC on silica gel (petroleum ether/ethyl acetate=2:1, (v/v)) yielded tert-butyl (S)-3-(5-([1,1'-biphenyl]-3-sulfonamido)-2-methylphenyl)-2-((tert-butoxycarbonyl)amino)propanoate (210 mg, 43% yield) as a yellow solid. TLC: Rf: 0.55 (petroleum ether/ethyl acetate=2:1, (v/v)); LC/MS/UV: Rt: 2.628 min, calculated for $C_{31}H_{38}N_2O_6S$ 566.25, found ESI (pos.) m/z=411.20 $[M-C_4H_8-CO_2-C_4H_8+H^+]^+$, 589.40 $[M+Na^+]^+$, ESI (neg.) m/z=565.35 $[M-H^+]^-$.

The protecting groups of the sulfonamide were removed in one step (Scheme 9). Global removal of the N-Boc-protection group and the tert-butyl ester group of tert-butyl (S)-3-(5-([1,1'-biphenyl]-3-sulfonamido)-2-methylphenyl)-2-((tert-butoxycarbonyl)amino)propanoate (210 mg, 0.37 mmol) was conducted through reaction with 50 vol-% TFA in DCM (4 mL) at room temperature for overnight. Evaporation of volatiles afforded crude compound (38). Purification by prep. HPLC and removal of the solvents by lyophilization yielded compound (38) (46 mg, 30% yield) as a colorless (white) solid. LC/MS/UV: Rt: 1.601 min, calculated for $C_{22}H_{22}N_2O_4S$ 410.13, ESI (pos.) m/z=411.15 $[M+H^+]^+$, ESI (neg.) m/z=409.10 $[M-H^+]^-$, 819.65 $[2M-H^+]^-$; HPLC/UV: Rt: 5.737 min (99.8% AUC at 220 nm, 99.5% AUC at 254 nm); $^1$H NMR (400 MHz, CD$_3$OD): δ 7.90 (s, 1H), 7.79 (d, J=7.6 Hz, 1H), 7.70 (dd, J=8.0, 1.6 Hz, 1H), 7.60-7.30 (m, 6H), 7.05 (d, J=8.0 Hz, 1H), 7.01 (d, J=2.4 Hz, 1H), 6.92 (dd, J=8.0, 2.4 Hz, 1H), 3.65 (dd, J=9.6, 4.8 Hz, 1H), 3.32-3.25 (m, 1H, superimposed by $^1$H NMR signal of NMR solvent), 2.81 (dd, J=14.8, 9.6 Hz, 1H), 2.27 (s, 3H). The $^1$H NMR signals of the amino group, the N—H acidic group, and the carboxyl group were not observed because of H-D exchange with the NMR solvent.

Example 39

(S)-2-Amino-3-(2-methyl-5-(N-naphthalen-1-yl)sulfamoyl)phenyl)propanoic Acid (39)

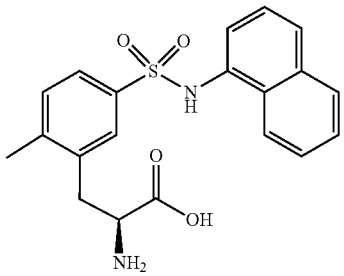

Compound (39) was synthesized by adapting methods described in Scheme 2, Scheme 3, and Scheme 9. Synthetic starting material 11 (SM-11), 3-iodo-4-methyl-benzenesulfonyl chloride [CAS No. 953725-14-9](500 mg, 1.58 mmol) in pyridine (5 mL) was reacted under a nitrogen atmosphere with commercial naphthalen-1-amine (1-naphthylamine) [CAS No. 134-32-7](339 mg, 2.37 mmol) at room temperature for overnight. Extractive aqueous workup and chromatographic purification by prep.-TLC on silica gel (petroleum ether/ethyl acetate=4:1, (v/v)) yielded 3-iodo-4-methyl-N-(naphthalen-1-yl)benzenesulfonamide (600 mg, 89% yield) as a yellow solid. TLC: Rf: 0.50 (petroleum ether/ethyl acetate=4:1, (v/v)); LC/MS/UV: Rt: 2.871 min, calculated for $C_{17}H_{14}INO_2S$ 422.98, found ESI (pos.) m/z=446.25 $[M+Na^+]^+$, ESI (neg.) m/z=422.15 $[M-H^+]^-$.

Synthetic 3-iodo-4-methyl-N-(naphthalen-1-yl)benzenesulfonamide (600 mg, 1.41 mmol) and starting material 3 (SM-3) tert-butyl (R)-2-((tert-butoxycarbonyl)amino)-3-iodopropanoate [CAS No. 1057341-65-7](562 mg, 1.41 mmol) were cross-coupled through Pd(0)-catalyzed Negishi-coupling using tris(dibenzylideneacetone)dipalladium ($Pd_2(dba)_3$) [CAS No. 51364-51-3](130 mg, 0.14 mmol) and dicyclohexylphosphino-2',6'-dimethoxybiphenyl (S-Phos) [CAS No. 657408-07-6](58 mg, 0.14 mmol) in the presence of an excess of zinc dust [CAS No. 7440-66-6](1.11 g, 17.0 mmol), pre-activated with elemental iodine ($I_2$) [CAS No. 7553-56-2](27 mg, 0.11 mmol) and trimethylchlorosilane (TMSCl) [CAS No. 75-77-4](60 µL, 51 mg, 0.47 mmol) in anhydrous DMF (10 mL+5 mL+10 mL) at 60° C. for overnight under a nitrogen atmosphere. Filtration over Celite®, evaporation of volatiles, and chromatographic purification on silica gel (petroleum ether/ethyl acetate=100:1 to 5:1, (v/v)) yielded tert-butyl (S)-2-((tert-butoxycarbonyl)amino)-3-(2-methyl-5-(N-(naphthalen-1-yl)sulfamoyl)phenyl)propanoate (400 mg, 52% yield) as a colorless (white) solid. TLC: Rf: 0.35 (petroleum ether/ethyl acetate=5:1, (v/v)); LC/MS/UV: Rt: 3.337 min, calculated for $C_{29}H_{36}N_2O_6S$ 540.23, found ESI (pos.) m/z=385.30 $[M-C_4H_8-CO_2-C_4H_8+H^+]^+$, 563.60 $[M+Na^+]^+$, ESI (neg.) m/z=539.50 $[M-H^+]^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(N-(naphthalen-1-yl)sulfamoyl)phenyl)propanoate (380 mg, 0.70 mmol) was conducted through reaction with 50 vol-% TFA in DCM (8 mL) at room temperature for overnight. Evaporation of volatiles afforded crude compound (39). Purification by prep. HPLC and removal of the solvents by lyophilization yielded compound (39) (57 mg, 21% yield) as a colorless (white) solid. LC/MS/UV: Rt: 1.468 min, calculated for $C_{20}H_{20}N_2O_4S$ 384.11, ESI (pos.) m/z=385.10 $[M+H^+]^+$, 769.30 $[2M+H^+]^+$, ESI (neg.) m/z=383.10 $[M-H^+]^-$, 767.50 $[2M-H^+]^-$; HPLC/UV: Rt: 5.381 min (99.9% AUC at 220 nm, 99.7% AUC at 254 nm); $^1$H NMR (400 MHz, DMSO-$d_6$): δ 8.07 (dd, J=7.2, 3.2 Hz, 1H), 7.87 (dd, J=9.2, 2.8 Hz, 1H), 7.74 (dd, J=8.4, 2.8 Hz, 1H), 7.60 (br s, 1H), 7.49-7.46 (m, 2H), 7.40-7.30 (m, 2H), 7.25 (dd, J=8.4, 2.8 Hz, 1H), 7.02 (dd, J=7.2, 2.8 Hz, 1H), 4.43-3.36 (br m, 1H), 3.20-3.14 (br m, 1H), 2.85-7.75 (br m, 1H), 2.31, (s, 3H). The $^1$H NMR signals of the amino group, the N—H acidic group, and the carboxyl group were not observed because of H-D exchange with the moisture in the NMR solvent.

Example 40

(S)-3-(5-(N-([1,1'-Biphenyl]-4-yl)sulfamoyl)-2-methylphenyl)-2-aminopropanoic Acid (40)

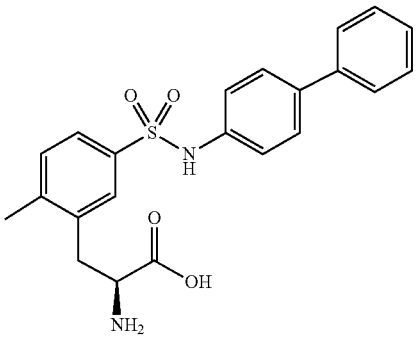

Compound (40) was synthesized by adapting methods described in Scheme 2, Scheme 3, and Scheme 9. Synthetic starting material 11 (SM-11), 3-iodo-4-methyl-benzenesulfonyl chloride [CAS No. 953725-14-9](500 mg, 1.58 mmol) in pyridine (5 mL) was reacted under a nitrogen atmosphere with commercial [1,1'-biphenyl]-4-amine (4-aminobiphenyl) [CAS No. 92-67-1](401 mg, 2.37 mmol) at room temperature for overnight. Extractive aqueous workup and chromatographic purification by prep.-TLC on silica gel (petroleum ether/ethyl acetate=5:1, (v/v)) yielded N-([1,1'-biphenyl]-4-yl)-3-iodo-4-methylbenzenesulfonamide (500 mg, 70% yield) as a yellow solid. TLC: Rf: 0.55 (petroleum ether/ethyl acetate=5:1, (v/v)); LC/MS/UV: Rt: 3.119 min, calculated for $C_{19}H_{16}INO_2S$ 448.99, found ESI (pos.) m/z=450.25 $[M+H^+]^+$, 921.40 $[2M+H^+]^+$, ESI (neg.) m/z=448.15 $[M-H^+]^-$.

Synthetic N-([1,1'-biphenyl]-4-yl)-3-iodo-4-methylbenzenesulfonamide (500 mg, 1.2 mmol) and starting material 3 (SM-3), tert-butyl (R)-2-((tert-butoxycarbonyl)amino)-3-iodopropanoate [CAS No. 1057341-65-7](413 mg, 1.2 mmol) were cross-coupled through Pd(0)-catalyzed Negishi-coupling using tris(dibenzylideneacetone)dipalladium ($Pd_2(dba)_3$) [CAS No. 51364-51-3](113 mg, 0.12 mmol) and dicyclohexylphosphino-2',6'-dimethoxybiphenyl (S-Phos) [CAS No. 657408-07-6](50 mg, 0.12 mmol) in the presence of an excess of zinc dust [CAS No. 7440-66-6](964 mg, 14.7 mmol), pre-activated with elemental iodine ($I_2$) [CAS No. 7553-56-2](23 mg, 0.09 mmol) and trimethylchlorosilane (TMSCl) [CAS No. 75-77-4](50 µL, 43 mg, 0.39 mmol) in anhydrous DMF (10 mL+5 mL+10 mL) at 60° C. for overnight under a nitrogen atmosphere. Filtration over Celite®, evaporation of volatiles and chromatographic purification on silica gel (petroleum ether/ethyl acetate=100:1 to 5:1, (v/v)) yielded tert-butyl (S)-3-(5-(N-([1,1'-biphenyl]-4-yl)sulfamoyl)-2-methylphenyl)-2-((tert-butoxycarbonyl)amino)propanoate (180 mg, 28% yield) as a colorless (white) solid. TLC: Rf: 0.30 (petroleum ether/ethyl acetate=5:1, (v/v)); LC/MS/UV: Rt: 3.328 min, calculated for $C_{31}H_{38}N_2O_6S$ 566.25, found ESI (pos.) m/z=411.35 $[M-C_4H_8-CO_2-C_4H_8+H^+]^+$, 589.55 $[M+Na^+]^+$, ESI (neg.) m/z=565.60 $[M-H^+]^-$.

The protecting groups of the sulfonamide were removed in one step (Scheme 9). Global removal of the N-Boc-protection group and the tert-butyl ester group of tert-butyl (S)-3-(5-(N-([1,1'-biphenyl]-4-yl)sulfamoyl)-2-methylphenyl)-2-((tert-butoxycarbonyl)amino)propanoate (180 mg, 0.32 mmol) was conducted through reaction with 50 vol-% TFA in DCM (4 mL) at room temperature for overnight. Evaporation of volatiles afforded crude compound (40). Purification by prep. HPLC and removal of the solvents by lyophilization yielded compound (40) (92 mg, 70% yield) as a colorless (white) solid. LC/MS/UV: Rt: 1.634 min, calculated for $C_{22}H_{22}N_2O_4S$ 410.13, ESI (pos) m/z=411.15 $[M+H^+]^+$, 821.30 $[2M+H^+]^+$, ESI (neg.) m/z=409.10 $[M-H^+]^-$, 819.70 $[2M-H^+]^-$; HPLC/UV: Rt: 5.788 min (99.9% AUC at 220 nm, 99.8% AUC at 254 nm); $^1$H NMR (400 MHz, DMSO-$d_6$): δ 7.71 (s, 1H), 7.55-7.40 (m, 6H), 7.39-7.31 (brt, J=7.6 Hz, 2H), 7.30-7.22 (m, 2H), 7.12 (d, J=8.0 Hz, 2H), 3.37-3.30 (m, 1H), 3.27-3.20 (m, 1H), 2.78 (dd, J=14.4, 8.8 Hz, 1H), 2.30 (s, 3H). The $^1$H NMR signals of the amino group and the carboxyl group were not observed because of H-D exchange with the moisture in the NMR solvent.

Example 41

(S)-2-Amino-3-(5-(N-butylsulfamoyl)-2-methylphenyl) propanoic Acid (41)

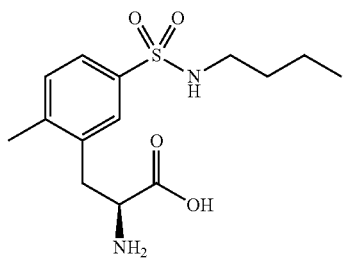

Compound (41) was synthesized by adapting methods described in Scheme 2, Scheme 3, and Scheme 9. Synthetic starting material 11 (SM-11), 3-iodo-4-methyl-benzenesulfonyl chloride [CAS No. 953725-14-9](500 mg, 1.58 mmol) in DCM (5 mL) was reacted in the presence of pyridine [CAS No. 110-86-1](255 μL, 250 mg, 3.16 mmol) with commercial butan-1-amine (n-butylamine, n-BuNH$_2$) [CAS No. 109-73-9](273 mg, 2.37 mmol) at room temperature for overnight under a nitrogen atmosphere. Evaporation of volatiles and chromatographic purification on silica gel (petroleum ether/ethyl acetate=100:1 to 20:1, (v/v)) yielded N-butyl-3-iodo-4-methylbenzenesulfonamide [CAS No. 1116332-52-2](450 mg, 73% yield) as a yellow solid. TLC: Rf: 0.40 (petroleum ether/ethyl acetate=4:1, v/v)); LC/MS: calculated for $C_{11}H_{16}INO_2S$ 352.99, found ESI (pos.) m/z=354.15 $[M+H^+]^+$; $^1$H NMR (400 MHz, CDCl$_3$): δ 8.25 (d, J=2.0 Hz, 1H), 7.71 (m, 1H), 7.34 (m, 1H), 4.41 (t, J=6.2 Hz, 1H), 2.93 (m, 2H), 2.48 (s, 3H), 1.44 (m, 2H), 1.33-1.23 (m, 2H), 0.85 (t, J=7.3 Hz, 3H).

Synthetic N-butyl-3-iodo-4-methylbenzenesulfonamide [CAS No. 1116332-52-2](450 mg, 1.27 mmol) and starting material 3 (SM-3), tert-butyl (R)-2-((tert-butoxycarbonyl) amino)-3-iodopropanoate [CAS No. 1057341-65-7](473 mg, 1.27 mmol) were cross-coupled through Pd(0)-catalyzed Negishi-coupling using tris(dibenzylideneacetone)dipalladium (Pd$_2$(dba)$_3$) [CAS No. 51364-51-3](117 mg, 0.13 mol) and tri(o-tolyl)phosphine (P(o-Tol)$_3$) [CAS No. 6163-58-2](39 mg, 0.13 mmol) in the presence of an excess of zinc dust [CAS No. 7440-66-6](1.0 g, 16.7 mmol), pre-activated with elemental iodine (I$_2$) [CAS No. 7553-56-2] (23 mg, 0.09 mmol) and trimethylchlorosilane (TMSCl) [CAS No. 75-77-4](50 L, 43 mg, 0.39 mmol) in anhydrous DMF (10 mL+5 mL+10 mL) at 60° C. for overnight under a nitrogen atmosphere. Filtration over Celite®, extractive aqueous workup, and chromatographic purification by prep.-TLC on silica gel (petroleum ether/ethyl acetate=3:1, (v/v)) yielded tert-butyl (S)-2-((tert-butoxycarbonyl)amino)-3-(5-(N-butylsulfamoyl)-2-methylphenyl)propanoate (305 mg, 54% yield) as a yellow oil. TLC: Rf: 0.20 (petroleum ether/ethyl acetate=3:1, (v/v)); LC/MS: Rt: calculated for $C_{23}H_{38}N_2O_6S$ 470.25, found ESI (pos.) m/z=493.45 $[M+Na^+]$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(N-butylsulfamoyl)-2-methylphenyl)propanoate (295 mg, 0.62 mmol) was conducted through reaction with 50 vol-% TFA in DCM (4 mL) at room temperature for overnight. Evaporation of volatiles afforded crude compound (41). Purification by prep. HPLC and removal of the solvents by lyophilization yielded compound (41) (56 mg, 21% yield) as a colorless (white) solid. LC/MS/UV: Rt: 1.313 min, calculated for $C_{14}H_{22}N_2O_4S$ 314.13, found ESI (pos) m/z=315.20 $[M+H^+]$, 629.35 $[2M+H^+]^+$, ESI (neg.) m/z=313.05 $[M-H^+]^-$, 627.40 $[2M-H^+]^-$; HPLC/UV: Rt: 5.309 min (99.8% AUC at 220 nm, 99.7% AUC at 254 nm); $^1$H NMR (400 MHz, CD$_3$OD): δ 7.72 (–s, 1H), 7.63 (br dd, J=8.4, 1.6 Hz, 1H), 3.76 (dd, J=9.2, 5.6 Hz, 1H), 4.44 (dd, J=14.4, 5.2 Hz, 1H), 3.02 (dd, J=14.4, 8.8 Hz, 1H), 2.82 (t, J=6.8 Hz, 2H), 2.46 (s, 3H), 1.50-1.38 (m, 2H), 1.38-1.25 (m, 2H), 0.87 (t, J=7.2 Hz, 3H). The $^1$H NMR signals of the amino group, the N—H acidic group, and the carboxyl group were not observed because of H-D exchange with the NMR solvent.

Example 42

(S)-2-Amino-3-(5-((2,6-dichlorophenyl)sulfonamido)-2-methylphenyl) propanoic Acid

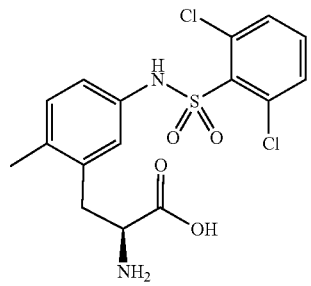

Compound (42) was synthesized by adapting methods described in Scheme 7 and Scheme 9. The aniline starting material 5 (SM-5), methyl (S)-3-(5-amino-2-methylphenyl)-2-((tert-butoxycarbonyl)amino)propanoate, (100 mg, 0.32 mmol) was reacted with commercial 2,6-dichlorobenzene-sulfonyl chloride [CAS No. 6579-54-0](88 mg, 0.36 mmol) in THF (5 mL) in the presence of triethylamine (Et$_3$N, TEA) [CAS No. 121-44-8](89 μL, 65 mg, 0.64 mmol) and 4-N, N-dimethylaminopyridine (DMAP) [CAS No. 1122-58-3](4 mg, 0.032 mmol) at room temperature for overnight. Extractive aqueous workup and chromatographic purification on silica gel (hexane/ethyl acetate=1:1, (v/v)) yielded methyl (S)-2-((tert-butoxycarbonyl)amino)-3-(5-((2,6-dichlorophenyl)sulfonamido)-2-methylphenyl)propanoate (120 mg, 72% yield) as a yellow oil. TLC: Rf 0.56 (hexane/ethyl acetate=1:1, (v/v)).

The protecting groups of the sulfonamide were removed in two steps (Scheme 9). Chemoselective removal of the N-Boc-protection group of methyl (S)-2-((tert-butoxycarbonyl)amino)-3-(5-((2,6-dichlorophenyl)sulfonamido)-2-methylphenyl)propanoate (120 mg, 0.23 mmol) (plus 80 mg of an additional batch of methyl (S)-2-((tert-butoxycarbonyl)amino)-3-(5-((2,6-dichlorophenyl)sulfonamido)-2-methylphenyl)propanoate of unknown purity) with 20 vol-% TFA in DCM (5 mL) at room temperature for about 2 h yielded crude methyl (S)-2-amino-3-(5-((2,6-dichlorophenyl)sulfonamido)-2-methylphenyl)propanoate. Evaporation of volatiles and hydrolysis of the methyl ester group with lithium hydroxide monohydrate (LiOH·H$_2$O) [CAS No. 1310-66-3](48 mg, 1.15 mmol) in THF/water (1:1, (v/v)) (5 mL) at room temperature for 2 h afforded crude compound (42). Evaporation of volatiles, purification by prep. HPLC, and removal of the solvents by lyophilization yielded compound (42) as a colorless (white) solid (110 mg in total). LC/MS/UV: Rt: 0.926 min, calculated for C$_{16}$H$_{16}$C$_{12}$N$_2$O$_4$S 402.02, found ESI (pos.) m/z=404.65 [M+H$^+$]$^+$, 806.35 [2M+H$^+$]$^+$, ESI (neg.) m/z=400.65 [M−H$^+$]$^−$, 804.15 [2M−H$^+$]$^−$; HPLC/UV: Rt: 8.269 min (97.9% AUC at 220 nm, 98.9% AUC at 254 nm); $^1$H NMR (300 MHz, CD$_3$OD): δ 7.53-7.46 (m, 2H), 7.40 (dd, J=9.0, 6.6 Hz, 1H), 7.10 (d, J=1.5 Hz, 1H), 7.05 (d, J=8.1 Hz, 1H), 6.96 (dd, J=8.1, 2.4 Hz, 1H), 3.69 (dd, J=9.9, 4.5 Hz, 1H), 3.32 (dd, J=14.7, 4.8 Hz, 1H, superimposed with the $^1$H NMR signal of NMR solvent), 2.83 (dd, J=14.7, 9.6 Hz, 1H), 2.27 (s, 3H). The $^1$H NMR signals of the amino group, the N—H acidic group, and the carboxyl group were not observed because of H-D exchange with the NMR solvent.

Example 43

(S)-2-Amino-3-(5-((3,5-dichlorophenyl)sulfonamido)-2-methylphenyl)propanoic Acid (43)

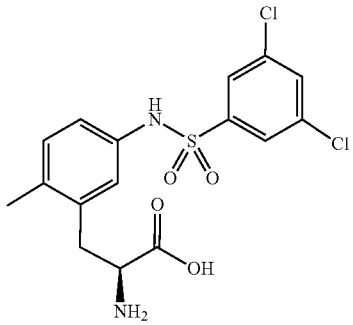

Compound (43) was synthesized by adapting methods described in Scheme 7 and Scheme 9. The aniline starting material 5 (SM-5), methyl (S)-3-(5-amino-2-methylphenyl)-2-((tert-butoxycarbonyl)amino)propanoate, (100 mg, 0.32 mmol) was reacted with commercial 3,5-dichlorobenzenesulfonyl chloride [CAS No. 16271-33-3](88 mg, 0.36 mmol) in THF (5 mL) in the presence of triethylamine (Et$_3$N, TEA) [CAS No. 121-44-8](89 µL, 65 mg, 0.64 mmol) and 4-N,N-dimethylaminopyridine (DMAP) [CAS No. 1122-58-3](4 mg, 0.032 mmol) at room temperature for overnight. Extractive aqueous workup and chromatographic purification on silica gel (hexane/ethyl acetate=7:3, (v/v)) yielded methyl (S)-2-((tert-butoxycarbonyl)amino)-3-(5-((3,5-dichlorophenyl)sulfonamido)-2-methylphenyl)propanoate (140 mg, ca. 85% yield) as a solid. TLC: Rf: 0.56 (hexane/ethyl acetate=7:3, (v/v)).

The protecting groups of the sulfonamide were removed in two steps (Scheme 9). Chemoselective removal of the N-Boc-protection group of methyl (S)-2-((tert-butoxycarbonyl)amino)-3-(5-((3,5-dichlorophenyl)sulfonamido)-2-methylphenyl)propanoate (140 mg, 0.27 mmol) with 20 vol-% TFA in DCM (5 mL) at room temperature for about 2 h yielded crude methyl (S)-2-amino-3-(5-((3,5-dichlorophenyl)sulfonamido)-2-methylphenyl)propanoate. Evaporation of volatiles and hydrolysis of the methyl ester group with LiOH·H$_2$O [CAS No. 1310-66-3](57 mg, 1.35 mmol) in THF/water (1:1, (v/v)) (5 mL) at room temperature for 2 h afforded crude compound (43). Evaporation of volatiles, purification by prep. HPLC, and removal of the solvents by lyophilization yielded compound (43) as a colorless (white) solid (80 mg, 73% yield). LC/MS/UV: Rt: 1.044 min, calculated for C$_{16}$H$_{16}$Cl$_2$N$_2$O$_4$S 402.02, found ESI (pos.) m/z=402.80 [M+H$^+$]$^+$, 806.35 [2M+H$^+$]$^+$, ESI (neg.) m/z=400.65 [M−H$^+$]$^−$, 804.15 [2M−H$^+$]$^−$; HPLC/UV: Rt: 9.225 min (93.3% AUC at 220 nm, 98.6% AUC at 254 nm); $^1$H NMR (300 MHz, CD$_3$OD): δ 7.68 (s, 3H, superimposed), 7.11 (d, J=8.1 Hz, 1H), 7.03 (d, J=2.4 Hz, 1H), 6.89 (dd, J=8.1, 3.2 Hz, 1H), 3.68 (dd, J=9.3, 4.5 Hz, 1H), 3.24 (dd, J=14.4, 4.5 Hz, 1H, superimposed with the $^1$H NMR signal of NMR solvent), 2.87 (dd, J=14.7, 9.6 Hz, 1H), 2.32 (s, 3H). The $^1$H NMR signals of the amino group, the N—H acidic group, and the carboxyl group were not observed because of H-D exchange with the NMR solvent.

Example 44

(S)-2-Amino-3-(5-(N-(4-methoxyphenyl)sulfamoyl)-2-methylphenyl)propanoic Acid (44)

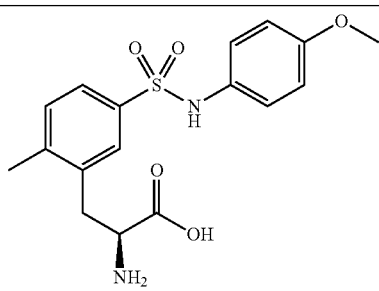

Compound (44) was synthesized by adapting methods described in Scheme 2, Scheme 3, and Scheme 9. Synthetic starting material 11 (SM-11), 3-iodo-4-methyl-benzenesulfonyl chloride [CAS No. 953725-14-9](3.08 g, 9.75 mmol) in pyridine [CAS No. 110-86-1](6 mL) was reacted with commercial 4-methoxyaniline (p-anisidine) [CAS No. 104-94-9](800 mg, 6.5 mmol) at room temperature for overnight under a nitrogen atmosphere. Evaporation of volatiles and chromatographic purification by prep.-TLC on silica gel (petroleum ether/ethyl acetate=4:1, (v/v)) yielded 3-iodo-N-(4-methoxyphenyl)-4-methylbenzenesulfonamide (770 mg, 29% yield) as a colorless (white) solid. TLC: Rf: 0.37 (petroleum ether/ethyl acetate=5:1, (v/v)); LC/MS: calculated for C$_{14}$H$_{14}$INO$_3$S 402.97, found ESI (neg.)

m/z=401.10 [M−H⁺]⁻; ¹H NMR (400 MHz, CDCl₃): δ 8.10 (d, J=2.0 Hz, 1H), 7.48 (dd, J=8.0, 2.0 Hz, 1H), 7.22 (d, J=0.8 Hz, 1H), 6.96 (d, J=9.0 Hz, 2H), 6.81-6.75 (m, 2H), 3.75 (s, 3H), 2.44 (s, 3H). The ¹H NMR signal of the N—H acidic group was not observed because of H-D exchange with moisture in the NMR solvent.

Synthetic 3-iodo-N-(4-methoxyphenyl)-4-methylbenzenesulfonamide (770 mg, 1.91 mmol) and starting material 3 (SM-3), tert-butyl (R)-2-((tert-butoxycarbonyl)amino)-3-iodopropanoate [CAS No. 1057341-65-7](710 mg, 1.91 mmol) were cross-coupled through Pd(0)-catalyzed Negishi-coupling using tris(dibenzylideneacetone)dipalladium (Pd₂(dba)₃) [CAS No. 51364-51-3](186 mg, 0.20 mol) and tri(o-tolyl)phosphine (P(o-Tol)₃) [CAS No. 6163-58-2](79 mg, 0.26 mmol) in the presence of an excess of zinc dust [CAS No. 7440-66-6](1.5 g, 22.9 mmol), pre-activated with elemental iodine (I₂) [CAS No. 7553-56-2](36 mg, 0.14 mmol) and trimethylchlorosilane (TMSCl) [CAS No. 75-77-4](36 µL, 31 mg, 0.29 mmol) in anhydrous DMF (10 mL+6 mL+10 mL) at 60° C. for overnight under a nitrogen atmosphere. Filtration over Celite® and chromatographic purification on silica gel (petroleum ether/ethyl acetate=9:1 to 3:1, (v/v)) yielded tert-butyl (S)-2-((tert-butoxycarbonyl)amino)-3-(5-(N-(4-methoxyphenyl)sulfamoyl)-2-methylphenyl)propanoate (342 mg, 24% yield) as a yellow oil. LC/MS: calculated for C₂₆H₃₆N₂O₇S 520.22, found ESI (neg.) m/z=519.25 [M−H⁺]⁻.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(N-(4-methoxyphenyl)sulfamoyl)-2-methylphenyl)propanoate (342 mg, 0.66 mmol) was conducted through reaction with 50 vol-% TFA in DCM (16 mL) at room temperature for overnight. Evaporation of volatiles afforded crude compound (44). Purification by prep. HPLC and removal of the solvents by lyophilization yielded compound (44) (53 mg, 22% yield) as a colorless (white) solid. LC/MS/UV: Rt: 1.346 min, calculated for C₁₇H₂₀N₂O₅S 364.11, ESI (pos) m/z=365.15 [M+H⁺]⁺, 729.30 [2M+H⁺]⁺, ESI (neg.) m/z=363.05 [M−H⁺]⁻, 727.50 [2M−H⁺]⁻; HPLC/UV: Rt: 4.701 min (99.8% AUC at 220 nm, 99.7% AUC at 254 nm); ¹H NMR (400 MHz, DMSO-d₆): δ 7.62 (br d, J=2.0 Hz, 1H), 7.35 (br dd, J=7.6, 2.0 Hz, 1H), 7.28 (d, J=8.4 Hz, 1H), 6.99 (br dd, J=8.8, 2.4 Hz, 1H), 6.79 (br dd, J=8.8, 2.8 Hz, 1H), 3.67 (s, 3H), 3.42 (dd, J=8.4, 5.2 Hz, 1H), 3.21 (dd, J=14.4, 5.6 Hz, 1H), 2.83 (dd, J=14.4, 8.4 Hz, 1H), 2.33 (s, 3H). The ¹H NMR signals of the amino group, the N—H acidic group, and the carboxyl group were not observed because of H-D exchange with moisture in the NMR solvent.

Example 45

((3-((S)-2-Amino-2-carboxyethyl)-4-methylphenyl)sulfonyl)-D-proline (45)

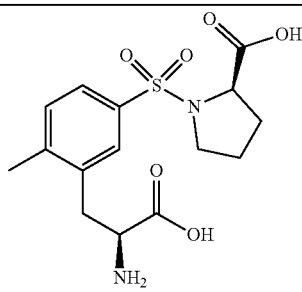

Compound (45) was synthesized by adapting methods described in Scheme 2, Scheme 3, and Scheme 9. Synthetic starting material 11 (SM-11), 3-iodo-4-methyl-benzenesulfonyl chloride [CAS No. 953725-14-9](500 mg, 1.58 mmol) in pyridine [CAS No. 110-86-1](5 mL) was reacted with commercial tert-butyl D-prolinate [CAS No. 90071-62-8](406 mg, 2.37 mmol) at room temperature for overnight under a nitrogen atmosphere. Extractive aqueous workup and chromatographic purification by prep.-TLC on silica gel (petroleum ether/ethyl acetate=5:1, (v/v)) yielded tert-butyl ((3-iodo-4-methylphenyl)sulfonyl)-D-prolinate (600 mg, 84% yield) as a yellow solid. TLC: Rf: 0.45 (petroleum ether/ethyl acetate=5:1, v/v)); LC/MS/UV: Rt: 3.124 min, calculated for C₁₆H₂₂INO₄S 451.03, found ESI (pos.) m/z=396.15 [M−C₄H₈+H⁺]⁺, 452.30 [M+H⁺]⁺, 925.60 [2M+Na⁺]⁺.

Synthetic tert-butyl ((3-iodo-4-methylphenyl)sulfonyl)-D-prolinate (600 mg, 1.32 mmol) and starting material 3 (SM-3), tert-butyl (R)-2-((tert-butoxycarbonyl)amino)-3-iodopropanoate [CAS No. 1057341-65-7](490 mg, 1.32 mmol) were cross-coupled through Pd(0)-catalyzed Negishi-coupling using tris(dibenzylideneacetone)dipalladium (Pd₂(dba)₃) [CAS No. 51364-51-3](121 mg, 0.13 mol) and 2-dicyclohexylphosphino-2',6'-dimethoxybiphenyl (S-Phos) [CAS No. 657408-07-6](54 mg, 0.13 mmol) in the presence of an excess of zinc dust [CAS No. 7440-66-6](1.03 g, 15.8 mmol), pre-activated with elemental iodine (I₂) [CAS No. 7553-56-2](25 mg, 0.1 mmol) and trimethylchlorosilane (TMSCl) [CAS No. 75-77-4](60 µL, 51 mg, 0.47 mmol) in anhydrous DMF (10 mL+5 mL+10 mL) at 60° C. for overnight under a nitrogen atmosphere. Filtration over Celite® and chromatographic purification on silica gel (petroleum ether/ethyl acetate=100:1 to 5:1, (v/v)) yielded tert-butyl ((3-((S)-3-(tert-butoxy)-2-((tert-butoxycarbonyl)amino)-3-oxopropyl)-4-methylphenyl)sulfonyl)-D-prolinate (300 mg, 39% yield) as a colorless (white) solid. TLC: Rf: 0.30 (petroleum ether/ethyl acetate=5:1, (v/v)); LC/MS/UV: Rt: 3.226 min, calculated for C₂₈H₄₄N₂O₈S 568.28, found ESI (neg.) m/z=591.60 [M+Na⁺]⁺.

The protecting groups of the sulfonamide were removed in one step (Scheme 9). Global removal of the N-Boc-protection group and the tert-butyl ester groups of tert-butyl ((3-((S)-3-(tert-butoxy)-2-((tert-butoxycarbonyl)amino)-3-oxopropyl)-4-methylphenyl)sulfonyl)-D-prolinate (280 mg, 0.49 mmol) was conducted through reaction with 50 vol-% TFA in DCM (6 mL) at room temperature for overnight. Evaporation of volatiles afforded crude compound (45). Purification by prep. HPLC and removal of the solvents by lyophilization yielded compound (45) (89 mg, 59% yield) as a colorless (white) solid. LC/MS/UV: Rt: 1.080 min, calculated for C₁₅H₂₀N₂O₆S 356.10, ESI (pos) m/z=357.15 [M+H⁺]⁺, 713.45 [2M+H⁺]⁺, ESI (neg.) m/z=355.05 [M−H⁺]⁻, 711.50 [2M−H⁺]⁻; HPLC/UV: Rt: 4.242 min (99.1% AUC at 220 nm, 99.7% AUC at 254 nm); ¹H NMR (400 MHz, DMSO-d₆): δ 7.56 (s, 1H), 7.49 (d, J=8.0 Hz, 1H), 7.34 (d, J=7.6 Hz, 1H), 4.02-3.96 (br m, 1H), 3.53 (br t, 1H), 3.27-3.20 (m, 2H, superimposed), 3.17 (dd, J=14.4, 7.2 Hz, 1H, superimposed), 2.90 (dd, J=15.6, 7.6 Hz, 1H), 2.35 (s, 3H), 2.00-1.90 m, 1H), 1.81-1.70 (m, 2H), 1.65-1.55 (m, 1H). The ¹H NMR signals of the amino group, and the carboxyl groups were not observed because of H-D exchange with moisture in the NMR solvent.

Example 46

(S)-2-Amino-3-(5-(N-isobutylsulfamoyl)-2-methylphenyl)propanoic Acid (46)

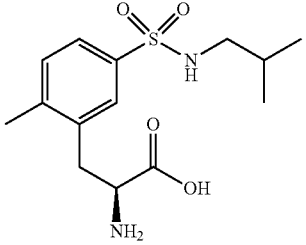

Compound (46) was synthesized by adapting methods described in Scheme 2, Scheme 3, and Scheme 9. Synthetic starting material 11 (SM-11), 3-iodo-4-methyl-benzenesulfonyl chloride [CAS No. 953725-14-9](500 mg, 1.58 mmol) in DCM (5 mL) was reacted with commercial 2-methylpropan-1-amine (isobutylamine) [CAS No. 78-81-9](173 mg, 2.37 mmol) in the presence of pyridine [CAS No. 110-86-1](255 µL, 250 mg, 3.16 mmol) at room temperature for overnight under a nitrogen atmosphere. Evaporation of volatiles and chromatographic purification by prep.-TLC on silica gel (petroleum ether/ethyl acetate=5:1, (v/v)) yielded 3-iodo-N-isobutyl-4-methylbenzenesulfonamide (383 mg, 68% yield) as a yellow solid. TLC: Rf: 0.70 (petroleum ether/ethyl acetate=4:1, v/v)); $^1$H NMR (400 MHz, CDCl$_3$): δ 8.25 (d, J=2.0 Hz, 1H), 7.70 (dd, J=8.0, 2.0 Hz, 1H), 7.34 (d, J=8.0 Hz, 1H), 4.44 (brt, J=6.8 Hz, 1H), 2.75-2.70 (m, 1H), 2.48 (s, 3H), 1.75-1.65 (m, 1H), 0.87 (d, J=6.8 Hz, 6H).

Synthetic 3-iodo-N-isobutyl-4-methylbenzenesulfonamide (380 mg, 1.08 mmol) and starting material 3 (SM-3), tert-butyl (R)-2-((tert-butoxycarbonyl)amino)-3-iodopropanoate [CAS No. 1057341-65-7](400 mg, 1.08 mmol) were cross-coupled through Pd(0)-catalyzed Negishi-coupling using tris(dibenzylideneacetone)dipalladium (Pd$_2$(dba)$_3$) [CAS No. 51364-51-3](99 mg, 0.11 mmol) and tri(o-tolyl)phosphine (P(o-tol)$_3$) [CAS No. 6163-58-2](33 mg, 0.11 mmol) in the presence of an excess of zinc dust [CAS No. 7440-66-6](844 mg, 12.9 mmol), pre-activated with elemental iodine (I$_2$) [CAS No. 7553-56-2](21 mg, 0.083 mmol) and trimethylchlorosilane (TMSCl) [CAS No. 75-77-4](21 µL, 18 mg, 0.16 mmol) in anhydrous DMF (3 mL+3 mL+5 mL) at 60° C. for overnight under a nitrogen atmosphere. Filtration over Celite®, extractive aqueous workup, and chromatographic purification by prep.-TLC on silica gel (petroleum ether/ethyl acetate=2:1, (v/v)) yielded tert-butyl (S)-2-((tert-butoxycarbonyl)amino)-3-(5-(N-isobutylsulfamoyl)-2-methylphenyl)propanoate (330 mg, 65% yield) as a yellow oil. TLC: Rf: 0.20 (petroleum ether/ethyl acetate=4:1, (v/v)); LC/MS/UV: Rt: 2.652 min, calculated for C$_{23}$H$_{38}$N$_2$O$_6$S 470.25, found ESI (pos.) m/z=963.55 [2M+Na$^+$]$^+$; ESI (neg.) m/z=469.20 [M−H$^+$]$^-$.

The protecting groups of the sulfonamide were removed in one step (Scheme 9). Global removal of the N-Boc-protection group and the tert-butyl ester groups of tert-butyl (S)-2-((tert-butoxycarbonyl)amino)-3-(5-(N-isobutylsulfamoyl)-2-methylphenyl)propanoate (320 mg, 0.68 mmol) was conducted through reaction with 50 vol-% TFA in DCM (6 mL) at room temperature for overnight. Evaporation of volatiles afforded crude compound (46). Purification by prep. HPLC and removal of the solvents by lyophilization yielded compound (46) (82 mg, 38% yield) as a colorless (white) solid. LC/MS/UV: Rt: 1.281 min, calculated for C$_{14}$H$_{22}$N$_2$O$_4$S 314.13, ESI (pos.) m/z=315.15 [M+H$^+$]$^+$, 627.45 [2M+H$^+$]$^+$, ESI (neg.) m/z=313.10 [M−H$^+$]$^-$, 711.50 [2M−H$^+$]$^-$; HPLC/UV: Rt: 5.289 min (99.9% AUC at 220 nm, 99.7% AUC at 254 nm); $^1$H NMR (400 MHz, DMSO-d$_6$): δ 7.68-7.65 (br m, 1H), 7.54-7.50 (br m, 1H), 7.34 (d, J=8.0 Hz, 1H), 3.36-3.26 (br m, 1H, superimposed with $^1$H NMR signal from NMR solvent), 2.79 (br dd, J=14.0, 8.4 Hz, 1H), 2.36 (s, 3H), 1.66-1.56 (m, 1H), 0.81 (d, J=6.4 Hz, 6H). The $^1$H NMR signals of the amino group, the N-acidic group, and the carboxyl groups were not observed because of H-D exchange with moisture in the NMR solvent. Some $^1$H NMR signals were not observed because they were obscured by the broad $^1$H NMR signal of the NMR solvent.

Example 47

(S)-2-Amino-3-(3,5-dichloro-4-(phenylsulfonamido)phenyl)propanoic Acid (47)

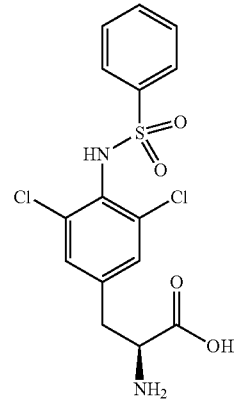

Compound (47) was synthesized by adapting methods described in Scheme 4, Scheme 7, and Scheme 9. Commercial 2,6-dichloro-4-iodoaniline [CAS No. 697-89-2](576 mg, 2.0 mmol) and starting material 3 (SM-3), tert-butyl (R)-2-((tert-butoxycarbonyl)amino)-3-iodopropanoate [CAS No. 1057341-65-7](1.11 g, 3.0 mmol) were cross-coupled through Pd(0)-catalyzed Negishi-coupling using tris(dibenzylideneacetone)dipalladium (Pd$_2$(dba)$_3$) [CAS No. 51364-51-3](46 mg, 0.05 mol) and tri(o-tolyl)phosphine (P(o-Tol)$_3$) [CAS No. 6163-58-2](61 mg, 0.2 mmol) in the presence of an excess of zinc dust [CAS No. 7440-66-6](1.2 g, 18.0 mmol), pre-activated with elemental iodine (I$_2$) [CAS No. 7553-56-2](114 mg, 0.45 mmol) and trimethylchlorosilane (TMSCl) [CAS No. 75-77-4](57 µL, 49 mg, 0.45 mmol) in anhydrous DMF (5 mL+5 mL+5 mL) at 60° C. for overnight under a nitrogen atmosphere. Filtration over Celite®, extractive aqueous workup, and chromatographic purification on silica gel (hexane/ethyl acetate=4:1, (v/v)) yielded tert-butyl (S)-3-(4-amino-3,5-dichlorophenyl)-2-((tert-butoxycarbonyl)amino)propanoate (530 mg, 65% yield) as a colorless solid. TLC: Rf: 0.45 (hexane/ethyl acetate=4:1, (v/v)).

The aniline coupling product tert-butyl (S)-3-(4-amino-3,5-dichlorophenyl)-2-((tert-butoxycarbonyl)amino)propanoate (200 mg, 0.49 mmol) in pyridine [CAS No. 110-86-1](10 mL) was reacted with commercial benzenesulfonyl chloride [CAS No. 98-09-9](262 mg, 1.48 mmol) at 80° C. for overnight under a nitrogen atmosphere. Evaporation of volatiles, extractive aqueous workup, and chromatographic purification on silica gel (hexane/ethyl acetate=7:3, (v/v)) yielded tert-butyl (S)-2-(tert-butoxycarbonyl)amino)-3-(3,5-dichloro-4-(phenylsulfonamido)phenyl)propanoate (90 mg, impure) as a solid. TLC: Rf: 0.46 (hexane/ethyl acetate=7:3, (v/v)).

The protecting groups of the sulfonamide were removed in one step (Scheme 9). Global removal of the N-Boc-protection group and the tert-butyl ester group of tert-butyl (S)-2-(tert-butoxycarbonyl)amino)-3-(3,5-dichloro-4-(phenylsulfonamido)phenyl)propanoate (90 mg, max. 0.16 mmol) was conducted through reaction with HCl in 1,4-dioxane (4 M in 1,4-dioxane, 5 mL, 20 mmol) at 40° C. for 3 h. Evaporation of volatiles afforded crude compound (47). Purification by prep. HPLC and removal of the solvents by lyophilization yielded compound (47) (35 mg) as a colorless (white) solid. LC/MS/UV: Rt: 0.843 min, calculated for $C_{15}H_{14}Cl_2N_2O_4S$ 388.01, found ESI (pos.) m/z=388.80 $[M+H^+]^+$, 778.25 $[2M+H^+]^+$, ESI (neg.) m/z=386.65 $[M-H^+]^-$, 776.15 $[2M-H^+]^-$; HPLC/UV: Rt: 7.912 min (99.8% AUC at 220 nm, 92.8% AUC at 254 nm); $^1$H NMR (300 MHz, CD$_3$OD): δ 7.80 (dd, J=7.5, 1.2 Hz, 2H), 7.63 (t, J=7.2 Hz, 1H), 7.53 (t, J=7.8 Hz, 2H), 7.38 (s, 2H), 3.90 (dd, J=8.1, 4.5 Hz, 1H), 3.22 (dd, J=14.7, 4.8 Hz, 1H), 3.02 (dd, J=14.7, 8.1 Hz, 1H). The $^1$H NMR signals of the amino group, the N—H acidic group, and the carboxyl group were not observed because of H-D exchange with the NMR solvent.

Example 48

(S)-2-Amino-3-(2-methyl-5-((4-methyl-N-tosylphenyl)sulfonamido)phenyl)propanoic Acid (48)

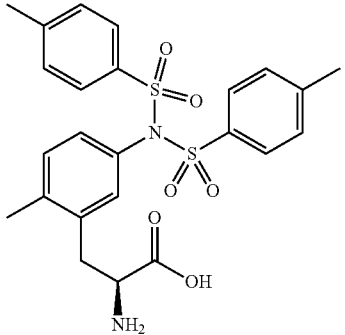

Compound (48) was synthesized by adapting methods described in Scheme 7 and Scheme 9. The aniline starting material 5 (SM-5), methyl (S)-3-(5-amino-2-methylphenyl)-2-((tert-butoxycarbonyl)amino)propanoate (100 mg, 0.32 mmol) was reacted with commercial 4-methyl-benzenesulfonyl chloride (tosyl chloride, TsCl) [CAS No. 98-59-9] (68 mg, 0.36 mmol) in DCM in the presence of triethylamine (Et$_3$N, TEA) [CAS No. 121-44-8](89 μL, 65 mg, 0.64 mmol)) and 4-N,N-dimethylaminopyridine (DMAP) [CAS No. 1122-58-3](4 mg, 0.03 mmol) at room temperature for 2 h. Reaction control showed methyl (S)-2-((tert-butoxycarbonyl)amino)-3-(2-methyl-5-((4-methyl-N-tosylphenyl)sulfonamido)phenyl)propanoate as the major reaction product and methyl (S)-2-((tert-butoxycarbonyl)amino)-3-(2-methyl-5-((4-methylphenyl)sulfonamido)phenyl)propanoate as the minor reaction product. Extractive aqueous workup and chromatographic purification on silica gel (hexane/ethyl acetate=7:3, v/v)) yielded methyl (S)-2-((tert-butoxycarbonyl)amino)-3-(2-methyl-5-((4-methyl-N-tosylphenyl)sulfonamido)phenyl)propanoate (130 mg, 66% yield). In a repeat reaction at the same scale, methyl (S)-2-((tert-butoxycarbonyl)amino)-3-(2-methyl-5-((4-methylphenyl)sulfonamido)phenyl)propanoate (130 mg, 88% yield) was obtained.

The protecting groups of the sulfonamide were removed in two steps (Scheme 9). Chemoselective removal of the N-Boc-protection group of methyl (S)-2-((tert-butoxycarbonyl)amino)-3-(2-methyl-5-((4-methyl-N-tosylphenyl)sulfonamido)phenyl)propanoate (130 mg, 0.21 mmol) was conducted with 20 vol-% TFA in DCM (5 mL) at room temperature for 2 h. After evaporation of volatiles, hydrolysis of the methyl ester group was conducted with lithium hydroxide monohydrate (LiOH·H$_2$O) (44 mg, 1.05 mmol) in THF/water (5 mL, 1:1, (v/v)) at room temperature yielded crude compound (48). Purification by prep. HPLC and removal of the solvents by lyophilization yielded pure compound (48) (80 mg, 76% yield) as a colorless (white) solid. LC/MS/UV: Rt: 1.190 min, calculated for $C_{24}H_{26}N_2O_6S_2$ 502.12, ESI (pos.) m/z=502.85 $[M+H^+]^+$, ESI (neg.) m/z=500.70 $[M-H^+]^-$; HPLC/UV: Rt: 10.168 min (94.9% AUC at 220 nm, 99.1% AUC at 254 nm); $^1$H NMR (300 MHz, CD$_3$OD): δ 7.78 (d, J=8.4 Hz, 2H), 7.69 (d, J=8.4 Hz, 2H), 7.48-7.36 (m, 4H), 7.23 (d, J=8.1 Hz, 1H), 6.97 (d, J=2.1 Hz, 1H), 6.78 (dd, J=8.4, 2.4 Hz, 1H), 3.65 (dd, J=10.5, 4.8 Hz, 1H), 3.41 (dd, J=14.7, 4.2 Hz, 1H), 2.84 (dd, J=14.7, 9.9 Hz, 1H), 4.49 (s, 3H), 2.48 (s, 3H), 2.43 (s, 3H). The $^1$H NMR signals of the amino-group, the N—H-acidic group, and the carboxyl group were not observed because of H-D exchange with the NMR solvent.

Example 49

(S)-2-Amino-3-(5-(N-(5-(dimethylamino)naphthalen-1-yl)sulfamoyl)-2-methylphenyl)propanoic Acid (49)

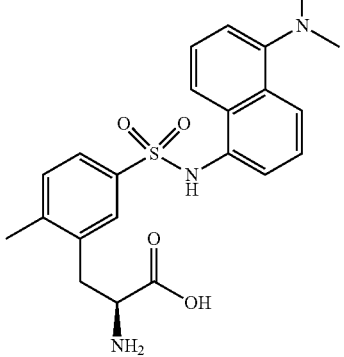

Following well-known literature procedures, $N^5,N^5$-dimethylnaphthalene-1,5-diamine was synthesized from commercial 1,5-dinitronaphthalene in three steps.

Commercial dinitro compound 1,5-dinitronaphthalene [CAS No. 605-71-0](5.0 g, 22.9 mmol) suspended in MeOH (75 mL) was partially reduced to 5-nitronaphthalene-1-amine in an aqueous solution of (anhydrous) sodium sulfide (Na$_2$S) [CAS No. 1313-82-2](7.9 g, 101 mmol)/sodium hydrogen carbonate (NaHCO$_3$) [CAS No. 144-55-8](3.85 g, 45.8 mmol) at 70° C. for 10-30 min. Extractive aqueous workup from an ice/water mixture and evaporation of volatiles yielded 5-nitronaphthalen-1-amine (1.3 g, crude, 30% yield) as a colorless (white) solid. LC/MS/UV: Rt: 2.595 min, calculated for $C_{10}H_8N_2O_2$ 188.06, found ESI (pos.) m/z=189.15 $[M+H^+]^+$. 5-Nitronaphthalene-1-amine is also commercially available [CAS No. 3272-91-1].

N,N-Dimethyl-5-nitro-naphthalen-1-amine was prepared by reacting nitronaphthalene-1-amine [CAS No. 3272-91-1](400 mg, 2.12 mmol) in DCM (8 mL) with commercial trimethyloxonium tetrafluoroborate [Meerwein's salt, $(Me_3O^+)BF_4^-$] [CAS No. 420-37-1](1.57 g, 10.6 mmol) at room temperature for overnight. Extractive aqueous workup and chromatographic purification by prep.-TLC on silica gel (petroleum ether/ethyl acetate=5:1, (v/v)) yielded N,N-dimethyl-5-nitronaphthalen-1-amine [CAS No. 10227-59-5] (162 mg, 53% yield) as a dark red oil. TLC: Rf: 0.70 (petroleum ether/ethyl acetate=4:1, (v/v)); LC/MS/UV: Rt: 2.736 min, calculated for $C_{12}H_{12}N_2O_2$ 216.09, found ESI (pos.) m/z=217.15 $[M+H^+]^+$.

$N^5,N^5$-dimethylnaphthalene-1,5-diamine was prepared through catalytic hydrogenation ($H_2$-balloon, 15 psi) of N,N-dimethyl-5-nitro-naphthalen-1-amine [CAS No. 10227-59-5](230 mg, 1.06 mmol) using a heterogenous catalyst palladium on carbon (Pd{C}) [CAS No. 7440-05-3](23 mg) in MeOH (3 mL) at 40° C. for 2 h. Filtration over Celite®, evaporation of volatiles, and chromatographic purification by prep.-TLC on silica gel (petroleum ether/ethyl acetate=5:1, (v/v)) yielded $N^5,N^5$-dimethylnaphthalene-1,5-diamine (124 mg, 50% yield) as a yellow solid. TLC: Rf: 0.50 (petroleum ether/ethyl acetate=4:1, (v/v)); LC/MS/UV: Rt: 0.571, min, calculated for $C_{12}H_{14}N_2$ 186.12, found ESI (pos.) m/z=187.20 $[M+H^+]^+$.

Synthetic sulfonyl chloride starting material 11 (SM-11), 3-iodo-4-methyl-benzenesulfonyl chloride [CAS No. 953725-14-9](212 mg, 0.67 mmol, 1.5 eq.) in DCM (2 mL) was reacted with synthetic $N^5,N^5$-dimethylnaphthalene-1,5-diamine (125 mg, 0.67 mmol) in the presence of pyridine [CAS No. 110-86-1](54 µL, 53 mg, 1.34 mmol) at room temperature for overnight under a nitrogen atmosphere. Evaporation of volatiles and chromatographic purification by prep.-TLC on silica gel (petroleum ether/ethyl acetate=5:1, (v/v)) yielded N-(5-(dimethylamino)naphthalen-1-yl)-3-iodo-4-methylbenzenesulfonamide (220 mg, 70% yield) as a yellow solid. TLC: Rf: 0.80 (petroleum ether/ethyl acetate=5:1, v/v)); LC/MS/UV: Rt: 3.265 min, calculated for $C_{19}H_{19}IN_2O_2S$ 466.02, found ESI (pos.) m/z=467.30 $[M+H^+]^+$, ESI (neg.) m/z=465.30 $[M-H^+]^-$.

Compound (49) was synthesized by adapting methods described in Scheme 4, Scheme 7, and Scheme 9. Synthetic N-(5-(dimethylamino)naphthalen-1-yl)-3-iodo-4-methyl-benzenesulfonamide (370 mg, 0.79 mmol) and starting material 3 (SM-3), tert-butyl (R)-2-((tert-butoxycarbonyl)amino)-3-iodopropanoate [CAS No. 1057341-65-7](295 mg, 0.79 mmol) were cross-coupled through Pd(0)-catalyzed Negishi-coupling using tris(dibenzylideneacetone)dipalladium ($Pd_2(dba)_3$) [CAS No. 51364-51-3] (73 mg, 0.079 mmol) and tri(o-tolyl)phosphine (P(o-Tol)$_3$) [CAS No. 6163-58-2](24 mg, 0.079 mmol) in the presence of an excess of zinc dust [CAS No. 7440-66-6](622 mg, 9.5 mmol), pre-activated with elemental iodine ($I_2$) [CAS No. 7553-56-2](15 mg, 0.06 mmol) and trimethylchlorosilane (TMSCl) [CAS No. 75-77-4](50 µL, 43 mg, 0.29 mmol) in anhydrous DMF (2 mL+5 mL+5 mL) at 60° C. for overnight under a nitrogen atmosphere. Filtration over Celite®, extractive aqueous workup, and chromatographic purification on silica gel (petroleum ether/ethyl acetate=50:1 to 10:1, (v/v)) yielded tert-butyl (S)-2-((tert-butoxycarbonyl)amino)-3-(5-(N-(5-(dimethylamino)naphthalen-1-yl)sulfamoyl)-2-methylphenyl)propanoate (120 mg, 26% yield) as a yellow solid. TLC: Rf: 0.30 (petroleum ether/ethyl acetate=5:1, (v/v)).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(N-(5-(dimethylamino)naphthalen-1-yl)sulfamoyl)-2-methylphenyl)propanoate (120 mg, 0.21 mmol) was conducted through reaction with 50 vol-% TFA in DCM (4 mL) at room temperature for overnight. Evaporation of volatiles afforded crude compound (49). Purification by prep. HPLC and removal of the solvents by lyophilization yielded compound (49) (73 mg, 81% yield) as a colorless (white) solid. LC/MS/UV: Rt: 2.205 min, calculated for $C_{22}H_{25}N_3O_4S$ 427.16, found 428.30 $[M+H^+]^+$, ESI (neg.) m/z=426.25 $[M-H^+]^-$; HPLC/UV: Rt: 4.713 min (100% AUC at 220 nm, 100% AUC at 254 nm); $^1$H NMR (400 MHz, DMSO-$d_6$): δ 7.98 (d, J=8.4 Hz, 1H), 7.79 (d, J=8.4 Hz, 1H), 7.63 (d, J=2.0 Hz, 1H), 7.44 (dd, J=8.0, 2.0 Hz, 1H), 7.40-7.25 (m, 3H), 7.10-7.05 (m, 2H), 3.37 (br s, 2H), 3.29 (dd, J=8.8, 5.2 Hz, 1H), 3.21 (dd, J=14.4, 5.2 Hz, 1H), 2.78 (s, 6H), 2.73 (dd, J=14.4, 8.4 Hz, 1H, superimposed), 2.33 (s, 3H). The $^1$H NMR signals of the N—H acidic group and the carboxyl group were not observed because of H-D exchange with the moisture in the NMR solvent.

Example 50

(S)-2-Amino-3-(2-methyl-5-(N-(quinolin-5-yl)sulfamoyl)phenyl) propanoic Acid (50)

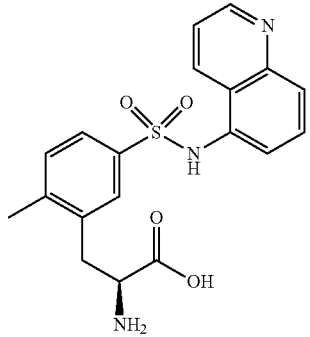

Compound (50) was synthesized by adapting methods described in Scheme 2, Scheme 3, and Scheme 9. Synthetic sulfonyl chloride starting material 11 (SM-11), 3-iodo-4-methyl-benzenesulfonyl chloride [CAS No. 953725-14-9] (500 mg, 1.58 mmol) was reacted with commercial 5-aminoquinoline (quinolin-5-amine) [CAS No. 611-34-7](342 mg, 2.37 mmol) in DCM (5 mL) in the presence of pyridine (246 µL, 250 mg, 3.16 mmol) at room temperature for 16 h. Trituration with a mixture of DCM and petroleum ether yielded 3-iodo-4-methyl-N-(quinolin-5-yl)benzenesulfonamide (805 mg, quant.) as a yellow solid. LC/MS/UV: Rt: 1.810 min, calculated for $C_{16}H_{13}IN_2O_2S$ 423.97, found ESI (pos.) 425.00 $[M+H^+]^+$, ESI (neg.) m/z=422.95 $[M-H^+]^-$.

Synthetic 3-iodo-4-methyl-N-(quinolin-5-yl)benzenesulfonamide (800 mg, 1.88 mmol) and starting material 3 (SM-3), tert-butyl (R)-2-((tert-butoxycarbonyl)amino)-3-iodopropanoate [CAS No. 1057341-65-7](700 mg, 1.88 mmol) were cross-coupled through Pd(0)-catalyzed Negishi-coupling using tris(dibenzylideneacetone)dipalladium ($Pd_2(dba)_3$) [CAS No. 51364-51-3](173 mg, 0.19 mmol) and tris(o-tolyl)phosphine (P(o-Tol)₃) [CAS No. 6163-58-2](57 mg, 0.19 mmol) in the presence of an excess of zinc dust [CAS No. 7440-66-6](1.5 g, 23.0 mol), pre-activated with elemental iodine (I₂) [CAS No. 7553-56-2](36 mg, 0.28 mmol) and trimethylchlorosilane (TMSCl) [CAS No. 75-77-4](80 µL, 69 mg, 0.63 mmol), in anhydrous DMF (4 mL+5 mL, 1×5 mL) at 60° C. for overnight under a nitrogen atmosphere. Filtration over Celite®, extractive aqueous work-up, and chromatographic purification over silica gel (petroleum ether/ethyl acetate=50:1 to 10:1, (v/v)) yielded tert-butyl (S)-2-((tert-butoxycarbonyl)amino)-3-(2-methyl-5-(N-(quinolin-5-yl)sulfamoyl)phenyl)propanoate (310 mg, 30% yield) as a yellow solid. TLC: Rf: 0.80 (petroleum ether/ethyl acetate=5:1 (v/v)); LC/MS/UV: Rt: 2.087 min, calculated for C₂₈H₃₅N₃O₆S 541.22, found ESI (pos.) 542.40 [M+H⁺]⁺, ESI (neg.) 540.30 [M+H⁺]⁻.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(N-(quinolin-5-yl)sulfamoyl)phenyl)propanoate (310 mg, 0.55 mmol) was conducted through reaction of with 50 vol-% TFA in DCM (8 mL) at room temperature for overnight to afford crude compound (50). Purification by prep. HPLC and removal of the solvents by lyophilization yielded pure compound (50) (61 mg, 28% yield) as a colorless (white) solid. LC/MS/UV: Rt: 1.055 min, calculated for C₁₉H₁₉N₃O₄S 385.11, found ESI (pos.) m/z=386.10 [M+H⁺]⁺, 770.80 [2M+H⁺]⁺, ESI (neg.) m/z=384.10 [M−H⁺]⁻, 769.35 [2M−H⁺]⁻; HPLC/UV: Rt: 4.510 min (100% AUC at 220 nm, 100% AUC at 254 nm); ¹H NMR (400 MHz, CD₃OD): δ 8.80 (d, J=4.4 Hz, 1H), 8.56 (d, J=8.4 Hz, 1H), 7.90 (d, J=8.4H, 1H), 7.68-7.57 (m, 2H), 7.50 (dd, J=8.6, 4.3 Hz, 1H), 7.31 (d, J=7.9 Hz, 1H), 7.23 (d, J=8.0 Hz, 1H), 7.18 (d, J=7.5 Hz, 1H), 3.71 (t, J=7.3 Hz, 1H), 3.35-3.29 (m, 1H, superimposed by NMR solvent signal), 2.98 (dd, J=14.7, 8.2 Hz, 1H), 2.41 (s, 3H). The ¹H NMR signals of the amino-group, the N—H-acidic group, and the carboxyl group were not observed because of H-D-exchange with the NMR solvent.

Example 51

(R)-2-Amino-3-(5-(N-(4-chlorophenyl)sulfamoyl)-2-methylphenyl) propanoic Acid (51)

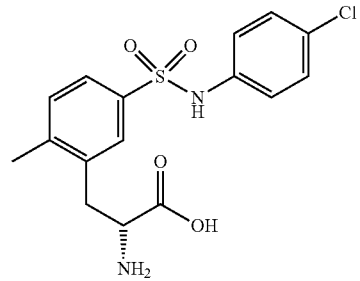

Compound (51) was synthesized by adapting methods described in Scheme 2, Scheme 3, and Scheme 9. Commercial 3-bromo-4-methylbenzenesulfonyl chloride [CAS No. 1029145-99-0](2.70 g, 10.0 mmol) was reacted with commercial 4-chloroaniline [CAS No. 106-47-8](2.55 g, 20.0 mmol) in pyridine (30 mL) in the presence of 4-N,N-dimethylpyridine (DMAP) [CAS No. 1122-58-3](122 mg, 1.0 mmol) at room temperature for overnight. Evaporation of volatiles, extractive aqueous work-up, and chromatographic purification on silica gel (hexane/ethyl acetate=6:1, (v/v)) yielded 3-bromo-N-(4-chlorophenyl)-4-methylbenzenesulfonamide (2.53 g, 70% yield) as a honey-colored oil that solidified at room temperature to a beige solid. TLC: Rf: 0.32 (hexane/ethyl acetate=6:1, (v/v)); LC/MS/UV: Rt: 1.776 min, calculated for C₁₃H₁₁BrClNO₂S 358.94, found ESI (pos.) m/z=361.75 [M+H⁺]⁺, ESI (neg.) 359.60 [M−H⁺]⁻; HPLC/UV: Rt: 13.439 min (99.1% AUC at 220 nm, 99.3% at 254 nm); ¹H NMR (300 MHz, CDCl₃): δ 7.95 (d, J=2.1 Hz, 1H), 7.54 (dd, J=7.8, 1.8 Hz, 1H), 7.29 (d, J=8.1 Hz, 1H), 7.26-7.20 (m, 2H), 7.06-7.00 (m, 2H), 6.90 (br. s, 1H), 3.42 (s, 3H).

Synthetic 3-bromo-N-(4-chlorophenyl)-4-methylbenzenesulfonamide (800 mg, 1.88 mmol) and starting material 2 (SM-2), methyl (S)-2-((tert-butoxycarbonyl)amino)-3-iodo-propanoate [CAS No. 170848-34-7](500 mg, 1.39 mmol) were cross-coupled through Pd(0)-catalyzed Negishi-coupling using tris(dibenzylideneacetone)dipalladium (Pd₂(dba)₃) [CAS No. 51364-51-3](32 mg, 0.035 mmol) and tris(o-tolyl)phosphine (P(o-Tol)₃) [CAS No. 6163-58-2](42 mg, 0.14 mmol) in the presence of an excess of zinc dust [CAS No. 7440-66-6](585 mg, 9.0 mol), pre-activated with elemental iodine (I₂) [CAS No. 7553-56-2](57 mg, 0.23 mmol) and trimethylchlorosilane (TMSCl) [CAS No. 75-77-4](29 µL, 25 mg, 0.23 mmol) in anhydrous DMF (5 mL+5 mL) at 60° C. for overnight under a nitrogen atmosphere. Filtration over Celite®, extractive aqueous work-up, and chromatographic purification over silica gel (hexane/ethyl acetate=7:3, (v/v)) yielded methyl (R)-2-((tert-butoxycarbonyl)amino)-3-(5-(N-(4-chlorophenyl)sulfamoyl)-2-methylphenyl)propanoate (290 mg, 43% yield). TLC: Rf: 0.25 (hexane/ethyl acetate=7:3, (v/v)).

The protecting groups of the sulfonamide were removed in two steps (Scheme 9). Chemoselective removal of the N-Boc-protection group of methyl (R)-2-((tert-butoxycarbonyl)amino)-3-(5-(N-(4-chlorophenyl)sulfamoyl)-2-methylphenyl)propanoate (290 mg, 0.60 mmol) was conducted with 20 vol-% TFA in DCM (5 mL) at room temperature. Evaporation of volatiles, hydrolysis of the methyl ester group with lithium hydroxide monohydrate (LiOH·H₂O) [CAS No. 1310-66-3](165 mg, 3.93 mmol) in THF/water (5 mL, 1:1, v/v)) at room temperature yielded the crude compound (51). Purification by prep. HPLC and removal of the solvents by lyophilization yielded pure compound (51) (140 mg, 63% yield) as a colorless (white) solid. LC/MS/UV: Rt: 1.030 min, calculated for C₁₆H₁₇ClN₂O₄S 368.06, ESI (pos.) m/z=368.95 [M+H⁺]⁺, 737.15 [2M+H⁺]⁺, ESI (neg.) m/z=366.75 [M−H⁺]⁻, 734.40 [2M−H⁺]⁻; HPLC/UV: Rt: 9.082 min (97.1% AUC at 220 nm, 97.8% AUC at 254 nm); ¹H NMR (300 MHz, CD₃OD): δ 7.71 (d, J=1.8 Hz, 1H), 7.45 (dd, J=7.5, 1.5 Hz, 1H), 7.29 (d, J=8.4 Hz, 1H), 7.23-7.17 (m, 2H), 7.12-7.06 (m, 2H), 3.72 (dd, J=8.7, 5.7 Hz, 1H), 3.36 (dd, J=14.7, 5.7 Hz, 1H), 3.00 (dd, J=15.0, 8.7 Hz, 1H), 2.41 (s, 3H). The ¹H NMR signals of the amino-group, the N—H-acidic group, and the carboxyl group were not observed because of H-D exchange with the NMR solvent.

Example 52

(S)-2-Amino-3-(5-(N-(4-chlorophenyl)sulfamoyl)-2-methylphenyl)propanoic Acid (52)

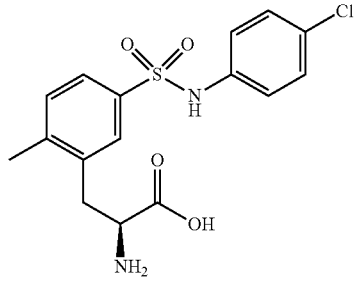

Compound (52) was synthesized by adapting methods described in Scheme 2, Scheme 3, and Scheme 9. Sulfonyl chloride starting material 9 (SM-9), tert-butyl (S)-2-((tert-butoxycarbonyl)amino)-3-(5-(chlorosulfonyl)-2-methylphenyl)propanoate, (868 mg, 2.0 mmol) was reacted with commercial 4-chloroaniline [CAS No. 106-47-8](1.02 g, 8.0 mmol) in pyridine (12 mL) and in the presence of 4-N,N-dimethylaminopyridine (DMAP) [CAS No. 122-58-3](59 mg, 0.48 mmol) at room temperature for overnight. Evaporation of the volatiles, acidic aqueous work-up, and chromatographic purification on silica gel (hexane/ethyl acetate=3:1 to 5:2, (v/v)) yielded tert-butyl (S)-2-((tert-butoxycarbonyl)amino)-3-(5-(N-(4-chlorophenyl)sulfamoyl)-2-methylphenyl)propanoate (1.00 g, 96% yield) as a colorless foam. TLC: Rf: 0.22 (hexane/ethyl acetate=3:1 (v/v)); LC/MS/UV: Rt: 2.034 min, calculated for $C_{25}H_{33}ClN_2O_6S$ 524.17, found ESI (pos.) m/z=546.85 [M+Na$^+$]$^+$, ESI (neg.) m/z=522.75 [M–H$^+$]$^-$; HPLC/UV: Rt: 14.473 min (98.8% AUC at 254 nm); $^1$H NMR (300 MHz, CDCl$_3$): δ 7.61 (br s, 1H), 7.45 (br d, J=8.1 Hz, 1H), 7.19 (d, J=8.4 Hz, 1H), 7.11-7.07 (m, 1H), 7.02 (br d, J=8.7 Hz, 2H), 6.92 (br s, 1H), 6.63-6.58 (m, 2H), 5.09 (d, J=8.7 Hz, 1H), 4.48-4.38 (m, 1H), 3.10 (dd, J=13.8, 6.6 Hz, 1H), 2.95 (dd, J=13.2, 7.2 Hz, 1H), 2.39 (s, 3H), 1.39-1.36 (2×s, 2×9H).

Intermediate tert-butyl (S)-2-((tert-butoxycarbonyl)amino)-3-(5-(N-(4-chlorophenyl)sulfamoyl)-2-methylphenyl)propanoate was also prepared by an alternative synthetic route.

Synthetic sulfonyl chloride starting material 11 (SM-11), 3-iodo-4-methyl-benzenesulfonyl chloride [CAS No. 953725-14-9](800 mg, 2.53 mmol) was reacted with commercial 4-chloroaniline [CAS No. 106-47-8](484 mg, 3.79 mmol) in pyridine [CAS No. 110-86-1](8 mL) at room temperature for overnight under a nitrogen atmosphere. Extractive aqueous workup and chromatographic purification by prep.-TLC on silica gel (petroleum ether/ethyl acetate=5:1, (v/v)) yielded N-(4-chlorophenyl)-3-iodo-4-methylbenzenesulfonamide (500 mg, 48% yield) as a yellow solid. TLC: Rf: 0.50 (petroleum ether/ethyl acetate=5:1, (v/v)); LC/MS: calculated for $C_{13}H_{11}ClINO_2S$ 406.92, found ESI (pos.) m/z=407.95 [M+H$^+$]$^+$.

Synthetic N-(4-chlorophenyl)-3-iodo-4-methylbenzenesulfonamide (500 mg, 1.20 mmol) and starting material 3 (SM-3), tert-butyl (R)-2-((tert-butoxycarbonyl)amino)-3-iodopropanoate [CAS No. 1057341-65-7](456 mg, 1.20 mmol) were cross-coupled through Pd(0)-catalyzed Negishi-coupling using tris(dibenzylideneacetone)dipalladium (Pd$_2$(dba)$_3$) [CAS No. 51364-51-3](113 mg, 0.12 mmol) and 2-dicyclohexylphosphino-2',6'-dimethoxybiphenyl (S-Phos) [CAS No. 657408-07-6](51 mg, 0.12 mmol) in the presence of an excess of zinc dust [CAS No. 7440-66-6](964 mg, 14.7 mmol), pre-activated with elemental iodine (I$_2$) [CAS No. 7553-56-2](23 mg, 0.18 mmol) and trimethylchlorosilane (TMSCl) [CAS No. 75-77-4](50 μL, 43 mg, 0.39 mmol) in anhydrous DMF (10 mL+5 mL+10 mL) at 60° C. for overnight under a nitrogen atmosphere. Filtration over Celite®, evaporation of volatiles, and chromatographic purification on silica gel with petroleum ether/ethyl acetate mixtures yielded tert-butyl (S)-2-((tert-butoxycarbonyl)amino)-3-(5-(N-(4-chlorophenyl)sulfamoyl)-2-methylphenyl)propanoate (150 mg, 23% yield) as a colorless (white) solid. The analytical data correspond to the analytical data of tert-butyl (S)-2-((tert-butoxycarbonyl)amino)-3-(5-(N-(4-chlorophenyl)sulfamoyl)-2-methylphenyl)propanoate obtained through the synthetic route disclosed above.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(N-(4-chlorophenyl)sulfamoyl)-2-methylphenyl)propanoate (1.0 g, 1.91 mmol) in 1,4-dioxane (2 mL) was conducted through reaction with commercial HCl in 1,4-dioxane [CAS No. 7647-01-0](4 M in 1,4-dioxane, 12 mL, 48 mmol) at 40° C. for overnight. Evaporation of the volatiles afforded the crude compound (52). Purification by prep. HPLC and removal of the solvents by lyophilization yielded compound (52) (580 mg, 74% yield) as a colorless (white) solid. LC/MS/UV: Rt: 1.089 min, calculated for $C_{16}H_{17}ClN_2O_4S$ 368.06, ESI (pos.) m/z=368.90 [M+H$^+$]$^+$, 736.55 [2M+H$^+$]$^+$, ESI (neg.) m/z=366.75 [M–H$^+$]$^-$, 736.15 [2M–H$^+$]$^-$; HPLC/UV: Rt: 9.162 min (99.5% AUC at 220 nm, 99.0% AUC at 254 nm); $^1$H NMR (300 MHz, CD$_3$OD): δ 7.71 (br s, 1H), 7.46 (br d, J=8.1H, 1H), 7.28 (d, J=7.8 Hz, 1H), 7.19 (d, J=9.0 Hz, 2H), 7.08 (d, J=8.7 Hz, 2H), 3.75-3.66 (m, 1H), 3.38-3.31 (m, 1H, superimposed with $^1$H NMR signal of NMR solvent), 3.00 (dd, J=14.1, 8.4 Hz, 1H), 2.41 (s, 3H). The $^1$H NMR signals of the amino-group, the N—H-acidic group, and the carboxyl group were not observed because of H-D exchange with the NMR solvent.

Example 53

(S)-2-Amino-3-(5-(N-cyclohexylsulfamoyl)-2-methylphenyl)propanoic Acid (53)

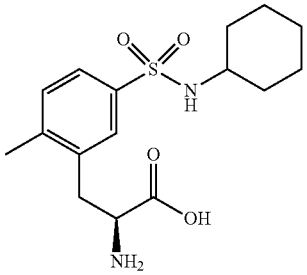

Compound (53) was synthesized by adapting methods described in Scheme 2, Scheme 3, and Scheme 9. Sulfonyl chloride starting material 11 (SM-11), 3-iodo-4-methyl-benzenesulfonyl chloride, (800 mg, 2.53 mmol) was reacted with commercial cyclohexylamine [CAS No. 108-91-8](376 mg, 3.79 mmol) in DCM (8 mL) in the presence of pyridine (407 µL, 400 mg, 5.06 mmol) at room temperature for overnight under a nitrogen atmosphere. Evaporation of the volatiles and chromatographic purification by prep.-TLC on silica gel yielded N-cyclohexyl-3-iodo-4-methylbenzenesulfonamide (605 mg, 63% yield) as a yellow solid. TLC: Rf: 0.28 (petroleum ether/ethyl acetate=4:1, (v/v)); LC/MS/UV: Rt: 2.957 min, calculated for $C_{13}H_{18}INO_2S$ 379.01, found ESI (pos.) m/z=402.05 [M+Na$^+$]$^+$, 781.20 [2M+Na$^+$]$^+$, ESI (neg.) m/z=378.10 [M–H$^+$]$^-$; $^1$H NMR (400 MHz, CDCl$_3$): δ 8.29 (d, J=1.9 Hz, 1H), 7.74 (dd, J=8.0, 1.9 Hz, 1H), 7.35 (d, J=7.9 Hz, 1H), 4.47 (d, J=7.4 Hz, 1H), 3.31-3.00 (m, 1H), 2.49 (s, 3H), 1.85-1.73 (m, 2H), 1.69-1.45 (m, 4H), 1.27-1.12 (m, 4H).

Synthetic N-cyclohexyl-3-iodo-4-methylbenzenesulfonamide (595 mg, 1.57 mmol) and aniline starting material 3 (SM-3), tert-butyl (R)-2-((tert-butoxycarbonyl)amino)-3-iodopropanoate [CAS No. 1057341-65-7](500 mg, 1.39 mmol) were cross-coupled through Pd(0)-catalyzed Negishi-coupling using tris(dibenzylideneacetone)dipalladium (Pd$_2$(dba)$_3$) [CAS No. 51364-51-3](144 mg, 0.16 mmol) and 2-dicyclohexylphosphino-2',6'-dimethoxybiphenyl (S-Phos) [CAS No. 657408-07-6](64 mg, 0.16 mmol) in the presence of an excess of zinc dust [CAS No. 7440-66-6](1.23 g, 18.8 mol), pre-activated with elemental iodine (I$_2$) [CAS No. 7553-56-2](30 mg, 0.23 mmol) and trimethylchlorosilane (TMSCl) [CAS No. 75-77-4](30 µL, 26 mg, 0.23 mmol) in anhydrous DMF (10 mL+5 mL, +1×5 mL) at 60° C. for overnight under a nitrogen atmosphere. Filtration over Celite®, extractive aqueous work-up, and chromatographic purification over silica gel (hexane/ethyl acetate=50:1 to 10:1, (v/v)) yielded tert-butyl (S)-2-((tert-butoxycarbonyl)amino)-3-(5-(N-cyclohexylsulfamoyl)-2-methylphenyl)propanoate (353 mg, 45% yield) as a yellow solid. TLC: Rf: 0.30 (petroleum ether/ethyl acetate=5:1, (v/v)); LC/MS/UV: Rt: 2.935 min, calculated for $C_{25}H_{40}N_2O_6S$ 496.26, found ESI (pos.) m/z=519.30 [M+Na$^+$]$^+$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(N-cyclohexylsulfamoyl)-2-methylphenyl)propanoate (342 mg, 0.69 mmol) was conducted through reaction with 50 vol-% TFA in DCM (4 mL) at room temperature for overnight. Evaporation of volatiles yielded the crude compound (53). Purification by prep. HPLC and removal of the solvents by lyophilization yielded compound (53) as a colorless (white) solid (73 mg, 31% yield). LC/MS/UV: Rt: 1.361 min, calculated for $C_{16}H_{24}N_2O_4S$ 340.15, ESI (pos.) m/z=341.20 [M+H$^+$]$^+$, 382.20 [M+H$^+$+MeCN]$^+$, 681.35 [2M+H$^+$]$^+$, ESI (neg.) m/z=339.10 [M–H$^+$]$^-$, 679.55 [2M–H$^+$]$^-$; HPLC/UV: Rt: 4.794 min (100% AUC at 220 nm, 100% AUC at 254 nm); $^1$H NMR (400 MHz, CD$_3$OD): δ 7.74 (br. s, 1H), 7.68 (d, J=8.0 Hz), 7.39 (d, J=8.0 Hz, 1H), 4.64-4.62 (br. m, 1H), 3.79-3.76 (m, 1H), 3.48-3.34 (m, 1H), 3.10-2.98 (m, 1H), 2.45 (s, 3H), 1.80-1.65 (br m, 4H), 1.65-1.45 (br m, 1H), 1.25-1.10 (br m, 5H). The $^1$H NMR signals of the amine-group, the N—H acidic group, and the carboxyl-group were not observed because of H-D exchange with the NMR solvent.

Example 54

(S)-2-Amino-3-(2-methyl-5-(((phenylmethyl)sulfonamido)methyl)phenyl)propanoic Acid (54)

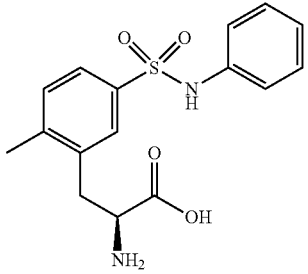

Following well-known literature procedures, (3-iodo-4-methylphenyl)methanamine [CAS No. of HCl salt 1803588-29-5] was prepared from commercial 3-iodo-4-methyl-benzoic acid [CAS No. 82998-57-0] in 3 steps. (3-Iodo-4-methylphenyl)methanol [CAS No. 165803-89-4] was prepared as described for Example (55) and is also commercially available.

2-(3-Iodo-4-methylbenzyl)isoindoline-1,3-dione was prepared from benzylic alcohol (3-iodo-4-methylphenyl)methanol (2.0 g, 8.06 mmol) through Mitsunobu-coupling with phthalimide [CAS No. 85-41-6](1.19 g, 8.06 mmol), triphenylphosphine (PPh$_3$) [CAS No. 603-35-0](2.5 g, 9.67 mmol), and diethyl diazenedicarboxylate (diethyl azodicarboxylate, DEAD) [CAS No. 1972-28-7](1.68 g, 9.67 mmol) in THF (40 mL) at 0° C.-10° C. for 2 h. Extractive aqueous work-up and chromatographic purification on silica gel (petroleum ether/ethyl acetate=10:1 to 5:1, (v/v)) yielded 2-(3-iodo-4-methylbenzyl)isoindoline-1,3-dione (2.3 g, 75% yield). TLC: Rf: 0.45 (petroleum ether/ethyl acetate=5:1, (v/v)); $^1$H NMR (400 MHz, CDCl$_3$): δ 7.88-7.82 (m, 3H), 7.74-7.70 (m, 2H), 7.32-7.30 (m, 1H), 7.17 (d, J=7.8 Hz, 1H), 4.76 (s, 2H), 2.38 (s, 3H).

(3-Iodo-4-methyl-phenyl)methanamine was prepared through hydrazinolysis of the synthetic imide 2-(3-iodo-4-methylbenzyl)isoindoline-1,3-dione (2.0 g, 5.11 mmol) with hydrazine hydrate (H$_2$N—NH$_2$—H$_2$O) [CAS No. 7803-57-8](85 wt-%, 2.6 g, 51.1 mmol) in a mixture of anhydrous THF and MeOH (160 mL, 1:1, (v/v)) at 65° C. for 6 h. Removal of the precipitate by filtration, evaporation of volatiles, and chromatographic purification on silica gel (DCM/MeOH=100:1, (v/v), with 1 vol-% of NH$_3$(aq.)) yielded (3-iodo-4-methyl-phenyl)methanamine (760 mg, 58% yield) as an off-white solid. TLC: Rf: 0.25 (DCM/MeOH=20:1, (v/v)); $^1$H NMR (400 MHz, CD$_3$OD): δ 7.91 (br s, 1H), 7.34-7.30 (m, 2H), 3.97 (s, 2H), 2.41 (s, 3H). The $^1$H NMR signal of the amino-group was not observed because of H-D exchange with the NMR solvent.

Commercial benzylsulfonyl chloride [CAS No. 1939-99-7](190 mg, 1.03 mmol) was reacted with (3-iodo-4-methylphenyl)methanamine (170 mg, 0.68 mmol) in DCM (6 mL) in the presence of pyridine (137 µL, 135 mg, 1.36 mmol) at room temperature for overnight. Evaporation of the volatiles and chromatographic purification on silica gel (DCM/MeOH=20:1, (v/v)) yielded N-(3-iodo-4-methylbenzyl)-1-phenylmethanesulfonamide (150 mg, 54% yield) as a yellow oil. TLC: Rf: 0.60 (DCM/MeOH=20:1, (v/v)); LC/MS: calculated for $C_{15}H_{16}INO_2S$ 400.99, found ESI (pos.) m/z=402.15 [M+H$^+$]$^+$; $^1$H NMR (400 MHz, CDCl$_3$): δ 8.31 (d, J=7.6 Hz, 1H), 7.93-7.83 (m, 3H), 7.83-7.53 (m, 5H), 7.46-7.40 (m, 1H, superimposed with $^1$H NMR signal of NMR solvent), 6.26 (br s, 1H), 4.62 (d, J=5.6 Hz, 2H), 2.41 (s, 3H).

N-(3-Iodo-4-methylbenzyl)-1-phenylmethanesulfonamide (1.0 g, 2.49 mmol, 1.0 eq.) and aniline starting material 3 (SM-3), tert-butyl (R)-2-((tert-butoxycarbonyl)amino)-3-iodopropanoate [CAS No. 1057341-65-7](925 mg, 2.49 mmol) were cross-coupled through Pd(0)-catalyzed Negishi-coupling using tris(dibenzylideneacetone)dipalladium (Pd$_2$(dba)$_3$) [CAS No. 51364-51-3](280 mg, 0.25 mmol) and 2-dicyclohexylphosphino-2',6'-dimethoxybiphenyl (S-Phos) [CAS No. 657408-07-6](130 mg, 0.25 mmol) in the presence of an excess of zinc dust [CAS No. 7440-66-6](3.17 g, 48.5 mol), pre-activated with elemental iodine (I$_2$) [CAS No. 7553-56-2](130 mg, 0.51 mmol) and trimethylchlorosilane (TMSCl) [CAS No. 75-77-4](76 µL, 65 mg, 0.51 mmol), in anhydrous DMF (10 mL+6 mL) at 60° C. for overnight under a nitrogen atmosphere. Filtration over Celite®, extractive aqueous work-up, and chromatographic purification over silica gel (petroleum ether/ethyl acetate mixtures) yielded tert-butyl (S)-2-((tert-butoxycarbonyl) amino)-3-(2-methyl-5-(((phenylmethyl)sulfonamido) methyl)phenyl)propanoate (344 mg, 34% yield). LC/MS: Calculated for C$_{27}$H$_{38}$N$_2$O$_6$S 518.25, found ESI (pos.) m/z=519.40 [M+H$^+$]$^+$; $^1$H NMR (400 MHz, CD$_3$OD): δ 8.30-8.20 (m, 1H), 7.97-7.86 (m, 2H), 7.64-7.60 (m, 1H), 7.54-7.47 (m, 1H), 7.22-7.15 (m, 3H), 4.57 (s, 2H), 4.26-4.20 (m, 1H), 3.10-3.04 (m, 1H), 2.90-2.84 (m, 1H), 2.34 (s, 3H), 1.35 (2×s, 2×9H). The $^1$H NMR signal of one of the benzylic groups was not observed because of superposition with the residual $^1$H NMR signal of the NMR solvent. The $^1$H NMR signals of the N—H-acidic groups were not observed because of H-D exchange with the NMR solvent).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(((phenylmethyl)sulfonamido)methyl)phenyl)propanoate (100 mg, 0.19 mmol) was conducted through reaction with 50 vol-% TFA in DCM (4 mL) at room temperature for 5 h. Evaporation of volatiles yielded crude compound (54). Purification by prep. HPLC and removal of the solvents by lyophilization yielded pure compound (54) (18 mg, 26% yield) as a colorless (white) solid. LC/MS/UV: Rt: 2.178 min, calculated for C$_{18}$H$_{22}$N$_2$O$_4$S 362.13, ESI (pos.) m/z=363.25 [M+H$^+$], 725.60 [2M+H$^+$]$^+$, ESI (neg.) m/z=361.20 [M−H$^+$]$^-$, 724.55 [2M−H$^+$]$^-$; HPLC/UV: Rt: 5.515 min (97.9% AUC at 220 nm, 100% AUC at 254 nm); $^1$H NMR (400 MHz, DMSO-d$_6$): δ 8.15-8.12 (m, 1H), 8.00-7.94 (m, 2H), 7.65-7.52 (m, 3H), 7.23 (s, 1H), 7.15 (s, 1H), 4.78 (br s, 2H), 4.46 (s, 2H), 3.47-3.44 (m, 1H), 3.28-3.21 (m, 1H), 2.80-2.72 (m, 1H), 2.26 (s, 3H). The $^1$H NMR signal of one benzylic group was not observed because of superposition with the $^1$H NMR signal of the NMR solvent. The $^1$H NMR signals of the N—H-acidic group and the carboxylic acid group were not observed because of H-D exchange with the moisture in the NMR solvent.

Example 55

(S)-2-Amino-3-(5-((benzylthio)methyl)-2-methylphenyl)propanoic Acid (55)

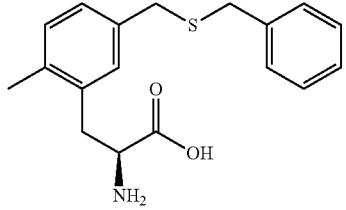

(3-Iodo-4-methylphenyl)methanol [CAS No. 165803-89-4] is commercially available. (3-Iodo-4-methylphenyl) methanol was also prepared through reduction of commercial 3-iodo-4-methylbenzoic acid [CAS No. 82998-57-0] (10.0 g, 38.2 mmol) with borane dimethylsulfide complex (BH$_3$·SMe$_2$) [CAS No. 13292-87-0](2 M in THF, 76 mL, 152 mmol) in THF (100 mL) from 0° C. to 50° C. for overnight. Quenching of the reaction with MeOH (90 mL), evaporation of volatiles, and chromatographic purification on silica gel (petroleum ether/ethyl acetate=100:0 to 2:1, (v/v)) yielded (3-iodo-4-methylphenyl)methanol (9.0 g, 95% yield) as a colorless (white) solid the in near quantitative yield. TLC: Rf: 0.50 (petroleum ether/ethyl acetate=2: 1, (v/v)).

(3-Iodo-4-methylphenyl)methanol (1.0 g, 4.03 mmol) and aniline starting material 3 (SM-3), tert-butyl (R)-2-((tert-butoxycarbonyl)amino)-3-iodopropanoate [CAS No. 1057341-65-7](1.49 g, 4.03 mmol) were cross-coupled through Pd(0)-catalyzed Negishi-coupling using tris(dibenzylideneacetone)dipalladium (Pd$_2$(dba)$_3$) [CAS No. 51364-51-3](370 mg, 0.10 mmol) and 2-dicyclohexylphosphino-2',6'-dimethoxybiphenyl (S-Phos) [CAS No. 657408-07-6] (140 mg, 0.10 mmol) in the presence of an excess of zinc dust [CAS No. 7440-66-6](3.15 g, 47.0 mol), pre-activated with elemental iodine (I$_2$) [CAS No. 7553-56-2](77 mg, 0.6 mmol) and trimethylchlorosilane (TMSCl) [CAS No. 75-77-4](100 µL, 86 mg, 0.51 mmol) in anhydrous DMF (10 mL+6 mL) at 60° C. for overnight under a nitrogen atmosphere. Filtration over Celite®, extractive aqueous work-up, and chromatographic purification over silica gel (petroleum ether/ethyl acetate mixtures) yielded tert-butyl (S)-2-((tert-butoxycarbonyl)amino)-3-(5-(hydroxymethyl)-2-methylphenyl)propanoate (800 mg, 54% yield) as a yellow oil. TLC: Rf: 0.2 (petroleum ether/ethyl acetate=4:1, (v/v)). LC/MS: calculated for C$_{20}$H$_{31}$NO$_5$ 365.22, found ESI (pos.) m/z=388.25 [M+Na$^+$]$^+$.

The benzylic alcohol tert-butyl (S)-2-((tert-butoxycarbonyl)amino)-3-(5-(hydroxymethyl)-2-methylphenyl)propanoate (2.0 g, 5.47 mmol) was reacted with commercial tetrabromomethane (carbon tetrabromide, CBr$_4$) [CAS No. 558-13-4](3.62 g, 10.9 mmol) and triphenylphosphine (Ph$_3$P) [CAS No. 603-35-0](2.9 g, 10.9 mmol) in DCM (20 mL) at 0° C. for 2 h. Evaporation of the volatiles and chromatographic purification on silica gel (petroleum ether/ ethyl acetate=4:1, (v/v)) yielded tert-butyl (S)-3-(5-(bromomethyl)-2-methylphenyl)-2-((tert-butoxycarbonyl) amino)propanoate (1.6 g, 68% yield) as a yellow solid. TLC: Rf: 0.75 (petroleum ether/ethyl acetate=4:1, (v/v)). LC/MS: calculated for C$_{20}$H$_{30}$BrNO$_4$ 427.14, found ESI (pos.) m/z=450.15 [M+Na$^+$]$^+$.

Synthetic benzylic bromide tert-butyl (S)-3-(5-(bromomethyl)-2-methylphenyl)-2-((tert-butoxycarbonyl)amino)propanoate (2.2 g, 5.14 mmol) was reacted with commercial benzyl mercaptan (BnSH) [CAS No. 100-53-8](957 mg, 7.70 mmol) in the presence of potassium carbonate ($K_2CO_3$) [CAS No. 584-08-7](3.35 g, 10.3 mmol) in anhydrous DMF (22 mL) at 80° C. for overnight. Evaporation of volatiles, extractive aqueous work-up, and chromatographic purification on silica gel (petroleum ether/ethyl acetate=15:1, (v/v)) yielded tert-butyl (S)-3-(5-((benzylthio)methyl)-2-methylphenyl)-2-((tert-butoxycarbonyl)amino)propanoate (1.5 g, 61% yield) as a yellow solid. TLC: Rf: 0.40 (petroleum ether/ethyl acetate=15:1, (v/v)). LC/MS: calculated for $C_{27}H_{37}NO_4S$ 471.24, found ESI (pos.) m/z=494.35 [M+Na$^+$]$^+$.

The protecting groups of the bisbenzylic thioether were removed in one step (Scheme 9). Global removal of the N-Boc-protection group and the tert-butyl ester group of tert-butyl (5)-3-(5-((benzylthio)methyl)-2-methylphenyl)-2-((tert-butoxycarbonyl)amino)propanoate (100 mg, 0.21 mmol) in 1,4-dioxane (1 mL) was conducted through reaction with commercial HCl in 1,4-dioxane [CAS No. 7647-01-0](4 M in 1,4-dioxane, 5 mL, 20 mmol) at 40° C. for overnight. Evaporation of volatiles yielded crude compound (55). Purification by prep. HPLC and removal of the solvents by lyophilization yielded compound (55) as a colorless solid (23 mg, 34% yield). LC/MS/UV: Rt: 2.064 min, calculated for $C_{18}H_{21}NO_2S$. 315.13, ESI (pos.) m/z=316.05 [M+H$^+$]$^+$, ESI (neg.) m/z=314.00 [M–H$^+$]$^-$; HPLC/UV: Rt: 6.058 min (100% AUC at 220 nm, 100% AUC at 254 nm); $^1$H NMR (400 MHz, CD$_3$OD): δ 7.28-7.15 (br m, 4H), 7.15-7.06 (br m, 3H), 3.72 (dd, J=10.3, 4.1 Hz, 1H), 3.62 (s, 2H), 3.57 (s, 2H), 3.41 (dd, J=14.7, 4.4 Hz, 1H), 2.87 (dd, J=14.8, 10.3 Hz, 1H), 2.35 (s, 3H). The $^1$H NMR signals of the amine-group, the N—H acidic group, and the carboxyl-group were not observed because of H-D exchange with the NMR solvent.

Example 56

(S)-2-Amino-3-(5-((benzylsulfonyl)methyl)-2-methylphenyl)propanoic Acid (56)

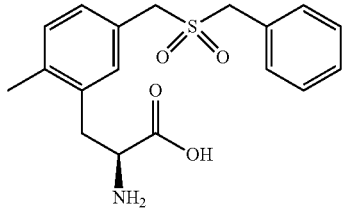

Compound (56) was synthesized by adapting methods described in Scheme 6 and Scheme 9. The bis-benzylic thioether was prepared as described in Example 55.

Synthetic tert-butyl (S)-3-(5-((benzylthio)methyl)-2-methylphenyl)-2-((tert-butoxycarbonyl)amino)propanoate (200 mg, 0.42 mmol) was fully oxidized to the corresponding sulfone with meta-chloroperbenzoic acid (mCPBA, 3-chloroperbenzoic acid) [CAS No. 937-14-4](439 mg, 2.54 mmol) in DCM (2 mL) at 0° C. to 25° C. for 16 h. Extractive aqueous work-up and chromatographic purification on silica gel (petroleum ether/ethyl acetate=10:1, (v/v)) yielded tert-butyl (S)-3-(5-((benzylsulfonyl)methyl)-2-methylphenyl)-2-((tert-butoxycarbonyl)amino)propanoate (110 mg, 51% yield) as a colorless (white) solid. LC/MS: calculated for $C_{27}H_{37}NO_6S$ 503.23, found ESI (pos.) m/z=526.70 [M+Na$^+$].

The protecting groups of the bisbenzylic sulfone were removed in one step (Scheme 9). Global removal of the N-Boc-protection group and the tert-butyl ester group of tert-butyl (S)-3-(5-((benzylsulfonyl)methyl)-2-methylphenyl)-2-((tert-butoxycarbonyl)amino)propanoate (110 mg, 0.22 mmol, 1.0 eq.) in 1,4-dioxane (1 mL) was conducted through reaction with commercial HCl in 1,4-dioxane [CAS No. 7647-01-0](4 M in 1,4-dioxane, 5 mL, 20 mmol) at 40° C. for overnight. Evaporation of volatiles yielded crude compound (56). Purification by prep. HPLC and removal of the solvents by lyophilization yielded compound (56) (33 mg, 44% yield) as a colorless solid. LC/MS/UV: Rt: 1.800 min, $C_{18}H_{21}NO_4S$ 347.12, ESI (pos.) m/z=348.05 [M+H$^+$]$^+$, 695.20 [2M+H$^+$]$^+$, ESI (neg.) m/z=346.10 [M–H$^+$]$^-$, 693.25 [2M–H$^+$]$^-$; HPLC/UV: Rt: 5.333 min (99.2% AUC at 220 nm, 99.1% AUC at 254 nm); H NMR (400 MHz, DMSO-d$_6$): δ 7.45-7.32 (br m, 5H), 7.26-7.14 (m, 3H), 5.76 (d, J=3.4 Hz, 2H), 4.45 (d, J=2.5 Hz, 1H), 4.40-4.28 (m, 2H), 2.78-2.70 (m, 2H), 2.30 (s, 3H). The $^1$H NMR signals of the amino-group and the carboxyl-group were not observed because of exchange with the NMR solvent.

Example 57

(S)-2-Amino-3-(5-((4-methoxyphenyl)sulfonamido)-2-methylphenyl)propanoic Acid (57)

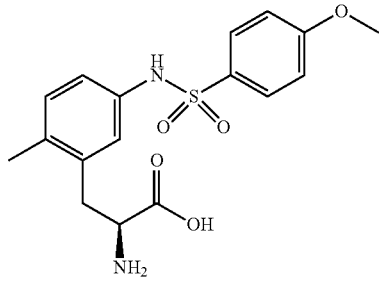

Compound (57) was synthesized by adapting methods described in Scheme 2, Scheme 3, and Scheme 9. Aniline starting material 6 (SM-6), tert-butyl (S)-3-(5-amino-2-methylphenyl)-2-((tert-butoxycarbonyl)amino)propanoate, (400 mg, 1.14 mmol) was reacted with commercial 4-methoxybenzenesulfonyl chloride [CAS No. 98-68-0] (354 mg, 1.71 mmol) in DCM (16 mL) in the presence of pyridine [CAS No. 110-86-1](212 μL, 180 mg, 2.28 mmol) at room temperature for overnight. Evaporation of the volatiles, acidic aqueous work-up, and chromatographic purification on silica gel (petroleum ether/ethyl acetate=5:1, (v/v)) yielded tert-butyl (S)-2-((tert-butoxycarbonyl)amino)-3-(5-((4-methoxyphenyl)sulfonamido)-2-methylphenyl)propanoate (390 mg, 65% yield). TLC: Rf: 0.55 (petroleum ether/ethyl acetate=4:1, (v/v)); LC/MS: calculated for $C_{26}H_{36}N_2O_7S$ 520.22, found ESI (neg.) m/z=519.45 [M–H$^+$]$^-$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-((4-methoxyphenyl)sulfonamido)-2-methylphenyl)propanoate (100 mg, 0.19 mmol) in 1,4-dioxane (4 mL) was conducted through reaction with commercial HCl in 1,4-dioxane [CAS No.

7647-01-0](4 M in 1,4-dioxane, 6 mL, 24 mmol) at room temperature for overnight. Evaporation of volatiles yielded to crude compound (57). Purification by prep. HPLC and removal of the solvents by lyophilization yielded compound (57) (59 mg, 83% yield) as a solid. LC/MS/UV: Rt: 1.389 min, calculated for $C_{17}H_{20}N_2O_5S$. 364.42 ESI (pos.) m/z=365.10 [M+H$^+$]$^+$, 729.25 [2M+H$^+$]$^+$, ESI (neg.) m/z=363.05 [M–H$^+$]$^-$, 727.40 [2M–H$^+$]$^-$; HPLC/UV: Rt: 5.375 min (97.2% AUC at 220 nm, 98.6% AUC at 254 nm); $^1$H NMR (400 MHz, CD$_3$OD): δ 7.68 (d, J=8.4 Hz, 2H), 7.06-6.94 (m, 4H), 6.89-6.82 (m, 1H), 3.81 (s, 3H), 3.78-3.70 (m, 1H), 3.70-3.62 (br m, 1H), 2.88-2.80 (m, 1H), 2.28 (s, 3H). The $^1$H NMR signals of the amino-group, the N—H acidic group, and the carboxyl group were not observed because of H-D exchange with the NMR solvent.

Example 58

(S)-2-Amino-3-(5-butylsulfonamido)-2-methylphenyl)propanoic Acid (58)

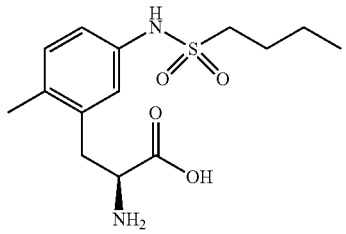

Compound (58) was synthesized by adapting methods described in Scheme 7 and Scheme 9. Aniline starting material 6 (SM-6), tert-butyl (S)-3-(5-amino-2-methylphenyl)-2-((tert-butoxycarbonyl)amino)propanoate, (400 mg, 1.14 mmol) was reacted with commercial 1-butanesulfonyl chloride [CAS No. 2386-60-9](235 mg, 1.50 mmol) in DCM (16 mL) in the presence of pyridine [CAS No. 110-86-1] (183 μL, 180 mg, 2.28 mmol) at room temperature for overnight. Evaporation of the volatiles and chromatographic purification on silica gel (petroleum ether/ethyl acetate=5:1, (v/v)) yielded tert-butyl (S)-2-((tert-butoxycarbonyl)amino)-3-(5-(butylsulfonamido)-2-methylphenyl)propanoate (330 mg, 61% yield). TLC: Rf: 0.50 (petroleum ether/ethyl acetate=4:1, (v/v)). LC/MS/UV: Rt: 3.103 min, calculated for $C_{23}H_{38}N_2O_6S$ 470.25, found ESI (pos.) m/z=483.40 [M+H$^+$]$^+$, ESI (neg.) m/z=469.45 [M–H$^+$]$^-$; $^1$H NMR (400 MHz, CD$_3$OD): δ 7.08 (d, J=8.0 Hz, 1H), 7.03 (d, J=2.4 Hz, 1H), 6.98 (dd, J=8.0, 2.4 Hz, 1H), 4.24-4.15 (m, 1H), 3.02 (dd, 1H, superimposed), 3.05-2.98 (m, 2H, superimposed), 2.83 (dd, J=14.0, 8.8 Hz, 1H), 2.29 (s, 3H), 1.75-1.68 (m, 2H), 1.45-1.38 (m, 2H, superimposed), 1.37 (2×s, 2×9H, superimposed), 0.88 (t, J=7.6 Hz, 3H). The $^1$H NMR signals of the N—H acidic groups were not observed because of H-D exchange with the NMR solvent.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(butylsulfonamido)-2-methylphenyl)propanoate (100 mg, 0.19 mmol) in 1,4-dioxane (4 mL) was conducted through reaction with commercial HCl in 1,4-dioxane [CAS No. 7647-01-0](4 M in 1,4-dioxane, 6 mL, 24 mmol) at room temperature for overnight. Evaporation of volatiles yielded crude compound (58). Purification by prep. HPLC and removal of the solvents by lyophilization yielded compound (58) (52 mg, 79% yield) as a colorless (white) solid. LC/MS/UV: Rt: 1.327 min, calculated for $C_{14}H_{22}N_2O_4S$ 314.13, found ESI (pos.) m/z=315.10 [M+H$^+$]$^+$, ESI (neg.) m/z=313.10 [M–H$^+$]$^-$, 627.30 [2M–H$^+$]$^-$; HPLC/UV: Rt: 5.209 min (100% AUC at 220 nm, 100% AUC at 254 nm); $^1$H NMR (400 MHz, CD$_3$OD): 7.16 (d, J=8.4 Hz, 1H), 7.10 (br s, 1H), 7.04 (br d, J=8.0 Hz, 1H), 3.75-3.66 (m, 1H), 3.39-3.33 (m, 1H), 3.08-3.01 (m, 2H), 2.93-2.83 (m, 1H), 2.33 (s, 3H), 1.80-1.68 (m, 2H), 1.45-1.32 (m, 2H), 0.89 (t, J=7.2 Hz, 3H). The $^1$H NMR signals of the amino-group, the N—H acidic group, and the carboxyl group were not observed because of H-D exchange with the NMR solvent.

Example 59

(S)-2-Amino-3-(5-(benzylthio)-2-methylphenyl)propanoic Acid (59)

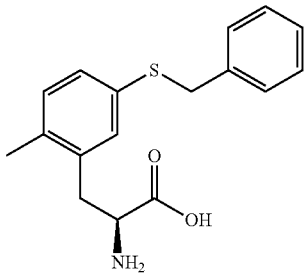

Compound (59) was synthesized by adapting methods described in Scheme 6 and Scheme 9. The benzylic thioether tert-butyl (S)-3-(5-benzylsulfanyl-2-methylphenyl)-2-(tert-butoxycarbonylamino)propanoate was prepared as described for the preparation of starting material 9 (SM-9).

The protecting groups of the benzylic thioether were removed in one step (Scheme 9). Global removal of the N-Boc-protection group and the tert-butyl ester group of tert-butyl (S)-3-(5-benzylsulfanyl-2-methylphenyl)-2-(tert-butoxycarbonylamino)propanoate (150 mg, 0.33 mmol) in 1,4-dioxane (2 mL) was conducted through reaction with commercial HCl in 1,4-dioxane (4 M in 1,4-dioxane, 7.5 mL, 30 mmol) at 40° C. for overnight. Evaporation of volatiles yielded the crude compound (59). Purification by prep. HPLC and removal of the solvents by lyophilization yielded compound (59) (32 mg, 32% yield) as a colorless (white) solid. LC/MS/UV: Rt: 1.598 min, calculated for $C_{17}H_{19}NO_2S$ 301.11, ESI (pos.) m/z=302.10 [M+H$^+$]$^+$, 603.35 [2M+H$^+$]$^+$, ESI (neg.) m/z=300.05 [M–H$^+$]$^-$, 601.30 [2M–H$^+$]$^-$; HPLC/UV: Rt: 5.987 min (100% AUC at 220 nm, 100% AUC at 254 nm); $^1$H NMR (400 MHz, CD$_3$OD): δ 7.36-7.17 (m, 6H), 7.15-7.05 (m, 2H), 4.11 (s, 2H), 3.70 (dd, J=9.9, 4.8 Hz, 1H), 3.36 (dd, J=14.6, 4.7 Hz, 1H), 2.86 (dd, J=14.6, 9.8 Hz, 1H), 2.33 (s, 3H). The $^1$H NMR signals of the amino-group, the N—H acidic group, and the carboxyl group were not observed because of H-D exchange with the NMR solvent.

Example 60

(2S)-2-Amino-3-(5-((benzylsulfinyl)methyl)-2-methylphenyl)propanoic Acid (60)

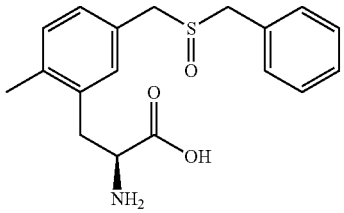

Compound (60) was synthesized by adapting methods described in Scheme 6 and Scheme 9. tert-Butyl (S)-3-(5-((benzylthio)methyl)-2-methylphenyl)-2-((tert-butoxycarbonyl)amino)propanoate was prepared as described for the preparation of Example 55 (Compound (55)).

Partial oxidation of the bis-benzylic thioether (300 mg, 0.64 mmol) was accomplished with 30 wt-% aq. $H_2O_2$ (65 µL, 72 mg (21.6 mg $H_2O_2$), 0.64 mmol) in HOAc (3 mL) at 0° C. to room temperature for 2 h. Extractive aqueous work-up and chromatographic purification on silica gel (petroleum ether/ethyl acetate=10:1, (v/v) yielded tert-butyl (2S)-3-(5-((benzylsulfinyl)methyl)-2-methylphenyl)-2-((tert-butoxycarbonyl)amino)propanoate (250 mg, 80% yield) as a colorless (white) solid. LC/MS/UV: Rt: 2.782 min, calculated for $C_{27}H_{37}NO_5S$ 487.24, found ESI (pos.) m/z=388.60 [M−$C_4H_8$—$CO_2$+H$^+$]$^+$, 510.35 [M+Na$^+$]$^+$.

The protecting groups of the bis-benzylic sulfoxide were removed in one step (Scheme 9). Global removal of the N-Boc-protection group and the tert-butyl ester group of tert-butyl (2S)-3-(5-((benzylsulfinyl)methyl)-2-methylphenyl)-2-((tert-butoxycarbonyl)amino)propanoate (230 mg, 0.47 mmol) was conducted through reaction with 50 vol-% TFA in DCM (6 mL) at room temperature for overnight. Evaporation of volatiles yielded crude compound (60). Purification by prep. HPLC and removal of the solvents by lyophilization yielded compound (60) (58 mg, 37% yield) as a colorless solid and as a mixture of diastereomers. LC/MS/UV: 1.743 min, calculated for $C_{18}H_{21}NO_3S$ 331.12, ESI (pos.) m/z=332.10 [M+H$^+$]$^+$, 663.30 [2M+H$^+$]$^+$, ESI (neg.) m/z=330.05 [M−H$^+$]$^-$, 661.25 [2M−H$^+$]$^-$; HPLC/UV: Rt: 5.276 (100% AUC at 220 nm, 100% AUC at 254 nm); $^1$H NMR (400 MHz, CD$_3$OD): δ 7.49-7.30 (m, 5H), 7.28-7.08 (m, 3H), 4.24-4.12 (m, 2H), 4.01-3.84 (m, 2H), 3.79-3.71 (m, 1H), 3.48-3.40 (m, 1H), 2.96-2.84 (m, 1H), 2.39 and 2.39 (2×s, 3H, diastereomers). The $^1$H NMR signals of the amino-group, the N—H acidic groups, and the carboxyl group were not observed because of H-D exchange with the moisture in the NMR solvent.

Example 61

(S)-2-Amino-3-(3,5-di(methylsulfonamido)phenyl)propanoic Acid (61)

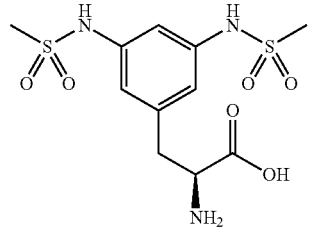

5-Bromobenzene-1,3-diamine is commercially available [CAS No. 33786-90-2]. Following well-known literature methods, the compound was also prepared from commercial 1-bromo-3,5-dinitrobenzene [CAS No. 18242-39-2](5.0 g, 20.2 mmol) through reduction of the nitro groups with iron powder (Fe) [CAS No. 7439-89-6] (9.06 g, 162 mmol) in the presence of ammonium chloride (NH$_4$Cl) [CAS No. 12125-02-9](2.17 g, 40.6 mmol) in a mixture of EtOH and water (360 mL, 2:1, (v/v)) at 90° C. for overnight. Filtration and evaporation of volatiles yielded crude 5-bromobenzene-1,3-diamine (3.3 g, 88% yield) as a dark red oil. LC/MS: calculated for $C_6H_7BrN_2$ 185.98, found ESI (pos.) m/z=187.00 [M+H$^+$]$^+$; $^1$H NMR (400 MHz, CDCl$_3$): δ 6.24 (s, 2H), 5.89 (s, 1H), 2.57 (br s, 4H).

5-Bromobenzene-1,3-diamine [CAS No. 33786-90-2](3.3 g, 17.6 mmol) and starting material 3 (SM-3), tert-butyl (R)-2-((tert-butoxycarbonyl)amino)-3-iodopropanoate [CAS No. 1057341-65-7](5.1 g, 13.7 mmol, 1.0 eq) were cross-coupled through Pd(0)-catalyzed Negishi-coupling using tris(dibenzylideneacetone)dipalladium (Pd$_2$(dba)$_3$) [CAS No. 51364-51-3](1.26 g, 1.37 mmol) and 2-dicyclohexylphosphino-2',6'-dimethoxybiphenyl (S-Phos) [CAS No. 657408-07-6](563 mg, 1.37 mmol) in the presence of an excess of zinc dust [CAS No. 7440-66-6](10.8 g, 165 mol), pre-activated with elemental iodine (I$_2$) [CAS No. 7553-56-2](261 mg, 2.06 mmol) and trimethylchlorosilane (TMSCl) [CAS No. 75-77-4](300 µL, 257 mg, 2.36 mmol) in anhydrous DMF (30 mL+20 mL+10 mL) at 60° C. for overnight under a nitrogen atmosphere. Filtration over Celite®, extractive aqueous work-up, and chromatographic purification over silica gel (petroleum ether/ethyl acetate=10/1 to 3/1, (v/v)) yielded tert-butyl (S)-2-((tert-butoxycarbonyl)amino)-3-(3,5-diaminophenyl)propanoate (1.67 g, 28% yield) as a yellow oil. TLC: Rf: 0.25 (petroleum ether/ethyl acetate=1:1, (v/v)); LC/MS/UV: Rt: 1.411 min, calculated for $C_{18}H_{29}N_3O_4$ 351.22, found m/z=352.25 [M+H$^+$]$^+$; $^1$H NMR (400 MHz, CD$_3$OD): δ 6.03 (s, 1H), 5.99 (s, 2H), 4.18-4.08 (br m, 1H), 2.79 (br dd, J=13.2, 6.4 Hz, 1H), 2.68 (br dd, J=13.2, 6.8 Hz, 1H), 1.40 (s, 9H), 1.29 (s, 9H). The $^1$H NMR signals of the aromatic amino groups (anilines) and the N—H acidic group were not observed because of H-D exchange with the NMR solvent.

The bis-aniline coupling product tert-butyl (S)-2-((tert-butoxycarbonyl)amino)-3-(3,5-diaminophenyl)propanoate (425 mg, 1.21 mmol) was reacted with commercial methanesulfonyl chloride (MsCl) [CAS No. 124-63-0](415 mg, 3.63 mmol) in DCM (4 mL) in the presence of pyridine [CAS No. 110-86-1](390 µL, 383 mg, 4.84 mmol) at room temperature for overnight under a nitrogen atmosphere. Evaporation of volatiles and chromatographic purification (petroleum ether/ethyl acetate=30:1 to 5:1, (v/v)) yielded tert-butyl (S)-2-((tert-butoxycarbonyl)amino)-3-(3,5-di(methylsulfonamido)phenyl)propanoate (471 mg, 76% yield). TLC: Rf: 0.45 (petroleum ether/ethyl acetate=4:1, (v/v)); LC/MS/UV: Rt: 2.753 min, calculated for $C_{20}H_{33}N_3O_8S_2$ 507.17, found ESI (pos.) m/z=530.30 [M+Na$^+$]$^+$, ESI (neg.) m/z=506.35 [M−H$^+$]$^-$; $^1$H NMR (400 MHz, CD$_3$OD): δ 7.07-7.04 (m, 1H), 6.90-6.84 (m, 2H), 4.26-4.20 (m, 1H), 3.02-2.92 (m, 1H, superimposed), 2.96 (s, 6H), 2.85-2.75 (m, 1H), 1.41 (s, 9H), 1.38 (s, 9H).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(3,5-di(methylsulfonamido)phenyl)propanoate (220 mg, 0.43 mmol) was conducted through reaction with 50 vol-% TFA in DCM (4 mL) at room temperature for overnight. Evaporation of volatiles yielded the crude compound (61). Purification by prep. HPLC and removal of the solvents by lyophilization yielded compound (61) (35 mg, 23% yield) as a colorless (white) solid. LC/MS/UV: Rt: 1.068 min, calculated for $C_{11}H_{17}N_3O_6S_2$ 351.40, ESI (pos.) m/z=352.10 [M+H$^+$]$^+$, 703.30 [2M+H$^+$]$^+$, ESI (neg.) m/z=350.00 [M−H$^+$]$^-$, 701.30 [2M−H$^+$]$^-$; HPLC/UV: Rt: 3.852 min (100% AUC at 220 nm, 100% AUC at 254 nm); $^1$H NMR (400 MHz, DMSO-d$_6$): 7.00 (s, 1H), 6.84 (s, 2H), 3.43 (dd, J=8.0, 4.8 Hz, 1H), 3.03 (dd, J=14.0, 4.8 Hz, 1H), 2.99 (s, 6H), 2.78 (dd, J=14.4, 8.8 Hz, 1H), 2.51 (s, 3H). The $^1$H NMR signals of the amino-group, the N—H acidic groups, and the carboxyl group were not observed because of H-D exchange with the moisture in the NMR solvent.

Example 62

(S)-2-Amino-3-(3,5-bis(phenylsulfonamido)phenyl)propanoic Acid (62)

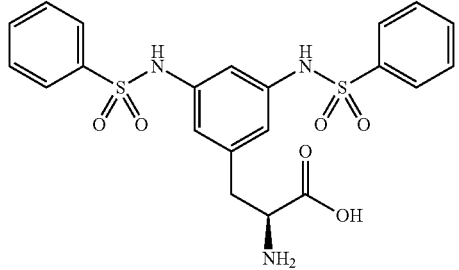

The bis-aniline coupling product tert-butyl (S)-2-((tert-butoxycarbonyl)amino)-3-(3,5-diaminophenyl)propanoate (see Example 61) (320 mg, 0.91 mmol) was reacted with commercial benzenesulfonyl chloride (PhSO$_2$Cl) [CAS No. 98-09-9](482 mg, 2.73 mmol) in DCM (3 mL) in the presence of pyridine [CAS No. 110-86-1](293 µL, 288 mg, 3.64 mmol) at room temperature for overnight under a nitrogen atmosphere. Evaporation of volatiles and chromatographic purification (petroleum ether/ethyl acetate=30:1 to 5:1, (v/v)) yielded tert-butyl (S)-3-(3,5-bis(phenylsulfonamido)phenyl)-2-((tert-butoxycarbonyl)amino)propanoate (283 mg, 49% yield) as a yellow oil. TLC: Rf: 0.65 (petroleum ether/ethyl acetate=4:1, (v/v)); LC/MS: calculated for $C_{30}H_{37}N_3O_8S_2$ 631.20, found ESI (pos.) m/z=654.20 [M+Na$^+$]$^+$; $^1$H NMR (400 MHz, CD$_3$OD): δ 7.68 (d, J=8.4 Hz, 4H), 7.55 (t, J=7.2 Hz, 2H), 7.43 (t, J=7.6 Hz, 4H), 7.03-6.97 (m, 1H), 6.58 (d, J=1.6 Hz, 2H), 4.10-3.95 (m, 1H), 2.82-2.72 (dd, J=13.6, 5.6 Hz, 1H), 2.70-2.62 (dd, J=14.4, 8.0 Hz, 1H), 1.39 (s, 9H), 1.28 (s, 9H).

The protecting groups of the sulfonamide were removed in one step (Scheme 9). Global removal of the N-Boc-protection group and the tert-butyl ester group of tert-butyl (S)-3-(3,5-bis(phenylsulfonamido)phenyl)-2-((tert-butoxycarbonyl)amino)propanoate (200 mg, 0.32 mmol) in 1,4-dioxane (1 mL) was conducted through reaction with commercial HCl in 1,4-dioxane [CAS No. 7647-01-0] (4 M in 1,4-dioxane, 8 mL, 32 mmol) at 40° C. for overnight. Evaporation of volatiles yielded the crude compound (62). Purification by prep. HPLC and removal of the solvents by lyophilization yielded compound (62) (34 mg, 22% yield) as a colorless (white) solid. LC/MS/UV: Rt: 1.192 min, calculated for $C_{21}H_{21}N_3O_6S_2$ 475.09, ESI (pos.) m/z=476.15 [M+H$^+$]$^+$, 951.35 [2M+H$^+$]$^+$, ESI (neg.) m/z=474.10 [M−H$^+$]$^-$, 949.50 [2M−H$^+$]$^-$; HPLC/UV: Rt: 5.648 min (98.4% AUC at 220 nm, 99.0% AUC at 254 nm); H NMR (400 MHz, CD$_3$OD): δ 7.72 (d, J=7.2 Hz, 4H), 7.56 (t, J=7.6 Hz, 2H), 7.45 (t, J=8.0 Hz, 4H), 7.09 (br t, J=2.0 Hz, 1H), 6.63 (d, J=2.0 Hz, 2H), 3.59 (dd, J=9.2, 4.4 Hz, 2H), 3.08 (dd, J=14.8, 4.4 Hz, 1H), 2.74 (dd, J=14.8, 8.8 Hz, 1H). The $^1$H NMR signals of the amino-group, the N—H acidic groups, and the carboxyl group were not observed because of H-D exchange with the NMR solvent.

Example 63

(S)-2-Amino-3-(3,5-bis((4-methylphenyl)sulfonamido)phenyl)propanoic Acid (63)

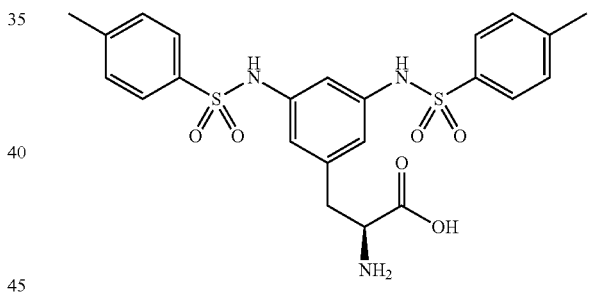

The bis-aniline coupling product tert-butyl (S)-2-((tert-butoxycarbonyl)amino)-3-(3,5-diaminophenyl)propanoate (see Example 61) (300 mg, 0.85 mmol) was reacted with commercial 4-methylbenzenesulfonyl chloride (4-toluenesulfonyl chloride, p-toluenesulfonyl chloride, toluene-p-sulfonyl chloride, TsCl) [CAS No. 98-59-9](488 mg, 2.55 mmol) in DCM (4 mL) in the presence of pyridine [CAS No. 110-86-1](275 µL, 270 mg, 3.41 mmol) at room temperature for overnight under a nitrogen atmosphere. Evaporation of volatiles and chromatographic purification (petroleum ether/ethyl acetate=30:1 to 10:1, (v/v)) yielded tert-butyl (S)-3-(3,5-bis((4-methylphenyl)sulfonamido)phenyl)-2-((tert-butoxycarbonyl)amino)propanoate (493 mg, 87% yield) as a colorless (white) solid. TLC: Rf: 0.65 (petroleum ether/ethyl acetate=4:1, (v/v)); LC/MS/UV: Rt: 2.846 min, calculated for $C_{32}H_{41}N_3O_8S_2$ 659.23, found ESI (pos.) m/z=682.25 [M+Na$^+$]$^+$; $^1$H NMR (400 MHz, CD$_3$OD): δ 7.57 (d, J=8.4 Hz, 4H), 7.24 (d, J=8.4 Hz, 4H), 7.00 (br t., J=2.0 Hz, 1H), 6.55 (d, J=1.6 Hz, 2H), 4.10-3.95 (br m, 1H), 2.75 (dd, J=14.0, 6.8 Hz, 1H), 2.67 (dd, J=13.6, 8.8 Hz, 1H), 2.36 (s, 6H), 1.39 (s, 9H), 1.27 (s, 9H).

The protecting groups of the sulfonamide were removed in one step (Scheme 9). Global removal of the N-Boc-protection group and the tert-butyl ester group of tert-butyl (S)-3-(3,5-bis((4-methylphenyl)sulfonamido)phenyl)-2-((tert-butoxycarbonyl)amino)propanoate (200 mg, 0.30 mmol) in 1,4-dioxane (1 mL) was conducted through reaction with commercial HCl in 1,4-dioxane [CAS No. 7647-01-0](4 M in 1,4-dioxane, 8 mL, 32 mmol) at 40° C. for overnight. Evaporation of volatiles yielded the crude compound (63). Purification by prep. HPLC and removal of the solvents by lyophilization yielded compound (63) (28 mg, 18% yield) as a light yellow solid. LC/MS/UV: Rt: 1.968 min, calculated for $C_{23}H_{25}N_3O_6S_2$ 503.12, ESI (pos.) m/z=504.20 [M+H$^+$]$^+$, ESI (neg.) m/z=502.15 [M–H$^+$]$^-$; HPLC/UV: Rt: 5.978 min (98.8% AUC at 220 nm, 99.0% AUC at 254 nm); $^1$H NMR (400 MHz, CD$_3$OD): δ 7.60 (d, J=8.4 Hz, 4H), 7.25 (d, J=8.8 Hz, 4H), 7.09 (t, J=2.0 Hz, 1H), 6.61 (d, J=2.0 Hz, 2H), 3.59 (dd, J=9.2, 4.4 Hz, 1H), 3.07 (dd, J=14.8, 4.0 Hz, 1H), 2.73 (dd, J=14.4, 8.4 Hz, 1H), 2.36 (s, 6H). The $^1$H NMR signals of the amino-group, the N—H acidic groups, and the carboxyl group were not observed because of H-D exchange with the NMR solvent.

Example 64

(2S)-2-Amino-3-(5-(benzylsulfinyl)-2-methylphenyl)propanoic Acid (64)

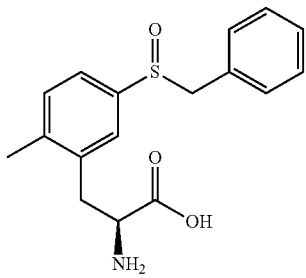

Compound (64) was synthesized by adapting methods described in Scheme 6 and Scheme 9. The phenylic-benzylic thioether tert-butyl (S)-3-(5-(benzylthio)-2-methylphenyl)-2-((tert-butoxycarbonyl)amino)propanoate was prepared as described for the preparation of sulfonyl chloride starting material 9 (SM-9).

Partial oxidation of the phenylic-benzylic thioether (370 mg, 0.81 mmol) was accomplished with 30 wt-% aq. hydrogen peroxide (H$_2$O$_2$) (30 µL, 33 mg (10 mg H$_2$O$_2$), 0.29 mmol) in acetic acid (HOAc) (2 mL) at 0° C. to room temperature for 2 h. Extractive aqueous work-up with chloroform (CHCl$_3$) yielded tert-butyl (2S)-3-(5-(benzylsulfinyl)-2-methylphenyl)-2-((tert-butoxycarbonyl)amino)propanoate (290 mg, 76% yield). LC/MS/UV: Rt: 3.127 min, calculated for $C_{26}H_{35}NO_5S$ 473.22, found ESI (pos.) m/z=496.25 [M+Na$^+$]$^+$, m/z=969.60 [2M+H$^+$]$^+$.

The protecting groups of the sulfoxide were removed in one step (Scheme 9). Global removal of the N-Boc-protection group and the tert-butyl ester group of tert-butyl (2S)-3-(5-(benzylsulfinyl)-2-methylphenyl)-2-((tert-butoxycarbonyl)amino)propanoate (250 mg, 0.53 mmol) in 1,4-dioxane (4 mL) was conducted through reaction with commercial HCl in 1,4-dioxane [CAS No. 7647-01-0](4 M in 1,4-dioxane, 15 mL, 60 mmol) at 40° C. for overnight. Evaporation of volatiles yielded the crude compound (64). Purification by prep. HPLC and removal of the solvents by lyophilization yielded compound (64) (9 mg, 5% yield) as a colorless (white) solid. LC/MS/UV: Rt: 1.683 min, calculated for $C_{17}H_{19}NO_3S$. 317.11, ESI (pos.) m/z=318.25 [M+H$^+$]$^+$, 635.50 [2M+H$^+$]$^+$; HPLC/UV: Rt: 4.311 min (100% AUC at 220 nm, 100% AUC at 254 nm); $^1$H NMR (400 MHz, CD$_3$OD): δ 7.37-7.25 (m, 6H), 7.13-7.08 (m, 2H), 5.52-5.49 (br m, 2H), 4.19-4.14 (br m, 1H), 3.93-3.89 (m, 1H), 3.72-3.68 (m, 1H), 2.44 (s, 3H). The $^1$H NMR signals of the amino-group, the N—H acidic groups, and the carboxyl group were not observed because of H-D exchange with the NMR solvent.

Example 65

(2S)-2-Amino-3-(5-(benzylsulfonyl)-2-methylphenyl)propanoic Acid (65)

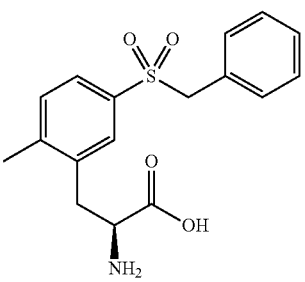

Compound (65) was synthesized by adapting methods described in Scheme 6 and Scheme 9. The phenylic-benzylic thioether tert-butyl (S)-3-(5-(benzylthio)-2-methylphenyl)-2-((tert-butoxycarbonyl)amino)propanoate was prepared as described for the preparation of sulfonyl chloride starting material 9 (SM-9).

Full oxidation of the phenylic-benzylic thioether (150 mg, 0.33 mmol) was accomplished with 3-chloroperbenzoic acid (meta-chloroperbenzoic acid, mCPBA) [CAS No. 937-14-4](339 mg, 1.96 mmol) in DCM (6 mL) at 0° C. to room temperature for 4 h. Extractive aqueous work-up yielded tert-butyl (S)-3-(5-(benzylsulfonyl)-2-methylphenyl)-2-((tert-butoxycarbonyl)amino)propanoate (120 mg, 74% yield). LC/MS/UV: Rt: 3.744 min, calculated for $C_{26}H_{35}NO_6S$ 489.22, found ESI (pos.) m/z=507.65 [M+H$_2$O+H$^+$]$^+$; $^1$H NMR (400 MHz, CDCl$_3$): δ 7.42 (d, J=1.9 Hz, 1H), 7.34-7.25 (m, 4H), 7.19 (d, J=7.9 Hz, 1H), 7.10 (d, J=8.3 Hz, 2H), 5.02 (d, J=9.4 Hz, 1H), 4.39 (dd, J=17.2, 6.8 Hz, 1H), 4.24 (s, 2H), 3.10 (dd, J=15.2, 4.8 Hz, 1H), 2.90 (dd, J=13.6, 7.6 Hz, 1H), 2.42 (s, 3H), 1.41 (s, 9H), 1.37 (s, 9H).

The protecting groups of the sulfone were removed in one step (Scheme 9). Global removal of the N-Boc-protection group and the tert-butyl ester group of tert-butyl (S)-3-(5-(benzylsulfonyl)-2-methylphenyl)-2-((tert-butoxycarbonyl)amino)propanoate (120 mg, 0.25 mmol) in 1,4-dioxane (4 mL) was conducted through reaction with commercial HCl in 1,4-dioxane [CAS No. 7647-01-0](4 M in 1,4-dioxane, 6 mL, 24 mmol) at 40° C. for overnight. Evaporation of volatiles yielded the crude compound (65). Purification by prep. HPLC and removal of the solvents by lyophilization yielded compound (65) (55 mg, 60% yield) as a yellow solid. LC/MS/UV: Rt: 1.737 min, calculated for $C_{17}H_{19}NO_4S$. 333.10, found $C_{17}H_{19}NO_4S$. 333.40 g/mol. ESI (pos) m/z=334.15 [M+H$^+$]$^+$, ESI (neg) m/z=333.10 [M–H$^+$]$^-$; HPLC/UV: 4.430 min (97.8% AUC at 220 nm); $^1$H NMR (400 MHz, CD$_3$OD): δ 7.58 (s, 1H), 7.41 (d, J=7.8

Hz, 1H), 7.34 (d, J=9.3 Hz, 1H), 7.32-7.21 (m, 3H), 7.19-7.12 (d, J=7.2 Hz, 2H), 4.46 (s, 2H), 3.69 (dd, J=10.8, 4.8 Hz, 1H), 3.00-2.90 (m, 2H), 2.46 (s, 3H). The $^1$H NMR signals of the amino-group, the N—H acidic groups, and the carboxyl group were not observed because of H-D exchange with the NMR solvent.

Example 66

(S)-2-Amino-3-(2-methyl-5-(((4-methylphenyl)sulfonamido)methyl)phenyl)propanoic Acid (66)

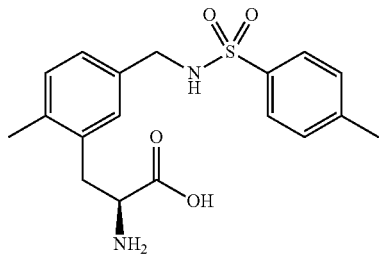

Compound (66) was synthesized by adapting methods described in Scheme 1, Scheme 3, and Scheme 9. Following well-known literature procedures, (3-iodo-4-methylphenyl)methanamine [CAS No. of HCl salt 1803588-29-5] was prepared from commercial 3-iodo-4-methyl-benzoic acid [CAS No. 82998-57-0] in 3 steps or commercial 3-iodo-4-methylphenyl)methanol [CAS No. 165803-89-4] as described for Example (54) (compound (54)).

Commercial 4-methylbenzenesulfonyl chloride (4-toluenesulfonyl chloride, p-toluenesulfonyl chloride, toluene-p-sulfonyl chloride, TsCl) [CAS No. 98-59-9](413 mg, 2.16 mmol) was reacted with (3-iodo-4-methyl-phenyl)methanamine (400 mg, 1.44 mmol) in pyridine [CAS No. 110-86-1](4 mL) at room temperature for overnight. Evaporation of the volatiles, extractive aqueous work-up and chromatographic purification by prep.-TLC on silica gel (petroleum ether/ethyl acetate=5:1, (v/v)) yielded N-(3-iodo-4-methyl-benzyl)-4-methylbenzenesulfonamide (300 mg, 46% yield) as a yellow solid. TLC: Rf: 0.45 (petroleum ether/ethyl acetate=5:1, (v/v)); LC/MS/UV: Rt: 2.454 min, calculated for $C_{15}H_{16}INO_2S$ 400.99, found ESI (pos.) m/z=402.05 [M+H$^+$]$^+$, m/z=803.15 [2M+H$^+$]$^+$, ESI (neg.) m/z=400.00 [M−H$^+$]$^-$; $^1$H NMR (400 MHz, CDCl$_3$): δ 7.71 (d, J=8.4 Hz, 2H), 7.51 (s, 1H), 7.28 (d, J=8.4 Hz, 2H), 7.14-7.02 (m, 2H), 4.61 (brt, J=6.4 Hz, 1H), 4.03 (d, J=6.4 Hz, 2H), 2.43 (s, 3H), 2.35 (s, 3H).

Synthetic N-(3-iodo-4-methylbenzyl)-4-methylbenzenesulfonamide (1.0 g, 2.49 mmol) and starting material 3 (SM-3), tert-butyl (R)-2-((tert-butoxycarbonyl)amino)-3-iodopropanoate [CAS No. 1057341-65-7](350 mg, 0.87 mmol) were cross-coupled through Pd(0)-catalyzed Negishi-coupling using tris(dibenzylideneacetone)dipalladium (Pd$_2$(dba)$_3$) [CAS No. 51364-51-3](80 mg, 0.09 mmol) and 2-dicyclohexylphosphino-2',6'-dimethoxybiphenyl (S-Phos) [CAS No. 657408-07-6](36 mg, 0.09 mmol) in the presence of an excess of zinc dust [CAS No. 7440-66-6](684 mg, 10.5 mmol), pre-activated with elemental iodine (I$_2$) [CAS No. 7553-56-2](17 mg, 0.13 mmol) and trimethylchlorosilane (TMSCl) [CAS No. 75-77-4](40 µL, 34 mg, 0.13 mmol) in anhydrous DMF (4 mL+3 mL) at 60° C. for overnight under a nitrogen atmosphere. Filtration over Celite®, extractive aqueous work-up, and chromatographic purification over silica gel (petroleum ether/ethyl acetate mixtures) yielded tert-butyl (S)-2-((tert-butoxycarbonyl)amino)-3-(2-methyl-5-(((4-methylphenyl)sulfonamido)methyl)phenyl)propanoate (150 mg, 52% yield) as a yellow oil. TLC: Rf: 0.30 (petroleum ether/ethyl acetate=4:1, (v/v)); LC/MS/UV: Rt: 2.873 min, calculated for $C_{27}H_{38}N_2O_6S$ 518.25, found ESI (pos.) m/z=541.30 [M+Na$^+$]$^+$, ESI (neg.) m/z=517.30 [M−H$^+$]$^-$; $^1$H NMR (400 MHz, CDCl$_3$): δ 7.69 (d, J=8.0 Hz, 2H), 7.25 (d, J=8.0 Hz, 2H), 6.99 (d, J=7.6 Hz, 1H), 6.89 (d, J=7.6 Hz, 1H), 6.23 (s, 1H), 4.90 (d, J=8.0 Hz, 1H), 4.50 (br s, 1H), 4.32 (q, J=7.6 Hz, 1H), 3.96 (br s, 2H), 2.93 (dd, J=18.8, 6.4 Hz, 1H), 2.80 (dd, J=18.8, 9.6 Hz, 1H), 2.38 (s, 3H), 2.24 (s, 3H), 1.30 (2×s, 2×9H, superimposed).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(((4-methylphenyl)sulfonamido)methyl)phenyl)propanoate (150 mg, 0.29 mmol) in 1,4-dioxane (2 mL) was conducted through reaction with commercial HCl in 1.4-dioxane [CAS No. 7647-01-0](4 M in 1,4-dioxane, 7 mL, 28 mmol) at 40° C. for overnight. Evaporation of volatiles yielded the crude compound (66). Purification by prep. HPLC and removal of the solvents by lyophilization yielded compound (66) (38 mg, 36% yield) as a colorless (white) solid. LC/MS/UV: Rt: 1.649 min, calculated for $C_{18}H_{22}N_2O_4S$ 362.13, found ESI (pos.) m/z=363.15 [M+H$^+$]$^+$, 725.30 [2M+H$^+$]$^+$, ESI (neg.) m/z=361.10 [M−H$^+$]$^-$, 723.55 [2M−H$^+$]$^-$; HPLC/UV: Rt: 5.655 min (100% AUC at 220 nm), 100% AUC at 254 nm); $^1$H NMR (400 MHz, DMSO-d$_6$): δ 7.68 (d, J=8.4 Hz, 2H), 7.39 (d, J=8.4 Hz, 2H), 7.08-6.96 (m, 3H), 3.85 (s, 2H), 3.33 (dd, J=9.6, 4.4 Hz, 1H), 3.19 (dd, J=14.8, 4.0 Hz, 1H), 2.68 (dd, J=14.4, 9.6 Hz, 1H), 2.39 (s, 3H), 2.24 (s, 3H). The $^1$H NMR signals of the N—H-acidic group, the amino-group, and the carboxylic acid group were not observed because of H-D exchange with the moisture in the NMR solvent.

Example 67

(S)-2-Amino-3-(2-methyl-5-(methylsulfonamido)phenyl)propanoic Acid (67)

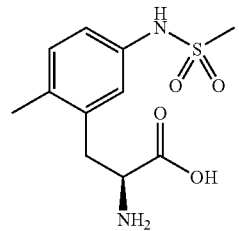

Compound (67) was synthesized by adapting methods described in Scheme 7 and Scheme 9. Commercial methanesulfonyl chloride (MsCl) [CAS No. 124-63-0](50 µL, 74 mg, 0.65 mmol) was reacted with starting material 5 (SM-5), methyl (S)-3-(5-amino-2-methylphenyl)-2-((tert-butoxycarbonyl)amino)propanoate, (200 mg, 0.65 mmol) in THF (4 mL) in the presence of triethylamine (Et$_3$N, TEA) [CAS No. 121-44-8](90 µL, 65 mg, 0.65 mmol) at room temperature for 2 h under a nitrogen atmosphere. Extractive aqueous work-up and chromatographic purification on silica gel (hexane/ethyl acetate=1:1, (v/v)) yielded methyl (S)-2-((tert-butoxycarbonyl)amino)-3-(2-methyl-5-(methylsulfonamido)phenyl)propanoate (200 mg, 80% yield) as an oil. TLC: Rf: 0.25 (hexane/ethyl acetate=1:1, (v/v)).

The protecting groups of the sulfonamide were removed in two steps (Scheme 9). Chemoselective removal of the N-Boc-protection group of methyl (S)-2-((tert-butoxycarbonyl)amino)-3-(2-methyl-5-(methylsulfonamido)phenyl)propanoate (200 mg, 0.52 mmol) was conducted with 20 vol-% TFA in DCM (5 mL) at room temperature for 1 h. Evaporation of volatiles and hydrolysis of the methyl ester group with lithium hydroxide monohydrate (LiOH·H$_2$O) [CAS No. 1310-66-3](109 mg, 2.6 mmol) in THF/water (1:1, (v/v)) (5 mL) at room temperature for 1 h yielded crude compound (67). Evaporation of volatiles, purification by prep. HPLC, and removal of the solvents by lyophilization yielded compound (67) (85 mg, 60% yield) as a colorless solid. LC/MS/UV: Rt: 0.431 min, calculated for C$_{11}$H$_{16}$N$_2$O$_4$S. 272.08, found ESI (pos.) m/z=273.10 [M+H$^+$]$^+$, 544.90 [2M+H$^+$]$^+$, ESI (neg) m/z=270.90 [M−H$^+$]-542.75 [2M−H$^+$]$^-$; HPLC/UV: Rt: 5.723 min (97.9% AUC at 220 nm); $^1$H NMR (300 MHz, CD$_3$OD): δ 7.17 (d, J=8.1 Hz, 1H), 7.13 (d, J=1.8 Hz, 1H), 7.07 (dd, J=8.4, 2.4 Hz, 1H), 3.74 (dd, J=9.3, 5.4 Hz, 1H), 3.38 (dd, J=14.7, 5.4 Hz, 1H), 2.94 (s, 3H), 2.92 (dd, J=14.7, 9.9 Hz, 1H), 2.35 (s, 3H). The $^1$H NMR signals of the amino-group, N—H-acidic group, and the carboxylic acid group were not observed because of H-D exchange with the NMR solvent.

Example 68

(S)-2-Amino-3-(3-(methylsulfonamido)phenyl)propanoic Acid (68)

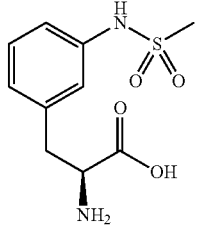

Commercial methanesulfonyl chloride (MsCl) [CAS No. 124-63-0](31 µL, 46 mg, 0.39 mmol) in THF (5 mL) was reacted with synthetic aniline starting material tert-butyl (S)-3-(3-aminophenyl)-2-((tert-butoxycarbonyl)amino)propanoate (see Example 37) (110 mg, 0.33 mmol, 1.0 eq.) in THF (5 mL) with triethylamine (Et$_3$N, TEA) [CAS No. 121-44-8](92 µL, 65 mg, 0.66 mmol) at room temperature for 2 h under a nitrogen atmosphere. Extractive aqueous work-up and chromatographic purification on silica gel (hexane/ethyl acetate=1:1, (v/v)) yielded tert-butyl (S)-2-((tert-butoxycarbonyl)amino)-3-(3-(methylsulfonamido)phenyl)propanoate (110 mg, 81% yield) as an oil. TLC: Rf: 0.50 (hexane/ethyl acetate=1:1, (v/v)).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(3-(methylsulfonamido)phenyl)propanoate (110 mg, 0.27 mmol) was conducted through reaction with commercial HCl in 1,4-dioxane [CAS No. 7647-01-0](4 M in 1,4-dioxane, 5 mL, 20 mmol) at 40° C. for 4 h. Evaporation of volatiles yielded the crude compound (68). Purification by prep. HPLC and removal of the solvents by lyophilization yielded pure compound (68) as a colorless (white) solid (55 mg, 79% yield). LC/MS/UV: Rt: 0.334 min, calculated for C$_{10}$H$_{14}$N$_2$O$_4$S 258.07, ESI (pos) m/z=259.05 [M+H$^+$]$^+$, 516.80 [2M+H$^+$]$^+$, ESI (neg.) m/z=256.85 [M−H$^+$]$^-$, 514.65 [2M−H$^+$]$^-$; HPLC/UV: Rt: 4.720 min (98.2% AUC at 220 nm); $^1$H NMR (300 MHz, CD$_3$OD): δ 7.32 (t, J=7.8 Hz, 1H), 7.21-7.14 (br m, 2H), 7.09 (d, J=7.5 Hz, 1H), 3.78 (dd, J=8.1, 4.5 Hz, 1H), 3.28 (dd, J=14.7, 4.8 Hz, 1H), 3.01 (dd, J=14.7, 8.7 Hz, 1H), 2.98 (s, 3H). The $^1$H NMR signals of the amino-group, the N—H-acidic group, and the carboxylic acid group were not observed because of H-D exchange with the NMR solvent.

Example 69

(S)-2-Amino-3-(2-methyl-5-(phenylsulfonamidomethyl)phenyl)propanoic Acid (69)

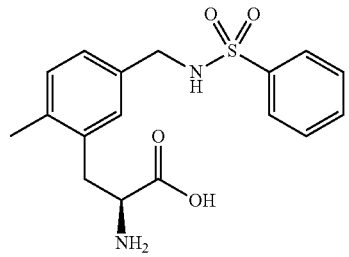

Compound (69) was synthesized by adapting methods described in Scheme 1, Scheme 3, and Scheme 9. Following well-known literature procedures, (3-iodo-4-methylphenyl)methanamine [CAS No. of HCl salt 1803588-29-5] was prepared from commercial 3-iodo-4-methyl-benzoic acid [CAS No. 82998-57-0] in 3 steps or from commercial 3-iodo-4-methylphenyl)methanol [CAS No. 165803-89-4] as described for Example (54) (Compound (54)).

Commercial benzenesulfonyl chloride (PhSO$_2$Cl) [CAS No. 98-09-9](536 mg, 3.03 mmol) was reacted with (3-iodo-4-methyl-phenyl)methanamine (500 mg, 2.02 mmol) in pyridine [CAS No. 110-86-1] (5 mL) at room temperature for overnight. Evaporation of the volatiles, extractive aqueous work-up, and chromatographic purification by prep.-TLC on silica gel (petroleum ether/ethyl acetate=5:1, (v/v)) yielded N-(3-iodo-4-methylbenzyl)benzenesulfonamide (440 mg, 63% yield) as a yellow solid. TLC: Rf: 0.50 (petroleum ether/ethyl acetate=5:1, (v/v)); LC/MS/UV: Rt: 2.354 min, calculated for C$_{14}$H$_{14}$INO$_2$S 386.98, found ESI (pos.) m/z=388.00 [M+H$^+$]$^+$, m/z=775.05 [2M+H$^+$]$^+$, ESI (neg.) m/z=385.95 [M−H$^+$]$^-$; $^1$H NMR (400 MHz, CDCl$_3$): δ 7.78 (d, J=7.2 Hz, 2H), 7.55-7.49 (m, 2H), 7.48-7.42 (m, 2H), 7.08-6.98 (m, 2H), 4.66 (brt, J=5.6 Hz, 1H), 4.00 (d, J=6.4 Hz, 2H), 2.30 (s, 3H).

Synthetic N-(3-Iodo-4-methylbenzyl)benzenesulfonamide (440 mg, 1.13 mmol) and starting material 3 (SM-3), tert-butyl (R)-2-((tert-butoxycarbonyl)amino)-3-iodopropanoate [CAS No. 1057341-65-7](422 mg, 1.13 mmol) were cross-coupled through Pd(0)-catalyzed Negishi-coupling using tris(dibenzylideneacetone)dipalladium (Pd$_2$(dba)$_3$) [CAS No. 51364-51-3](104 mg, 0.11 mol) and 2-dicyclohexylphosphino-2',6'-dimethoxybiphenyl (S-Phos) [CAS No. 657408-07-6](47 mg, 0.11 mmol) in the presence of an excess of zinc dust [CAS No. 7440-66-6](891 mg, 13.6 mmol), pre-activated with elemental iodine (I$_2$) [CAS No. 7553-56-2](22 mg, 0.09 mmol) and trimethylchlorosilane (TMSCl) [CAS No. 75-77-4](50 µL, 43 mg, 0.39 mmol) in anhydrous DMF (5 mL+3 mL) at 60° C. for overnight under a nitrogen atmosphere. Filtration over Celite®, extractive aqueous work-up, and chromatographic purification over silica gel (petroleum ether/ethyl acetate mixtures) yielded tert-butyl (S)-2-((tert-butoxycarbonyl)amino)-3-(2-methyl-5-(phenylsulfonamidomethyl)phenyl)propanoate (300 mg, 52% yield) as a yellow oil. TLC: Rf: 0.35 (petroleum ether/ethyl acetate=4:1, (v/v)); LC/MS/UV: Rt: 2.513 min, calculated for $C_{26}H_{36}N_2O_6S$ 504.23, found ESI (pos.) m/z=505.35 [M+H$^+$]$^+$, ESI (neg.) m/z=503.30 [M+H$^-$]$^+$.

The protecting groups of the sulfonamide were removed in one step (Scheme 9). Global removal of the N-Boc-protection group and the tert-butyl ester group of tert-butyl (S)-2-((tert-butoxycarbonyl)amino)-3-(2-methyl-5-(phenylsulfonamidomethyl)phenyl)propanoate (300 mg, 0.59 mmol) in 1,4-dioxane (3 mL) was conducted through reaction with commercial HCl in 1,4-dioxane [CAS No. 7647-01-0](4 M in 1,4-dioxane, 15 mL, 28 mmol) at 40° C. for overnight. Evaporation of volatiles yield the crude compound (69). Purification by prep. HPLC and removal of the solvents by lyophilization yielded compound (69) (84 mg, 40% yield) as a colorless (white) solid. LC/MS/UV: Rt: 1.430 min, calculated for $C_{17}H_{20}N_2O_4S$ 348.11, ESI (pos.) m/z=349.10 [M+H$^+$]$^+$, ESI (neg.) m/z=347.05 [M-H$^+$]$^-$, 695.55 [2M-H$^+$]$^-$; HPLC/UV: Rt: 5.429 min (99.0% AUC at 220 nm), 99.1% AUC at 254 nm); $^1$H NMR (400 MHz, DMSO-d$_6$): δ 7.80 (d, J=6.8 Hz, 2H), 7.66-7.57 (m, 3H), 7.07 (d, J=8.0 Hz, 1H), 7.02-6.97 (m, 2H), 3.89 (s, 2H), 3.40 (dd, J=9.2, 4.4 Hz, 1H), 3.19 (dd, J=14.8, 4.4 Hz, 1H), 2.71 (dd, J=14.4, 9.2 Hz, 1H), 2.42 (s, 3H). The $^1$H NMR signals of the amino-group, the N—H-acidic group, and the carboxylic acid group were not observed because of H-D exchange with the moisture in the NMR solvent.

Example 70

(S)-2-Amino-3-(4-(methylsulfonamido)phenyl)propanoic Acid (70)

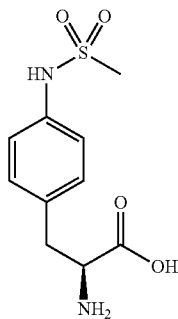

Compound (70) was synthesized by adapting methods described in Scheme 4, Scheme 7, and Scheme 9. Commercial 4-iodoaniline [CAS No. 540-37-5](500 mg, 2.28 mmol) and starting material 1 (SM-1), methyl (R)-2-((tert-butoxycarbonyl)amino)-3-iodopropanoate [CAS No. 93267-04-0] (800 mg, 2.43 mmol) were cross-coupled through Pd(0)-catalyzed Negishi-coupling using tris(dibenzylideneacetone)dipalladium (Pd$_2$(dba)$_3$) [CAS No. 51364-51-3](52 mg, 0.06 mol) and tri(o-tolyl)phosphine (P(o-tol)$_3$) [CAS No. 6163-58-2](70 mg, 0.23 mmol) in the presence of an excess of zinc dust [CAS No. 7440-66-6](948 mg, 14.6 mmol), pre-activated with elemental iodine (I$_2$) [CAS No. 7553-56-2](93 mg, 0.36 mmol) and trimethylchlorosilane (TMSCl) [CAS No. 75-77-4](46 μL, 39 mg, 0.36 mmol) in anhydrous DMF (5 mL) at 60° C. for overnight under a nitrogen atmosphere. Filtration over Celite®, extractive aqueous work-up, and chromatographic purification over silica gel (hexane/ethyl acetate=1:1, (v/v)) yielded methyl (S)-3-(4-aminophenyl)-2-((tert-butoxycarbonyl)amino)propanoate (480 mg, 72% yield) as an oil. TLC: Rf: 0.45 (hexane/ethyl acetate=1:1, (v/v)).

Commercial methanesulfonyl chloride (MsCl) [CAS No. 124-63-0](152 μL, 225 mg, 2.0 mmol) in THF (5 mL) was reacted with synthetic methyl (S)-3-(4-aminophenyl)-2-((tert-butoxycarbonyl)amino)propanoate (480 mg, 1.6 mmol) in THF (5 mL) with triethylamine (Et$_3$N, TEA) [CAS No. 121-44-8](445 μL, 323 mg, 3.2 mmol) at room temperature for 2 h under a nitrogen atmosphere. Extractive aqueous work-up and evaporation of volatiles yielded crude methyl (S)-2-((tert-butoxycarbonyl)amino)-3-(4-(methylsulfonamido)phenyl)propanoate together with the bis-sulfonamide product methyl (S)-2-((tert-butoxycarbonyl)amino)-3-(4-(N-(methylsulfonyl)methylsulfonamido)phenyl)propanoate (270 mg) as an oil which was used directly in the next step. TLC: Rf: 0.65 (hexane/ethyl acetate=1:1, (v/v)).

The protecting groups of the sulfonamides were removed in two steps (Scheme 9).

Chemoselective removal of the N-Boc-protection group of the methyl (S)-2-((tert-butoxycarbonyl)amino)-3-(4-(methylsulfonamido)phenyl)propanoate and methyl (S)-2-((tert-butoxycarbonyl)amino)-3-(4-(N-(methylsulfonyl)methylsulfonamido)phenyl)propanoate mixture was conducted with 20 vol-% TFA in DCM (5 mL) at room temperature for 1 h. Evaporation of the volatiles and hydrolysis of the methyl ester groups with lithium hydroxide monohydrate (LiOH·H$_2$O) [CAS No. 1310-66-3](126 mg, 3.0 mmol) in THF/water (1:1, (v/v)) (5 mL) at room temperature for 2 h afforded the crude compound (70). One of the methylsulfonamide groups of methyl (S)-2-amino-3-(4-(N-(methylsulfonyl)methylsulfonamido)phenyl)propanoate also hydrolyzed off during the 2$^{nd}$ deprotection step to yield mostly (S)-2-amino-3-(4-(methylsulfonamido)phenyl)propanoic acid. Evaporation of volatiles, purification by prep. HPLC, and removal of the solvents by lyophilization yielded compound (70) (80 mg) as a colorless solid. LC/MS/UV: Rt: 0.326 min, calculated for $C_{10}H_{14}N_2O_4S$ 258.07, ESI (pos.) m/z=259.05 [M+H$^+$]$^+$, 516.85 [2M+H$^+$]$^+$, ESI (neg.) m/z=256.85 [M-H$^+$]$^-$, 514.70 [2M-H$^+$]$^-$; HPLC/UV: Rt: 4.849 min (99.1% AUC at 220 nm, 98.0% AUC at 254 nm); $^1$H NMR (300 MHz, DMSO-d$_6$): δ 7.19 (d, J=8.4 Hz, 1H), 7.09 (d, J=8.1 Hz, 1H), 3.32 (dd, J=8.1, 4.2 Hz, 1H), 3.07 (dd, J=14.1, 4.2 Hz, 1H), 2.93 (s, 3H), 2.77 (dd, J=14.1, 8.1 Hz, 1H). The $^1$H NMR signals of the amino-group, the N—H acidic group, and the carboxylic acid group were not observed because of H-D exchange with the moisture in the NMR solvent.

Example 71

(S)-2-Amino-3-(3-sulfamoylphenyl)propanoic Acid (71)

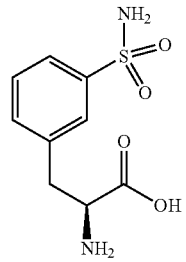

Compound (71) was synthesized by adapting methods described in Scheme 2, Scheme 3, and Scheme 9 using well-known literature procedures.

3-Bromobenzenesulfonamide [CAS No. 89599-01-9] is also commercially available. 3-bromobenzenesulfonamide [CAS No. 89599-01-9] was also prepared from commercial 3-bromobenzenesulfonyl chloride [CAS No. 2905-24-0] (500 mg, 1.96 mmol) and a 28-30 wt-% aqueous ammonia solution (ammonium hydroxide, NH$_4$OH) [CAS No. 1336-21-6](5 mL) in water (5 mL) at room temperature in 2 h. Extractive work-up yielded and evaporation of volatiles yielded 3-bromobenzenesulfonamide (470 mg, crude) as a colorless (white) solid that was of sufficient purity to be used directly in the next step. TLC: Rf: 0.50 (hexane/ethyl acetate=1:1, (v/v)).

Synthetic 3-bromobenzenesulfonamide [CAS No. 89599-01-9](420 mg, 2.0 mmol) and starting material 1 (SM-1), methyl (R)-2-((tert-butoxycarbonyl)amino)-3-iodopropanoate [CAS No. 93267-04-0](987 mg, 3.0 mmol) were cross-coupled through Pd(0)-catalyzed Negishi-coupling using tris(dibenzylideneacetone)dipalladium (Pd$_2$(dba)$_3$) [CAS No. 51364-51-3](46 mg, 0.05 mol) and tri(o-tolyl)phosphine (P(o-toly)$_3$) [CAS No. 6163-58-2](61 mg, 0.2 mmol) in the presence of an excess of zinc dust [CAS No. 7440-66-6] (1.17 g, 18.0 mmol), pre-activated with elemental iodine (I$_2$) [CAS No. 7553-56-2](114 mg, 0.45 mmol) and trimethylchlorosilane (TMSCl) [CAS No. 75-77-4](57 µL, 49 mg, 0.45 mmol) in anhydrous DMF (5 mL+5 mL) at 60° C. for overnight under a nitrogen atmosphere. Filtration over Celite®, extractive aqueous work-up, and chromatographic purification over silica gel (hexane/ethyl acetate=1:1, (v/v)) yielded methyl (S)-2-((tert-butoxycarbonyl)amino)-3-(3-sulfamoylphenyl)propanoate (300 mg, 42% yield) as an oil that solidified to a solid. TLC: Rf: 0.15 (hexane/ethyl acetate=1:1, (v/v)).

The protecting groups of the sulfonamide were removed in two steps (Scheme 9). Chemoselective removal of the N-Boc-protection group of methyl (S)-2-((tert-butoxycarbonyl)amino)-3-(3-sulfamoylphenyl)propanoate (300 mg, 0.84 mmol) was conducted with 20 vol-% TFA in DCM (5 mL) at room temperature for 1 h. Evaporation of volatiles and hydrolysis of the methyl ester group with lithium hydroxide monohydrate (LiOH·H$_2$O) [CAS No. 1310-66-3](176 mg, 4.2 mmol) in THF/water (1:1, (v/v)) (5 mL) at room temperature for 2 h afforded crude compound (71). Evaporation of volatiles, purification by prep. HPLC, and removal of the solvents by lyophilization yielded compound (71) (57 mg, 28% yield) as a colorless (white) solid. LC/MS/UV: Rt: 0.481 min, calculated for C$_9$H$_{12}$N$_2$O$_4$S 244.05, ESI (pos.) m/z=245.10 [M+H$^+$]$^+$, 488.85 [2M+H$^+$]$^+$, ESI (neg.) m/z=242.90 [M−H$^+$]$^−$, 486.70 [2M−H$^+$]$^−$; HPLC/UV: Rt: 3.895 min (98.9% AUC at 220 nm, 97.8% AUC at 254 nm); $^1$H NMR (300 MHz, DMSO-d$_6$): δ 7.72 (br s, 1H), 7.68-7.63 (m, 1H), 7.50-7.44 (m, 1H), 7.29 (br s, 1H), 3.47 (dd, J=7.8, 4.8 Hz, 1H), 3.19 (dd, J=14.1, 4.5 Hz, 1H), 2.91 (dd, J=14.7, 8.4 Hz, 1H). The $^1$H NMR signals of the amino-group, the N—H-acidic group, and the carboxylic acid group were not observed because of H-D exchange with the moisture in the NMR solvent.

Example 72

(S)-2-Amino-3-(3-(N-methylsulfamoyl)phenyl)propanoic Acid (72)

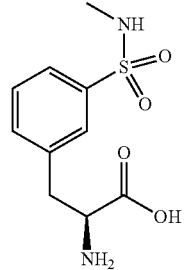

Compound (72) was synthesized by adapting methods described in Scheme 2, Scheme 3, and Scheme 9 using well-known literature procedures.

3-Bromo-N-methylbenzenesulfonamide [CAS No. 153435-79-1] is commercially available. 3-Bromo-N-methylbenzenesulfonamide [CAS No. 153435-79-1] was also prepared from commercial 3-bromobenzenesulfonyl chloride [CAS No. 2905-24-0](500 mg, 1.96 mmol) and methylamine (MeNH$_2$) [CAS No. 74-89-5](2 M in THF, 1.96 mL, 3.92 mmol) in THF (5 mL) at 0° C. to room temperature in 2 h. Extractive work-up yielded 3-bromo-N-methylbenzenesulfonamide (580 mg, crude) as a colorless (white) solid that was of sufficient purity to be used directly in the next step. TLC: Rf: 0.70 (hexane/ethyl acetate=1:1, (v/v)).

Synthetic 3-bromo-N-methylbenzenesulfonamide [CAS No. 153435-79-1](580 mg, 2.3 mmol) and starting material 1 (SM-1), methyl (R)-2-((tert-butoxycarbonyl)amino)-3-iodopropanoate [CAS No. 93267-04-0](987 mg, 3.0 mmol) were cross-coupled through Pd(0)-catalyzed Negishi-coupling using tris(dibenzylideneacetone)dipalladium (Pd$_2$(dba)$_3$) [CAS No. 51364-51-3](53 mg, 0.06 mol) and tri(o-tolyl)phosphine (P(o-Tol)$_3$) [CAS No. 6163-58-2](70 mg, 0.23 mmol) in the presence of an excess of zinc dust [CAS No. 7440-66-6](1.17 g, 18.0 mmol), pre-activated with elemental iodine (I$_2$) [CAS No. 7553-56-2](114 mg, 0.45 mmol) and trimethylchlorosilane (TMSCl) [CAS No. 75-77-4](57 µL, 49 mg, 0.45 mmol) in anhydrous DMF (5 mL+5 mL) at 60° C. for overnight under a nitrogen atmosphere. Filtration over Celite®, extractive aqueous work-up, and chromatographic purification over silica gel (hexane/ethyl acetate=1:1, (v/v)) yielded methyl (S)-2-((tert-butoxycarbonyl)amino)-3-(3-(N-methylsulfamoyl)phenyl)propanoate (350 mg, 41% yield) as an oil. TLC: Rf: 0.20 (hexane/ethyl acetate=1:1, (v/v)).

The protecting groups of the sulfonamide were removed in two steps (Scheme 9). Chemoselective removal of the N-Boc-protection group of methyl (S)-2-((tert-butoxycarbonyl)amino)-3-(3-(N-methylsulfamoyl)phenyl)propanoate (350 mg, 0.94 mmol) was conducted with 20 vol-% TFA in DCM (5 mL) at room temperature for 2 h. Evaporation of volatiles and hydrolysis of the methyl ester group with lithium hydroxide monohydrate (LiOH·H$_2$O) [CAS No. 1310-66-3](198 mg, 4.7 mmol, 5 eq.) in THF/water (1:1, (v/v)) (5 mL) at room temperature for 2 h yielded crude compound (72). Evaporation of volatiles, purification by prep. HPLC, and removal of the solvents by lyophilization yielded compound (72) (110 mg, 45% yield) as a colorless (white) solid. LC/MS/UV: Rt: 0.522 min, calculated for C$_{10}$H$_{14}$N$_2$O$_4$S 258.07, found ESI (pos.) m/z=259.05

[M+H⁺]⁺, 516.90 [2M+H⁺]⁺, ESI (neg.) m/z=256.90 [M−H⁺]⁻, 514.75 [2M−H⁺]⁻; HPLC/UV: Rt: 5.068 min (98.0% AUC at 220 nm, 100% AUC at 254 nm); H NMR (300 MHz, CD$_3$OD): δ 7.83-7.72 (m, 2H), 7.61-7.53 (m, 2H), 4.06 (brt, J=6.9 Hz, 1H), 3.37 (dd, J=14.7, 5.4 Hz, 1H), 3.22 (dd, J=14.1, 6.9 Hz, 1H), 2.53 (s, 3H). The $^1$H NMR signals of the N—H-acidic group, the amino-group, and the carboxylic acid group were not observed because of H-D exchange with the NMR solvent.

Example 73

(S)-2-Amino-3-(3-(N,N-dimethylsulfamoyl)phenyl)propanoic Acid (73)

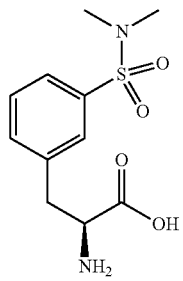

Compound (73) was synthesized by adapting methods described in Scheme 2, Scheme 3, and Scheme 9 using well-known literature procedures.

3-Bromo-N,N-dimethylbenzenesulfonamide [CAS No. 153435-80-4] is commercially available. 3-Bromo-N,N-dimethylbenzenesulfonamide [CAS No. 153435-80-4] was also prepared from commercial 3-bromobenzenesulfonyl chloride [CAS No. 2905-24-0](500 mg, 1.96 mmol) and dimethylamine (Me$_2$NH) [CAS No. 124-40-3](2 M in THF, 1.96 mL, 3.92 mmol) in THF (5 mL) at room temperature in 2 h. Extractive work-up yielded 3-bromo-N,N-dimethylbenzenesulfonamide (510 mg, crude) as a colorless (white) solid that was of sufficient purity to be used directly in the next step. TLC: Rf: 0.65 (hexane/ethyl acetate=1:1, (v/v)).

3-Bromo-N,N-dimethylbenzenesulfonamide [CAS No. 153435-80-4](510 mg, 1.93 mmol, 1.0 eq.) and starting material 1 (SM-1), methyl (R)-2-((tert-butoxycarbonyl)amino)-3-iodopropanoate [CAS No. 93267-04-0](921 mg, 2.8 mmol, 1.0 eq.) were cross-coupled through Pd(0)-catalyzed Negishi-coupling using tris(dibenzylideneacetone)dipalladium (Pd$_2$(dba)$_3$) [CAS No. 51364-51-3](44 mg, 0.05 mol, 0.025 eq.) and tri(o-tolyl)phosphine [CAS No. 6163-58-2](59 mg, 0.19 mmol, 0.1 eq.) in the presence of an excess of zinc dust [CAS No. 7440-66-6](1.1 g, 16.8 mmol, 6.0 eq.), pre-activated with elemental iodine (I$_2$) [CAS No. 7553-56-2](107 mg, 0.42 mmol, 0.15 eq.) and trimethylchlorosilane (TMSCl) [CAS No. 75-77-4](53 μL, 45 mg, 0.42 mmol, 0.15 eq.), in DMF (5 mL+5 mL) at 60° C. for overnight. Filtration over Celite®, extractive aqueous work-up, and chromatographic purification over silica gel (hexane/ethyl acetate=1:1, (v/v)) yielded methyl (S)-2-((tert-butoxycarbonyl)amino)-3-(3—(N,N-dimethylsulfamoyl)phenyl)propanoate (250 mg, 33% yield) as an oil. TLC: Rf: 0.45 (hexane/ethyl acetate=1:1, (v/v)).

The protecting groups of the sulfonamide were removed in two steps (Scheme 9). Chemoselective removal of the N-Boc-protection group of methyl (S)-2-((tert-butoxycarbonyl)amino)-3-(3-(N,N-dimethylsulfamoyl)phenyl)propanoate (250 mg, 0.65 mmol) was conducted with 20 vol % TFA in DCM (5 mL) at room temperature for 2 h. Hydrolysis of the methyl ester group with LiOH·H$_2$O [CAS No. 1310-66-3](136 mg, 3.2 mmol, 5 eq.) in THF/water (1:1, (v/v)) (5 mL) at room temperature for 2 h afforded crude compound (73). Evaporation of volatiles, purification by prep. HPLC, and removal of the solvents by lyophilization yielded compound (73) (105 mg, 59% yield) as a colorless (white) solid. LC/MS/UV: Rt: 0.569 min, calculated for C$_{11}$H$_{16}$N$_2$O$_4$S 272.08, found ESI (pos.) m/z=273.05 [M+H⁺]⁺, 544.85 [2M+H⁺]⁺, ESI (neg.) m/z=270.90 [M−H⁺]⁻, 542.70 [2M−H⁺]⁻; HPLC/UV: Rt: 5.923 min (97.0% AUC at 220 nm, 98.5% AUC at 254 nm); $^1$H NMR (300 MHz, CD$_3$OD): δ 7.75 (br s, 1H), 7.73-7.68 (m, 1H), 7.65-7.56 (m, 2H), 3.84 (dd, J=7.5, 4.5 Hz, 1H), 3.37 (dd, J=14.7, 5.4 Hz, 1H), 3.16 (dd, J=14.4, 8.4 Hz, 1H), 2.70 (s, 6H). The $^1$H NMR signals of the N—H-acidic group, the amino-group, and the carboxylic acid group were not observed because of H-D exchange with the NMR solvent.

Example 74

(S)-2-Amino-3-(4-sulfamoylphenyl)propanoic acid (74)

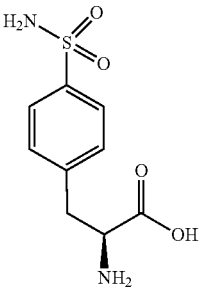

Compound (74) was synthesized by adapting methods described in Scheme 2, Scheme 3, and Scheme 9 using well-known literature procedures.

4-Iodobenzenesulfonamide [CAS No. 825-86-5] is commercially available. 4-Iodobenzenesulfonamide [CAS No. 825-86-5] was also prepared from commercial 4-iodobenzenesulfonyl chloride [CAS No. 98-61-3](500 mg, 1.65 mmol) and a 28-30 wt-% aqueous ammonia solution (ammonium hydroxide, NH$_4$OH) [CAS No. 1336-21-6](5 mL) in water/acetonitrile (5 mL, 6:4, (v/v)) at room temperature in 2 h. Extractive work-up yielded 4-iodobenzenesulfonamide (460 mg, crude) as a colorless (white) solid that was of sufficient purity to be used directly in the next step. TLC: Rf: 0.50 (hexane/ethyl acetate=1:1, (v/v)).

4-Iodobenzenesulfonamide [CAS No. 825-86-5](460 mg, 1.6 mmol) and starting material 1 (SM-1), methyl (R)-2-((tert-butoxycarbonyl)amino)-3-iodopropanoate [CAS No. 93267-04-0](658 mg, 2.0 mmol) were cross-coupled through Pd(0)-catalyzed Negishi-coupling using tris(dibenzylideneacetone)dipalladium (Pd$_2$(dba)$_3$) [CAS No. 51364-51-3](37 mg, 0.04 mol) and tri(o-tolyl)phosphine (P(o-Tol)$_3$) [CAS No. 6163-58-2](49 mg, 0.16 mmol) in the presence of an excess of zinc dust [CAS No. 7440-66-6](740 mg, 12.0 mmol), pre-activated with elemental iodine (I$_2$) [CAS No. 7553-56-2](76 mg, 0.3 mmol) and trimethylchlorosilane (TMSCl) [CAS No. 75-77-4](38 μL, 33 mg, 0.3 mmol) in anhydrous DMF (5 mL+5 mL) at 60° C. for overnight. Filtration over Celite®, extractive aqueous work-up, and chromatographic purification over silica gel (hexane/ethyl acetate=1:1, (v/v)) yielded methyl (S)-2-

((tert-butoxycarbonyl)amino)-3-(4-sulfamoylphenyl)propanoate (290 mg, 51% yield) as an oil that solidified to a solid. TLC: Rf: 0.30 (hexane/ethyl acetate=1:1, (v/v)).

The protecting groups of the sulfonamide were removed in two steps (Scheme 9). Chemoselective removal of the N-Boc-protection group of methyl (S)-2-((tert-butoxycarbonyl)amino)-3-(4-sulfamoylphenyl)propanoate (290 mg, 0.81 mmol) was conducted with 20 vol-% TFA in DCM (5 mL) at room temperature for 2 h. Evaporation of volatiles and hydrolysis of the methyl ester group with lithium hydroxide monohydrate (LiOH·H$_2$O) [CAS No. 1310-66-3](120 mg, 4.0 mmol) in THF/water (1:1, (v/v)) (5 mL) at room temperature for 2 h afforded crude compound (74). Evaporation of volatiles, purification by prep. HPLC, and removal of the solvents by lyophilization yielded compound (74) (95 mg, 48% yield) as a colorless (white) solid. LC/MS/UV: Rt: 0.363 min, calculated for C$_9$H$_{12}$N$_2$O$_4$S 244.05, ESI (pos.) m/z=245.10 [M+H$^+$]$^+$, 488.85 [2M+H$^+$]$^+$, ESI (neg.) m/z=242.90 [M−H$^+$]$^−$, 486.70 [2M−H$^+$]$^−$; HPLC/UV: Rt: 4.857 min (99.1% AUC at 220 nm, 99.4% AUC at 254 nm); $^1$H NMR (300 MHz, CD$_3$OD): δ 7.89 (d, J=8.7 Hz, 2H), 7.48 (d, J=8.7 Hz, 2H), 4.29 (dd, J=7.8, 6.6 Hz, 1H), 3.38 (dd, J=14.4, 5.7 Hz, 1H), 3.24 (dd, J=14.7, 7.8 Hz, 1H). The $^1$H NMR signals of the amino-group, the N—H-acidic group, and the carboxylic acid group were not observed because of H-D exchange with the NMR solvent.

Example 75

(S)-2-Amino-3-(5-(N-(2-bromophenyl)sulfamoyl)-2-methylphenyl)propanoic Acid (75)

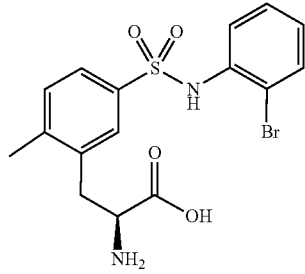

Compound (75) was synthesized by adapting methods described in Scheme 8 and Scheme 9. Sulfonyl chloride starting material tert-butyl (S)-2-((tert-butoxycarbonyl)amino)-3-(5-(chlorosulfonyl)-2-methylphenyl)propanoate 9 (SM-9) (217 mg, 0.5 mmol) was reacted with commercial 2-bromoaniline [CAS No. 615-26-1](172 mg, 1.0 mmol) in neat pyridine [CAS No. 110-86-1](2 mL) in the presence of 4-N,N-dimethylaminopyridine (DMAP) [CAS No. 1122-58-3](6 mg, 0.05 mmol) at room temperature for overnight. Evaporation of volatiles, extractive aqueous work-up, and chromatographic purification on silica gel (hexane/ethyl acetate=4:1, (v/v)) yielded tert-butyl (S)-3-(5-(N-(2-bromophenyl)sulfamoyl)-2-methylphenyl)-2-((tert-butoxycarbonyl)amino)propanoate (222 mg, 78% yield) as a pale yellow foam. TLC: Rf: 0.50 (hexane/ethyl acetate=3:1, (v/v)).

The protecting groups of the sulfonamide were removed in one step (Scheme 9). Global removal of the N-Boc-protection group and the tert-butyl ester group of tert-butyl (S)-3-(5-(N-(2-bromophenyl)sulfamoyl)-2-methylphenyl)-2-((tert-butoxycarbonyl)amino)propanoate (222 mg, 0.39 mmol) in 1,4-dioxane (0.5 mL) was conducted through reaction with commercial HCl in 1,4-dioxane [CAS No. 7647-01-0](4 M in 1,4-dioxane, 3 mL, 12 mmol) at 40° C. for overnight. Evaporation of volatiles afforded the crude compound (75). Purification by prep. HPLC and removal of the solvents by lyophilization yielded compound (75) (103 mg, 64% yield) as a colorless (white) solid. LC/MS/UV: Rt: 0.882 min, calculated for C$_{16}$H$_{17}$BrN$_2$O$_4$S. 412.01 g/mol, found ESI (pos.): m/z=414.70 [M+H$^+$]$^+$, 826.25 [2M+H$^+$]$^+$; ESI (neg.) m/z=412.60 [M−H$^+$]$^−$, 824.20 [2M−H$^+$]$^−$. HPLC/UV: Rt: 8.488 min (94.5% AUC at 220 nm, 96.4% AUC at 254 nm); $^1$H NMR (300 MHz, CD$_3$OD): δ 7.69 (d, J=1.8 Hz, 1H), 7.53-7.44 (m, 3H), 7.34-7.26 (m, 2H), 7.10-7.03 (m 1H), 3.72 (dd, J=9.9, 5.1 Hz, 1H), 3.42 (dd, J=14.7, 5.4 Hz, 1H), 2.94 (dd, J=14.7, 9.3 Hz, 1H), 2.44 (s, 3H). The $^1$H NMR signals of the amino-group, the N—H-acidic group, and the carboxylic acid group were not observed because of H-D exchange with the NMR solvent.

Example 76

(S)-2-Amino-3-(5-(N-(3-bromophenyl)sulfamoyl)-2-methylphenyl)propanoic Acid (76)

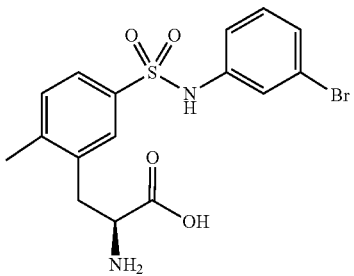

Compound (76) was synthesized by adapting methods described in Scheme 8 and Scheme 9. Sulfonyl chloride starting material tert-butyl (S)-2-((tert-butoxycarbonyl)amino)-3-(5-(chlorosulfonyl)-2-methylphenyl)propanoate 9 (SM-9) (217 mg, 0.5 mmol) was reacted with commercial 3-bromoaniline [CAS No. 591-19-5](172 mg, 1.0 mmol) in neat pyridine [CAS No. 110-86-1](2 mL) in the presence of 4-N,N-dimethylaminopyridine (DMAP) [CAS No. 1122-58-3](6 mg, 0.05 mmol) at room temperature for overnight. Evaporation of volatiles, extractive aqueous work-up, and chromatographic purification on silica gel (hexane/ethyl acetate=3:1, (v/v)) yielded tert-butyl (S)-3-(5-(N-(3-bromophenyl)sulfamoyl)-2-methylphenyl)-2-((tert-butoxycarbonyl)amino)propanoate (243 mg, 85% yield) as an almost colorless foam. TLC: Rf: 0.40 (hexane/ethyl acetate=3:1, (v/v)).

The protecting groups of the sulfonamide were removed in one step (Scheme 9). Global removal of the N-Boc-protection group and the tert-butyl ester group of tert-butyl (S)-3-(5-(N-(3-bromophenyl)sulfamoyl)-2-methylphenyl)-2-((tert-butoxycarbonyl)amino)propanoate (243 mg, 0.43 mmol) in 1,4-dioxane (0.5 mL) was conducted through reaction with commercial HCl in 1,4-dioxane [CAS No. 7647-01-0](4 M in 1,4-dioxane, 3 mL, 12 mmol) at 40° C. for overnight. Evaporation of volatiles afforded the crude compound (76). Purification by prep. HPLC and removal of the solvents by lyophilization yielded compound (76) (110 mg, 62% yield) as a colorless (white) solid. LC/MS/UV: Rt: 0.983 min, calculated for C$_{16}$H$_{17}$BrN$_2$O$_4$S 412.01, found ESI (pos.) m/z=414.75 [M+H$^+$]$^+$, 826.25 [2M+H$^+$]$^+$; ESI (neg.) m/z=412.60 [M–H+]−, 824.15 [2M–H+]−. HPLC/UV: Rt: 9.057 min (96.9% AUC at 220 nm, 97.9% AUC at 254 nm); ¹H NMR (300 MHz, CD₃OD): δ 7.73 (d, J=1.8 Hz, 1H), 7.51 (dd, J=8.1, 2.4 Hz, 1H), 7.35-7.28 (m, 2H), 7.21-7.05 (m, 3H), 3.72 (dd, J=9.3, 5.7 Hz, 1H), 3.39 (dd, J=14.7, 5.7 Hz, 1H), 2.99 (dd, J=14.7, 9.0 Hz, 1H), 2.42 (s, 3H). The ¹H NMR signals of the amino-group, the N—H-acidic group, and the carboxylic acid group were not observed because of H-D exchange with the NMR solvent.

Example 77

(S)-2-Amino-3-(5-(N-(4-bromophenyl)sulfamoyl)-2-methylphenyl) propanoic Acid (77)

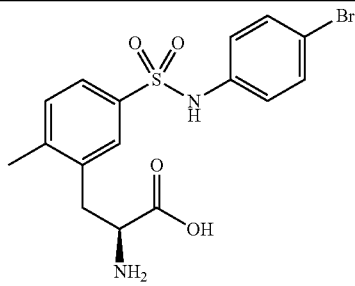

Compound (77) was synthesized by adapting methods described in Scheme 8 and Scheme 9. Sulfonyl chloride starting material tert-butyl (S)-2-((tert-butoxycarbonyl)amino)-3-(5-(chlorosulfonyl)-2-methylphenyl)propanoate 9 (SM-9) (217 mg, 0.5 mmol) was reacted with commercial 4-bromoaniline [CAS No. 106-40-1](172 mg, 1.0 mmol) in neat pyridine [CAS No. 110-86-1](2 mL) in the presence of 4-N,N-dimethylaminopyridine (DMAP) [CAS No. 1122-58-3](6 mg, 0.05 mmol) at room temperature for overnight. Evaporation of volatiles, extractive aqueous work-up, and chromatographic purification on silica gel (hexane/ethyl acetate=3:1, (v/v)) yielded tert-butyl (S)-3-(5-(N-(4-bromophenyl)sulfamoyl)-2-methylphenyl)-2-((tert-butoxycarbonyl)amino)propanoate (242 mg, 85% yield) as a colorless foam. TLC: Rf: 0.35 (hexane/ethyl acetate=3:1, (v/v)).

The protecting groups of the sulfonamide were removed in one step (Scheme 9). Global removal of the N-Boc-protection group and the tert-butyl ester group of tert-butyl (S)-3-(5-(N-(4-bromophenyl)sulfamoyl)-2-methylphenyl)-2-((tert-butoxycarbonyl)amino)propanoate (222 mg, 0.39 mmol) in 1,4-dioxane (0.5 mL) was conducted through reaction with commercial HCl in 1,4-dioxane [CAS No. 7647-01-0](4 M in 1,4-dioxane, 3 mL, 12 mmol) at 40° C. for overnight. Evaporation of volatiles afforded the crude compound (77). Purification by prep. HPLC and removal of the solvents by lyophilization yielded compound (77) as a colorless (white) solid (87 mg, 50% yield). LC/MS/UV: Rt: 0.957 min, calculated for C₁₆H₁₇BrN₂O₄S 412.01, found ESI (pos.) m/z=414.75 [M+H+]+, ESI (neg.) m/z=412.65 [M–H+]−, 824.15 [2M–H+]−. HPLC/UV: Rt: 9.137 min (98.6% AUC at 220 nm, 99.0% AUC at 254 nm); ¹H NMR (300 MHz, CD₃OD): δ 7.71 (d, J=1.8 Hz, 1H), 7.47 (dd, J=4.5, 1.8 Hz, 1H), 7.34 (d, J=8.7 Hz, 2H), 7.29 (d, J=8.4 Hz, 1H), 7.03 (d, J=9.0 Hz, 1H), 3.71 (dd, J=8.4, 6.0 Hz, 1H), 3.40-3.30 (m, 1H, superimposed with the ¹H NMR signal of the NMR solvent), 3.00 (dd, J=14.4, 8.1 Hz, 1H), 2.41 (s, 3H). The ¹H NMR signals of the amino-group, the N—H-acidic group, and the carboxylic acid group were not observed because of H-D exchange with the NMR solvent.

Example 78

(S)-2-Amino-3-(3-(piperidin-1-ylsulfonyl)phenyl)propanoic Acid (78)

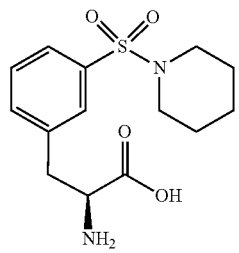

Compound (78) was synthesized by adapting methods described in Scheme 2, Scheme 3, and Scheme 9 using well-known literature procedures.

1-((3-Bromophenyl)sulfonyl)piperidine [CAS No. 871269-12-4] is commercially available. 1-((3-Bromophenyl)sulfonyl)piperidine [CAS No. 871269-12-4] was also prepared from commercial 3-bromobenzenesulfonyl chloride [CAS No. 2905-24-0](500 mg, 1.96 mmol) and commercial piperidine ((CH₂)₅NH) [CAS No. 110-89-4](333 mg, 3.92 mmol) in THF (10 mL) at room temperature in 2 h. Extractive aqueous work-up yielded 1-((3-bromophenyl)sulfonyl)piperidine (670 mg, crude) as a colorless (white) solid that was of sufficient purity to be used directly in the next step.

Synthetic 1-((3-bromophenyl)sulfonyl)piperidine [CAS No. 871269-12-4](304 mg, 1.0 mmol) and starting material 1 (SM-1), methyl (R)-2-((tert-butoxycarbonyl)amino)-3-iodopropanoate [CAS No. 93267-04-0](395 mg, 1.2 mmol) were cross-coupled through Pd(0)-catalyzed Negishi-coupling using tris(dibenzylideneacetone)dipalladium (Pd₂(dba)₃) [CAS No. 51364-51-3](23 mg, 0.025 mol) and tri(o-tolyl)phosphine (P(o-Tol)₃) [CAS No. 6163-58-2](30 mg, 0.1 mmol) in the presence of an excess of zinc dust [CAS No. 7440-66-6](471 mg, 7.2 mmol), pre-activated with elemental iodine (I₂) [CAS No. 7553-56-2](46 mg, 0.18 mmol) and trimethylchlorosilane (TMSCl) [CAS No. 75-77-4](23 µL, 20 mg, 0.18 mmol) in anhydrous DMF (5 mL+5 mL) at 60° C. for overnight under a nitrogen atmosphere. Filtration over Celite®, extractive aqueous work-up, and chromatographic purification over silica gel (hexane/ethyl acetate=7:3, (v/v)) yielded impure (>85%) methyl (S)-2-((tert-butoxycarbonyl)amino)-3-(3-(piperidin-1-ylsulfonyl)phenyl)propanoate (150 mg, 35% yield) as an oil. TLC: Rf: 0.33 (hexane/ethyl acetate=7:3, (v/v)).

The protecting groups of the sulfonamide were removed in two steps (Scheme 9). Chemoselective removal of the N-Boc-protection group of methyl (S)-2-((tert-butoxycarbonyl)amino)-3-(3-(piperidin-1-ylsulfonyl)phenyl)propanoate (150 mg, impure, max. 0.35 mmol) was conducted with 20 vol-% TFA in DCM (5 mL) at room temperature for 2 h. Evaporation of volatiles and hydrolysis of the methyl ester group with lithium hydroxide monohydrate (LiOH·H₂O) [CAS No. 1310-66-3](74 mg, 1.75 mmol) in THF/water (1:1, (v/v)) (5 mL) at room temperature for 2 h afforded the crude compound (78). Evaporation of volatiles, purification by prep. HPLC, and removal of the solvents by lyophilization yielded compound (78) (45 mg, 41% yield) as a colorless (white) solid. LC/MS/UV: Rt: 0.861 min, calculated for $C_{14}H_{20}N_2O_4S$ 312.11, found ESI (pos.) m/z=313.00 [M+H⁺]⁺, 624.80 [2M+H⁺]⁺, ESI (neg.) m/z=310.90 [M−H⁺]⁻, 622.70 [2M−H⁺]⁻; HPLC/UV: Rt: 7.744 min (95.1% AUC at 220 nm, 99.4% AUC at 254 nm); ¹H NMR (300 MHz, CD₃OD): δ 7.76-7.54 (m, 4H), 3.88-3.78 (m, 1H), 3.38 (dd, J=14.1, 4.8 Hz, 1H) 3.38 (dd, J=14.1, 4.8 Hz, 1H), 3.13 (dd, J=14.1, 6.0 Hz, 1H), 2.99 (t, J=5.1 Hz, 4H), 1.72-1.56 (m, 4H), 1.50-38 (m, 2H). The ¹H NMR signals for the amino-group and the carboxyl group were not observed because of H-D exchange with the NMR solvent.

Example 79

(S)-2-Amino-3-(3-(N-(4-chlorophenyl)sulfamoyl)phenyl)propanoic Acid (79)

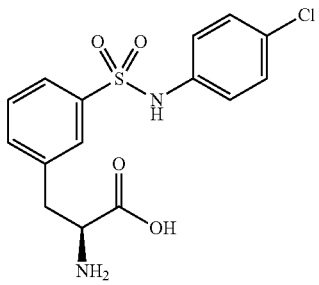

Compound (79) was synthesized by adapting methods described in Scheme 2, Scheme 3, and Scheme 9 using well-known literature procedures.

3-Bromo-N-(4-chlorophenyl)benzenesulfonamide was prepared from commercial 3-bromobenzenesulfonyl chloride [CAS No. 2905-24-0](500 mg, 1.96 mmol) and 4-chloroaniline [CAS No. 106-47-8](500 mg, 3.92 mmol) in THF (5 mL) at room temperature in 2 h. Extractive aqueous work-up yielded 3-bromo-N-(4-chlorophenyl)benzenesulfonamide (510 mg, crude) as a yellowish solid that was of sufficient purity to be used directly in the next step. TLC: Rf: 0.50 (hexane/ethyl acetate=1:1, (v/v). TLC: Rf: 0.58 (DCM).

Synthetic 3-bromo-N-(4-chlorophenyl)benzenesulfonamide (320 mg, 0.92 mmol) and starting material 1 (SM-1), methyl (R)-2-((tert-butoxycarbonyl)amino)-3-iodopropanoate [CAS No. 93267-04-0](395 mg, 1.2 mmol) were cross-coupled through Pd(0)-catalyzed Negishi-coupling using tris(dibenzylideneacetone)dipalladium (Pd₂(dba)₃) [CAS No. 51364-51-3](21 mg, 0.023 mol) and tri(o-tolyl)phosphine (P(o-Tol)₃) [CAS No. 6163-58-2](28 mg, 0.092 mmol) in the presence of an excess of zinc dust [CAS No. 7440-66-6](468 mg, 7.2 mmol), pre-activated with elemental iodine (I₂) [CAS No. 7553-56-2](46 mg, 0.18 mmol) and trimethylchlorosilane (TMSCl) [CAS No. 75-77-4](23 µL, 20 mg, 0.092 mmol) in anhydrous DMF (5 mL+3 mL) at 60° C. for overnight under a nitrogen atmosphere. Filtration over Celite®, extractive aqueous work-up, and chromatographic purification over silica gel (hexane/ethyl acetate=7:3, (v/v)) yielded (impure) methyl (S)-2-((tert-butoxycarbonyl)amino)-3-(3-(N-(4-chlorophenyl)sulfamoyl)phenyl)propanoate (160 mg, impure, 37% yield) as a solid. TLC: Rf: 0.25 (hexane/ethyl acetate=7:3, (v/v)).

The protecting groups of the sulfonamide were removed in two steps (Scheme 9). Chemoselective removal of the N-Boc-protection group of methyl (S)-2-((tert-butoxycarbonyl)amino)-3-(3-(N-(4-chlorophenyl)sulfamoyl)phenyl)propanoate (160 mg, impure, max. 0.34 mmol) was conducted with 20 vol-% TFA in DCM (5 mL) at room temperature for 1 h. Evaporation of volatiles and hydrolysis of the methyl ester group with lithium hydroxide monohydrate (LiOH·H₂O) [CAS No. 1310-66-3](72 mg, 1.7 mmol) in THF/water (1:1, (v/v)) (5 mL) at room temperature for 2 h yielded the crude compound (79). Evaporation of volatiles, purification by prep. HPLC, and removal of the solvents by lyophilization yielded compound (79) (74 mg, 61% yield) as a colorless (white) solid. LC/MS/UV: Rt: 0.969 min, calculated for $C_{15}H_{15}ClN_2O_4S$ 354.04, ESI (pos.) m/z=354.85 [M+H⁺]⁺, 708.55 [2M+H⁺]⁺, ESI (neg.) m/z=352.75 [M−H⁺]⁻, 708.20 [2M−H⁺]⁻; HPLC/UV: Rt: 8.741 min (99.3% AUC at 220 nm, 99.4% AUC at 254 nm); ¹H NMR (300 MHz, CD₃OD): δ 7.81-7.77 (m, 1H), 7.63-7.58 (m, 2H), 7.45 (br d, J=7.8 Hz, 1H), 7.24-7.17 (m, 2H), 7.12-7.06 (m, 2H), 3.79 (dd, J=8.1, 5.4 Hz, 1H), 3.28 (dd, J=14.7, 5.4 Hz, 1H), 3.10 (dd, J=14.7, 8.1 Hz, 1H). The ¹H NMR signals for the amino-group, the N—H acidic group, and the carboxyl group were not observed because of H-D exchange with the NMR solvent.

Example 80

(S)-2-Amino-3-(4-(N-(4-chlorophenyl)sulfamoyl)phenyl)propanoic Acid (80)

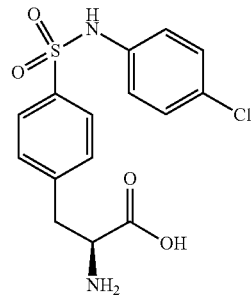

Compound (80) was synthesized by adapting methods described in Scheme 2, Scheme 3, and Scheme 9 using well-known literature procedures.

N-(4-Chlorophenyl)-4-iodobenzenesulfonamide was prepared from commercial 4-iodobenzenesulfonyl chloride [CAS No. 98-61-3](500 mg, 1.65 mmol) and 4-chloroaniline [CAS No. 106-47-8](317 mg, 2.48 mmol) in neat pyridine [CAS No. 110-86-1](5-10 mL) at 40° C. for overnight. Evaporation of volatiles, extractive aqueous workup, and chromatographic purification on silica gel (100% DCM) yielded N-(4-chlorophenyl)-4-iodobenzenesulfonamide (490 mg, 76% yield) as a colorless (white) solid. TLC: Rf: 0.43 (DCM).

N-(4-Chlorophenyl)-4-iodobenzenesulfonamide (490 mg, 1.24 mmol) and starting material 1 (SM-1), methyl (R)-2-((tert-butoxycarbonyl)amino)-3-iodopropanoate [CAS No. 93267-04-0](494 mg, 1.5 mmol) were cross-coupled through Pd(0)-catalyzed Negishi-coupling using tris(dibenzylideneacetone)dipalladium (Pd₂(dba)₃) [CAS No. 51364-51-3](28 mg, 0.03 mol) and tri(o-tolyl)phosphine (P(o-Tol)₃) [CAS No. 6163-58-2](36 mg, 0.12 mmol) in the presence of an excess of zinc dust [CAS No. 7440-66-6](585 mg, 9.0 mmol), pre-activated with elemental iodine (I₂) [CAS No. 7553-56-2](57 mg, 0.23 mmol) and trimethylchlorosilane (TMSCl) [CAS No. 75-77-4](29 µL, 25 mg, 0.23 mmol) in anhydrous DMF (5 mL+5 mL) at 60° C. for overnight under a nitrogen atmosphere. Filtration over Celite®, extractive aqueous work-up, and chromatographic purification over silica gel (hexane/ethyl acetate=7:3, (v/v)) yielded methyl (S)-2-((tert-butoxycarbonyl)amino)-3-(4-(N-(4-chlorophenyl)sulfamoyl)phenyl)propanoate (120 mg, 21% yield) as a yellow solid. TLC: Rf: 0.43 (hexane/ethyl acetate=7:3, (v/v)).

The protecting groups of the sulfonamide were removed in two steps (Scheme 9). Chemoselective removal of the N-Boc-protection group of methyl (S)-2-((tert-butoxycarbonyl)amino)-3-(4-(N-(4-chlorophenyl)sulfamoyl)phenyl)propanoate (120 mg, 0.26 mmol) was conducted with 20 vol-% TFA in DCM (5 mL) at room temperature for 2 h. Evaporation of volatiles and hydrolysis of the methyl ester group with lithium hydroxide monohydrate (LiOH·H$_2$O) [CAS No. 1310-66-3](57 mg, 1.28 mmol) in THF/water (1:1, (v/v)) (5 mL) at room temperature for 2 h yielded the crude compound (80). Evaporation of volatiles, purification by prep. HPLC, and removal of the solvents by lyophilization yielded compound (80) (60 mg, 65% yield) as a colorless (white) solid. LC/MS/UV: Rt: 1.036 min, calculated for $C_{15}H_{15}ClN_2O_4S$ 354.04, ESI (pos) m/z=354.90 M+H$^+$]$^+$, 708.55 [2M+H$^+$]$^+$, ESI (neg) m/z=352.75 [M–H$^+$]$^-$, 708.15 [2M–H$^+$]$^-$; HPLC/UV: Rt 8.553 min (99.1% AUC at 220 nm, 99.7% AUC at 254 nm); $^1$H NMR (300 MHz, CD$_3$OD): 7.77-7.71 (m, 2H), 7.44 (d, J=8.1 Hz, 2H), 7.23-7.17 (m, 2H), 7.11-7.05 (m, 2H), 3.79 (dd, J=8.1, 4.8 Hz, 1H), 3.28 (dd, J=14.1, 4.8 Hz, 1H), 3.07 (dd, J=14.1, 8.1 Hz, 1H). The $^1$H NMR signals for the amino-group, the N—H acidic group, and the carboxyl group were not observed because of H-D exchange with the NMR solvent.

Example 81

(S)-2-Amino-3-(2-(N-(4-chlorophenyl)sulfamoyl)phenyl)propanoic Acid (81)

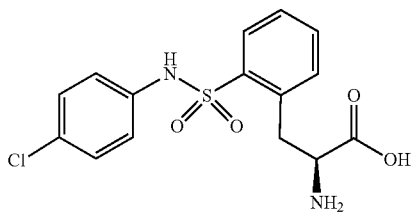

Compound (81) was synthesized by adapting methods described in Scheme 2, Scheme 3, and Scheme 9 using well-known literature procedures.

N-(4-Chlorophenyl)-2-iodobenzenesulfonamide was prepared from commercial 2-iodobenzenesulfonyl chloride [CAS No. 63059-29-0](500 mg, 1.65 mmol) and 4-chloroaniline [CAS No. 106-47-8](317 mg, 2.48 mmol) in neat pyridine [CAS No. 110-86-1](5-10 mL) at 40° C. for overnight. Evaporation of volatiles, extractive aqueous work-up, and chromatographic purification on silica gel (hexane/ethyl acetate=7:3, (v/v)) yielded N-(4-chlorophenyl)-2-iodobenzenesulfonamide (580 mg, 89% yield) as a colorless solid. TLC: Rf: 0.43 (hexane/ethyl acetate=7:3, (v/v)).

N-(4-Chlorophenyl)-2-iodobenzenesulfonamide (580 mg, 1.47 mmol) and starting material 1 (SM-1), methyl (R)-2-((tert-butoxycarbonyl)amino)-3-iodopropanoate [CAS No. 93267-04-0](494 mg, 1.5 mmol) were cross-coupled through Pd(0)-catalyzed Negishi-coupling using tris(dibenzylideneacetone)dipalladium (Pd$_2$(dba)$_3$) [CAS No. 51364-51-3](34 mg, 0.037 mol) and tri(o-tolyl)phosphine (P(o-Tol)$_3$) [CAS No. 6163-58-2](45 mg, 0.15 mmol) in the presence of an excess of zinc dust [CAS No. 7440-66-6](585 mg, 9.0 mmol), pre-activated with elemental iodine (I$_2$) [CAS No. 7553-56-2](57 mg, 0.23 mmol) and trimethylchlorosilane (TMSCl) [CAS No. 75-77-4](29 µL, 25 mg, 0.23 mmol) in anhydrous DMF (5 mL+5 mL) at 60° C. for overnight under a nitrogen atmosphere. Filtration over Celite®, extractive aqueous work-up, and chromatographic purification over silica gel (hexane/ethyl acetate=7:3, (v/v)) yielded (impure) methyl (S)-2-((tert-butoxycarbonyl)amino)-3-(2-(N-(4-chlorophenyl)sulfamoyl)phenyl)propanoate (117 mg, impure). TLC: Rf: 0.24 (hexane/ethyl acetate=7:3, (v/v)).

The protecting groups of the sulfonamide were removed in two steps (Scheme 9). Chemoselective removal of the N-Boc-protection group of methyl (S)-2-((tert-butoxycarbonyl)amino)-3-(2-(N-(4-chlorophenyl)sulfamoyl)phenyl)propanoate (117 mg, impure, max. 0.25 mmol) was conducted with 20 vol-% TFA in DCM (5 mL) at room temperature for 2 h. Evaporation of volatiles and hydrolysis of the methyl ester group with lithium hydroxide monohydrate (LiOH·H$_2$O) [CAS No. 1310-66-3](52 mg, 1.25 mmol) in THF/water (1:1, (v/v)) (5 mL) at room temperature for 2 h yielded the crude compound (81). Evaporation of volatiles, purification by prep. HPLC, and removal of the solvents by lyophilization yielded compound (81) (14 mg, 16% yield) as a colorless (white) solid. LC/MS/UV: Rt: 1.049 min, calculated for $C_{15}H_{15}ClN_2O_4S$ 354.04, ESI (pos.): m/z=354.85 [M+H$^+$]$^+$, 708.55 [2M+H$^+$]$^+$, ESI (neg.) m/z=352.75 [M–H$^+$]$^-$, 708.15 [2M–H$^{+-}$; HPLC/UV: Rt: 8.716 min (99.5% AUC at 220 nm, 98.5% AUC at 254 nm); $^1$H NMR (300 MHz, CD$_3$OD): δ 7.97 (dd, J=7.5, 1.2 Hz, 1H), 7.62-7.39 (m, 3H), 7.22-7.16 (m, 2H), 7.10-7.04 (m, 2H), 3.98 (dd, J=9.9 Hz, 4.5 Hz, 1H), 3.80 (dd, J=14.4, 4.5 Hz, 1H). The $^1$H NMR signal of the CH-group was not observed because of superposition with the $^1$H NMR solvent signal of the NMR solvent. The $^1$H NMR signals for the amino-group, the N—H acidic group, and the carboxyl group were not observed because of H-D exchange with the NMR solvent.

Example 82 tert-Butyl (S)-2-amino-3-(5-(N-(4-chlorophenyl)sulfamoyl)-2-methylphenyl)propanoate (82)

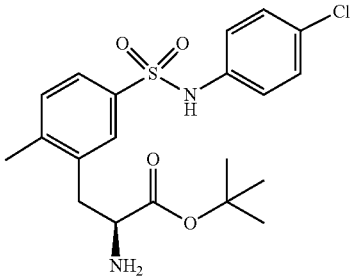

The N-Boc-protecting group of the sulfonamide tert-butyl (S)-2-((tert-butoxycarbonyl)amino)-3-(5-(N-(4-chlorophenyl)sulfamoyl)-2-methylphenyl)propanoate (see intermediate for Example 52 (compound (52)) was chemoselectively removed in one step (Scheme 9). Reaction of sulfonamide tert-butyl (S)-2-((tert-butoxycarbonyl)amino)-3-(5-(N-(4- chlorophenyl)sulfamoyl)-2-methylphenyl)propanoate (247 mg, 0.47 mmol) with 9 vol-% TFA in DCM 4.4 mL) at room temperature for 1 h to afford crude compound (82). Evaporation of volatiles, purification by prep. HPLC, and removal of the solvents by lyophilization yielded compound (82) as a colorless solid (108 mg, 54% yield). LC/MS/UV: Rt: 0.976 min, calculated for $C_{20}H_{25}ClN_2O_4S$ 424.12 g/mol, ESI (pos.) m/z=368.90 [M−$C_4H_8$+H$^+$]$^+$, 424.90 [M+H$^+$]$^+$, ESI (neg.) m/z=422.80 [M−H$^+$]$^-$; HPLC/UV: Rt: 10.714 min; $^1$H NMR (300 MHz, CD$_3$OD): δ 7.58-7.7.53 (m, 2H), 7.32 (br d, J=7.8 Hz, 1H), 7.23-7.17 (m, 2H), 7.10-7.05 (m, 2H), 3.72 (br dd, J=8.1, 6.9 Hz, 1H), 3.06 (dd, J=13.5, 8.1 Hz, 1H), 2.97 (dd, J=13.5, 6.9 Hz, 1H), 2.39 (s, 3H), 1.29 (s, 9H). The $^1$H NMR signals for the amino-group and the N—H acidic group were not observed because of H-D exchange with the NMR solvent.

Example 83

(S)-2-Amino-3-(5-(N-(3,4-dichlorophenyl)sulfamoyl)-2-methylphenyl)propanoic Acid (83)

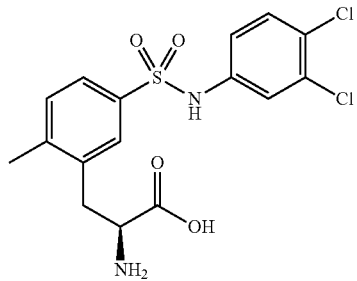

Compound (83) was synthesized by adapting methods described in Scheme 8 and Scheme 9. Sulfonyl chloride stating material 9 (SM-9), tert-butyl (S)-2-((tert-butoxycarbonyl)amino)-3-(5-(chlorosulfonyl)-2-methylphenyl)propanoate, (217 mg, 0.5 mmol) was reacted with commercial 3,4-dichloroaniline [CAS No. 95-76-1](162 mg, 1.0 mmol) in neat pyridine [CAS No. 110-86-1](2 mL) in the presence of 4-N,N-dimethylaminopyridine (DMAP) [CAS No. 1122-58-3](12 mg, 0.1 mmol) at 40° C. for overnight. Evaporation of volatiles, extractive aqueous work-up, and chromatographic purification on silica gel (hexane/ethyl acetate=4:1, (v/v)) yielded tert-butyl (S)-2-((tert-butoxycarbonyl)amino)-3-(5-(N-(3,4-dichlorophenyl)sulfamoyl)-2-methylphenyl)propanoate contaminated with 3,4-dichloroaniline (337 mg, mixture) as a pale yellow oil. TLC: Rf: 0.42 (hexane/ethyl acetate=3:1, (v/v)).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(N-(3,4-dichlorophenyl)sulfamoyl)-2-methylphenyl)propanoate (337 mg, impure, max. 0.5 mmol) in 1,4-dioxane (0.5 mL) was conducted through reaction with commercial HCl in 1,4-dioxane [CAS No. 7647-01-0](4 M in 1,4-dioxane, 3 mL, 12 mmol) at 40° C. for overnight. Evaporation of volatiles afforded the crude compound (83). Purification by prep. HPLC and removal of the solvents by lyophilization yielded compound (83) (95 mg, 47% yield) as a colorless (white) solid. LC/MS/UV: Rt: 1.077 min, calculated for $C_{16}H_{16}Cl_2N_2O_4S$ 402.02 g/mol, ESI (pos.) m/z=402.85 [M+H$^+$]$^+$, 806.30 [2M+H$^+$]$^+$, ESI (neg.) m/z=400.65 [M−H$^+$]$^-$, 804.20 [2M−H$^+$]$^-$; HPLC/UV: Rt: 9.740 min (96.6% AUC at 220 nm, 97.9% AUC at 254 nm); $^1$H NMR (300 MHz, CD$_3$OD): δ 7.74 (d, J=2.4 Hz, 1H), 7.50 (dd, J=8.1, 1.8 Hz, 1H), 7.36-7.28 (m, 3H), 7.05 (dd, J=8.7, 3.0 Hz, 1H), 3.72 (dd, J=8.7, 5.7 Hz, 1H), 3.67 (dd, J=14.7, 6.0 Hz, 1H), 3.02 (dd, J=14.7, 8.1 Hz, 1H), 2.42 (s, 3H). The $^1$H NMR signals for the amino-group, the N—H acidic group, and the carboxyl-group were not observed because of H-D exchange with the NMR solvent.

Example 84

(S)-2-Amino-3-(5-(N-(4-chlorophenyl)-N-methylsulfamoyl)-2-methylphenyl)propanoic Acid (84)

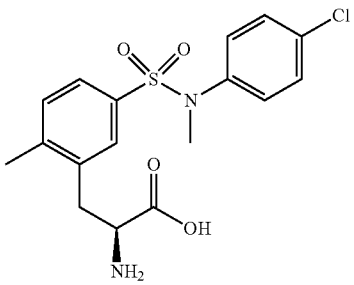

Compound (84) was synthesized by adapting methods described in Scheme 8 and Scheme 9. Sulfonyl chloride starting material 9 (SM-9), tert-butyl (S)-2-((tert-butoxycarbonyl)amino)-3-(5-(chlorosulfonyl)-2-methylphenyl)propanoate, (217 mg, 0.5 mmol) was reacted with commercial 4-chloro-N-methyl aniline [CAS No. 932-96-7](142 mg, 1.0 mmol) in neat pyridine [CAS No. 110-86-1](2 mL) in the presence of 4-N,N-dimethylaminopyridine (DMAP) [CAS No. 1122-58-3](12 mg, 0.1 mmol) at 40° C. for overnight (Scheme 8). Evaporation of volatiles, extractive aqueous work-up, and chromatographic purification on silica gel (hexane/ethyl acetate=6:1, (v/v)) yielded tert-butyl (S)-2-((tert-butoxycarbonyl)amino)-3-(5-(N-(4-chlorophenyl)-N-methylsulfamoyl)-2-methylphenyl)propanoate (337 mg) as a pale yellow oil. TLC: Rf: 0.50 (hexane/ethyl acetate=3:1, (v/v)).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(N-(4-chlorophenyl)-N-methylsulfamoyl)-2-methylphenyl)propanoate (224 mg, 0.42 mmol) in 1,4-dioxane (0.5 mL) was conducted through reaction with commercial HCl in 1,4-dioxane [CAS No. 7647-01-0](4 M in 1,4-dioxane, 3 mL, 12 mmol) at 40° C. for overnight. Evaporation of volatiles afforded the crude compound (84). Purification by prep. HPLC and removal of the solvents by lyophilization yielded impure material (75 mg, impure) which was further purified through a second prep. HPLC to yield compound (84) (16 mg, 10% yield) as a white solid. LC/MS/UV: Rt: 1.091 min, calculated for $C_{17}H_{19}ClN_2O_4S$ 382.08, found ESI (pos.) m/z=382.95 [M+H$^+$]$^+$, 763.90 [2M+H$^+$]$^+$, ESI (neg.) m/z=380.70 [M−H$^+$]$^-$, 762.30 [2M−H$^+$]$^-$; HPLC/UV: Rt: 9.485 min (94.9% AUC at 220 nm, 95.0% AUC at 254 nm); $^1$H NMR (300 MHz, CD$_3$OD): δ 7.50 (d, J=2.4 Hz, 1H), 7.37-7.23 (m, 5H), 7.15-7.09 (m, 1H), 3.69 (dd, J=8.1, 6.3 Hz, 1H), 3.37 (dd, J=14.1, 6.0 Hz, 1H), 3.17 (s, 3H), 3.00 (dd, J=14.7, 9.0

Hz, 1H), 2.47 (s, 3H). The $^1$H NMR signals for the amino-group, the N—H acidic group, and the carboxyl-group were not observed because of H-D exchange with the NMR solvent.

Example 85

(S)-2-Amino-3-(4-(N-(4-chlorophenyl)sulfamoyl)-2-methylphenyl)propanoic Acid (85)

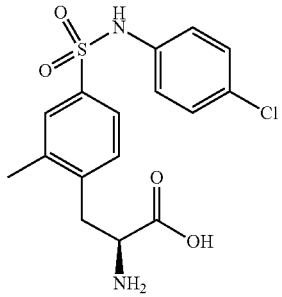

Compound (85) was synthesized by adapting methods described in Scheme 2, Scheme 3, and Scheme 9 using well-known literature procedures.

4-Bromo-N-(4-chlorophenyl)-3-methylbenzenesulfonamide was prepared from commercial 4-bromo-3-methylbenzenesulfonyl chloride [CAS No. 72256-93-0](1.0 g, 3.71 mmol) and 4-chloroaniline [CAS No. 106-47-8](0.95 mg, 7.42 mmol) in neat pyridine [CAS No. 110-86-1](15 mL) and in the presence of 4-N,N-dimethylaminopyridie (DMAP) [CAS No. 1122-58-3](45 mg, 0.37 mmol) at room temperature for overnight. Evaporation of volatiles, extractive aqueous, and chromatographic purification on silica gel (hexane/ethyl acetate=6:1, (v/v)) yielded 4-bromo-N-(4-chlorophenyl)-3-methylbenzenesulfonamide (553 mg, 41% yield) as a beige solid. TLC: Rf: 0.28 (hexane/ethyl acetate=6:1, (v/v)).

4-Bromo-N-(4-chlorophenyl)-3-methylbenzenesulfonamide (543 mg, 1.5 mmol) and starting material 1 (SM-1), methyl (R)-2-((tert-butoxycarbonyl)amino)-3-iodopropanoate [CAS No. 93267-04-0](658 mg, 2.0 mmol) were cross-coupled through Pd(0)-catalyzed Negishi-coupling using tris(dibenzylideneacetone)dipalladium (Pd$_2$(dba)$_3$) [CAS No. 51364-51-3](34 mg, 0.033 mmol) and tri(o-tolyl)phosphine (P(o-Tol)$_3$) [CAS No. 6163-58-2](46 mg, 0.15 mmol) in the presence of an excess of zinc dust [CAS No. 7440-66-6](780 mg, 12.0 mmol), pre-activated with elemental iodine (I$_2$) [CAS No. 7553-56-2](76 mg, 0.3 mmol) and trimethylchlorosilane (TMSCl) [CAS No. 75-77-4](38 µL, 33 mg, 0.3 mmol) in anhydrous DMF (5 mL+2 mL) at 60° C. for overnight under a nitrogen atmosphere. Filtration over Celite®, extractive aqueous work-up, and chromatographic purification over silica gel (hexane/ethyl acetate=4:1, (v/v)) yielded (impure) methyl (S)-2-((tert-butoxycarbonyl)amino)-3-(4-(N-(4-chlorophenyl)sulfamoyl)-2-methylphenyl)propanoate (80 mg, impure). TLC: Rf: 0.22 (hexane/ethyl acetate=7:3, (v/v)).

The protecting groups of the sulfonamide were removed in two steps (Scheme 9). Chemoselective removal of the N-Boc-protection group of methyl (S)-2-((tert-butoxycarbonyl)amino)-3-(4-(N-(4-chlorophenyl)sulfamoyl)-2-methylphenyl)propanoate (80 mg, impure, max. 0.17 mmol) was conducted with 20 vol-% TFA in DCM (5 mL) at room temperature for 2 h. Hydrolysis of the methyl ester group with lithium hydroxide monohydrate (LiOH·H$_2$O) [CAS No. 1310-66-3](35 mg, 0.83 mmol) in THF/water (1:1, (v/v)) (4 mL) at room temperature for 2 h yielded the crude compound (85). Evaporation of volatiles, purification by prep. HPLC, and removal of the solvents by lyophilization yielded compound (85) (32 mg, 51% yield) as a colorless (white) solid. LC/MS/UV: Rt: 8.389 min, calculated for C$_{16}$H$_{17}$ClN$_2$O$_4$S 368.06, found ESI (pos.) m/z=368.95 [M+H$^+$]$^+$, 737.10 [2M+H$^+$]$^+$, ESI (neg.) m/z=366.75 [M−H$^+$]$^-$, 736.15 [2M−H$^+$]$^-$; HPLC/UV: Rt: 8.389 min (94.7% AUC at 254 nm); $^1$H NMR (300 MHz, CD$_3$OD): δ 7.54 (d, J=2.4 Hz, 1H), 7.47 (dd, J=8.1, 2.4 Hz, 1H), 7.36 (br d, J=7.5 Hz, 1H), 7.30-7.24 (m, 2H), 7.13-7.06 (m, 2H), 3.21 (dd, J=15.3, 4.2 Hz, 1H), 2.75 (dd, J=14.7, 9.0 Hz, 1H), 2.30 (s, 3H). The $^1$H NMR signal of the CH-group was not observed because of superposition with the NMR solvent signal. The $^1$H NMR signals for the amino-group, the N—H acidic group, and the carboxyl-group were not observed because of H-D exchange with the NMR solvent.

Example 86

(S)-2-Amino-3-(5-(N-(4-chloroophenyl)sulfamoyl)-2-isopropylphenyl)propanoic Acid (86)

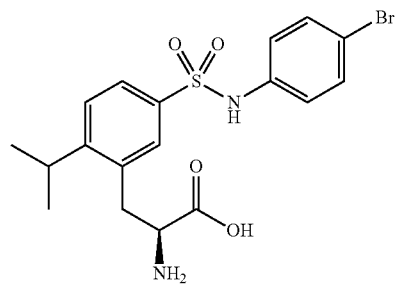

Compound (86) was synthesized by adapting methods described in Scheme 8 and Scheme 9. Sulfonyl chloride starting material 10 (SM-10), tert-butyl (S)-2-((tert-butoxycarbonyl)amino)-3-(5-(chlorosulfonyl)-2-isopropylphenyl)propanoate, (360 mg, 0.78 mmol) was reacted with commercial 4-chloro-N-methyl aniline [CAS No. 932-96-7](198 mg, 1.56 mmol) in neat pyridine [CAS No. 110-86-1](5 mL) at 60° C. for 2 h. Evaporation of volatiles, extractive aqueous work-up, and chromatographic purification on silica gel (hexane/ethyl acetate=7:3, (v/v)) yielded tert-butyl (S)-2-((tert-butoxycarbonyl)amino)-3-(5-(N-(4-chlorophenyl)sulfamoyl)-2-isopropylphenyl)propanoate (300 mg, 69% yield) as a solid. TLC: Rf: 0.47 (hexane/ethyl acetate=7:3, (v/v)).

The protecting groups of the sulfonamide were removed in one step (Scheme 9). Global removal of the N-Boc-protection group and the tert-butyl ester group of tert-butyl (S)-2-((tert-butoxycarbonyl)amino)-3-(5-(N-(4-chlorophenyl)sulfamoyl)-2-isopropylphenyl)propanoate (300 mg, 0.54 mmol) was conducted through reaction with commercial HCl in 1,4-dioxane [CAS No. 7647-01-0](4 M in 1,4-dioxane, 5 mL, 20 mmol) at 40° C. for 6 h. Evaporation of volatiles yielded the crude compound (86). Purification by prep. HPLC and removal of the solvents by lyophilization yielded compound (86) (110 mg, 51% yield) as a colorless (white) solid. LC/MS/UV: Rt: 1.072 min, calculated for $C_{18}H_{21}ClN_2O_4S$ 396.09, ESI (pos.) m/z=396.85 [M+H$^+$]$^+$, 792.60 [2M+H$^+$]$^+$, ESI (neg.) m/z=394.75 (M–H$^+$)$^-$, 792.15 (2M–H$^+$)$^-$; HPLC/UV: Rt: 9.663 min (97.7% AUC at 220 nm, 95.7% AUC at 254 nm); H NMR (300 MHz, CD$_3$OD): δ 7.70 (d, J=1.8 Hz, 1H), 7.56 (dd, J=8.1, 1.8 Hz, 1H), 7.45 (d, J=9.0 Hz, 1H), 7.24-7.18 (m, 2H), 7.13-7.07 (m, 2H), 3.64 (dd, J=8.7, 5.7 Hz, 1H), 3.44 (dd, J=14.7, 6.0 Hz, 1H), 3.28-3.23 (m, 1H, superimposed with the $^1$H NMR signal of the NMR solvent), 2.98 (dd, J=14.1, 8.7 Hz, 1H), 1.28-1.20 (2×d, J=7.2 Hz and 6.6 Hz, 6H). The $^1$H NMR signals for the amino-group, the N—H acidic group, and the carboxyl-group were not observed because of H-D exchange with the NMR solvent.

Example 87

(S)-2-Amino-3-(5-((4-(tert-butyl)phenyl)sulfonamido)-2-methylphenyl)propanoic Acid (87)

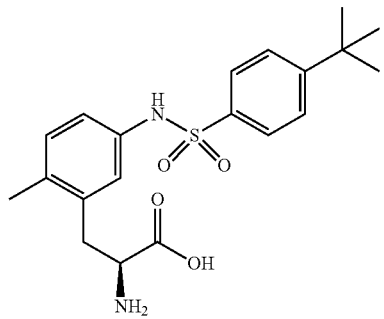

Compound (87) was synthesized by adapting methods described in Scheme 7 and Scheme 9. Commercial 4-(tert-butyl)benzenesulfonyl chloride [CAS No. 15084-51-2](233 mg, 1.0 mmol) was reacted with starting material 5 (SM-5), methyl (S)-3-(5-amino-2-methylphenyl)-2-((tert-butoxycarbonyl)amino)propanoate (308 mg, 1.0 mmol, 1.0 eq.) in neat pyridine [CAS No. 110-86-1](5 mL) at room temperature for 2 h. Evaporation of volatiles, extractive aqueous work-up, and chromatographic purification on silica gel (hexane/ethyl acetate=1:1, (v/v)) yielded methyl (S)-2-((tert-butoxycarbonyl)amino)-3-(5-((4-(tert-butyl)phenyl)sulfonamido)-2-methylphenyl)propanoate (430 mg, 85% yield) as a solid. TLC: Rf: 0.72 (hexane/ethyl acetate=1:1, (v/v)).

The protecting groups of the sulfonamide were removed in two steps (Scheme 9). Chemoselective removal of the N-Boc-protection group of methyl (S)-2-((tert-butoxycarbonyl)amino)-3-(5-((4-(tert-butyl)phenyl)sulfonamido)-2-methylphenyl)propanoate (430 mg, 0.85 mmol) was conducted with 20 vol-% TFA in DCM (5 mL) at room temperature for 2 h. Evaporation of volatiles and hydrolysis of the methyl ester group with lithium hydroxide monohydrate (LiOH·H$_2$O) [CAS No. 1310-66-3](179 mg, 4.3 mmol) in THF/water (1:1, (v/v)) (10 mL) at room temperature for 2 h yielded the crude compound (87). Evaporation of volatiles, purification by prep. HPLC, and removal of the solvents by lyophilization yielded compound (87) (190 mg, 57% yield) as a colorless (white) solid. LC/MS/UV: Rt: 1.112 min, calculated for $C_{20}H_{26}N_2O_4S$ 390.16, ESI (pos.) m/z=390.95 [M+H$^+$]$^+$, 780.70 [2M+H$^+$]$^+$; ESI (neg.) m/z=388.80 [M–H$^+$]$^-$, 778.60 [2M–H$^+$]$^-$; HPLC/UV: Rt: 9.049 min (99.0% AUC at 220 nm, 98.7% AUC at 254 nm); $^1$H NMR (300 MHz, CD$_3$OD): δ 7.73-7.67 (m, 2H), 7.54-7.48 (m, 2H), 7.05 (br s, 1H), 7.03 (br d, J=4.8 Hz, 1H), 6.90 (dd, J=8.4, 2.4 Hz, 1H), 3.73 (dd, J=9.9, 4.5 Hz, 1H), 3.32 (dd, J=13.5, 5.4 Hz, 1H), 2.86 (dd, J=14.7, 9.3 Hz, 1H), 2.28 (s, 3H), 1.29 (s, 9H). The $^1$H NMR signals for the amino-group, the N—H acidic group, and the carboxyl-group were not observed because of H-D exchange with the NMR solvent.

Example 88

(S)-2-Amino-3-(5-((4-chlorophenyl)sulfonamido)-2-methylphenyl)propanoic Acid (88)

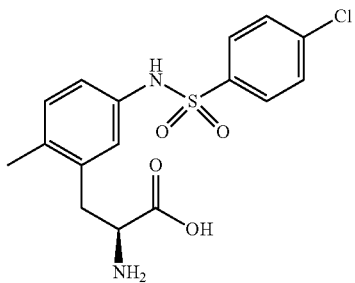

Compound (88) was synthesized by adapting methods described in Scheme 7 and Scheme 9. Commercial 4-chlorobenzenesulfonyl chloride [CAS No. 98-6-2](226 mg, 1.07 mmol) was reacted with starting material 5 (SM-5), methyl-(S)-3-(5-amino-2-methylphenyl)-2-((tert-butoxycarbonyl)amino)propanoate, (165 mg, 0.54 mmol) in neat pyridine [CAS No. 110-86-1](2 mL) in the presence of 4-N,N-dimethyaminopyridine (DMAP) [CAS No. 1122-58-3](13 mg, 0.11 mmol) at room temperature for overnight. Evaporation of volatiles, extractive aqueous work-up, and chromatographic purification on silica gel (hexane/ethyl acetate=3:1, (v/v)) yielded methyl (S)-2-((tert-butoxycarbonyl)amino)-3-(5-((4-chlorophenyl)sulfonamido)-2-methylphenyl)propanoate (150 mg, 58% yield) as a solid. TLC: Rf: 0.28 (hexane/ethyl acetate=3:1, (v/v)).

The protecting groups of the sulfonamide were removed in two steps (Scheme 9). Chemoselective removal of the N-Boc-protection group of methyl (S)-2-((tert-butoxycarbonyl)amino)-3-(5-((4-chlorophenyl)sulfonamido)-2-methylphenyl)propanoate (150 mg, 0.31 mmol) was conducted with 20 vol-% TFA in DCM (5 mL) at room temperature for 2 h. Evaporation of volatiles and hydrolysis of the methyl ester group with lithium hydroxide monohydrate (LiOH·H$_2$O) [CAS No. 1310-66-3](65 mg, 1.55 mmol) in THF/water (1:1, (v/v)) (5 mL) at room temperature for 2 h yielded the crude compound (88). Evaporation of volatiles, purification by prep. HPLC, and removal of the solvents by lyophilization yielded compound (88) (88 mg, 77% yield) as a colorless (white) solid. LC/MS/UV: Rt: 0.972 min, calculated for $C_{16}H_{17}ClN_2O_4S$ 368.06, ESI (pos.) m/z=368.55 [M+H$^+$]$^+$, 736.50 [2M+H$^+$]$^+$, ESI (neg.) m/z=366.75 [M–H$^+$]$^-$, 736.15 [2M–H$^+$]$^-$; HPLC/UV: Rt: 8.906 min (99.2 AUC at 220 nm, 98.9% AUC at 254 nm); $^1$H NMR (300 MHz, DMSO-d$_6$): δ 7.77-7.70 (m, 2H), 7.62-7.54 (m, 2H), 7.00 (d, J=2.4 Hz, 1H), 6.96 (d, J=8.1 Hz, 1H), 6.76 (dd, J=8.1, 2.4 Hz, 1H), 3.21 (dd, J=9.6, 5.4 Hz, 1H), 3.09 (dd, J=14.4, 4.5 Hz, 1H), 2.62 (dd, J=14.4, 9.0H, 1H), 2.16 (s, 3H). The $^1$H NMR signals for the amino-group, the N—H acidic group, and the carboxyl-group were not observed because of H-D exchange with moisture in the NMR solvent or superposition with the ¹H NMR signal of the NMR solvent.

Example 89

(S)-2-Amino-3-(5-(N-(4-chlorophenyl)sulfamoyl)-2-methylphenyl) propanoic Acid (89)

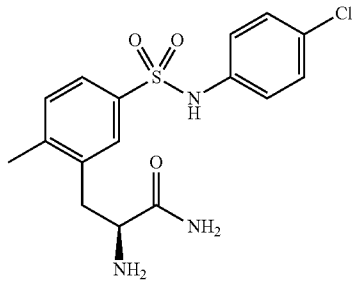

Compound (89) was synthesized by adapting well known methods described in the literature and in Scheme 9 and Scheme 10. Carboxylic acid starting material 12 (SM-12), (S)-2-((tert-butoxycarbonyl)amino)-3-(5-(N-(4-chlorophenyl)sulfamoyl)-2-methylphenyl)propanoic acid, (100 mg, 0.21 mmol) was activated with neat isobutyl chloroformate (IBCF) [CAS No. 543-27-1](35 µL, 37 mg, 0.26 mmol) in the presence of N-methyl morpholine (NMM) [CAS No. 109-02-4](46 µL, 42 mg, 0.42 mmol) in tetrahydrofuran (THF) at room temperature for about 30 min to yield (S)—(S)-2-((tert-butoxycarbonyl)amino)-3-(5-(N-(4-chlorophenyl)sulfamoyl)-2-methylphenyl)propanoic (isobutyl carbonic) anhydride. The intermittent mixed anhydride was reacted with commercial concentrated aqueous ammonia (ammonium hydroxide) ($NH_{3(aq)}$ or $NH_4OH$) (1 mL, 28-30 wt-%) to yield tert-butyl N-((1S)-2-amino-1-((5-((4-chlorophenyl)sulfamoyl)-2-methyl-phenyl)methyl)-2-oxo-ethyl) carbamate (80 mg) after chromatographic purification on silica gel (hexanes/ethyl acetate=1:1 (v/v)). TLC: Rf: 0.3 (hexanes/ethyl acetate=1:1 (v/v)).

The N-Boc protecting group was removed in one step (Scheme 9). Removal of the N-Boc-protection group was conducted through reaction of the sulfonamide (80 mg, 0.17 mmol) with 20 vol-% TFA in DCM (5 mL) at room temperature for overnight to yield the crude compound (89). Purification by prep. HPLC and removal of the solvents by lyophilization yielded the pure compound (89) (10 mg, 16% yield) as a colorless (white) solid. LC/MS/UV: Rt: 0.585 min, calculated for $C_{16}H_{18}ClN_3O_3S$ 367.08, found ESI (pos.) m/z=367.90 [M+H⁺]⁺, ESI (neg.) m/z=365.80 [M−H⁺]⁻; HPLC/UV: Rt: 8.581 min (99.1% AUC at 220 nm; 98.0% AUC at 254 nm); ¹H NMR (300 MHz, $CD_3OD$): δ 7.64 (d, J=1.8 Hz, 1H), 7.57 (dd, J=8.4, 1.8 Hz, 1H), 7.35 (d, J=8.1 Hz, 1H), 7.24-7.17 (m, 2H), 7.10-7.03 (m, 2H), 3.95 (t, J=7.5 Hz, 1H), 3.20-3.10 (m, 2H), 2.42 (s, 3H). The ¹H NMR signal of acidic N—H group was not observed because of H-D exchange with the NMR solvent.

Example 90

(S)-2-Amino-3-(5-(N-(4-chlorophenyl)sulfamoyl)-2-methylphenyl) -N-methylpropanamide (90)

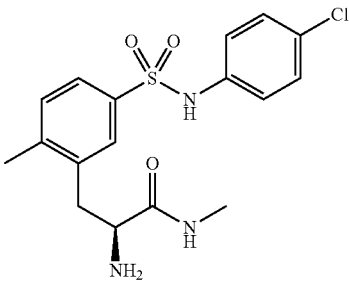

Compound (90) was synthesized by adapting well known methods described in the literature and as described in Schemes 9 and 10. Carboxylic acid (S)-2-((tert-butoxycarbonyl)amino)-3-(5-(N-(4-chlorophenyl)sulfamoyl)-2-methylphenyl)propanoic acid 12 (SM-12) (100 mg, 0.21 mmol) was coupled with commercial methylamine ($H_2NCH_3$) [CAS No. 74-89-5](2.0 M in THF, 315 µL, 0.63 mmol) in DCM (5 mL) in the presence of EDAC HCl [CAS No. 25952-53-8](121 mg, 0.63 mmol), N,N-diisopropylethylamine (DIEA) [CAS No. 7087-68-5](183 µL, 136 mg, 1.05 mmol), and 4-N,N-dimethylpyridine (DMAP) [CAS No. 1122-58-3](13 mg, 0.11 mmol) at room temperature for overnight. Aqueous work-up and chromatographic purification on silica gel (hexanes/ethyl acetate=1:1, (v/v)) yielded tert-butyl (S)-(3-(5-(N-(4-chlorophenyl)sulfamoyl)-2-methylphenyl)-1-(methylamino)-1-oxopropan-2-yl)carbamate (60 mg, 59% yield) as a colorless (white) sticky solid. TLC: Rf: 0.25 (hexanes/ethyl acetate=1:1 (v/v)).

The N-Boc-protecting group of the sulfonamide was removed in one step (Scheme 9). Removal of the N-Boc-protection group was conducted through reaction of sulfonamide (60 mg, 0.12 mmol) with 20 vol-% TFA in DCM (5 mL) at room temperature for overnight to yield the crude compound (90). Purification by prep. HPLC and removal of the solvents by lyophilization yielded the pure compound (90) (26 mg, 57% yield) as a colorless (white) solid. LC/MS/UV: Rt: 0.854 min, calculated for $C_{17}H_{20}ClN_3O_3S$ 381.09, found (ESI (pos.) 381.80 [M+H⁺]⁺, 762.55 [2M+H⁺]⁺, ESI (neg.) m/z=379.75 [M−H⁺]⁻, 760.45 [2M−H⁺]⁻; HPLC/UV: Rt: 8.689 min (99.4% AUC at 220 nm, 99.7% AUC at 254 nm); H NMR (300 MHz, $CD_3OD$): δ 7.55-7.48 (m, 2H), 7.28 (d, J=8.4 Hz, 1H), 7.19 (br d, J=8.7 Hz, 2H), 7.05 (br d, J=8.7 Hz, 2H), 3.41 (t, J=6.9 Hz, 1H), 2.99 (dd, J=13.5, 7.5 Hz, 1H), 2.83 (dd, J=13.5, 6.6 Hz, 1H), 2.71 (s, 3H), 2.37 (s, 3H). The acidic N—H protons were not observed because of H-D exchange with the NMR solvent.

Example 91

(S)-2-Amino-3-(5-(N-(4-chlorophenyl)sulfamoyl)-2-methylphenyl)-N,N-dimethylpropanamide (91)

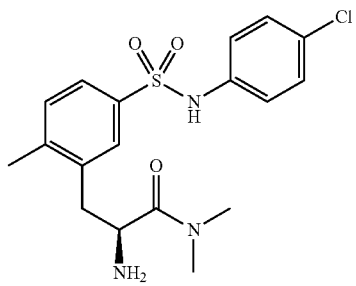

Compound (91) was synthesized by adapting well known methods described in the literature and in Scheme 9 and Scheme 10. Carboxylic acid (S)-2-((tert-butoxycarbonyl)amino)-3-(5-(N-(4-chlorophenyl)sulfamoyl)-2-methylphenyl)propanoic acid 12 (SM-12) (100 mg, 0.21 mmol) was coupled with commercial dimethylamine (HN(CH$_3$)$_2$) [CAS No. 124-40-3](2.0 M in THF, 315 µL, 0.63 mmol) in DCM (5 mL) in the presence of EDAC HCl [CAS No. 25952-53-8](121 mg, 0.63 mmol), N,N-diisopropylethylamine (DIEA) [CAS No. 7087-68-5](183 µL, 136 mg, 1.05 mmol), and 4-N,N-dimethylpyridine (DMAP) [CAS No. 1122-58-3](13 mg, 0.11 mmol) at room temperature for overnight. After removal of the volatiles, direct chromatographic purification on silica gel (dichloromethane/ethyl acetate=1:1, (v/v)) yielded tert-butyl (S)-(3-(5-(N-(4-chlorophenyl)sulfamoyl)-2-methylphenyl)-1-(dimethylamino)-1-oxopropan-2-yl)carbamate (40 mg, 38% yield) as a colorless (white) solid. TLC: Rf 0.65 (dichloromethane/ethyl acetate=1:1 (v/v)).

The N-Boc-protecting group of the sulfonamide was removed in one step (Scheme 9). Removal of the N-Boc-protection group was conducted through reaction of the sulfonamide (40 mg, 0.081 mmol) with 20 vol-% TFA in DCM (5 mL) at 25° C. for 1 h to yield the crude compound (91). Purification by prep. HPLC and removal of the solvents by lyophilization yielded the pure compound (91) (28 mg, 87% yield) as a colorless (white) solid. LC/MS/UV: Rt: 0.870 min, calculated for C$_{18}$H$_{22}$ClN$_3$O$_3$S 395.11, found (ESI (pos.) 395.85 [M+H$^+$]$^+$, 790.65 [2M+H$^+$]$^+$, ESI (neg.) m/z=393.75 [M−H$^+$]$^-$, 788.50 [2M−H$^+$]$^-$; HPLC/UV: Rt: 8.964 min (99.2% AUC at 220 nm, 99.4% AUC at 254 nm); $^1$H NMR (300 MHz, CD$_3$OD): δ 7.58 (dd, J=8.1, 1.5 Hz, 1H), 7.49 (d, J=1.8 Hz, 1H), 7.33 (br d, J=8.4 Hz, 1H), 7.21 (br d, J=8.7 Hz, 2H), 7.07 (br d, J=8.7 Hz, 2H), 4.20-4.08 (br m, 1H), 3.04 (dd, J=13.5, 5.4 Hz, 1H), 2.92 (dd, J=13.5, 9.9 Hz, 1H), 2.77 (s, 3H), 2.39 (s, 3H), 2.34 (s, 3H). The $^1$H NMR signal of the acidic N—H groups was not observed because of H-D exchange with the NMR solvent.

Example 92

(S)-2-Amino-3-(5-(N-(4-chlorophenyl)sulfamoyl)-2-methylphenyl)-N-isopropylpropanamide (92)

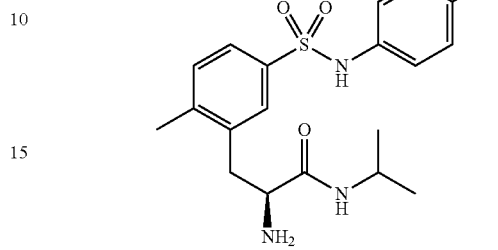

Compound (92) was synthesized by adapting well known methods described in the literature and in Scheme 9 and Scheme 10. Carboxylic acid (S)-2-((tert-butoxycarbonyl)amino)-3-(5-(N-(4-chlorophenyl)sulfamoyl)-2-methylphenyl)propanoic acid 12 (SM-12) (150 mg, 0.32 mmol) was coupled with neat commercial isopropylamine (H$_2$NCH(CH$_3$)$_2$) [CAS No. 75-31-0](82 µL, 57 mg, 0.96 mmol) in DCM (5 mL) in the presence of EDAC HCl [CAS No. 25952-53-8](184 mg, 0.96 mmol), N,N-diisopropylethylamine (DIEA) [CAS No. 7087-68-5](158 µL, 117 mg, 0.96 mmol), and 4-N,N-dimethylpyridine (DMAP) [CAS No. 1122-58-3](12 mg, 0.10 mmol) at room temperature for overnight. Extractive aqueous work-up and chromatographic purification on silica gel (hexanes/ethyl acetate=1:1 (v/v)) yielded tert-butyl (S)-(3-(5-(N-(4-chlorophenyl)sulfamoyl)-2-methylphenyl)-1-(isopropylamino)-1-oxopropan-2-yl)carbamate (110 mg, 67% yield) as a colorless (white) solid. TLC: Rf: 0.45 (hexane/ethyl acetate=1:1 (v/v)).

The N-Boc-protecting group of the sulfonamide was removed in one step (Scheme 9). Removal of the N-Boc-protection group was conducted through reaction of the sulfonamide (110 mg, 0.22 mmol) with 20 vol-% TFA in DCM (5 mL) at room temperature for 1 h to yield the crude compound (92). Purification by prep. HPLC and removal of the solvents by lyophilization yielded the pure compound (92) (60 mg, 67% yield) as a colorless (white) solid. LC/MS/UV: Rt: 0.876 min, calculated for C$_{19}$H$_{24}$ClN$_3$O$_3$S 409.12, found (ESI (pos.) 409.8 [M+H$^+$]$^+$, ESI (neg.) m/z=408.70 [M−H$^+$]$^-$; HPLC/UV: Rt: 9.296 min (99.7% AUC at 220 nm, 99.6% AUC at 254 nm); $^1$H NMR (300 MHz, CD$_3$OD): δ 7.60 (dd, J=8.1, 2.4 Hz, 1H), 7.54 (br d, J=1.8 Hz, 1H), 7.36 (d, J=8.1 Hz, 1H), 7.23-7.17 (m, 2H), 7.10-7.03 (m, 2H), 3.57-3.54 (m, 2H), 3.16 (dd, J=13.2, 5.7 Hz, 1H), 3.06 (dd, J=12.9, 9.9 Hz, 1H), 2.41 (s, 3H), 1.04 (d, J=6.3 Hz, 3H), 0.76 (d, J=6.3 Hz, 3H). The $^1$H NMR signals of the N—H acidic groups were not observed because of H-D exchange with the NMR solvent.

Example 93

(S)-2-Amino-3-(5-(N-(4-chlorophenyl)sulfamoyl)-2-methylphenyl)-N-hydroxypropanamide (93)

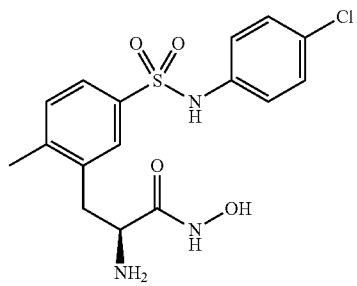

Compound (93) was synthesized by adapting well known methods described in the literature and in Scheme 9 and Scheme 10. Carboxylic acid (S)-2-((tert-butoxycarbonyl)amino)-3-(5-(N-(4-chlorophenyl)sulfamoyl)-2-methylphenyl)propanoic acid 12 (SM-12) (190 mg, 0.41 mmol) was coupled with commercial hydroxylamine hydrochloride (hydroxylammonium chloride) ($H_2NOH$ HCl) [CAS No. 5470-11-1](85 mg, 1.21 mmol) in DCM (10 mL) in the presence of EDAC HCl [CAS No. 25952-53-8](232 mg, 1.21 mmol), N,N-diisopropylethylamine (DIEA) [CAS No. 7087-68-5] (406 μL, 301 mg, 2.46 mmol), and 4-N,N-dimethylpyridine (DMAP) [CAS No. 1122-58-3](15 mg, 0.12 mmol) at room temperature for overnight. Extractive aqueous work-up and chromatographic purification on silica gel (hexanes/ethyl acetate=1:1 (v/v)) yielded tert-butyl (S)-(3-(5-(N-(4-chlorophenyl)sulfamoyl)-2-methylphenyl)-1-(methoxy(methyl)amino)-1-oxopropan-2-yl)carbamate (30 mg, 15% yield) as a colorless (white) solid (Scheme 10). TLC: Rf: 0.15 (hexane/ethyl acetate=1:1 (v/v)).

The N-Boc-protecting group of the sulfonamide was removed in one step (Scheme 9). Removal of the N-Boc-protection group was conducted through reaction of the sulfonamide (110 mg, 0.22 mmol) with 20 vol-% TFA in DCM (5 mL) at 25° C. for 1 h to afford only trace amounts of crude compound (93) (Scheme 9). Calculated for $C_{16}H_{18}ClN_3O_4S$ 383.07.

Example 94

(S)-2-Amino-3-(5-(N-(4-chlorophenyl)sulfamoyl)-2-methylphenyl)-N-methoxy-N-methylpropanamide (94)

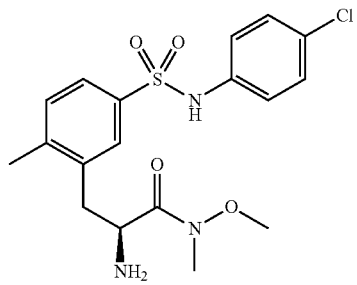

Compound (94) was synthesized by adapting well known methods described in the literature and in Scheme 9 and Scheme 10. Carboxylic acid (S)-2-((tert-butoxycarbonyl)amino)-3-(5-(N-(4-chlorophenyl)sulfamoyl)-2-methylphenyl)propanoic acid 12 (SM-12) (200 mg, 0.43 mmol) was coupled with commercial N,O-dimethylhydroxylamine hydrochloride ($HN(CH_3)(OCH_3)$ HCl) [CAS No. 6638-79-5] (125 mg, 1.28 mmol) in DCM (10 mL) in the presence of EDAC HCl [CAS No. 25952-53-8](165 mg, 0.86 mmol), N,N-diisopropylethylamine (DIEA) [CAS No. 7087-68-5] (426 μL, 316 mg, 2.58 mmol), and 4-N,N-dimethylpyridine (DMAP) [CAS No. 1122-58-3](32 mg, 0.26 mmol) at room temperature for overnight. Aqueous work-up and chromatographic purification on silica gel (hexanes/ethyl acetate=1:1 (v/v)) yielded tert-butyl (S)-(3-(5-(N-(4-chlorophenyl)sulfamoyl)-2-methylphenyl)-1-(methoxy(methyl)amino)-1-oxopropan-2-yl)carbamate (100 mg, 45% yield) as a colorless (white) solid (Scheme 10). TLC: Rf: 0.38 (hexane/ethyl acetate=1:1 (v/v)).

The N-Boc-protecting group of the sulfonamide was removed in one step (Scheme 9). Removal of the N-Boc-protection group was conducted through reaction of the sulfonamide (50 mg, 0.1 mmol) with 20 vol-% TFA in DCM (5 mL) at room temperature for 1 h to yield the crude compound (94). Purification by prep. HPLC and removal of the solvents by lyophilization yielded the pure compound (94) (26 mg, 63% yield) as a colorless (white) solid. LC/MS/UV: Rt: 0.957 min, calculated for $C_{18}H_{22}ClN_3O_4S$ 411.10, found (ESI pos.) 411.90 [M+H$^+$]$^+$, ESI (neg.) m/z=409.75 [M−H$^+$]$^-$; HPLC/UV: Rt: 9.364 min (99.9% AUC at 220 nm, 99.6% AUC at 254 nm); $^1$H NMR (300 MHz, DMSO-d$_6$): δ 8.30-8.00 (br s, 2H), 7.53 (dd, J=7.8, 1.8 Hz, 1H), 7.47 (br s, 1H), 7.36 (br d, J=7.5 Hz, 1H), 7.31-7.24 (m, 2H), 7.10-7.04 (m, 2H), 4.31 (t, J=8.1 Hz, 1H), 3.07 (dd, J=13.5, 6.6 Hz, 1H), 2.96 (dd, J=13.5, 9.0 Hz, 1H), 2.94 (s, 3H), 2.32 (s, 3H). The $^1$H NMR signal of the N—H acidic group was not observed because of H-D exchange with the moisture in the NMR solvent. One of the CH$_3$-singlets appeared to be superimposed with the $^1$H NMR signal of the NMR solvent.

Example 95

(S)-3-(2-Amino-4-methyl-3-oxopentyl)-N-(4-chlorophenyl)-4-methylbenzenesulfonamide (95)

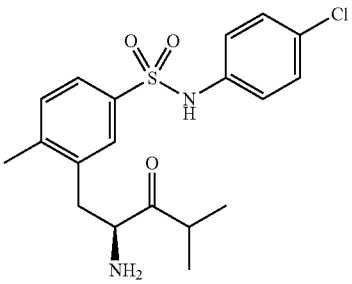

Compound (95) was synthesized by adapting methods described in the literature and in Scheme 9 and Scheme 11. Synthesized tert-butyl (S)-(3-(5-(N-(4-chlorophenyl)sulfamoyl)-2-methylphenyl)-1-(methoxy(methyl)amino)-1-oxopropan-2-yl)carbamate (see compound (94), Example 94) was reacted with isopropyl lithium (iPrLi) [CAS No. 1888-75](e.g., 0.7 M in pentane) or isopropylmagnesium bromide (iPrMgBr) (e.g., 0.75 M in THF) in ethereal solvents such as diethyl ether (Et₂O) or tetrahydrofuran (THF at temperatures from about −78° C. to about room temperature to yield tert-butyl (S)-(1-(5-(N-(4-chlorophenyl)sulfamoyl)-2-methylphenyl)-4-methyl-3-oxopentan-2-yl)carbamate.

The N-protecting group of the sulfonamide was removed in one step (Scheme 9). Removal of the N-Boc-protection group was conducted through reaction with 20-50 vol-% TFA in DCM room temperature for about 1 h to 24 h to afford the crude compound (95). Evaporation of volatiles, purification by prep. HPLC, and removal of the solvents by lyophilization yielded pure compound (95). $C_{19}H_{23}ClN_2O_3S$. M.W.: 394.92 g/mol.

Example 96

(2S)-2-Amino-3-(2-methyl-5-((p-tolylsulfinyl)amino)phenyl)propanoic Acid (96)

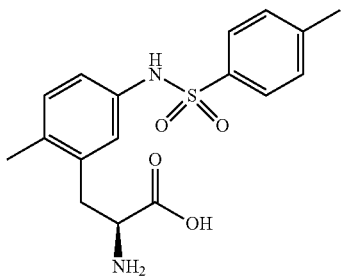

Compound (96) was synthesized by adapting well known methods described in the literature and in Scheme 7 and Scheme 9. Aniline starting material 6 (SM-6), tert-butyl (S)-3-(5-amino-2-methylphenyl)-2-((tert-butoxycarbonyl)amino)propanoate, was reacted with commercial 4-methylsulfonylbenzenesulfonyl chloride (tosyl chloride, TsCl) [CAS No. 82964-91-8] in the presence of reducing triphenylphosphine (PPh₃) [CAS No. 603-35-0] to yield tert-butyl (2S)-2-((tert-butoxycarbonyl)amino)-3-(2-methyl-5-((p-tolylsulfinyl)amino)phenyl)propanoate.

The N-Boc- and tert-butyl ester protecting groups of the sulfinamide were removed in one step (Scheme 9). Removal of the N-Boc-protection group and the tert-butyl ester of tert-butyl (2S)-2-((tert-butoxycarbonyl)amino)-3-(2-methyl-5-((p-tolylsulfinyl)amino)phenyl)propanoate was conducted through reaction with 20-50 vol-% TFA in DCM at room temperature for about 1 h to about 24 h to yield the crude compound (96). Evaporation of volatiles, purification by prep. HPLC, and removal of the solvents by lyophilization yielded the pure compound (96). $C_{17}H_{20}N_2O_3S$. 332.42 g/mol.

Example 97

(2S)-2-Amino-3-(5-(((4-chlorophenyl)amino)sulfinyl)-2-methylphenyl)propanoic Acid (97)

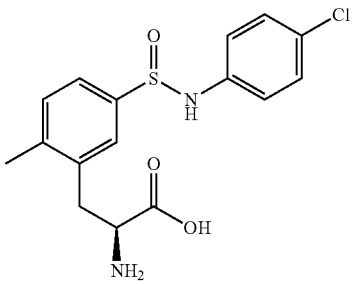

Compound (97) was synthesized by adapting well known methods described in the literature and as described in Schemes 8 and 9. Sulfonyl chloride starting material 9 (SM-9), tert-butyl (S)-2-((tert-butoxycarbonyl)amino)-3-(5-(chlorosulfonyl)-2-methylphenyl)propanoate, was reacted with commercial 4-chloroaniline [CAS No. 106-47-8] in the presence of reducing triphenylphosphine (PPh₃) [CAS No. 603-35-0] to yield tert-butyl (2S)-2-((tert-butoxycarbonyl)amino)-3-(5-(((4-chlorophenyl)amino)sulfinyl)-2-methylphenyl)propanoate.

The N-Boc- and tert-butyl ester protecting groups of the sulfinamide were removed in one step (Scheme 9). Removal of the N-Boc-protection group and the tert-butyl ester of tert-butyl (2S)-2-((tert-butoxycarbonyl)amino)-3-(5-(((4-chlorophenyl)amino)sulfinyl)-2-methylphenyl)propanoate was conducted through reaction with 20-50 vol-% TFA in DCM at room temperature for about 1 h to about 24 h to yield the crude compound (97). Evaporation of volatiles, purification by prep. HPLC, and removal of the solvents by lyophilization yielded the pure compound (97). $C_{16}H_{17}ClN_2O_3S$. 352.84 g/mol.

Example 98

(S)-2-Amino-3-(5-(((4-chlorophenyl)sulfonamido)oxy)-2-methylphenyl)propanoic Acid (98)

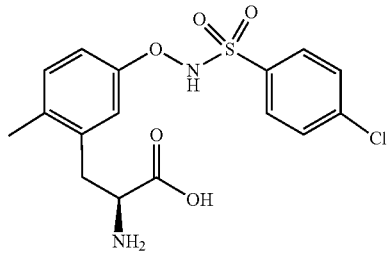

Compound (98) was synthesized by adapting methods described in literature. R-Iodo alanine derivative 3 (SM-3), tert-butyl (R)-2-((tert-butoxycarbonyl)amino)-3-iodopropanoate [CAS No. 1057341-65-7], was reacted with commercial 3-iodo-4-methylphenol [CAS No. 626250-54-2] under Negishi-coupling conditions, e.g., as described in US patent publication U.S. Pat. No. 9,783,487 and references cited therein, with tris(dibenzylideneacetone)dipalladium(0) [Pd₂(dba)₃][CAS No. 51364-51-3] and tri(o-tolyl)phosphine (P(o-Tol)₃) [CAS No. 6163-58-2] in the presence of an excess of activated zinc [Zn*][CAS No. 7440-66-6], pre-activated with elemental iodine (I₂) [CAS No. 7553-56-2] and chlorotrimethylsilane (TMSCl) [CAS No. 75-77-4] prior to use, in anhydrous DMF at 60° C. for overnight under a nitrogen atmosphere. Filtration over Celite®, evaporation of solvents, extractive aqueous workup and chromatographic purification on silica gel with hexane and ethyl acetate mixtures yielded tert-butyl (S)-2-((tert-butoxycarbonyl)amino)-3-(5-hydroxy-2-methylphenyl)propanoate.

The synthetic phenol tert-butyl (S)-2-((tert-butoxycarbonyl)amino)-3-(5-hydroxy-2-methylphenyl)propanoate was reacted with commercial 0-(2,4,6-trimethylbenzenesulfonyl)hydroxylamine (O-(mesitylsulfonyl)hydroxylamine) [CAS No. 36016-40-7] to yield tert-butyl (S)-3-(5-aminooxy-2-methylphenyl)-2-(tert-butoxycarbonylamino)propanoate using methods well-known in the art.

The aromatic hydroxylamine tert-butyl (S)-3-(5-aminooxy-2-methylphenyl)-2-(tert-butoxycarbonylamino)propanoate was reacted with commercial 4-chlorobenzenesulfonyl chloride [CAS No. 98-60-2] in neat pyridine [CAS No. 110-86-1] in the presence of 4-N,N-dimethylaminopyridine (DMAP) [CAS No. 112258-3] at room temperature for overnight to yield tert-butyl (S)-2-((tert-butoxycarbonyl)amino)-3-(5-(((4-chlorophenyl)sulfonamido)oxy)-2-methylphenyl)propanoate.

The N-Boc- and tert-butyl ester protecting groups of the sulfonamide were removed in one step (Scheme 9). Removal of the N-Boc-protection group and the tert-butyl ester of tert-butyl (S)-2-((tert-butoxycarbonyl)amino)-3-(5-(((4-chlorophenyl)sulfonamido)oxy)-2-methylphenyl)propanoate was conducted through reaction with 20-50 vol-% TFA in DCM at room temperature for about 1 h to about 24 h to yield the crude compound (98). Evaporation of volatiles, purification by prep. HPLC, and removal of the solvents by lyophilization yielded the pure compound (98). C₁₆H₁₇ClN₂O₅S. 384.83 g/mol.

Example 99

(S)-2-Amino-3-(5-((N-(4-chlorophenyl)sulfamoyl)amino)-2-methylphenyl)propanoic Acid (99)

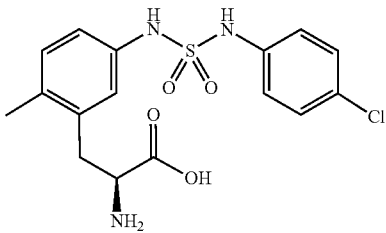

Compound (99) was synthesized by adapting methods described in the literature and in Scheme 7 and Scheme 9. Aniline starting material 6 (SM-6), tert-butyl (S)-3-(5-amino-2-methylphenyl)-2-((tert-butoxycarbonyl)amino)propanoate was reacted with commercial N-(4-chlorophenyl)sulfamoyl chloride [CAS No. 172662-89-4] in neat pyridine [CAS No. 110-86-1] at room temperature for overnight. Evaporation of volatiles, extractive aqueous workup and chromatographic purification on silica gel with hexane and ethyl acetate mixtures yield tert-butyl (S)-2-((tert-butoxycarbonyl)amino)-3-(5-((N-(4-chlorophenyl)sulfamoyl)amino)-2-methylphenyl)propanoate.

The N-Boc- and tert-butyl ester protecting groups of the protected sulfamoylamino compound are removed in one step (Scheme 9). Removal of the N-Boc-protection group and the tert-butyl ester of tert-butyl (S)-2-((tert-butoxycarbonyl)amino)-3-(5-((N-(4-chlorophenyl)sulfamoyl)amino)-2-methylphenyl)propanoate was conducted through reaction with 20-50 vol-% TFA in DCM at room temperature for 1 h to about 24 h to afford crude compound (99). Evaporation of volatiles, purification by prep. HPLC, and removal of the solvents by lyophilization yielded the pure compound (99). C₁₆H₁₈ClN₃O₄S. 383.85 g/mol.

Example 100

Methyl (S)-2-amino-3-(5-(N-(4-chlorophenyl)sulfamoyl)-2-methylphenyl)propanoate (100)

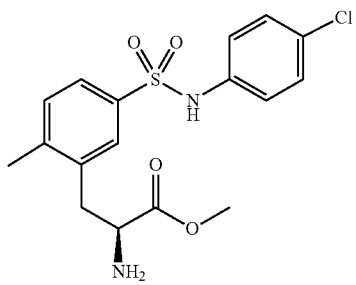

Compound (100) was synthesized by adapting methods described in Scheme 2, Scheme 3, and Scheme 9.

For the synthesis and analytical data of 3-bromo-N-(4-chlorophenyl)-4-methylbenzenesulfonamide see Example 51. Synthetic 3-bromo-N-(4-chlorophenyl)-4-methylbenzenesulfonamide (1.0 g, 2.8 mmol) and starting material 1 (SM-1), methyl (R)-2-((tert-butoxycarbonyl)amino)-3-iodopropanoate [CAS No. 93267-04-0](500 mg, 1.39 mmol) were cross-coupled through Pd(0)-catalyzed Negishi-coupling using tris(dibenzylideneacetone)dipalladium (Pd₂(dba)₃) [CAS No. 51364-51-3](63 mg, 0.07 mmol) and tris(o-tolyl)phosphine (P(o-Tol)₃) [CAS No. 6163-58-2](85 mg, 0.28 mmol) in the presence of an excess of zinc dust [CAS No. 7440-66-6](1.3 g, 20.2 mmol), pre-activated with elemental iodine (I₂) [CAS No. 7553-56-2](128 mg, 0.5 mmol) and trimethylchlorosilane (TMSCl) [CAS No. 75-77-4](63 μL, 54 mg, 0.5 mmol) in anhydrous DMF (5 mL+5 mL) at 60° C. for overnight under a nitrogen atmosphere. Filtration over Celite®, extractive aqueous work-up, and chromatographic purification over silica gel (hexane/ethyl acetate=7:3, (v/v)) yielded methyl (S)-2-((tert-butoxycarbonyl)amino)-3-(5-(N-(4-chlorophenyl)sulfamoyl)-2-methylphenyl)propanoate (709 mg, 52% yield). TLC: Rf: 0.40 (hexane/ethyl acetate=7:3, (v/v)).

The amino protecting group of the sulfonamide was removed in one step (Scheme 9). Chemoselective removal of the N-Boc-protection group of methyl (S)-2-((tert-butoxycarbonyl)amino)-3-(5-(N-(4-chlorophenyl)sulfamoyl)-2-methylphenyl)propanoate (100 mg, 0.21 mmol) was conducted with 20 vol-% TFA in DCM (5 mL) at room temperature. Evaporation of volatiles and hydrolysis of the methyl ester group with lithium hydroxide monohydrate (LiOH·H₂O) (165 mg, 3.93 mmol, 5.0 eq.) in THF/water (5 mL, 1:1, v/v)) at room temperature yielded crude compound (100). Purification by prep. HPLC and removal of the solvents by lyophilization yielded pure compound (100) (50 mg, 62% yield) as a colorless (white) solid. LC/MS/UV: Rt: 1.140 min, calculated for $C_{17}H_{19}ClN_2O_4S$ 382.08, found (ESI (pos.) m/z=382.85 $[M+H^+]^+$, 764.50 $[2M+H^+]^+$, ESI (neg.) m/z=380.75 $[M-H^+]^-$, 762.35 $[2M-H^+]^-$; HPLC/UV: Rt: 8.713 min (96.5% AUC at 220 nm, 98.1% AUC at 254 nm); $^1$H NMR (300 MHz, DMSO-$d_6$): δ 7.54 (d, J=2.4 Hz, 1H), 7.52 (s, 1H), 7.35 (d, J=7.5 Hz, 1H), 7.30-7.23 (m, 2H), 7.10-03 (m, 2H), 4.07 (dd, J=8.7, 6.6 Hz, 1H), 3.50 (s, 3H), 3.10 (dd, J=14.1, 6.3 Hz, 1H, superimposed), 3.02 (dd, J=14.1, 8.1 Hz, superimposed), 2.30 (s, 3H). The $^1$H NMR signals of the amino group, N—H acidic group, and the carboxyl group were not observed because of H-D exchange with the moisture in the NMR solvent.

Example 101

Ethyl (S)-2-amino-3-(5-(N-(4-chlorophenyl)sulfamoyl)-2-methylphenyl)propanoate (101)

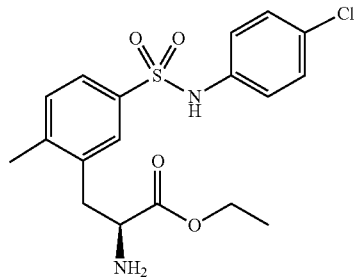

Ethyl (S)-2-amino-3-(5-(N-(4-chlorophenyl)sulfamoyl)-2-methylphenyl)propanoate was synthesized from (S)-2-amino-3-(5-(N-(4-chlorophenyl)sulfamoyl)-2-methylphenyl)propanoic acid (Example 52) in one step.

(S)-2-Amino-3-(5-(N-(4-chlorophenyl)sulfamoyl)-2-methylphenyl)propanoic acid (Example 52) (51 mg, 0.14 mmol) suspended in ethanol (EtOH) [CAS No. 64-17-5] (2.5 mL) was reacted with thionylchloride (SOCl$_2$) [CAS No. 7719-09-7] (500 µL, 819 mg, 6.9 mmol) at room temperature for overnight. Evaporation of volatiles yielded crude compound (101). Purification by prep. HPLC under neutral conditions and removal of the solvents by lyophilization yielded pure compound (101) (23 mg, 41% yield) as a white solid. LC/MS/UV: Rt: 1.207 min, calculated for $C_{18}H_{21}ClN_2O_4S$ 396.09, found (ESI (pos.) m/z=396.85 $[M+H^+]^+$, 792.50 $[2M+H^+]^+$, ESI (neg.) m/z=394.70 $[M-H^+]^-$; HPLC/UV: Rt: 9.301 min (96.5% AUC at 220 nm, 98.8% AUC at 254 nm); $^1$H NMR (300 MHz, DMSO-$d_6$): δ 7.53 (d, J=2.4 Hz, 1H), 2.48 (dd, J=8.4, 1.2 Hz, 1H), 7.31 (d, J=8.1 Hz, 1H), 7.28-7.23 (m, 2H), 7.10-7.04 (m, 2H), 3.92-3.80 (m, 2H), 3.65 (t, J=7.2 Hz, 1H), 2.89 (d, J=7.2 Hz, 2H), 2.29 (s, 3H), 0.95 (t, J=6.9 Hz, 3H). The $^1$H NMR signals of the amino group, N—H acidic group, and the carboxyl group were not observed because of H-D exchange with the moisture in the NMR solvent.

Example 102

(S)-2-Amino-3-(4-((5-amino-2-phenylbenzo[d]oxazol-7-yl)methoxy)-3,5-dichlorophenyl)propanoic Acid (102)

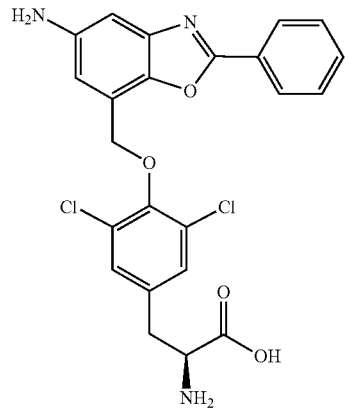

(S)-2-Amino-3-(4-((5-amino-2-phenylbenzo[d]oxazol-7-yl)methoxy)-3,5-dichlorophenyl)propanoic acid (100) [CAS No. 1037592-40-7] is commercially available. The synthesis of (S)-2-amino-3-(4-((5-amino-2-phenylbenzo[d]oxazol-7-yl)methoxy)-3,5-dichlorophenyl)propanoic acid, also referred to as JPH203, is described in PCT International Publication No. WO 2008081537 A1.

JPH203 exhibited an IC$_{50}$ of 19±6 nM in the LAT1 uptake inhibition assay described in Example 103.

JPH203 exhibited an LC$_{50}$ of 20±10 µM in the amino acid starvation assay described in Example 104.

Example 103

LAT1 Uptake Inhibition Assay

The ability of compounds to interact with LAT1 was measured using a radiolabeled competition uptake assay with [$^3$H]-Gabapentin ([$^3$H]-GP) (Perkin Elmer) in 96-well plates with LN229 cells (ATCC®). Ten (10)×10' (10,000) cells/well were plated in white, clear bottom plates and were allowed to grow for three (3) days. On the fourth day, the cells were washed and then incubated with 50,000 counts per minute (cpm) of [$^3$H]-GP in phosphate buffered saline (PBS) (VWR International) with increasing concentrations of test compounds in at least triplicate for 15 min. At end of the assay time, the incubation solution was removed, and plates were washed three times (3×) with 100 µL of ice-cold PBS buffer. One-hundred fifty (150) L of scintillation fluid (VWR International) was added to each well, and the radioactivity retained within the cells was measured on a 96-well scintillation counter. Background uptake ([$^3$H]-GP uptake in the presence of 10 mM non-radiolabeled gabapentin (GP)) (MedKoo) was subtracted and data were normalized to the DMSO control ([$^3$H]-GP uptake in the absence of any competitor). Data were fitted to the Michaelis-Menten equation using GraphPad Prism (Version 8.2.0).

Compounds (30), (44), (52), (76), (77), and (86) exhibited an IC$_{50}$, the concentration of test compound at which the [$^3$H]-GP uptake was inhibited by 50%, at a concentration of less than or equal to 0.020 µM.

Compounds (21), (29), (35), (38), (39), and (40) exhibited an IC$_{50}$, the concentration of test compound at which the

[³H]-GP uptake was inhibited by 50%, at a concentration of less than or equal to 0.100 μM and more than 0.020 μM.

Compounds (10), (41), (49), (53), (79), (82), (84), and (87) exhibited an $IC_{50}$, the concentration of test compound at which the [³H]-GP uptake was inhibited by 50%, at a concentration of less than or equal to 0.100 μM and more than 0.020 μM.

Compounds (2), (3), (7), (43), (46), (55), (65), and (75) exhibited an $IC_{50}$, the concentration of test compound at which the [³H]-GP uptake was inhibited by 50%, at a concentration of less than or equal to 1.00 μM and more than 0.100 μM.

Compounds (6), (17) (23), (50), (59), and (83) exhibited an $IC_{50}$, the concentration of test compound at which the [³H]-GP uptake was inhibited by 50%, at a concentration of less than or equal to 1.00 μM and more than 0.100 μM.

Compounds (16), (26), (27), (32), (48), and (57) exhibited an $IC_{50}$, the concentration of test compound at which the [³H]-GP uptake was inhibited by 50%, at a concentration of less than or equal to 1.00 μM and more than 0.100 μM.

Compounds (15), (56), (58), and (69) exhibited an $IC_{50}$, the concentration of test compound at which the [³H]-GP uptake was inhibited by 50%, at a concentration of less than or equal to 1.00 μM and more than 0.100 μM.

Compounds (5), (19), (28), (33), (37), (42), (60), (66), and (85) exhibited an $IC_{50}$, the concentration of test compound at which the [³H]-GP uptake was inhibited by 50%, at a concentration of less than or equal to 1.00 μM and more than 0.100 μM.

Compounds (4), (8), (9), (11), (12), (13), (14), (20), (22), (24), (25), (34), (36), (54), (63), (64), (73), (78), (80), and (81) exhibited an $IC_{50}$, the concentration of test compound at which the [³H]-GP uptake was inhibited by 50%, at a concentration of less than or equal to 10.00 μM and more than 1.00 μM.

Compounds (1), (18), (31), (45), (47), (51), (61), (62), (67), (68), (70), (71), (72), and (74) exhibited an $IC_{50}$, the concentration of test compound at which the [³H]-GP uptake was inhibited by 50%, at a concentration of equal to or more than 10.00 μM.

Example 104

Amino Acid Starvation Assay

The ability of compounds to inhibit amino acid uptake interact with LAT1 was measured using an antiproliferation assay with LN229 cells (ATCC®). LN229 cells were cultured in DMEM medium (VWR International). Two (2)×10' (2,000) cells/well were plated in clear bottom 96-well plates (CellBIND®, Corning 3340) and were allowed to attach overnight. The next day, cells were washed once with PBS buffer (VWR International). F12K medium (200 L) (VWR International) with increasing concentrations of test compounds in at least triplicate was added. Cells were incubated for six (6) days at 37° C. and 5% $CO_2$. At end of the assay, 140 μL of supernatant medium were removed from each well and 60 μL of CellTiter-Glo® (Promega) were added. Cell lysis was induced by placing the plates for three (3) minutes on an orbital shaker. Plates were incubated for 10 min at 25° C. to stabilize the luminesce signal. Luminescence was recorded using an EnSpire® Multimode Plate Reader (Perkin Elmer). Background (luminescence from wells incubated in the presence of 100 M of commercial LAT1 inhibitor JPH203 (MedKoo) was subtracted, and data were normalized to the DMSO control (proliferation in the absence of any competitor). Data were fitted to the Michaelis-Menten equation using GraphPad Prism (Version 8.2.0).

Compounds (44), (52), (76), (77), and (86) exhibited an $LC_{50}$, the concentration of test compound at which the proliferation was inhibited by 50%, at a concentration of less than 30 μM.

Compounds (10), (21), (29), (30), (35), (38), (39), (40) and (41) exhibited an $LC_{50}$, the concentration of test compound at which the proliferation was inhibited by 50%, at a concentration of less than 100 μM and more or equal than 30 μM.

Compounds (49), (53), (79), (53), (82) and (87) exhibited an $LC_{50}$, the concentration of test compound at which the proliferation was inhibited by 50%, at a concentration of more or equal than 100 μM. The structure and activity of various LAT1-targeted inhibitors is summarized in Table 1.

TABLE 1

Structure and activity of LAT1-targeted inhibitors.

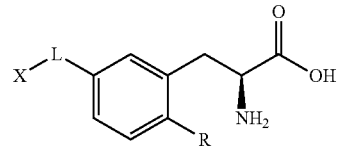

| Compound | Moiety (X) | Linker (L) | R | LAT1 inhibition $IC_{50}$ (nM ± SE) | Anti-proliferation $LC_{50}$ (μM ± SE) |
|---|---|---|---|---|---|
| 76 | 3-Bromophenyl—* | *—NH—SO$_2$— | —Me | 9 ± 3 | 11 ± 1 |
| 44 | 4-Methoxyphenyl—* | *—NH—SO$_2$— | —Me | 10 ± 3 | 20 ± 6 |
| 86 | 4-Chlorophenyl—* | *—NH—SO$_2$— | —iPr | 10 ± 1 | 4 ± 0.7 |
| 77 | 4-Bromophenyl—* | *—NH—SO$_2$— | —Me | 12 ± 4 | 13 ± 1 |
| 52 | 4-Chlorophenyl—* | *—NH—SO$_2$— | —Me | 12 ± 2 | 9.7 ± 0.7 |
| 30 | Benzyl—* | *—NH—SO$_2$— | —Me | 20 ± 4 | 38 ± 2 |
| 39 | 1-Napthyl—* | *—NH—SO$_2$— | —Me | 24 ± 9 | 32 ± 2 |
| 40 | 4-Phenylphenyl—* | *—NH—SO$_2$— | —Me | 25 ± 8 | 60 ± 20 |
| 35 | Phenyl—* | *—NH—SO$_2$— | —Me | 30 ± 8 | 40 ± 10 |
| 29 | 3-Bromophenyl—* | *—SO$_2$—NH— | —Me | 40 ± 10 | 90 ± 30 |
| 38 | 3-Phenylphenyl—* | *—SO$_2$—NH— | —Me | 40 ± 10 | 52 ± 2 |
| 21 | 5-Dimethylamino-1-naphthyl—* | *—SO$_2$—NH— | —iPr | 50 ± 10 | 49 ± 1 |
| 41 | 1-Butyl—* | *—NH—SO$_2$— | —Me | 56 ± 9 | 36 ± 10 |
| 53 | Cyclohexyl—* | *—NH—SO$_2$— | —Me | 60 ± 10 | 100 ± 10 |

TABLE 1-continued

Structure and activity of LAT1-targeted inhibitors.

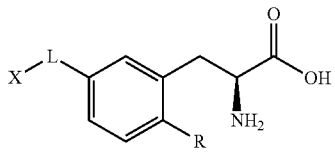

| Compound | Moiety (X) | Linker (L) | R | LAT1 inhibition IC$_{50}$ (nM ± SE) | Anti-proliferation LC$_{50}$ (μM ± SE) |
|---|---|---|---|---|---|
| 79 | 4-Chlorophenyl—* | *—NH—SO$_2$— | —H | 80 ± 10 | 100 ± 20 |
| 49 | 5-Dimethylamino-1-naphthyl—* | *—NH—SO$_2$— | —Me | 80 ± 20 | 100 ± 10 |
| 10 | Phenyl—* | *—SO$_2$—NH— | —Me | 100 ± 40 | 70 ± 20 |
| 87 | 4-tert-Butylphenyl—* | *—SO$_2$—NH— | —Me | 100 ± 20 | 100 ± 20 |

*Bonding between X and L moieties.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A compound having the structure of Formula (3):

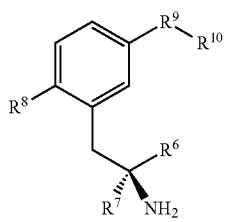

(3)

or a pharmaceutically acceptable salt thereof, wherein,
$R^6$ is selected from —COOH, —COOR$^a$, —COR$^a$, and —CON(R$^b$)$_2$, wherein,
$R^a$ is C$_{1-4}$ alkyl; and
each R$^b$ is independently selected from hydrogen, —OH, C$_{1-4}$ alkyl, and C$_{1-4}$ alkoxy;
$R^7$ is selected from hydrogen and methyl;
$R^8$ is selected from hydrogen, halogen, C$_{1-3}$ alkyl, and C$_{1-3}$ alkoxy;
$R^9$ is selected from —S(O)$_2$—NR— and —NR—S(O)$_2$—, wherein R is selected from hydrogen and methyl;
$R^{10}$ is selected from C$_{6-10}$ aryl, substituted C$_{6-10}$ aryl, C$_{5-6}$ cycloalkyl, and biphenyl; and
each substituent is independently selected from halogen, phenyl, —N(—R)$_2$, C$_{1-4}$ alkoxy, and C$_{1-4}$ alkyl, wherein each R is independently selected from hydrogen and methyl.

2. The compound of claim 1, wherein $R^6$ is —COOH.
3. The compound of claim 1, wherein $R^7$ is hydrogen.
4. The compound of claim 1, wherein $R^8$ is methyl.
5. The compound of claim 1, wherein $R^9$ is —S(O)$_2$—NR—.
6. The compound of claim 1, wherein $R^9$ is —NR—S(O)$_2$—.
7. The compound of claim 1, wherein $R^9$ is —S(O)$_2$—NH—.
8. The compound of claim 1, wherein $R^9$ is —NH—S(O)$_2$—.
9. The compound of claim 1, wherein $R^{10}$ is phenyl.
10. The compound of claim 1, wherein $R^{10}$ is substituted phenyl.
11. The compound of claim 10, wherein the substituted phenyl is 4-substituted phenyl.
12. The compound of claim 10, wherein the substituted phenyl is 3-substituted phenyl.
13. The compound of claim 10, wherein the substituent is selected from Cl, Br, methoxy, and benzyl.
14. The compound of claim 1, wherein $R^{10}$ is naphthyl.
15. The compound of claim 1, wherein $R^{10}$ is substituted naphthyl.
16. The compound of claim 15, wherein the substituted naphthyl is 5-substituted naphthyl.
17. The compound of claim 15, wherein the substituent is —N(R)$_2$.
18. The compound of claim 15, wherein the substituent is —N(—CH$_3$)$_2$.
19. The compound of claim 1, wherein $R^{10}$ is biphenyl.
20. The compound of claim 1, wherein $R^{10}$ is cyclohexyl.
21. The compound of claim 1, wherein
$R^6$ is —COOH;
$R^7$ is hydrogen;
$R^8$ is methyl; and
$R^9$ is —S(O)$_2$—NH—.
22. The compound of claim 1, wherein
$R^6$ is —COOH;
$R^7$ is hydrogen;
$R^8$ is methyl; and
$R^9$ is —NH—S(O)$_2$—.
23. The compound of claim 1, wherein the compound is selected from:
(S)-2-amino-3-(5-((5-(dimethylamino)naphthalene)-1-sulfonamido)-2-methylphenyl)propanoic acid (2);
(S)-2-amino-3-(3-((5-(dimethylamino)naphthalene)-1-sulfonamido)phenyl)propanoic acid (3);
(S)-2-amino-3-(2-methyl-5-((4-methylphenyl)sulfonamido)phenyl)propanoic acid (7);
(S)-2-amino-3-(2-methyl-5-(phenylsulfonamido)phenyl)propanoic acid (10);
(S)-2-amino-3-(5-((5-(dimethylamino)naphthalene)-1-sulfonamido)-2-isopropylphenyl)propanoic acid (21);
(S)-2-amino-3-(5-((3-bromophenyl)sulfonamido)-2-methylphenyl)propanoic acid (29);

(S)-2-amino-3-(5-(N-benzylsulfamoyl)-2-methylphenyl) propanoic acid (30);
(S)-2-amino-3-(2-methyl-5-(N-phenylsulfamoyl)phenyl) propanoic acid hydrochloride (35);
(S)-3-(5-([1,1'-biphenyl]-3-sulfonamido)-2-methylphenyl)-2-aminopropanoic acid (38);
(S)-2-amino-3-(2-methyl-5-(N-(naphthalen-1-yl)sulfamoyl)phenyl)propanoic acid (39);
(S)-3-(5-(N-([1,1'-biphenyl]-4-yl)sulfamoyl)-2-methylphenyl)-2-aminopropanoic acid (40);
(S)-2-amino-3-(5-((3,5-dichlorophenyl)sulfonamido)-2-methylphenyl)propanoic acid (43);
(S)-2-amino-3-(5-(N-(4-methoxyphenyl)sulfamoyl)-2-methylphenyl)propanoic acid (44);
(S)-2-amino-3-(5-(N-(5-(dimethylamino)naphthalen-1-yl)sulfamoyl)-2-methylphenyl)propanoic acid (49);
(S)-2-amino-3-(5-(N-(4-chlorophenyl)sulfamoyl)-2-methylphenyl)propanoic acid (52);
(S)-2-amino-3-(5-(N-cyclohexylsulfamoyl)-2-methylphenyl)propanoic acid (53);
(S)-2-amino-3-(5-((benzylthio)methyl)-2-methylphenyl) propanoic acid (55);
(S)-2-amino-3-(5-(benzylsulfonyl)-2-methylphenyl)propanoic acid (65);
(S)-2-amino-3-(5-(N-(3-bromophenyl)sulfamoyl)-2-methylphenyl)propanoic acid (76);
(S)-2-amino-3-(5-(N-(4-bromophenyl)sulfamoyl)-2-methylphenyl)propanoic acid (77);
(S)-2-amino-3-(3-(N-(4-chlorophenyl)sulfamoyl)phenyl) propanoic acid (79);
tert-butyl (S)-2-amino-3-(5-(N-(4-chlorophenyl)sulfamoyl)-2-methylphenyl)propanoate (82);
(S)-2-amino-3-(5-(N-(4-chlorophenyl)-N-methylsulfamoyl)-2-methylphenyl)propanoic acid (84);
(S)-2-amino-3-(5-(N-(4-chlorophenyl)sulfamoyl)-2-isopropylphenyl)propanoic acid (86); and
(S)-2-amino-3-(5-((4-(tert-butyl)phenyl)sulfonamido)-2-methylphenyl)propanoic acid (87);
or a pharmaceutically acceptable salt of any of the foregoing.

24. A pharmaceutical composition comprising the compound of claim 1 or a pharmaceutically acceptable salt thereof; and a pharmaceutically acceptable vehicle.

25. A method of treating an organ transplant rejection, an acute graft-vs-host-disease, or a chronic graft-vs-host-disease in a patient comprising administering to a patient in need of such treatment a therapeutically effective amount of the compound of claim 1 or a pharmaceutically acceptable salt thereof.

26. A method of treating a disease in a patient comprising administering to a patient in need of such treatment a therapeutically effective amount of the compound of claim 1 or a pharmaceutically acceptable salt thereof, wherein the disease is selected from alopecia, pemphigus, psoriasis, scleroderma, vitiligo, dermatitis, asthma, fibrosis, rheumatoid arthritis, lupus, Crohn's disease, ulcerative colitis, and Celiac disease.

27. A method of treating an organ transplant rejection, an acute graft-vs-host-disease, or a chronic graft-vs-host-disease in a patient comprising administering to a patient in need of such treatment a therapeutically effective amount of the pharmaceutical composition of claim 24.

28. A method of treating a disease in a patient comprising administering to a patient in need of such treatment a therapeutically effective amount of the pharmaceutical composition of claim 24, wherein the disease is selected from alopecia, pemphigus, psoriasis, scleroderma, vitiligo, dermatitis, asthma, fibrosis, rheumatoid arthritis, lupus, Crohn's disease, ulcerative colitis, and Celiac disease.

* * * * *